US008796253B2

(12) United States Patent
Boyer et al.

(10) Patent No.: US 8,796,253 B2
(45) Date of Patent: Aug. 5, 2014

(54) HETEROARYL SUBSTITUTED PYRAZOLE DERIVATIVES USEFUL FOR TREATING HYPER-PROLIFERATIVE DISORDERS AND DISEASES ASSOCIATED WITH ANGIOGENESIS

(75) Inventors: Stephen Boyer, Bethany, CT (US); Michael Härter, Leverkusen (DE); Philip Wickens, Richmond Hill (CA); Manoj Patel, Berlin, CT (US); Ellalahewage Sathyajith Kumarasinghe, Franklin, MA (US); Ajay Kumar Bhargava, Woodbridge, CT (US); Karl-Heinz Thierauch, Berlin (DE); Hartmut Beck, Köln (DE); Susanne Greschat, Düsseldorf (DE); Peter Ellinghaus, Melle (DE); Patrick Paulus, Frankfurt am Main (DE); Holger Hess-Stumpp, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 633 days.

(21) Appl. No.: 12/600,640

(22) PCT Filed: May 8, 2008

(86) PCT No.: PCT/EP2008/003681
§ 371 (c)(1),
(2), (4) Date: Jun. 1, 2010

(87) PCT Pub. No.: WO2008/141731
PCT Pub. Date: Nov. 27, 2008

(65) Prior Publication Data
US 2010/0249085 A1    Sep. 30, 2010

Related U.S. Application Data

(60) Provisional application No. 60/930,816, filed on May 18, 2007.

(51) Int. Cl.
| C07D 403/04 | (2006.01) |
| C07D 413/04 | (2006.01) |
| C07D 413/14 | (2006.01) |
| C07D 471/04 | (2006.01) |
| C07D 491/04 | (2006.01) |

(52) U.S. Cl.
USPC .......... 514/210.2; 514/230.8; 514/234.5; 514/254.06; 514/303; 514/322; 514/326; 514/340; 514/364; 514/374; 514/397; 544/138; 544/370; 546/118; 546/199; 546/210; 546/269.4; 548/131; 548/217; 548/238; 548/301.7; 548/306.1

(58) Field of Classification Search
None
See application file for complete search history.

(56) References Cited

U.S. PATENT DOCUMENTS

| 6,162,819 A | 12/2000 | Schindler et al. |
| 2003/0022924 A1 | 1/2003 | Pillarisetti et al. |
| 2005/0187276 A1 | 8/2005 | Park et al. |
| 2012/0028950 A1* | 2/2012 | Harter et al. ............... 514/210.2 |

FOREIGN PATENT DOCUMENTS

| WO | 0157024 A1 | 8/2001 |
| WO | 02100826 A2 | 12/2002 |
| WO | 03051833 A2 | 6/2003 |
| WO | 2004058176 A2 | 7/2004 |
| WO | 2004089303 A1 | 10/2004 |
| WO | 2006088903 A2 | 8/2006 |
| WO | 2006114313 A1 | 11/2006 |
| WO | 2007002559 A1 | 1/2007 |
| WO | 2007034279 A2 | 3/2007 |

OTHER PUBLICATIONS

IARC International Agency for Research on Caner: Globocan 2002.
American Cancer Society: Cancer Facts and Figures 2007.
Gibbs, JB: Mechanism-based target identification and drug discovery in cancer research, Science 2000, 297 (5460), 1969-1973.
Semenza, GL and Wang, GL.: A nuclear factor induced by hypoxia via de novo proten sythesis binds to the human erythropoetin gene enhancer at a sit required for transcriptional activation, Mol. Cell. Biol. 1992, 12 (12) 5447-5454.
Wang, GL and Semenza GL: Purification and characterization of hypoxia-inducible factor 1, J. Biol. Chem. 1995, 270 (3), 1230-1237.
Wang, GL et al.: Hypoxia-inducible factor 1 is a basic-helix-loop-helix-PAS heterdimer regulated by cellular O2 tension, PNAS 1995, 92 (12), 5510-5514.
Jiang, BH et al., Dimerization, DNA binding, transactivation properties of hypoxia-inducible factor 1, J. Biol. Chem. 1996, 271 (30), 17771-17778.
Makino,YC et al.: Nature 2001, 414 (6863), 550-554.
Jiang, BH et al.: Hypoxia-inducible factor 1 levels vary exponentially over a physiologically relevant range of O2 tension, Am. J. Physiol. 1996, 271, 1172-1180.
Maxwell PH et al.: The tumor suppressor protein VHL targets hypoxia-inducible facotrs for oxygen-dependent proteolysis, Nature 1999, 399 (6733), 271-275.
Hirota, K. and Semenza, GL: Regulation of angiogenesis by hypoxia-inducible factor 1, Crit. Rev. Oncol. Hematol. 2006, 59 (1), 15-26.
Chen, J. et al.:Dominant-negative hypoxia-inducible factor-1 alpha reduces tumorigenicity of pancreatic cancer cells through the suppression of glucose metabolism, Am. J. Pathol. 2003, 162 (4), 1283-1291.
Stoeltzing, O. et al.: Role of hypoxia-inducible factor-1alpha in gastric cancer cell growth, angio-genesis, and vessel maturation, J. Natl. Cancer Inst. 2004, 96 (12), 946-956.
Li, L. et al.: Evaluating hypoxia-inducible factor-1alpha as a cancer therapeutic target via inducible RNA interference in vivo, Cancer Res. 2005, 65 (16), 7249-7258.

(Continued)

Primary Examiner — Kamal Saeed

(57) ABSTRACT

This invention relates to novel heteroaryl substituted pyrazole compounds, pharmaceutical compositions containing such compounds and the use of those compounds or compositions for treating hyper-proliferative and/or angiogenesis disorders, as a sole agent or in combination with other active ingredients or therapeutic measures.

20 Claims, No Drawings

(56) References Cited

OTHER PUBLICATIONS

Mizukami, Y. et al.: Induction of interleukin-8 preserves the angiogenic response in HIF-1alpha-deficient colon cancer cells, Nat. Med. 2005, 11 (9), 992-997.

Li., S. et al.: Knockdown of hypoxia-inducible factor-1alpha in breast carcinoma MCF-7 cells results in reduced tumor growth and increased sensitivity to methotrexate, Biochem. Biophys. Res. Commun. 2006, 342, 1341-1351.

Borioni, A. et al.: Synthesis of new 4-heteroaryl-2-phenylquinolines and their pharmacological activity as NK-2/NK-3 receptor ligands, Archive Der Pharmazie, vol. 340, (1), Jan. 2007, pp. 17-25.

International Search Report, Appl. No. PCT/EP2008/003681, dated Sep. 26, 2008.

Database Registry, Chemical Abstract Service: XP002497423-XP002497431.

* cited by examiner

HETEROARYL SUBSTITUTED PYRAZOLE DERIVATIVES USEFUL FOR TREATING HYPER-PROLIFERATIVE DISORDERS AND DISEASES ASSOCIATED WITH ANGIOGENESIS

FIELD OF THE INVENTION

This invention relates to novel heteroaryl substituted pyrazole compounds, pharmaceutical compositions containing such compounds and the use of those compounds or compositions for treating hyper-proliferative and/or angiogenesis disorders, as a sole agent or in combination with other active ingredients or therapeutic measures.

BACKGROUND OF THE INVENTION

Cancer is a disease resulting from an abnormal growth of tissue. Certain cancers have the potential to invade into local tissues and also metastasize to distant organs. This disease can develop in a wide variety of different organs, tissues and cell types. Therefore, the term "cancer" refers to a collection of over a thousand different diseases.

Over 4.4 million people worldwide were diagnosed with breast, colon, ovarian, lung, or prostate cancer in 2002 and over 2.5 million people died of these devastating diseases (Globocan 2002 Report). In the United States alone, over 1.25 million new cases and over 500,000 deaths from cancer were predicted in 2005. The majority of these new cases were expected to be cancers of the colon (~100,000), lung (~170,000), breast (~210,000) and prostate (~230,000). Both the incidence and prevalence of cancer is predicted to increase by approximately 15% over the next ten years, reflecting an average growth rate of 1.4% (American Cancer Society, Cancer Facts and Figures 2005).

Cancer treatments are of two major types, either curative or palliative. The main curative therapies for cancer are surgery and radiation. These options are generally successful only if the cancer is found at an early localized stage (Gibbs J B, 2000). Once the disease has progressed to locally advanced cancer or metastatic cancer, these therapies are less effective and the goal of therapy aims at symptom palliation and maintaining good quality of life. The most prevalent treatment protocols in either treatment mode involve a combination of surgery, radiation therapy and/or chemotherapy.

Cytotoxic drugs (also known as cytoreductive agents) are used in the treatment of cancer, either as a curative treatment or with the aim of prolonging life or palliating symptoms. Cytotoxics may be combined with radiotherapy and/or surgery, as neo-adjuvant treatment (initial chemotherapy aimed at shrinking the tumor, thereby rendering local therapy such as surgery and radiation more effective) or as adjuvant chemotherapy (used in conjunction or after surgery and/or localized therapy). Combinations of different drugs are frequently more effective than single drugs: they may provide an advantage in certain tumors of enhanced response, reduced development of drug resistance and/or increased survival. It is for these reasons that the use of combined cytotoxic regimens in the treatment of many cancers is very common.

Cytotoxic agents in current use employ different mechanisms to block proliferation and induce cell death. They can be generally categorized into the following groups based on their mechanism of action: the microtubule modulators that interfere with the polymerization or depolymerization of microtubules (e.g. docetaxel, paclitaxel, vinblastine, vinorelbine); anti-metabolites including nucleoside analogs and other inhibitors of key cellular metabolic pathways (e.g. capecitabine, gemcitabine, methotrexate); agents that interact directly with DNA (e.g. carboplatin, cyclophosphamide); anthracycline DNA interchalators that interfere with DNA polymerase and Topoisomerase II (e.g. doxorubicin, epirubicin); and the non-anthracycline inhibitors of Topoisomerase II and I enzymatic activity (e.g. topotecan, irinotecan, and etoposide). Even though different cytotoxic drugs act via different mechanisms of action, each generally leads to at least transient shrinkage of tumors.

Cytotoxic agents continue to represent an important component in an oncologist's arsenal of weapons for use in fighting cancer. The majority of drugs currently undergoing late Phase II and Phase III clinical trials are focusing on known mechanisms of action (tubulin binding agents, anti-metabolites, DNA processing), and on incremental improvements in known drug classes (for example the taxanes or the camptothecins). A small number of cytotoxic drugs based on novel mechanisms have recently emerged. Modes of action for these cytotoxics include inhibition of enzymes involved in DNA modification [e.g. histone deacetylase (HDAC)], inhibition of proteins involved in microtubule movement and cell cycle progression (e.g. kinesins, aurora kinase), and novel inducers of the apoptotic pathway (e.g. bcl-2 inhibitors).

Even though cytotoxic agents remain in the forefront of approaches to treat patients with advanced solid tumors, their limited efficacy and narrow therapeutic indices result in significant side effects. Moreover, basic research into cancer has led to the investigation of less toxic therapies based on the specific mechanisms central to tumor progression. Such studies could lead to effective therapy with improvement of the quality of life for cancer patients. Thus, a new class of therapeutic agents has emerged, referred to as cytostatics. Cytostatics direct their action on tumor stabilization and are generally associated with a more limited and less aggravating side effect profile. Their development has resulted from the identification of specific genetic changes involved in cancer progression and an understanding of the proteins activated in cancer such as tyrosine kinases and serine/threonine kinases.

Several new drugs that are directed at various molecular targets have been approved over the past several years for the treatment of cancer. Imatinib is an inhibitor of the Abl tyrosine kinase and was the first small molecule tyrosine kinase inhibitor to be approved for the treatment of chronic myeloid leukemia (CML). Based on additional activity of imatinib against the receptor tyrosine kinase activated in gastrointestinal stromal tumors (GIST), c-KIT, it was subsequently approved for the treatment of advanced GIST. Erlotinib, a small molecule inhibitor of EGFR, was approved in late 2004 for the treatment of non-small cell lung carcinoma (NSCLC). Sorafenib, an inhibitor of multiple kinases including c-Raf and VEGFR2 was approved for the treatment of advanced renal cell carcinoma (RCC) in December, 2005. Recently in January of 2006, Sunitinib, a multi-kinase inhibitor was approved for the treatment of refractory- or resistant-GIST and advanced RCC. These small molecule inhibitors demonstrate that targeted approaches are successful for the treatment of different types of cancers.

In addition to direct inhibition of tumor cell targets, cytostatic drugs are being developed to block the process of tumor angiogenesis. This process supplies the tumor with existing and new blood vessels to support continued nourishment and therefore help promote tumor growth.

Angiogenesis can be triggered by hypoxia, a common feature of the solid tumor micro-environment. Cancer cells adapt to hypoxia by reprogramming cellular metabolism to conserve energy and to generate ATP in the presence of reduced levels of $O_2$. In order to survive and proliferate under hypoxia, tumor cells produce angiogenesis stimulating factors that induce the formation of new blood vessels from the existing vasculature to increase $O_2$ delivery. This adaptive regulation of gene transcription under hypoxia is accomplished mostly by the induction of a transcription factor known as hypoxia inducible factor (HIF), a master activator of hypoxia responsive genes (Semenza and Wang 1992; Wang and Semenza 1995).

The HIF transcription factor is a heterodimer of an alpha and a beta subunit. There are three isoforms of the alpha subunit which form heterodimers with two beta isoforms (also known as ARNT1 and ARNT2 [aryl-hydrocarbon-receptor-nuclear translocator]). Both HIF subunits are members of the basic helix-loop-helix (HLH) containing PER_ARNT_SIM (PAS) domain family of transcription factors (Wang, Jiang et al. 1995). The HLH and PAS domains mediate heterodimer formation between the alpha and the beta subunits, which is necessary for DNA binding and transactivation of gene transcription (Jiang, Rue et al. 1996). In contrast to HIF-1α and HIF-2α, the HIF-3α is most likely a negative regulator which lacks gene transactivation properties (Makino, Cao et al. 2001). HIF-1α and HIF-2α show the greatest structural and functional similarity, as each of these proteins is hypoxia-induced and dimerize with HIF-1β. While HIF-1β is constitutively expressed, HIF-1α expression increases exponentially as $O_2$ concentration declines (Jiang, Semenza et al. 1996). In order to achieve a quick response to hypoxia, cells continuously synthesize, ubiquitinate, and degrade HIF-1α and HIF-2α proteins under normoxic conditions. Hydroxylation of two prolyl residues within the oxygen-dependent degradation domain (ODD) of HIF-1α and HIF-2α proteins mediates interactions with von Hippel-Lindau (VHL) E3 ubiquitin ligase complex that targets them for proteasomal degradation (Maxwell, Wiesener et al. 1999).

HIF-1α over expression is associated with increased microvessel density and/or VEGF expression in major tumor types including the colon and non-small-cell lung cancers (Hirota and Semenza 2006). HIF-1α loss-of-function resulted in varying degree of inhibition of tumor xenograft growth via suppression of angiogenesis and/or glucose metabolism in nude mice depending upon the tumor type (Chen, Zhao et al. 2003; Stoeltzing, McCarty et al. 2004; Li, Lin et al. 2005; Mizukami, Jo et al. 2005; Li, Shi et al. 2006). It is therefore anticipated that inhibitors of HIF pathway may act as anti-cancer therapeutics.

Despite advancements in the art, there remains a need for cancer treatments and anti-cancer compounds.

Compounds and compositions described herein, including salts, metabolites, solvates, solvates of salts, hydrates, prodrugs such as esters, polymorphs, and stereoisomeric forms thereof, exhibit anti-proliferative activity and are thus useful to prevent or treat the disorders associated with hyper-proliferation.

In EP 0908456-A1, WO 01/57024, WO 02/100826, WO 03/051833, WO 2004/058176, WO 2004/089303, WO 2006/088903, WO 2006/114313, WO 2007/002559 and WO 2007/034279, various 3-aryl and/or 3-heteroaryl substituted pyrazole derivatives and use thereof for the treatment of diseases have been disclosed.

DESCRIPTION OF THE INVENTION

One embodiment of this invention encompasses a compound having the Formula (I):

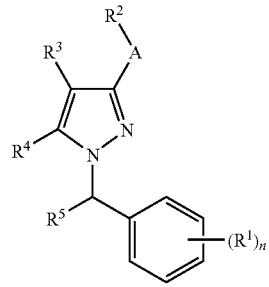

Formula I or a physiologically acceptable salt, solvate, hydrate or stereoisomer thereof, wherein:

A is heteroaryl optionally substituted with halogen or phenyl, or is heterocyclyl;

n is an integer from 0-3;

$R^1$ at each occurrence is independently halogen, —$NR^6C(O)R^7$, —$C(O)R^6$, —$C(O)OR^6$, —$OC(O)R^6$, —$OR^6$, —$SR^6$, —$S(O)R^6$, —$SO_2R^6$, cyano, nitro, —$C(O)NR^6R^7$, —$SO_2NR^6R^7$, or —$NR^6R^7$, or $R^1$ is independently aryl, heteroaryl, heterocyclyl, alkyl or cycloalkyl each optionally substituted with one or more halogen, $OR^6$ or $NR^6R^7$ groups;

$R^2$ is aryl optionally substituted with 1, 2 or 3 $R^8$ groups or heteroaryl optionally substituted with 1, 2 or 3 $R^8$ groups, when A is mono- or bicyclic heteroaryl or mono- or bicyclic heterocyclyl, or $R^2$ is hydrogen, halogen, cyano, alkyl optionally substituted with up to 3 fluoro atoms, alkyloxy optionally substituted with up to 3 fluoro atoms, cycloalkyl, aryloxy, aroyl, aralkyl optionally substituted with halogen, or heterocyclyl optionally substituted with alkyl, when A is bi- or tricyclic heteroaryl or mono-, bi- or tricyclic heterocyclyl;

$R^3$ and $R^4$ are each independently hydrogen, halogen, —$OR^6$, —$SR^6$, —$NR^6R^7$, alkyl optionally substituted with one or more halogen, $R^6$, —$OR^6$ or —$NR^6R^7$ groups, or cycloalkyl optionally substituted with one or more halogen, $R^6$, —$OR^6$ or —$NR^6R^7$ groups;

$R^5$ is hydrogen, oxo, or alkyl optionally substituted with one or more halogen, —$OR^6$ or —$NR^6R^7$ groups;

each occurrence of $R^6$ or $R^7$ may be the same or different and is independently hydrogen, or aryl, heteroaryl, heterocyclyl, alkyl, or cycloalkyl each of which may be optionally substituted with one or more hydrogen, halogen, —$OR^9$ or —$NR^9R^{10}$ groups;

each occurrence of $R^9$ may be the same or different and is independently hydrogen, halogen, —$NR^9C(O)R^{10}$, —$NR^9C(O)OR^{10}$, —$C(O)R^9$, —$C(O)OR^9$, —$OC(O)R^9$, —$OR^9$, —$SR^9$, —$S(O)R^9$, —$SO_2R^9$, cyano, nitro, —$C(O)NR^9R^{10}$, —$SO_2NR^9R^{10}$, —$NR^9R^{10}$, or aryl, heteroaryl, heterocyclyl, alkyl, or cycloalkyl, each of which may be optionally substituted with one or more halogen, $R^{11}$, —$OR^9$ or —$NR^9R^{10}$ groups;

each occurrence of $R^9$ and $R^{10}$ may be the same or different and is independently hydrogen, or aryl, heteroaryl, heterocyclyl, alkyl, cycloalkyl, aralkyl, or heterocyclylalkyl each of which may be optionally substituted with one or more hydrogen, halogen, hydroxyl, alkyloxy, cycloalkyloxy, aryloxy, amino, alkylamino, cycloalkylamino, arylamino, alkyl, cycloalkyl, alkylcarbonyl or alkoxycarbonyl groups;

each occurrence of $R^{11}$ may be the same or different and is independently hydrogen, oxo, aryl, heteroaryl, heterocyclyl, alkyl, cycloalkyl, —C(O)$R^9$, —C(O)O$R^9$, —$NR^{12}$C(O)$R^{13}$, —N[C(O)$R^{13}$]$_2$, —$NR^{12}$C(O)O$R^{13}$, or —N[C(O)O$R^{13}$]$_2$;

$R^{12}$ is hydrogen or alkyl; and $R^{13}$ is alkyl.

In another embodiment, the invention encompasses a compound of Formula (I), wherein A is mono- or bicyclic heteroaryl having 1 to 3 nitrogen, 0 or 1 oxygen and 0 or 1 sulfur ring heteroatoms;

n is an integer from 0-2;

$R^1$ at each occurrence is independently fluoro, chloro, bromo, cyano, —$NR^6$C(O)$R^7$, —C(O)O$R^6$, —O$R^6$, —S$R^6$, —S(O)$R^6$, —SO$_2R^6$, —C(O)$NR^6R^7$, or —SO$_2NR^6R^7$, or $R^1$ is independently alkyl, cycloalkyl or heterocyclyl each optionally substituted with one or more fluoro, O$R^6$ or $NR^6R^7$ groups;

$R^2$ is phenyl optionally substituted with 1 or 2 $R^8$ groups or heteroaryl optionally substituted with 1 or 2 $R^8$ groups, when A is mono- or bicyclic heteroaryl, or $R^2$ is cycloalkyl, phenoxy, benzoyl or phenylalkyl, when A is bicyclic heteroaryl;

$R^3$ and $R^4$ are each independently hydrogen, alkyloxy, amino, alkylamino, alkyl optionally substituted with one or more fluoro, hydroxy, alkyloxy, amino or alkylamino groups, or cycloalkyl optionally substituted with one or more fluoro, hydroxy, alkyloxy, amino or alkylamino groups;

$R^5$ is hydrogen or alkyl;

each occurrence of $R^6$ or $R^7$ may be the same or different and is independently hydrogen, or alkyl, cycloalkyl or heterocyclyl, each of which may be optionally substituted with one or more hydrogen, fluoro, —O$R^9$ or —$NR^9R^{10}$ groups;

each occurrence of $R^8$ may be the same or different and is independently hydrogen, fluoro, chloro, cyano, —$NR^9$C(O)$R^{10}$, —$NR^9$C(O)O$R^{10}$, —C(O)O$R^9$, —O$R^9$, —S$R^9$, —S(O)$R^9$, —SO$_2R^9$, —C(O)$NR^9R^{10}$, —SO$_2NR^9R^{10}$, —$NR^9R^{10}$, or alkyl, cycloalkyl, heterocyclyl or heteroaryl, each of which may be optionally substituted with one or more fluoro, chloro, $R^{11}$, —O$R^9$ or —$NR^9R^{10}$ groups;

each occurrence of $R^9$ and $R^{10}$ may be the same or different and is independently hydrogen, or alkyl, cycloalkyl, heterocyclyl or heterocyclylalkyl each of which may be optionally substituted with one or more hydrogen, fluoro, hydroxyl, alkyloxy, cycloalkyloxy, amino, alkylamino, cycloalkylamino, alkyl, cycloalkyl, alkylcarbonyl or alkoxycarbonyl groups;

each occurrence of $R^{11}$ may be the same or different and is independently hydrogen, oxo, alkyl, cycloalkyl, heterocyclyl, phenyl, heteroaryl, —C(O)$R^9$, —C(O)O$R^9$, —$NR^{12}$C(O)$R^{13}$, or —$NR^{12}$C(O)O$R^{13}$;

$R^{12}$ is hydrogen or alkyl; and $R^{13}$ is alkyl.

In a preferred embodiment, the invention encompasses a compound of Formula (I), wherein A is mono- or bicyclic heteroaryl having 1 to 3 nitrogen and 0 or 1 oxygen ring heteroatoms;

n is an integer from 0-2;

$R^1$ at each occurrence is independently fluoro, chloro, bromo, cyano, —$NR^6$C(O)$R^7$, C(O)O$R^6$, —O$R^6$, —S$R^6$, —S(O)$R^6$, —SO$_2R^6$, —C(O)$NR^6R^7$, or —SO$_2NR^6R^7$, or $R^1$ is independently alkyl or cycloalkyl each optionally substituted with one or more fluoro, hydroxy, alkyloxy, fluoroalkyloxy, amino or alkylamino groups;

$R^2$ is phenyl optionally substituted with 1 or 2 $R^8$ groups, or pyridyl, pyrimidinyl or pyrazinyl each optionally substituted with 1 or 2 $R^8$ groups;

$R^3$ is hydrogen;

$R^4$ is alkyloxy, amino, alkylamino, cyclopropyl, cyclobutyl, or alkyl optionally substituted with one or more fluoro, hydroxy or methoxy groups;

$R^5$ is hydrogen or methyl;

each occurrence of $R^6$ or $R^7$ may be the same or different and is independently hydrogen, or alkyl or cycloalkyl, each of which may be optionally substituted with one or more hydrogen, fluoro, hydroxy, alkyloxy, amino or alkylamino groups;

each occurrence of $R^8$ may be the same or different and is independently hydrogen, fluoro, chloro, cyano, —$NR^9$C(O)$R^{10}$, —$NR^9$C(O)O$R^{10}$, —C(O)O$R^9$, —O$R^9$, —S$R^9$, —S(O)$R^9$, —SO$_2R^9$, —C(O)$NR^9R^{10}$, —SO$_2NR^9R^{10}$, —$NR^9R^{10}$, or alkyl, cycloalkyl, monocyclic heterocyclyl or monocyclic heteroaryl, each of which may be optionally substituted with one or more fluoro, chloro, $R^{11}$, —O$R^9$ or —$NR^9R^{10}$ groups;

each occurrence of $R^9$ and $R^{10}$ may be the same or different and is independently hydrogen, or alkyl, cycloalkyl, monocyclic heterocyclyl or monocyclic heterocyclylmethyl each of which may be optionally substituted with one or more hydrogen, fluoro, hydroxyl, alkyloxy, cycloalkyloxy, alkyl, cycloalkyl, alkylcarbonyl or alkoxycarbonyl groups;

each occurrence of $R^{11}$ may be the same or different and is independently hydrogen, oxo, alkyl, cycloalkyl, monocyclic heterocyclyl, phenyl, monocyclic heteroaryl, alkylcarbonyl, alkoxycarbonyl, —NH—C(O)$R^{13}$, or —NH—C(O)O$R^{13}$; and $R^{13}$ is alkyl.

In a distinct embodiment, the invention encompasses a compound of Formula (I), wherein A is imidazol-2,4-diyl, 1,3-oxazol-2,4-diyl, 1,3-oxazol-2,5-diyl, 1,2,4-oxadiazol-3,5-diyl, 1,3,4-oxadiazol-2,5-diyl, 1H-benzimidazol-2,5-diyl, 1,3-benzoxazol-2,5-diyl, or 1,3-benzoxazol-2,6-diyl.

In another distinct embodiment, the invention encompasses a compound of Formula (I), wherein n is an integer from 0-2;

$R^1$ at each occurrence is independently fluoro, chloro, bromo, cyano, —$NR^6$C(O)$R^7$, —C(O)O$R^6$, —O$R^6$, —S$R^6$, —S(O)$R^6$, —SO$_2R^6$, —C(O)$NR^6R^7$, or —SO$_2NR^6R^7$, or $R^1$ is independently alkyl or cycloalkyl each optionally substituted with one or more fluoro, hydroxy, alkyloxy, fluoroalkyloxy, amino or alkylamino groups;

and $R^1$, if present, is located at the meta- and/or para-position of the phenyl ring relative to the linkage to the $CR^5$ group.

In a further distinct embodiment, the invention encompasses a compound of Formula (I), wherein $R^2$ is phenyl substituted with 1 $R^8$ group, or pyridyl substituted with 1 $R^8$ group, having the structure (a), (b), (c) or (d)

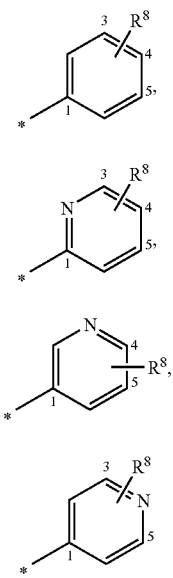

wherein
* denotes the linkage to group A;
$R^8$ is fluoro, chloro, cyano, —$NR^9C(O)R^{10}$, —$NR^9C(O)OR^{10}$, —$C(O)OR^9$, —$SR^9$, —$S(O)R^9$, —$SO_2R^9$, —$C(O)NR^9R^{10}$, —$SO_2NR^9R^{10}$, or —$NR^9R^{10}$; or
$R^8$ is alkyl, cycloalkyl, monocyclic heterocyclyl or monocyclic heteroaryl, each of which may be optionally substituted with one or more fluoro, chloro, $R^{11}$, —$OR^9$ or —$NR^9R^{10}$ groups;
and
$R^8$ is attached to a ring carbon atom in position 3, 4 or 5;
and wherein phenyl and pyridyl of structure (a), (b), (c) and (d) may be additionally substituted with fluoro, chloro or cyano.

In a particularly preferred embodiment, the invention encompasses a compound of Formula (I), wherein
A is imidazol-2,4-diyl, 1,3-oxazol-2,4-diyl, 1,2,4-oxadiazol-3,5-diyl or 1H-benzimidazol-2,5-diyl;
n is an integer of 0 or 1;
$R^1$ is fluoro, chloro, cyano, hydroxy, alkyloxy, fluoroalkyloxy, alkyl, fluoroalkyl, alkoxycarbonyl, or alkylcarbonylamino;
and
$R^1$, if present, is located at the meta- or para-position of the phenyl ring relative to the linkage to the $CR^5$ group;
$R^2$ is phenyl substituted with 1 $R^8$ group, having the structure (a)

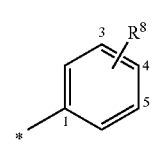

wherein
* denotes the linkage to group A;
$R^8$ is —$OR^9$, —$SR^9$, —$S(O)R^9$, or —$SO_2R^9$; or
$R^8$ is alkyl, cycloalkyl, oxetanyl, tetrahydrofuranyl, tetrahydropyranyl, pyrrolidinyl, piperidinyl, piperazinyl or morpholinyl, each of which may be optionally substituted with one or more fluoro, $R^{11}$, —$OR^9$ or —$NR^9R^{10}$ groups;
and
$R^8$ is attached to a ring carbon atom in position 3, 4 or 5;
$R^3$ is hydrogen;
$R^4$ is alkyl;
$R^5$ is hydrogen;
each occurrence of $R^9$ may be the same or different and is independently hydrogen, alkyl or fluoroalkyl;
$R^{10}$ is alkyl;
each occurrence of $R^{11}$ may be the same or different and is independently hydrogen, alkyl, pyrrolidinyl, piperidinyl, morpholinyl, pyrrolyl, pyrazolyl, imidazolyl or triazolyl.

A further embodiment of this invention encompasses a compound having the Formula (I), wherein
A is heteroaryl or heterocyclyl;
n is an integer from 0-3;
$R^1$ at each occurrence is independently halogen, —$NR^6C(O)R^7$, —$C(O)R^6$, —$C(O)OR^6$, —$OC(O)R^6$, —$OR^6$, —$SR^6$, cyano, nitro, —$C(O)NR^6R^7$, —$SO_2NR^6R^7$, or —$NR^6R^7$,
or
$R^1$ is independently aryl, heteroaryl, heterocyclyl, alkyl or cycloalkyl each optionally substituted with one or more halogen, $OR^6$ or $NR^6R^7$ groups;
$R^2$ is aryl optionally substituted with 1, 2 or 3 $R^8$ groups or heteroaryl optionally substituted with 1, 2 or 3 $R^8$ groups;
$R^3$ and $R^4$ are each independently hydrogen, halogen, —$OR^6$, —$SR^6$, —$NR^6R^7$, alkyl optionally substituted with one or more halogen, $R^6$, —$OR^6$ or —$NR^6R^7$ groups, or cycloalkyl optionally substituted with one or more halogen, $R^6$, —$OR^6$ or —$NR^6R^7$ groups;
$R^5$ is hydrogen, oxo, or alkyl optionally substituted with one or more halogen, —$OR^6$ or —$NR^6R^7$ groups;
each occurrence of $R^6$ or $R^7$ may be the same or different and is independently hydrogen, or aryl, heteroaryl, heterocyclyl, alkyl, or cycloalkyl each of which may be optionally substituted with one or more hydrogen, halogen, —$OR^9$ or —$NR^9R^{10}$ groups;
each occurrence of $R^8$ may be the same or different and is independently
hydrogen, halogen, —$NR^9C(O)R^{10}$, —$C(O)R^9$, —$C(O)OR^9$, —$OC(O)R^9$, —$OR^9$, —$SR^9$, cyano, nitro, —$C(O)NR^9R^{10}$, —$SO_2NR^9R^{10}$, —$NR^9R^{10}$, or
aryl, heteroaryl, heterocyclyl, alkyl, or cycloalkyl each of which may be optionally substituted with one or more halogen, $R^{11}$, —$OR^9$ or —$NR^9R^{10}$ groups;
each occurrence of $R^9$ and $R^{10}$ may be the same or different and is independently hydrogen, or aryl, heteroaryl, heterocyclyl, alkyl, or cycloalkyl each of which may be optionally substituted with one or more hydrogen, halogen, hydroxyl, alkyloxy, cycloalkyloxy, aryloxy, amino, alkylamino, cycloalkylamino, or arylamino groups; and
each occurrence of $R^{11}$ may be the same or different and is independently hydrogen, halogen, oxo, aryl, heteroaryl, heterocyclyl, alkyl, cycloalkyl, hydroxyl, alkyloxy, cycloalkyloxy, aryloxy, amino, alkylamino, cycloalkylamino, or arylamino groups.

In another embodiment, the invention encompasses a compound of Formula (I), wherein wherein $R^1$ at each occurrence is independently alkyl, halogen or —$OR^6$.

In still another embodiment, the invention encompasses a compound of Formula (I), wherein $R^4$ is alkyl.

In yet another embodiment, the invention encompasses a compound of Formula (I), wherein $R^3$ is hydrogen.

In yet still another embodiment, the invention encompasses a compound of Formula (I), wherein $R^2$ is aryl optionally substituted with 1, 2 or 3 $R^8$ groups.

In another embodiment, the invention encompasses a compound of Formula (I), wherein A is 1,2,4-oxadiazol-3,5-diyl, 1,3-benzoxazol-2,5-diyl, 1H-benzimidazol-2,5-diyl, imidazol-2,4-diyl or 1,3-oxazol-2,4-diyl.

In a distinct embodiment, the invention encompasses a compound of the formula (I-a)

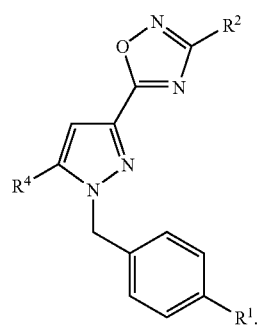

Formula (I-a)

In another embodiment, the invention encompasses a compound of formula (I-a), wherein
 $R^1$ is hydrogen, fluorine, chlorine, methyl, ethyl, propyl, isopropyl, tert.-butyl, cyclopropyl, methoxy, ethoxy, isopropoxy, trifluoromethyl, or trifluoromethoxy;
 $R^2$ is as defined for formula (I); and
 $R^4$ is hydrogen, fluorine, chlorine, methoxy, ethoxy, propoxy, isopropoxy, cyclopropyloxy, dimethylamino, methyl, ethyl, propyl, isopropyl, tert.-butyl, cyclopropyl, methoxymethyl, or methoxyethyl.

In still another embodiment, the invention encompasses a compound of formula (I-a), wherein $R^1$ and $R^4$ are methyl.

In another distinct embodiment, the invention encompasses a compound of the formula (I-b)

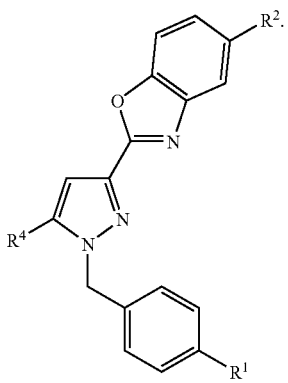

Formula (I-b)

In another embodiment, the invention encompasses a compound of formula (I-b), wherein
 $R^1$ is hydrogen, fluorine, chlorine, methyl, ethyl, propyl, isopropyl, tert.-butyl, cyclopropyl, methoxy, ethoxy, isopropoxy, trifluoromethyl, or trifluoromethoxy;
 $R^2$ is as defined for formula (I); and
 $R^4$ is hydrogen, fluorine, chlorine, methoxy, ethoxy, propoxy, isopropoxy, cyclopropyloxy, dimethylamino, methyl, ethyl, propyl, isopropyl, tert.-butyl, cyclopropyl, methoxymethyl, or methoxyethyl.

In yet another embodiment, the invention encompasses a compound of formula (I-b), wherein $R^1$ and $R^4$ are methyl.

In still another distinct embodiment, the invention encompasses a compound of the formula (I-c)

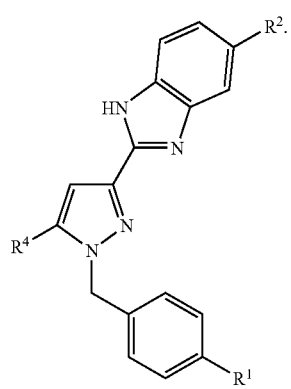

Formula (I-c)

In another embodiment, the invention encompasses a compound of formula (I-c), wherein
 $R^1$ is hydrogen, fluorine, chlorine, methyl, ethyl, propyl, isopropyl, tert.-butyl, cyclopropyl, methoxy, ethoxy, isopropoxy, trifluoromethyl, or trifluoromethoxy;
 $R^2$ is as defined for formula (I); and
 $R^4$ is hydrogen, fluorine, chlorine, methoxy, ethoxy, propoxy, isopropoxy, cyclopropyloxy, dimethylamino, methyl, ethyl, propyl, isopropyl, tert.-butyl, cyclopropyl, methoxymethyl, or methoxyethyl.

In yet another embodiment, the invention encompasses a compound of formula (I-c), wherein $R^1$ and $R^4$ are methyl.

In another embodiment, the invention encompasses a compound of the formula (I-d)

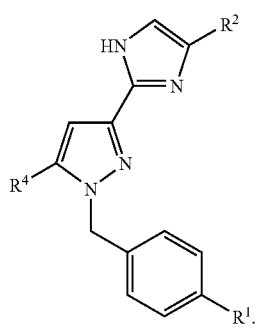

Formula (I-d)

In another embodiment, the invention encompasses a compound of formula (I-d), wherein
 $R^1$ is hydrogen, fluorine, chlorine, methyl, ethyl, propyl, isopropyl, tert.-butyl, cyclopropyl, methoxy, ethoxy, isopropoxy, trifluoromethyl, or trifluoromethoxy;
 $R^2$ is as defined for formula (I); and R⁴ is hydrogen, fluorine, chlorine, methoxy, ethoxy, propoxy, isopropoxy, cyclopropyloxy, dimethylamino, methyl, ethyl, propyl, isopropyl, tert.-butyl, cyclopropyl, methoxymethyl, or methoxyethyl.

In yet another embodiment, the invention encompasses a compound of formula (I-d), wherein R¹ and R⁴ are methyl.

In still another embodiment, the invention encompasses a compound of the formula (I-e)

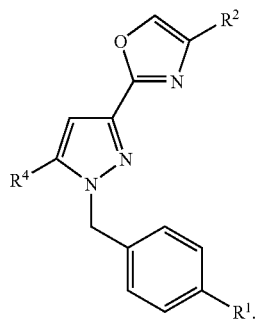

Formula (I-e)

In another embodiment, the invention encompasses a compound of formula (I-e), wherein
R¹ is hydrogen, fluorine, chlorine, methyl, ethyl, propyl, isopropyl, tert.-butyl, cyclopropyl, methoxy, ethoxy, isopropoxy, trifluoromethyl, or trifluoromethoxy;
R² is as defined for formula (I); and
R⁴ is hydrogen, fluorine, chlorine, methoxy, ethoxy, propoxy, isopropoxy, cyclopropyloxy, dimethylamino, methyl, ethyl, propyl, isopropyl, tert.-butyl, cyclopropyl, methoxymethyl, or methoxyethyl.

In still another embodiment, the invention encompasses a compound of formula (I-e), wherein R¹ and R⁴ are methyl.

In another embodiment, the invention encompasses a compound of formula (I), (I-a), (I-b), (I-c), (I-d) or (1-e), wherein R² is aryl optionally substituted with 1, 2 or 3 R⁸ groups.

In yet another embodiment, the invention encompasses a compound having the formula:
5-[5-methyl-1-(4-methylbenzyl)-1H-pyrazol-3-yl]-3-[4-(trifluoromethoxy)phenyl]-1,2,4-oxadiazole;
3-{4-[(4-chlorobenzyl)oxy]phenyl}-5-[5-methyl-1-(4-methylbenzyl)-1H-pyrazol-3-yl]-1,2,4-oxadiazole;
3-(4-bromophenyl)-5-[5-methyl-1-(4-methylbenzyl)-1H-pyrazol-3-yl]-1,2,4-oxadiazole;
3-(4-tert-butylphenyl)-5-[5-methyl-1-(4-methylbenzyl)-1H-pyrazol-3-yl]-1,2,4-oxadiazole;
5-[5-methyl-1-(4-methylbenzyl)-1H-pyrazol-3-yl]-3-[4-(trifluoromethoxy)biphenyl-4-yl]-1,2,4-oxadiazole;
3-methyl-1-(4-{5-[5-methyl-1-(4-methylbenzyl)-1H-pyrazol-3-yl]-1,2,4-oxadiazol-3-yl}phenyl)piperidine;
5-[5-methyl-1-(4-methylbenzyl)-1H-pyrazol-3-yl]-3-[4-(trifluoromethyl)phenyl]-1,2,4-oxadiazole;
3-(4-bromophenyl)-5-{5-methyl-1-[1-(4-methylphenyl)ethyl]-1H-pyrazol-3-yl}-1,2,4-oxadiazole;
5-[5-methyl-1-(4-methylbenzyl)-1H-pyrazol-3-yl]-3-phenyl-1,2,4-oxadiazole;
3-(4-fluorophenyl)-5-[5-methyl-1-(4-methylbenzyl)-1H-pyrazol-3-yl]-1,2,4-oxadiazole;
4-{5-[5-methyl-1-(4-methylbenzyl)-1H-pyrazol-3-yl]-1,2,4-oxadiazol-3-yl}pyridine;
3-(3-bromo-4-fluorophenyl)-5-[5-methyl-1-(4-methylbenzyl)-1H-pyrazol-3-yl]-1,2,4-oxadiazole;
3-{5-[5-methyl-1-(4-methylbenzyl)-1H-pyrazol-3-yl]-1,2,4-oxadiazol-3-yl}pyridine;
5-{5-[5-methyl-1-(4-methylbenzyl)-1H-pyrazol-3-yl]-1,2,4-oxadiazol-3-yl}-2-(trifluoromethyl)pyridine;
3-(4-cyclohexylphenyl)-5-[5-methyl-1-(4-methylbenzyl)-1H-pyrazol-3-yl]-1,2,4-oxadiazole;
1-(4-{5-[5-methyl-1-(4-methylbenzyl)-1H-pyrazol-3-yl]-1,2,4-oxadiazol-3-yl}-phenyl)piperidine;
3-(4-iodophenyl)-5-[5-methyl-1-(4-methylbenzyl)-1H-pyrazol-3-yl]-1,2,4-oxadiazole;
5-[5-methyl-1-(4-methylbenzyl)-1H-pyrazol-3-yl]-3-[4-(2,2,2-trifluoroethoxy)phenyl]-1,2,4-oxadiazole;
3-[4-(cyclopentyloxy)phenyl]-5-[5-methyl-1-(4-methylbenzyl)-1H-pyrazol-3-yl]-1,2,4-oxadiazole;
3-(4-isopropoxyphenyl)-5-[5-methyl-1-(4-methylbenzyl)-1H-pyrazol-3-yl]-1,2,4-oxadiazole;
4-(4-{5-[5-methyl-1-(4-methylbenzyl)-1H-pyrazol-3-yl]-1,2,4-oxadiazol-3-yl}-phenyl)morpholine;
5-[5-methyl-1-(4-methylbenzyl)-1H-pyrazol-3-yl]-3-(4-pyrrolidin-1-ylphenyl)-1,2,4-oxadiazole;
N,N-diethyl-4-{5-[5-methyl-1-(4-methylbenzyl)-1H-pyrazol-3-yl]-1,2,4-oxadiazol-3-yl}aniline;
1-(4-{5-[5-methyl-1-(4-methylbenzyl)-1H-pyrazol-3-yl]-1,2,4-oxadiazol-3-yl}-phenyl)pyrrolidin-2-one;
3-(4-{5-[5-methyl-1-(4-methylbenzyl)-1H-pyrazol-3-yl]-1,2,4-oxadiazol-3-yl}phenyl)-1,3-oxazolidin-2-one;
4-(4-{5-[5-methyl-1-(4-methylbenzyl)-1H-pyrazol-3-yl]-1,2,4-oxadiazol-3-yl}-phenyl)morpholin-3-one;
2-methoxy-N-(4-{5-[5-methyl-1-(4-methylbenzyl)-1H-pyrazol-3-yl]-1,2,4-oxadiazol-3-yl}phenyl)acetamide;
1-(4-{5-[5-methyl-1-(4-methylbenzyl)-1H-pyrazol-3-yl]-1,2,4-oxadiazol-3-yl}-phenyl)piperidin-2-one;
or a physiologically acceptable salt, solvate, hydrate or stereoisomer thereof.

In yet another embodiment, the invention encompasses a compound having the formula:
2-[5-methyl-1-(4-methylbenzyl)-1H-pyrazol-3-yl]-5-phenyl-1,3-benzoxazole;
2-[5-methyl-1-(4-methylbenzyl)-1H-pyrazol-3-yl]-6-phenoxy-1,3-benzoxazole;
2-[5-methyl-1-(4-methylbenzyl)-1H-pyrazol-3-yl]-1,3-benzoxazole;
2-[5-methyl-1-(4-methylbenzyl)-1H-pyrazol-3-yl]-5-(1-methyl-1-phenylethyl)-1,3-benzoxazole;
5-benzyl-2-[5-methyl-1-(4-methylbenzyl)-1H-pyrazol-3-yl]-1,3-benzoxazole;
5-(3-fluorophenyl)-2-[5-methyl-1-(4-methylbenzyl)-1H-pyrazol-3-yl]-1,3-benzoxazole;
5-(2-fluorophenyl)-2-[5-methyl-1-(4-methylbenzyl)-1H-pyrazol-3-yl]-1,3-benzoxazole;
5-(3-chlorophenyl)-2-[5-methyl-1-(4-methylbenzyl)-1H-pyrazol-3-yl]-1,3-benzoxazole;
or a physiologically acceptable salt, solvate, hydrate or stereoisomer thereof.

In another embodiment, the invention encompasses a compound having the formula:
6-bromo-2-[5-methyl-1-(4-methylbenzyl)-1H-pyrazol-3-yl]-1H-benzimidazole;
2-[5-methyl-1-(4-methylbenzyl)-1H-pyrazol-3-yl]-1H-benzimidazole;
6-methyl-2-[5-methyl-1-(4-methylbenzyl)-1H-pyrazol-3-yl]-1H-benzimidazole;
4-methyl-2-[5-methyl-1-(4-methylbenzyl)-1H-pyrazol-3-yl]-1H-benzimidazole;
6-chloro-2-[5-methyl-1-(4-methylbenzyl)-1H-pyrazol-3-yl]-1H-benzimidazole;
2-[5-methyl-1-(4-methylbenzyl)-1H-pyrazol-3-yl]-3H-imidazo[4,5-c]pyridine;

6-tert-butyl-2-[5-methyl-1-(4-methylbenzyl)-1H-pyrazol-3-yl]-1H-benzimidazole;
2-[5-methyl-1-(4-methylbenzyl)-1H-pyrazol-3-yl]-6-(trifluoromethyl)-1H-benzimidazole;
2-[5-methyl-1-(4-methylbenzyl)-1H-pyrazol-3-yl]-6-phenyl-1H-benzimidazole;
{2-[5-methyl-1-(4-methylbenzyl)-1H-pyrazol-3-yl]-1H-benzimidazol-6-yl}-(phenyl)methanone;
2-[5-methyl-1-(4-methylbenzyl)-1H-pyrazol-3-yl]-1H-naphtho[2,3-d]imidazole;
6-[5-methyl-1-(4-methylbenzyl)-1H-pyrazol-3-yl]-1,7-dihydroimidazo[4,5-f]indazole;
2-[5-methyl-1-(4-methylbenzyl)-1H-pyrazol-3-yl]-6-piperidin-1-yl-1H-benzimidazole;
2-[5-methyl-1-(4-methylbenzyl)-1H-pyrazol-3-yl]-6-(4-methylpiperazin-1-yl)-1H-benzimidazole;
6-cyclohexyl-2-[5-methyl-1-(4-methylbenzyl)-1H-pyrazol-3-yl]-1H-benzimidazole;
2-[5-methyl-1-(4-methylbenzyl)-1H-pyrazol-3-yl]-1H-[1]benzofuro[2,3-f]-benzimidazole;
2-[5-methyl-1-(4-methylbenzyl)-1H-pyrazol-3-yl]-6-morpholin-4-yl-1H-benzimidazole;
2-[5-methyl-1-(4-methylbenzyl)-1H-pyrazol-3-yl]-1H-benzimidazole-6-carbonitrile;
2,2-difluoro-6-[5-methyl-1-(4-methylbenzyl)-1H-pyrazol-3-yl]-5H-[1,3]dioxolo[4,5-f]-benzimidazole;
5-chloro-6-fluoro-2-[5-methyl-1-(4-methylbenzyl)-1H-pyrazol-3-yl]-1H-benzimidazole;
6-bromo-4-methyl-2-[5-methyl-1-(4-methylbenzyl)-1H-pyrazol-3-yl]-1H-benzimidazole;
6-(4-fluorophenyl)-2-[5-methyl-1-(4-methylbenzyl)-1H-pyrazol-3-yl]-1H-benzimidazole;
6-(2-fluorophenyl)-2-[5-methyl-1-(4-methylbenzyl)-1H-pyrazol-3-yl]-1H-benzimidazole;
6-(3-fluorophenyl)-2-[5-methyl-1-(4-methylbenzyl)-1H-pyrazol-3-yl]-1H-benzimidazole;
6-(2-chlorophenyl)-2-[5-methyl-1-(4-methylbenzyl)-1H-pyrazol-3-yl]-1H-benzimidazole;
6-(3-chlorophenyl)-2-[5-methyl-1-(4-methylbenzyl)-1H-pyrazol-3-yl]-1H-benzimidazole;
6-(4-chlorophenyl)-2-[5-methyl-1-(4-methylbenzyl)-1H-pyrazol-3-yl]-1H-benzimidazole;
2-[5-methyl-1-(4-methylbenzyl)-1H-pyrazol-3-yl]-6-(trifluoromethoxy)-1H-benzimidazole;
  or a physiologically acceptable salt, solvate, hydrate or stereoisomer thereof.

In still yet another embodiment, the invention encompasses a compound having the formula:
5-methyl-1-(4-methylbenzyl)-3-{4-[4-(trifluoromethoxy)phenyl]-1H-imidazol-2-yl}-1H-pyrazole;
3-(4,5-diphenyl-1H-imidazol-2-yl)-5-methyl-1-(4-methylbenzyl)-1H-pyrazole;
3-(4-biphenyl-4-yl-1H-imidazol-2-yl)-5-methyl-1-(4-methylbenzyl)-1H-pyrazole;
3-[4-(4-cyclohexylphenyl)-1H-imidazol-2-yl]-5-methyl-1-(4-methylbenzyl)-1H-pyrazole;
or a physiologically acceptable salt, solvate, hydrate or stereoisomer thereof.

In still another embodiment, the invention encompasses a compound having the formula:
2-[5-methyl-1-(4-methylbenzyl)-1H-pyrazol-3-yl]-4-phenyl-1,3-oxazole;
4-(4-bromophenyl)-2-[5-methyl-1-(4-methylbenzyl)-1H-pyrazol-3-yl]-1,3-oxazole;
4-(4'-chlorobiphenyl-4-yl)-2-[5-methyl-1-(4-methylbenzyl)-1H-pyrazol-3-yl]-1,3-oxazole;
4-(4-tert-butylphenyl)-2-[5-methyl-1-(4-methylbenzyl)-1H-pyrazol-3-yl]-1,3-oxazole;
2-[5-methyl-1-(4-methylbenzyl)-1H-pyrazol-3-yl]-4-[4-(trifluoromethoxy)phenyl]-1,3-oxazole;
1-(4-{2-[5-methyl-1-(4-methylbenzyl)-1H-pyrazol-3-yl]-1,3-oxazol-4-yl}-phenyl)piperidine;
4-(4-cyclohex-1-en-1-ylphenyl)-2-[5-methyl-1-(4-methylbenzyl)-1H-pyrazol-3-yl]-1,3-oxazole;
4-(4-cyclohex-1-ylphenyl)-2-[5-methyl-1-(4-methylbenzyl)-1H-pyrazol-3-yl]-1,3-oxazole;
  or a physiologically acceptable salt, solvate, hydrate or stereoisomer thereof.

DEFINITIONS

The term "halogen" refers to radicals of fluorine, chlorine, bromine and iodine.

The term "alkyl" refers to a straight or branched hydrocarbon chain radical, containing solely carbon and hydrogen atoms, having in the range from one up to eight carbon atoms, and which is attached to the rest of the molecule by a single bond, such as illustratively, methyl, ethyl, n-propyl, 1-methylethyl (iso-propyl), n-butyl, n-pentyl, and 1,1-dimethylethyl (tert-butyl).

The term "cycloalkyl" denotes a non-aromatic (i.e. saturated or partially unsaturated) mono- or multicyclic ring system having in the range of 3 up to 14 carbon atoms such as cyclopropyl, cyclobutyl, cyclopentyl, cyclopentenyl, cyclohexyl, cyclohexenyl, and cycloheptyl. Examples of multicyclic cycloalkyl groups include decahydronaphthyl. Examples of bridged cycloalkyl groups or spirobicycloalkyl groups include adamantyl, norbornyl, and spiro[4.4]nonyl groups.

The term "alkyloxy" or "alkoxy" denotes an alkyl group as defined herein attached via an oxygen linkage to the rest of the molecule. Representative examples of those groups are methoxy, ethoxy, n-propoxy, iso-propoxy, n-butoxy, and tert-butoxy.

The term "cycloalkyloxy" or "cycloalkoxy" denotes a cycloalkyl group as defined herein attached via an oxygen linkage to the rest of the molecule. Representative examples of those groups are cyclopropoxy, cyclobutoxy, cyclopentoxy, cyclohexoxy, and cycloheptoxy.

The term "fluoroalkyl" denotes an alkyl group as defined herein wherein one or more hydrogen atoms are replaced with fluoro atoms. This includes a per-fluoro substitution wherein all hydrogen atoms of the respective alkyl group are replaced with fluoro atoms. Representative examples of those groups are: fluoromethyl, difluoromethyl, trifluoromethyl, 2-fluoroethyl, 2,2,2-trifluoroethyl, and pentafluoroethyl.

The term "fluoroalkyloxy" or "fluoroalkoxy" denotes an alkoxy group as defined herein wherein one or more hydrogen atoms are replaced with fluoro atoms. This includes a per-fluoro substitution wherein all hydrogen atoms of the respective alkoxy group are replaced with fluoro atoms. Representative examples of those groups are: fluoromethoxy, difluoromethoxy, trifluoromethoxy, 2-fluoroethoxy, 2,2,2-trifluoroethoxy, and pentafluoroethoxy.

The term "aryl" refers to aromatic radicals having in the range of 6 up to 14 carbon atoms such as phenyl, naphthyl, indanyl, and biphenyl.

The term "aryloxy" denotes an aryl group as defined herein attached via an oxygen linkage to the rest of the molecule. Representative examples of those groups are phenoxy and naphthoxy.

The term "aroyl" denotes an aryl group as defined herein attached via a carbonyl linkage to the rest of the molecule. Representative examples of those groups are benzoyl and naphthoyl.

The term "aralkyl" denotes an aryl group as defined herein attached via a divalent alkyl linkage to the rest of the molecule. Representative examples of those groups are: benzyl, 1-phenethyl, 2-phenethyl, 2-phenyl-2-propyl, 3-phenyl-1-propyl, and 4-phenyl-1-butyl.

The term "heteroaryl" refers to a stable 5- to 13-membered aromatic heterocycle having in the range from 1 up to 4 heteroatoms from the group consisting of nitrogen, phosphorus, oxygen and sulfur, which ring or ring system can be linked via a carbon atom or a nitrogen atom, if such an atom is present. For purposes of this invention, the heteroaryl ring radical may be a monocyclic, bicyclic or tricyclic ring system. Examples of such heteroaryl radicals are: pyridyl, pyridyl N-oxide, pyrimidinyl, pyridazinyl, pyrazinyl, thienyl, furyl, pyrrolyl, pyrazolyl, imidazolyl, thiazolyl, oxazolyl, isoxazolyl, isothiazolyl, indolicenyl, indolyl, benzo[b]thienyl, benzo[b]furyl, benzoxazolyl, benzothiazolyl, benzothiadiazolyl, indazolyl, quinolyl, isoquinolyl, naphthyridinyl, quinazolinyl, oxadiazolyl, thiadiazolyl, tetrazolyl, triazolyl, benzimidazolyl, imidazo[4,5-c]pyridyl, naphtho[2,3-d]imidazolyl, and imidazo[4,5-f]indazolyl.

The term "heterocyclyl" refers to a stable 3- to 13-membered saturated or partially unsaturated heterocycle having in the range from 1 up to 4 heteroatoms from the group consisting of nitrogen, phosphorus, oxygen and sulfur, which ring or ring system can be linked via a carbon atom or a nitrogen atom, if such an atom is present. For purposes of this invention, the heterocyclic ring radical may be a monocyclic, bicyclic or tricyclic ring system, which may include fused, bridged or spiro ing systems. Examples of such heterocyclyl radicals are: tetrahydropyranyl, aziridyl, azepanyl, tetrahydrofuryl, oxetanyl, pyrrolidinyl, pyrrolinyl, piperidinyl, 1,2-dihydropyridinyl, 1,4-dihydropyridinyl, piperazinyl, morpholinyl, thiomorpholinyl, azepinyl, oxazolinyl, thiazolinyl, and 1,4-diazepinyl.

The term "heterocyclylalkyl" refers to a heterocyclyl group as defined herein attached via a divalent alkyl linkage to the rest of the molecule. Representative examples of those groups are: tetrahydrofuran-2-ylmethyl, pyrrolidin-2-ylmethyl, tetrahydropyran-4-ylmethyl, piperidin-2-ylmethyl, piperidin-4-ylmethyl, 2-(piperidin-4-yl)ethyl, 2-(morpholin-4-yl)ethyl, 3-(morpholin-4-yl)propyl, piperazin-2-ylmethyl, and 2-(piperazin-1-yl)ethyl.

The term "alkylamino" refers to an alkyl group as defined herein attached via an amino linkage to the rest of the molecule. The term alkylamino further includes dialkyl amino moieties in which two alkyl groups as defined herein are attached via a common amino linkage to the rest of the molecule. Representative examples of those groups are methylamino, ethylamino, dimethylamino, and diethylamino.

The term "cycloalkylamino" refers to a cycloalkyl group as defined herein attached via an amino linkage to the rest of the molecule. Representative examples of those groups are cyclopropylamino and cyclopentylamino.

The term "arylamino" refers to an aryl group as defined herein attached via an amino linkage to the rest of the molecule. Representative examples of those groups are phenylamino and naphthylamino.

The term "alkylcarbonyl" refers to an alkyl group as defined herein attached via a carbonyl linkage to the rest of the molecule. Representative examples of those groups are: acetyl, propionyl, n-butyryl, iso-butyryl, n-pentanoyl, pivaloyl, and n-hexanoyl.

The term "alkylcarbonylamino" refers to an alkylcarbonyl group as defined herein which is attached at its carbonyl group via an amino linkage to the rest of the molecule. Representative examples of those groups are: acetylamino, propionylamino, n-butyrylamino, iso-butyrylamino, n-pentanoylamino, pivaloylamino, and n-hexanoylamino.

The term "alkyloxycarbonyl" or "alkoxycarbonyl" refers to an alkoxy group as defined herein attached via a carbonyl linkage to the rest of the molecule. Representative examples of those groups are: methoxycarbonyl, ethoxycarbonyl, n-propoxycarbonyl, iso-propoxycarbonyl, n-butoxycarbonyl, and tert-butoxycarbonyl.

Where the plural form of the word compounds, salts, polymorphs, hydrates, solvates and the like, is used herein, this is taken to mean also a single compound, salt, polymorph, isomer, hydrate, solvate or the like.

The compounds of this invention may contain one or more asymmetric centers, depending upon the location and nature of the various substituents desired. Asymmetric carbon atoms may be present in the (R) or (S) configuration, resulting in racemic mixtures in the case of a single asymmetric center, and diastereomeric mixtures in the case of multiple asymmetric centers. In certain instances, asymmetry may also be present due to restricted rotation about a given bond, for example, the central bond adjoining two substituted aromatic rings of the specified compounds. Substituents on a ring may also be present in either cis or trans form. It is intended that all such configurations (including enantiomers and diastereomers), are included within the scope of the present invention. Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivitization, optimally chosen to maximize the separation of the enantiomers. Suitable chiral HPLC columns are manufactured by Daicel, e.g., Chiracel OD and Chiracel OJ among many others, all routinely selectable. Enzymatic separations, with or without derivitization, are also useful. The optically active compounds of this invention can likewise be obtained by chiral syntheses utilizing optically active starting materials or catalysts.

The present invention also relates to useful forms of the compounds as disclosed herein, such as pharmaceutically acceptable salts, co-precipitates, metabolites, hydrates, solvates and prodrugs of all the compounds of examples. The term "pharmaceutically acceptable salt" refers to a relatively non-toxic, inorganic or organic acid addition salt of a compound of the present invention. For example, see S. M. Berge, et al., "Pharmaceutical Salts," *J. Pharm. Sci.* 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and chorine salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

Representative salts of the compounds of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

A solvate for the purpose of this invention is a complex of a solvent and a compound of the invention in the solid state. Exemplary solvates would include, but are not limited to, complexes of a compound of the invention with ethanol or methanol. Hydrates are a specific form of solvate wherein the solvent is water.

Pharmaceutical Compositions of the Compounds of the Invention

This invention also relates to pharmaceutical compositions containing one or more compounds of the present invention. These compositions can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)-Part-1" *PDA Journal of Pharmaceutical Science & Technology* 1999, 53(6), 324-349; and Nema, S. et al, "Excipients and Their Use in Injectable Products" *PDA Journal of Pharmaceutical Science & Technology* 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC\text{---}CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, mono-thioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, crosslinked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilized powder for IV administration: A sterile preparation can be prepared with (i) 100-1000 mg of the desired compound of this invention as a lypholized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets; A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating HIF Transcription Disorders

The present invention also provides methods for the treatment of disorders associated with pathological or aberrant expression of HIF transcription factor, in particular HIF-1α and HIF-2α transcription factors.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the transcription factor and the disorder.

The phrase "aberrant expression of HIF transcription factor", or "aberrant expression of HIF-1α transcription factor", includes any abnormal expression or activity of the gene encoding the transcription factor or of the polypeptide it encodes. Examples of such aberrant activity, include, but are not limited to, over-expression of the gene or polypeptide; gene amplification; mutations which produce constitutively-active or hyperactive transcription factor activity; gene mutations, deletions, substitutions, additions, etc.

HIF-1α and HIF-2α are transcription factors regulating more than 100 genes. This includes, in addition to the angiogenically relevant factors, also those relevant for glucose, lipid and amino acid metabolism, cell migration, metastasis and DNA repair. The tumors thereby change functional tissues to the requirements of cell growth, suppressing apoptosis. It increases the probability for mutations and favors the occurrence of metastatic clones.

Via HIF, also suppression of the immune response in tumor tissue is induced. Inhibiting HIF will reduce the tolerance of the immune system towards the newly derived cancer cell clones with newly arising antigens.

In addition, there is an influence on stem cells, in particular on tumor stem cells which are reported to have an up-regulated HIF pathway. Thus, a class of tumor cells will be affected by HIF inhibitors which is not much affected by cytotoxic agents, as cancer stem cells do not proliferate vigorously.

Such changes of cellular metabolism brought about by HIF are not exclusive for cancer but may also occur during transient and chronic ischemic processes. Therefore, a HIF inhibitor may be useful for diseases which result from additional damage occurring through the adaptation of cells to hypoxic situations which results in improper functioning of a cell in concert with the tissue, instead of apoptosing. Such situations might be found in cardiovascular diseases where through thromboembolic events, inflammation, wounding, intoxication or other reasons ischemia is occurring in the heart and the brain, resulting in changes like improper action potential conduction leading to arrhythmia or cardiac heart failure (CHF). Such events also may be transient but chronically occurring as in apnoe.

Blockade of HIF effects will therefore be effective in diseases like developing CHF, arrhythmia, myocardial infarction, transplantation ischemia/reperfusion damage, apoplexy and macular degeneration, or in restoration of nerve function after traumatic crushing or severing.

As HIF-1 promotes the transition of epithelial to mesenchymal cells, diseases especially of the kidney and the lung associated with fibrosis are also targets of HIF pathway inhibitors which will inhibit the appearance or alleviate the aggravation of fibrotic disease.

Chuwash polycythemia is mediated by HIF-2α signalling during splenic erythropoiesis. Inhibitors of the HIF pathway will reduce the excessive proerythropoietic activity and thus relieve the appearance of the disease.

The present invention also provides for methods of modulating the HIF-1 pathway, especially the HIF-1α pathway, comprising administering an effective amount of a compound of the present invention, including salts, polymorphs, metabolites, hydrates, solvates, prodrugs (e.g.: esters) thereof, and diastereoisomeric forms thereof. The HIF-1 pathway can be modulated in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity (Aiello et al. *New Engl. J. Med.* 1994, 331, 1480; Peer et al. *Lab. Invest.* 1995, 72, 638), age-related macular degeneration (AMD; see, Lopez et al. *Invest. Opththalmol. Vis. Sci.* 1996, 37, 855), neovascular glaucoma, psoriasis, retrolental fibroplasias, angiofibroma, inflammation, rheumatoid arthritis (RA), restenosis, in-stent restenosis, vascular graft restenosis, etc. Also during transplantation, ischemia might occur, and survival of strongly damaged tissue cells might lead to a sluggish recovery of tissue cells versus stromal cells increasing scar formation. This might be especially important during the re-growth of damaged or even dissevered nerves. In addition, the increased blood supply associated with cancerous and neoplastic tissue, encourages growth, leading to rapid tumor enlargement and metastasis. Moreover, the growth of new blood and lymph vessels in a tumor provides an escape route for renegade cells, encouraging metastasis and the consequence spread of the cancer. New blood and lymph vessels are also deleterious for allografts in immune-restricted locations like the eye, leading, for example, to rejection of corneal transplants. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination Therapies

The compounds of this invention can be administered as the sole pharmaceutical agent or in combination with one or more other pharmaceutical agents where the combination causes no unacceptable adverse effects. For example, the compounds of this invention can be combined with known anti-hyperproliferative or other indication agents, and the like, as well as with admixtures and combinations thereof. The combination of the compounds of the present invention with other pharmaceutical agents used in cancer therapy and/ or with radiotherapy appears particularly beneficial due to the fact that tumor areas which are hypoxic do not respond well to conventional treatments. The compounds of this invention, however, are especially active in these regions of the tumor.

The additional pharmaceutical agent can be aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depo-medrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2α, interferon alfa-2B, interferon alfa-n1, interferon alfa-n3, interferon beta, interferon gamma-1α, interleukin-2, intron A, iressa, irinotecan, kytril, lentinan sulphate, letrozole, leucovorin, leuprolide, leuprolide acetate, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, rebif, rhenium-186 etidronate, rituximab, roferon-A, romurtide, salagen, sandostatin, sargramostim, semustine, sizofiran, sobuzoxane, solu-medrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, BAY 43-9006 (sorafenib), avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

Optional anti-hyperproliferative agents which can be added to the composition include but are not limited to compounds listed on the cancer chemotherapy drug regimens in the 11$^{th}$ Edition of the *Merck Index*, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyperproliferative agents suitable for use with the composition of the invention include but are not limited to those compounds acknowledged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyperproliferative agents suitable for use with the composition of the invention include but are not limited to other anti-cancer agents such as epothilone and its derivatives, irinotecan, raloxifen and topotecan.

HIF pathway inhibitors will render especially positive effects in combinations with other targeted therapies directed against angiogenesis like avastin, sorafenib, DAST, sunitinib, axitinib or AZD 2171, which are presently under development. Combinations with inhibitors of proteasomes and mTOR, anti-hormones or steroid metabolic enzyme inhibitors are especially favorable for patients due to the beneficial side effect profile of targeted therapies.

Generally, the use of cytotoxic and/or cytostatic agents in combination with a compound or composition of the present invention may serve to:
(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

EXPERIMENTAL

Abbreviations and Acronyms

A comprehensive list of the abbreviations used by organic chemists of ordinary skill in the art appears in The ACS Style Guide (third edition) or the Guidelines for Authors for the *Journal of Organic Chemistry*. The abbreviations contained in said lists, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meanings:
bs broad singlet
d doublet
DCI-MS direct chemical ionisation mass spectroscopy
dd doublet of doublet
DME 1,2-dimethoxyethane
DMF N,N-dimethylformamide
DMSO dimethylsulfoxide
EDCl 1-(3-dimethylaminopropyl)-3-ethylcarbodiimide hydrochloride
ES-MS electrospray mass spectroscopy
$Et_2O$ diethyl ether
EtOAc ethyl acetate
HOBT hydroxybenzotriazole
HPLC high performance/high pressure liquid chromatography
m multiplet
MPLC medium pressure liquid chromatography
NMR nuclear magnetic resonance
$Ph_3P$ triphenylphosphine
quart quartet
RT retention time (HPLC)
rt room temperature
s singlet
t triplet
THF tetrahydrofuran
$Tf_2O$ trifluoromethanesulfonic acid anhydride
TFA trifluoroacetic acid
tlc thin layer chromatography The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated under reduced pressure" refers to use of a Buchi rotary evaporator at approximately 15 mm of Hg. All temperatures are reported uncorrected in degrees Celsius (° C.). Thin layer chromatography (tlc) was performed on pre-coated glass-backed silica gel 60 A F-254 250 μm plates.

The structures of compounds of this invention were confirmed using one or more of the following procedures.
NMR NMR spectra were acquired for each compound and were consistent with the structures shown.

Routine one-dimensional NMR spectroscopy was performed on either 300 or 400 MHz Varian® Mercury-plus spectrometers. The samples were dissolved in deuterated solvents. Chemical shifts were recorded on the ppm scale and were referenced to the appropriate solvent signals, such as 2.49 ppm for DMSO-$d_6$, 1.93 ppm for $CD_3CN$, 3.30 ppm for $CD_3OD$, 5.32 ppm for $CD_2Cl_2$, and 7.26 ppm for $CDCl_3$ for 1H spectra.
LC/MS Unless otherwise noted, all retention times are obtained from the LC/MS and correspond to the molecular ion. High pressure liquid chromatography-electrospray mass spectra (LC/MS) were obtained using one of the following:

Method A

Hewlett-Packard 1100 HPLC equipped with a quaternary pump, a variable wavelength detector set at 254 nm, a Waters Sunfire C18 column (2.1×30 mm, 3.5 μm), a Gilson autosampler and a Finnigan LCQ ion trap mass spectrometer with electrospray ionization. Spectra were scanned from 120-1200 amu using a variable ion time according to the number of ions in the source. The eluents were A: 2% acetonitrile in water with 0.02% TFA, and B: 2% water in acetonitrile with 0.018% TFA. Gradient elution from 10% B to 95% B over 3.5 minutes at a flow rate of 1.0 mL/min was used with an initial hold of 0.5 minutes and a final hold at 95% B of 0.5 minutes. Total run time was 6.5 minutes.

Method B

Agilent 1100 HPLC system. The Agilent 1100 HPLC system was equipped with an Agilent 1100 autosampler, quaternary pump, a variable wavelength detector set at 254 nm. The HPLC column used was a Waters Sunfire C-18 column (2.1×30 mm, 3.5 μm). The HPLC eluent was directly coupled without splitting to a Finnigan LCQ DECA ion trap mass spectrometer with electrospray ionization. Spectra were scanned from 140-1200 amu using a variable ion time according to the number of ions in the source using positive ion mode. The eluents were A: 2% acetonitrile in water with 0.02% TFA, and B: 2% water in acetonirile with 0.02% TFA. Gradient elution from 10% B to 90% B over 3.0 minutes at a flow rate of 1.0 mL/min was used with an initial hold of 1.0 minutes and a final hold at 95% B of 1.0 minutes. Total run time was 7.0 minutes.

Method C

Agilent 1100 HPLC system. The Agilent 1100 HPLC system was equipped with an Agilent 1100 autosampler, quaternary pump, and a diode array. The HPLC column used was a Waters Sunfire C18 column (2.1×30 mm, 3.5 μm). The HPLC eluent was directly coupled with a 1:4 split to a Finnigan LTQ ion trap mass spectrometer with electrospray ionization. Spectra were scanned from 50-800 amu using a variable ion time according to the number of ions in the source using positive or negative ion mode. The eluents were A: water with 0.1% formic acid, and B: acetonitrile with 0.1% formic acid. Gradient elution from 10% B to 90% B over 3.0 minutes at a flowrate of 1.0 mL/min was used with an initial hold of 2.0 minutes and a final hold at 95% B of 1.0 minutes. Total run time was 8.0 minutes.

Method D

HPLC system: HP 1100 Series; UV DAD; Column: Phenomenex Gemini 3μ 30 mm×3.00 mm; Eluent A: 1 L water+0.5 mL 50% formic acid, Eluent B: 1 L acetonitrile+0.5 mL 50% formic acid; Gradient: 0.0 min 90% A→2.5 min 30% A→3.0 min 5% A→4.5 min 5% A; Flow rate: 0.0 min 1 mL/min, 2.5 min/3.0 min/4.5 min 2 mL/min; Oven: 50° C.; UV-Detection: 210 nm; MS system: Micromass ZQ; Electron spray ionisation.

Method E

HPLC system: Waters Alliance 2795; Column: Phenomenex Synergi 2.5μ MAX-RP 100A Mercury 20 mm×4 mm; Eluent A: 1 L water+0.5 mL 50% formic acid, Eluent B: 1 L acetonitrile+0.5 mL 50% formic acid; Gradient: 0.0 min 90% A→0.1 min 90% A→3.0 min 5% A→4.0 min 5% A→4.01 min 90% A; Flow rate: 2 mL/min; Oven: 50° C.; UV-Detection: 210 nm; MS system: Micromass ZQ; Electron spray ionisation.

Method F

HPLC system: Agilent Serie 1100; Column: Thermo Hypersil GOLD 3μ 20×4 mm; Eluent A: 1 L water+0.5 mL 50% formic acid; Eluent B: 1 L acetonitrile+0.5 mL 50% formic acid; Gradient: 0.0 min 100% A→3.0 min 10% A→4.0 min 10% A→4.01 min 100% A→5.00 min 100% A; Flow rate: 2.5 mL/min; Oven: 50° C.; UV-Detection: 210 nm; MS system: Micromass Quattro Micro MS; Electron spray ionisation.

Method K

HPLC system: Waters HPLC Acquity; Column: Thermo Hypersil GOLD 1.9μ 50 mm×1 mm; Eluent A: 1 L water+0.5 mL 50% formic acid; Eluent B: 1 L acetonitrile+0.5 mL 50% formic acid; Gradient: 0.0 min 90% A→0.1 min 90% A→1.5 min 10% A→2.2 min 10% A; Flow rate: 0.33 mL/min; Oven: 50° C.; UV-Detection: 210 nm; MS system: Micromass Quattro Premier; Electron spray ionisation.

Analytical HPLC and MS

Method G

HPLC system: HP 1100 with DAD detection; Column: Kromasil 100 RP-18, 60 mm×2.1 mm, 3.5 μm; Eluent: A=5 mL HClO$_4$ (70%)/L H$_2$O, B=acetonitrile; Gradient: 0 min 2% B, 0.5 min 2% B, 4.5 min 90% B, 9 min 90% B, 9.2 min 2% B, 10 min 2% B; Flow rate: 0.75 mL/min; Oven: 30° C.; Detection: UV 210 nm. MS system: M-40; Chemical ionisation (NH$_3$).

Method H

HPLC system: HP 1100 with DAD detection; Column: Kromasil 100 RP-18, 60 mm×2.1 mm, 3.5 μm; Eluent: A=5 mL HClO$_4$ (70%)/L H$_2$O, B=acetonitrile; Gradient: 0 min 2% B, 0.5 min 2% B, 4.5 min 90% B, 9 min 90% B, 9.2 min 2% B, 10 min 2% B; Flow rate: 0.75 mL/min; Oven: 30° C.; Detection: UV 210 nm. MS system: ZQ3; Electron spray ionisation.

Method I

HPLC system: HP 1100 with DAD detection; Column: Kromasil 100 RP-18, 60 mm×2.1 mm, 3.5 μm; Eluent: A=5 mL HClO$_4$ (70%)/L H$_2$O, B=acetonitrile; Gradient: 0 min 2% B, 0.5 min 2% B, 4.5 min 90% B, 6.5 min 90% B, 6.7 min 2% B, 7.5 min 2% B; Flow rate: 0.75 mL/min; Oven: 30° C.; Detection: UV 210 nm. MS system: M-40; Chemical ionisation (NH$_3$).

Method J

HPLC system: HP 1100 with DAD detection; Column: Kromasil 100 RP-18, 60 mm×2.1 mm, 3.5 μm; Eluent: A=5 mL HClO$_4$ (70%)/L H$_2$O, B=acetonitrile; Gradient: 0 min 2% B, 0.5 min 2% B, 4.5 min 90% B, 6.5 min 90% B, 6.7 min 2% B, 7.5 min 2% B; Flow rate: 0.75 mL/min; Oven: 30° C.; Detection: UV 210 nm. MS system: ZQ3; Electron spray ionisation.

Preparative HPLC:

Preparative HPLC was carried out in reversed phase mode, typically using a Gilson HPLC system equipped with two Gilson 322 pumps, a Gilson 215 Autosampler, a Gilson diode array detector, and a C-18 column (e.g. YMC Pro 20×150 mm, 120 A). Gradient elution was used with solvent A as water with 0.1% TFA, and solvent B as acetonitrile with 0.1% TFA. Following injection onto the column as a solution, the compound was typically eluted with a mixed solvent gradient, such as 10-90% Solvent B in Solvent A over 15 minutes with flow rate of 25 mL/min. The fraction(s) containing the desired product were collected by UV monitoring at 254 or 220 nm.

Preparative MPLC:

Preparative medium pressure liquid chromatography (MPLC) was carried out by standard silica gel "flash chromatography" techniques (e.g., Still, W. C. et al. *J. Org. Chem.* 1978, 43, 2923-5), or by using silica gel cartridges and devices such as the Biotage Flash systems. A variety of eluting solvents were used, as described in the experimental protocols.

General Preparative Methods

The particular process to be utilized in the preparation of the compounds used in this embodiment of the invention depends upon the specific compound desired. Such factors as the selection of the specific substituents play a role in the path to be followed in the preparation of the specific compounds of this invention. Those factors are readily recognized by one of ordinary skill in the art.

The compounds of the invention may be prepared by use of known chemical reactions and procedures. Nevertheless, the following general preparative methods are presented to aid the reader in synthesizing the compounds of the present invention, with more detailed particular examples being presented below in the experimental section describing the working examples.

The compounds of the invention can be made according to conventional chemical methods, and/or as disclosed below, from starting materials which are either commercially available or producible according to routine, conventional chemical methods. General methods for the preparation of the compounds are given below, and the preparation of representative compounds is specifically illustrated in examples.

Synthetic transformations that may be employed in the synthesis of compounds of this invention and in the synthesis of intermediates involved in the synthesis of compounds of this invention are known by or accessible to one skilled in the art. Collections of synthetic transformations may be found in compilations, such as:

J. March. *Advanced Organic Chemistry*, 4th ed.; John Wiley: New York (1992)
R. C. Larock. *Comprehensive Organic Transformations*, 2nd ed.; Wiley-VCH: New York (1999)
F. A. Carey; R. J. Sundberg. *Advanced Organic Chemistry*, 2nd ed.; Plenum Press: New York (1984)
T. W. Greene; P. G. M. Wuts. *Protective Groups in Organic Synthesis*, 3rd ed.; John Wiley: New York (1999)
L. S. Hegedus. *Transition Metals in the Synthesis of Complex Organic Molecules*, 2nd ed.; University Science Books: Mill Valley, Calif. (1994)
L. A. Paquette, Ed. *The Encyclopedia of Reagents for Organic Synthesis*; John Wiley: New York (1994)
A. R. Katritzky; O. Meth-Cohn; C. W. Rees, Eds. *Comprehensive Organic Functional Group Transformations*; Pergamon Press: Oxford, UK (1995)
G. Wilkinson; F. G A. Stone; E. W. Abel, Eds. *Comprehensive Organometallic Chemistry*; Pergamon Press: Oxford, UK (1982)
B. M. Trost; I. Fleming. *Comprehensive Organic Synthesis*; Pergamon Press: Oxford, UK (1991)
A. R. Katritzky; C. W. Rees Eds. *Comprehensive Heterocylic Chemistry*; Pergamon Press: Oxford, UK (1984)
A. R. Katritzky; C. W. Rees; E. F. V. Scriven, Eds. *Comprehensive Heterocylic Chemistry II*; Pergamon Press: Oxford, UK (1996)
C. Hansch; P. G. Sammes; J. B. Taylor, Eds. *Comprehensive Medicinal Chemistry*: Pergamon Press: Oxford, UK (1990).

In addition, recurring reviews of synthetic methodology and related topics include *Organic Reactions*; John Wiley: New York; *Organic Syntheses*; John Wiley: New York; *Reagents for Organic Synthesis*: John Wiley: New York; *The Total Synthesis of Natural Products*; John Wiley New York; *The Organic Chemistry of Drug Synthesis*; John Wiley: New York; *Annual Reports in Organic Synthesis*; Academic Press: San Diego Calif.; and *Methoden der Organischen Chemie* (Houben-Weyl); Thieme: Stuttgart, Germany. Furthermore, databases of synthetic transformations include *Chemical Abstracts*, which may be searched using either CAS OnLine or SciFinder, *Handbuch der Organischen Chemie* (Beilstein), which may be searched using SpotFire, and REACCS.

In general, the compounds of Formula I can be prepared through the use of the intermediate compounds of the Formula VI and compounds of the Formula VII, the preparation of which is shown in the Reaction Scheme 1 below. Following the method of Meyer, tert-butyl carbazate (II) is reacted with acetone in the presence of a dehydrating reagent, such as magnesium sulfate to furnish the compound of the Formula III (Meyer, K. G. *Synlett* 2004, 2355-2356). The resultant acetone adduct (III) is treated with a benzyl halide such as an optionally substituted benzyl bromide, in the presence of a base, for example potassium hydroxide, in a solvent such as toluene, preferably at elevated temperature to afford the compounds of Formula IV. The deprotection of the compounds of Formula IV to obtain the compounds of the formula V is typically carried out under acidic conditions, using an acid such as an aqueous solution of hydrochloric acid, and usually takes place in an organic solvent such as tetrahydrofuran. Cyclization of the resultant hydrazine salts (V) with a 1,3-dicarbonyl compound (e.g., 1,3-diketone, β-ketoester), for example methyl acetopyruvate, is normally conducted in a solvent such as acetic acid, preferably at elevated temperature, and furnishes the compounds of the Formula VI. The ester (VI) is hydrolyzed under basic conditions, using an aqueous solution of a base such as sodium hydroxide in an organic solvent such as ethanol. Acidic workup in the usual manner provides the compounds of the Formula VII.

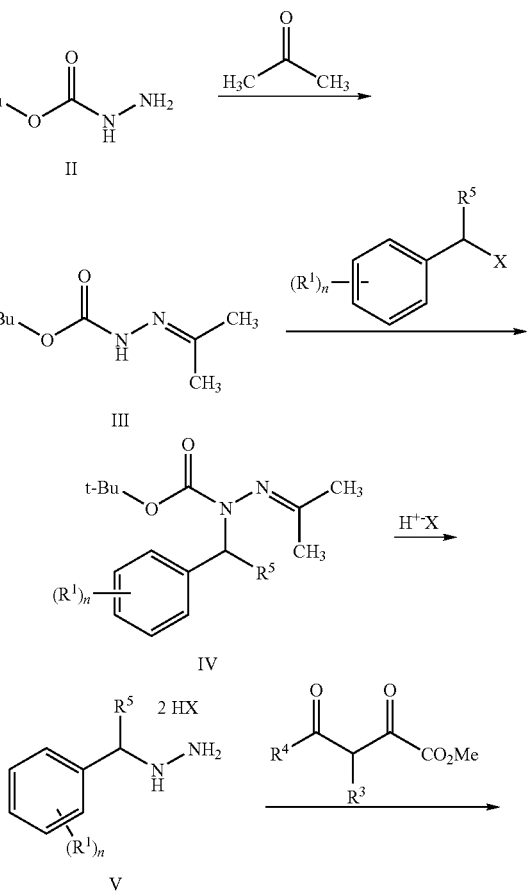

Reaction Scheme 1

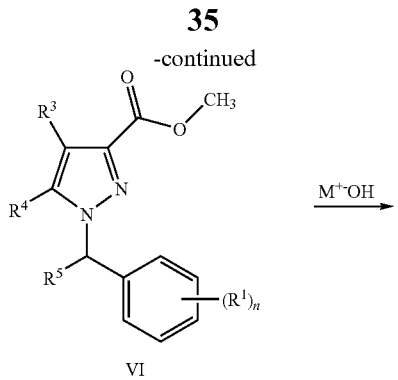

VI

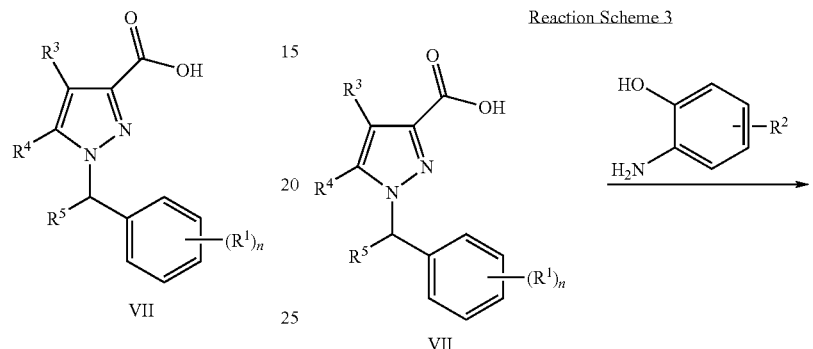

VII

A general synthesis of compounds of the Formula Ia is outlined in the Reaction Scheme 2 below. The compounds of Formula VII are reacted with an N'-hydroxyamidine in the presence of a coupling reagent, for example 1-(3-dimethylaminopropyl)-3-ethylcarbodiimide-hydrochloride (EDCl), and optionally in the presence of a promoting agent such as 1-hydroxybenzotriazole (HOBt), preferably at elevated temperature to obtain the oxadiazole compounds (Ia). Alternatively, compounds of the formula VII can be converted to the corresponding acid halide with a halogenating reagent such as thionyl chloride and then subsequently reacted with an N'-hydroxyamidine preferably at elevated temperature to afford the oxadiazole compounds (Ia).

Generally, compounds of the Formula Ib are synthesized from compounds of the Formula VII according to the procedure shown in Reaction Scheme 3 below. Optionally substituted 2-aminophenols and the compounds of Formula VII are suspended and/or dissolved in trimethylsilylpolyphosphate, and the mixture is stirred at elevated temperature to furnish, after an aqueous workup, the benzoxazole compounds of the Formula Ib.

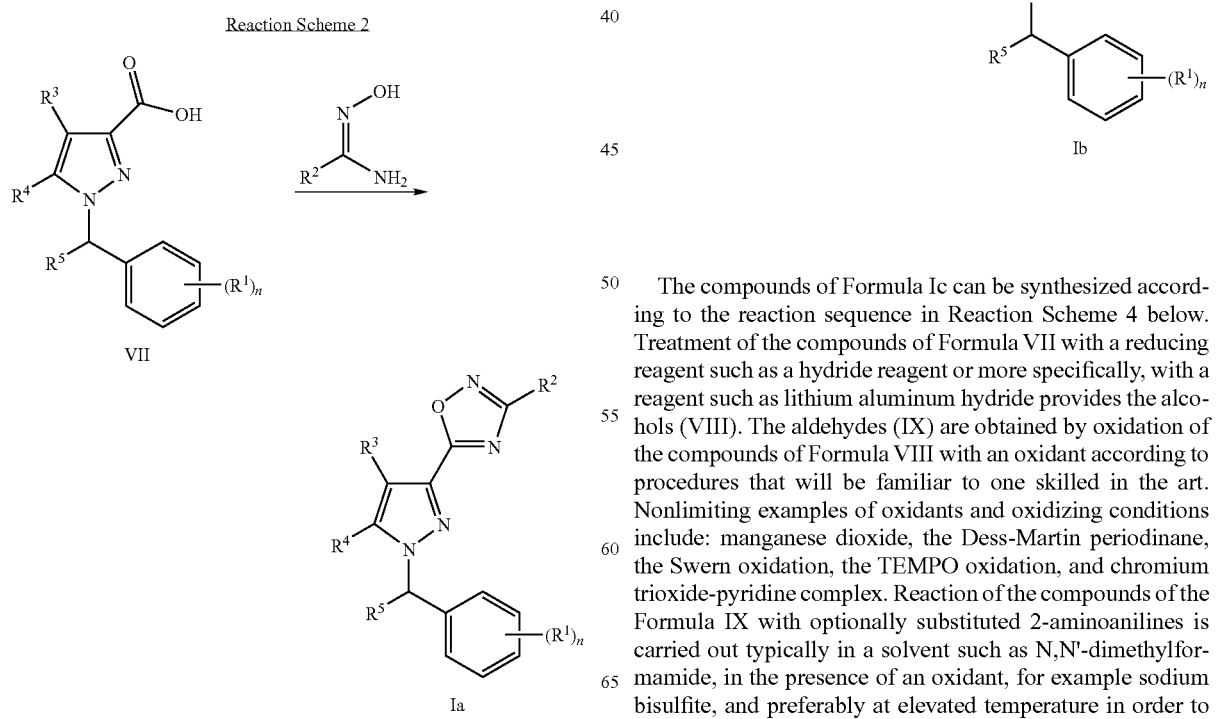

The compounds of Formula Ic can be synthesized according to the reaction sequence in Reaction Scheme 4 below. Treatment of the compounds of Formula VII with a reducing reagent such as a hydride reagent or more specifically, with a reagent such as lithium aluminum hydride provides the alcohols (VIII). The aldehydes (IX) are obtained by oxidation of the compounds of Formula VIII with an oxidant according to procedures that will be familiar to one skilled in the art. Nonlimiting examples of oxidants and oxidizing conditions include: manganese dioxide, the Dess-Martin periodinane, the Swern oxidation, the TEMPO oxidation, and chromium trioxide-pyridine complex. Reaction of the compounds of the Formula IX with optionally substituted 2-aminoanilines is carried out typically in a solvent such as N,N'-dimethylformamide, in the presence of an oxidant, for example sodium bisulfite, and preferably at elevated temperature in order to synthesize the benzimidazole compounds of the Formula Ic.

Reaction Scheme 4

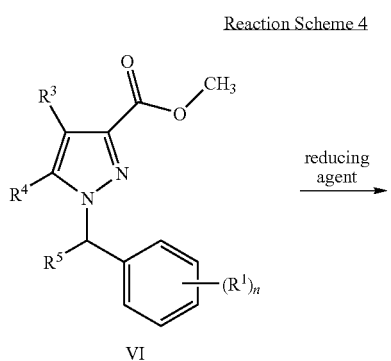

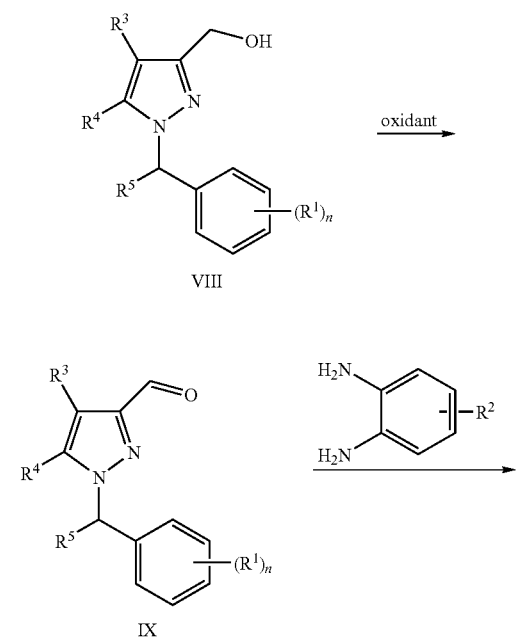

Alternatively, benzimidazole compounds of the formula Id are synthesized according to the route shown in Reaction Scheme 5. As described above, the reaction of the compounds of the Formula IX with halogen substituted 2-aminoanilines is carried out typically in a solvent such as N,N'-dimethylformamide, in the presence of an oxidant, for example sodium bisulfite, and preferably at elevated temperature in order to afford the benzimidazole compounds of the Formula X. The free benzimidazole N—H is protected with a suitable protecting group such as a [2-(trimethylsilyl)ethoxy]methyl (SEM) group by treating the compounds of the Formula X with [2-(trimethylsilyl)ethoxy]methyl chloride (SEMCl) in the presence of a base such as N,N'-diisopropylethylamine to provide the compounds of the Formula XI. Subsequently, phenyl substituted benzimidazoles of the Formula XII can be synthesized by coupling the compounds of the Formula XI with optionally substituted boronic acids under Suzuki-type conditions, for example in the presence of a palladium catalyst such as tetrakis(triphenylphosphine)palladium(0), using a base such as aqueous sodium carbonate, in an organic solvent such as dioxane and preferably at elevated temperature. Deprotection of the benzimidazoles of the Formula XII is carried out under acidic conditions, for example in a solution of dichloromethane/trifluoroacetic acid, and furnishes the compounds of the Formula Id.

Reaction Scheme 5

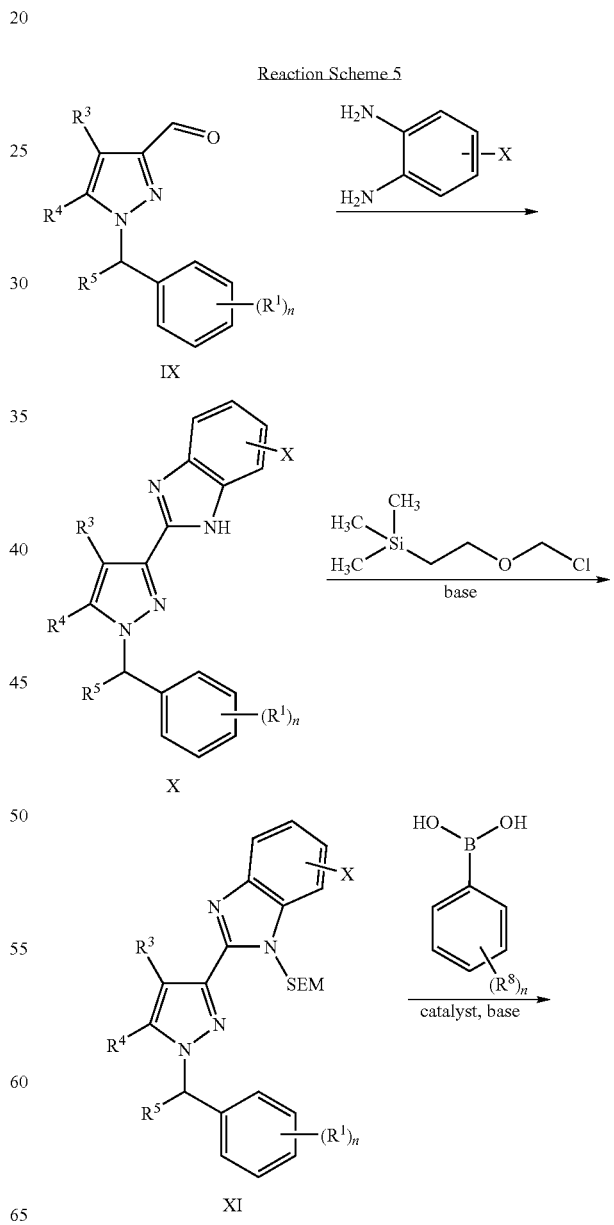

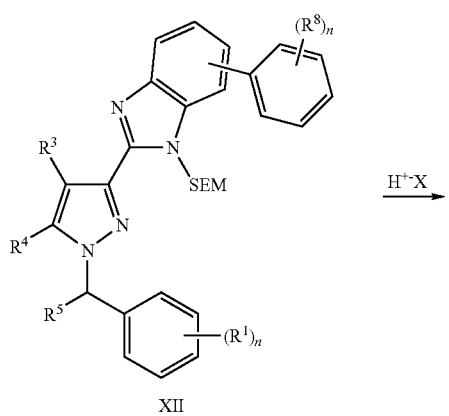

XII

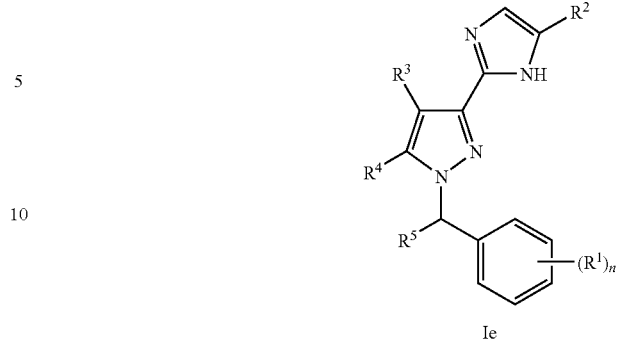

Ie

A general synthesis of the compounds of the Formula If and of the Formula Ig is shown in Reaction Scheme 7 below. The compounds of Formula VII are reacted with an optionally substituted 2-aminoethyl alcohol in the presence of a coupling reagent, for example O-(7-azabenzotriazol-1-yl)-N,N,N',N'-tetramethyluronium $PF_6$, and in the presence of a base such as triethylamine to obtain the compounds of the formula XIII. Cyclization of the amide (XIII) to produce the oxazoline compounds of the formula If is carried out with a cyclization reagent, for example carbomethoxysulfamoyltriethylammonium hydroxide inner salt (Burgess' reagent), in a solvent such as THF and preferably at elevated temperature. Conversion of the compounds of the Formula If to the compounds of the Formula Ig is conducted with an oxidizing agent, such as 2,3-dichloro-5,6-dicyano-1,4-benzoquinone (DDQ) or manganese dioxide, in a solvent such as dioxane or THF and preferably at elevated temperature.

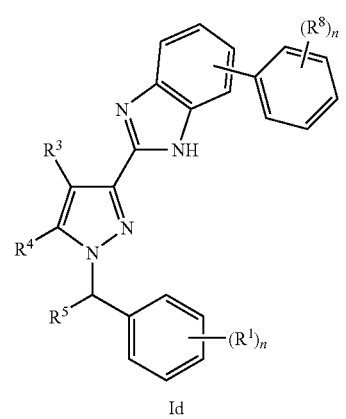

Id

Generally, the compounds of the Formula Ie are synthesized according to the sequence outlined in Reaction Scheme 6. First, the compounds of the Formula VII are treated with an optionally substituted 2-bromoethyl ketone and a base such as cesium carbonate. The resultant mixture is subsequently stirred in a solvent, such as xylene, with an excess amount of ammonium acetate, preferably at reflux to obtain the compounds of the Formula Ie.

Reaction Scheme 7

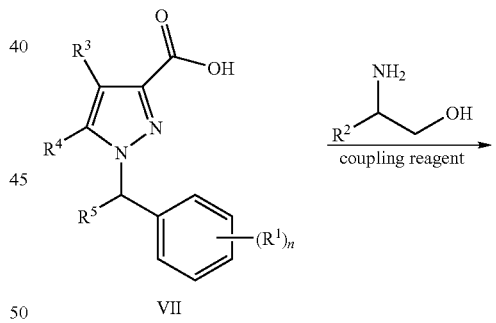

VII

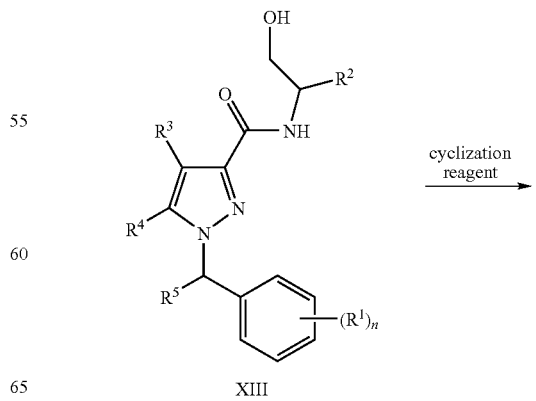

XIII

Reaction Scheme 6

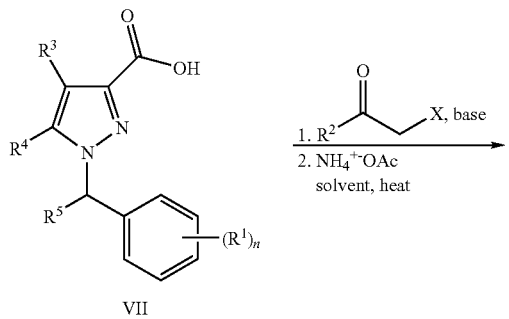

VII

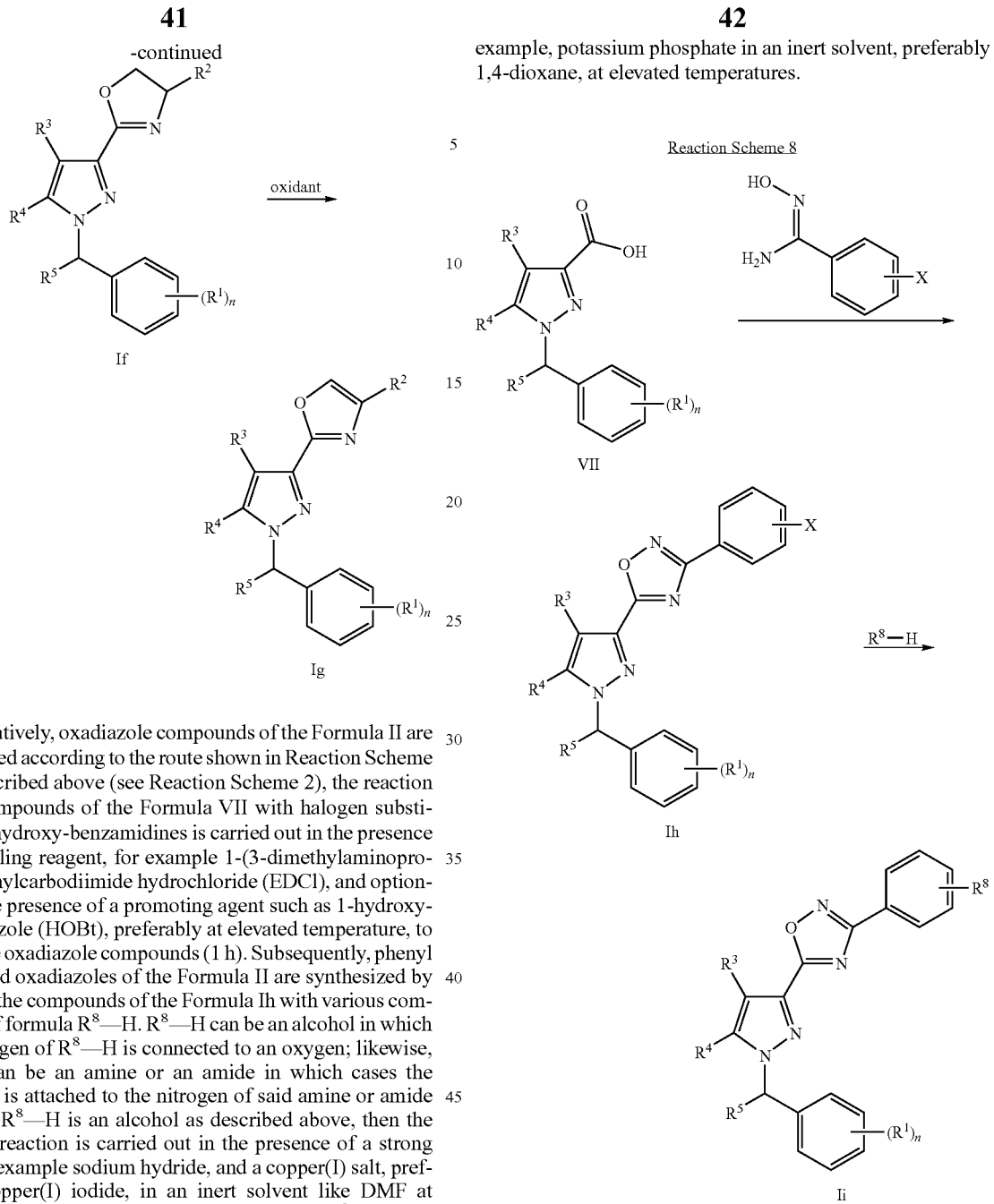

Alternatively, oxadiazole compounds of the Formula II are synthesized according to the route shown in Reaction Scheme 8. As described above (see Reaction Scheme 2), the reaction of the compounds of the Formula VII with halogen substituted N'-hydroxy-benzamidines is carried out in the presence of a coupling reagent, for example 1-(3-dimethylaminopropyl)-3-ethylcarbodiimide hydrochloride (EDCl), and optionally in the presence of a promoting agent such as 1-hydroxybenzotriazole (HOBt), preferably at elevated temperature, to obtain the oxadiazole compounds (1 h). Subsequently, phenyl substituted oxadiazoles of the Formula II are synthesized by coupling the compounds of the Formula Ih with various compounds of formula $R^8$—H. $R^8$—H can be an alcohol in which the hydrogen of $R^8$—H is connected to an oxygen; likewise, $R^8$—H can be an amine or an amide in which cases the hydrogen is attached to the nitrogen of said amine or amide group. If $R^8$—H is an alcohol as described above, then the coupling reaction is carried out in the presence of a strong base, for example sodium hydride, and a copper(I) salt, preferably copper(I) iodide, in an inert solvent like DMF at elevated temperatures. Alternatively, the alcohol $R^8$—H itself serves as the solvent and a catalyst system consisting of copper(I) iodide and phenanthroline in the presence of cesium carbonate as a base is employed. If $R^8$—H is an amine as described above, it is reacted with compounds of the formula Ih in the presence of a palladium catalyst consisting of a palladium source like, for example, tris(dibenzylideneacetone)dipalladium ($Pd_2(dba)_3$) or palladium(II) chloride, and a ligand like, for example, 2-(dicyclohexylphosphino)-2',4', 6'-tri-tert-butyl-1,1'-biphenyl or 2-(dicyclohexylphosphino)-1,1'-biphenyl, and a base like, for example, potassium carbonate or potassium phosphate in a solvent like, for example, DMF, tert.-butanol, 1,2-dimethoxyethane or mixtures thereof at elevated temperatures. If $R^8$—H is an amide as described above, the reaction with compounds of Formula Ih is brought about in the presence of a copper(I) salt, preferably copper(I) iodide, a 1,2-diaminoethane derivative like, for example, N,N'-dimethylenethylenediamine (DMEDA), a base like, for example, potassium phosphate in an inert solvent, preferably 1,4-dioxane, at elevated temperatures.

Another alternative route to compounds of Formula Ia is described in Reaction Scheme 9. It comprises the reaction of a pyrazole carboxylic acid of the Formula XIV with an N'-hydroxyamidine in the presence of a coupling reagent, for example 1-(3-dimethylaminopropyl)-3-ethylcarbodiimide hydrochloride (EDCl), and optionally in the presence of a promoting agent such as 1-hydroxybenzotriazole (HOBt), preferably at elevated temperature to give the oxadiazole compounds (XV). Further conversion of these oxadiazoles to the final product of Formula Ia is carried out with a benzylating agent, in which X represents a leaving group such as, for example, bromide or chloride, in the presence of a strong base such as potassium tert-butoxide in an inert solvent like, for example, THF.

Reaction Scheme 9

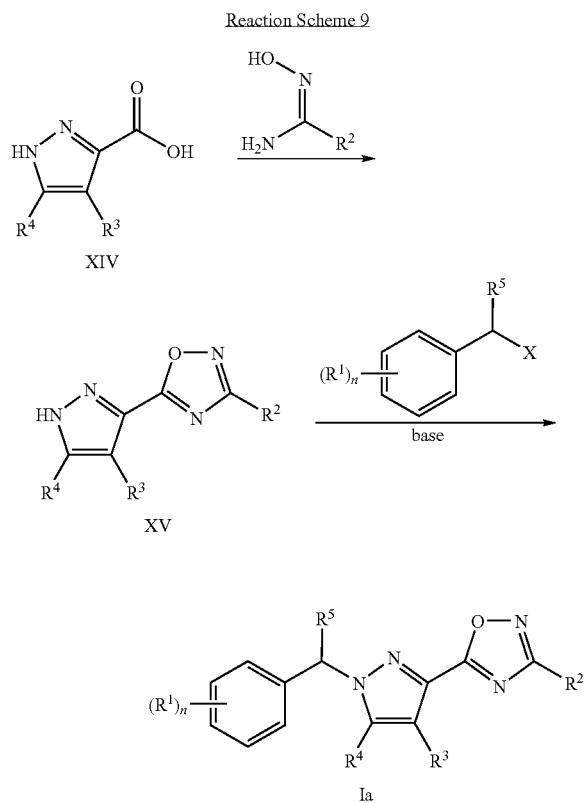

Reaction Scheme 10

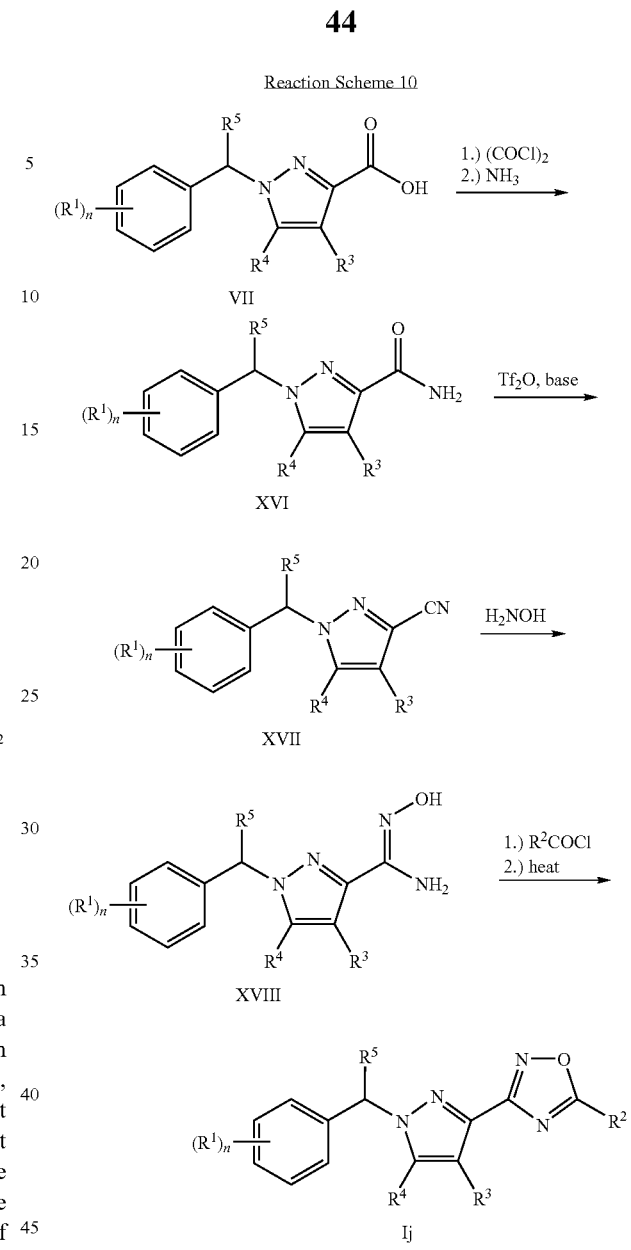

A general synthesis of compounds of Formula Ij is shown in Reaction Scheme 10 below. The compounds of Formula VII are converted to the corresponding amides via conversion to the acid chloride by the action of a chlorinating agent like, for example, oxalyl chloride or thionyl chloride in an inert solvent like, for example, dichloromethane, and subsequent reaction of the acid chloride with ammonia in a suitable solvent like, for example, THF or 1,4-dioxane, yielding the primary amides of Formula XVI. Dehydration by the aid of trifluoromethanesulfonic acid anhydride (Tf$_2$O) in the presence of a base like, for example, triethylamine or N,N-diisopropylethylamine in an inert solvent like, for example, dichloromethane, carried out at room temperature or below, for example 0° C., furnishes the nitriles of Formula XVII. The N'-hydroxyamidines of Formula XVIII are obtained by the addition of hydroxylamine. The reaction is best carried out in alcoholic solvents, for example ethanol, at elevated temperature. The sequence concludes with the reaction of compounds of Formula XVIII with acid chlorides R$^2$C(O)Cl in the presence of a base like, for example, triethylamine or N,N-diisopropylethylamine in an inert solvent like, for example, dichloromethane, THF or ethyl acetate at a temperature between −10° C. and room temperature. After the initial acylation step is complete and all volatiles are subsequently removed, cyclization to the oxadiazole is achieved by heating in a suitable solvent like, for example, DMSO or DMF to a temperature of about 140° C. to yield compounds of Formula Ij.

Certain compounds of the invention having the Formula Im can be prepared from compounds of Formula Ik provided that the residues R$^1$, R$^3$, R$^4$ and R$^5$ do not contain functional groups, like for example hydroxy, which are incompatible with the chemical transformations set forth in Reaction Scheme 11 below. Compounds of Formula Ik are converted to the bromides of Formula XIX by reaction with tetrabromomethane and triphenylphosphine in an inert solvent like, for example, dichloromethane or THF at room temperature or slightly below (0° C.). Compounds of Formula Im are obtained from these bromides by the reaction with amines H—NR$^9$R$^{10}$ or H—R$^{11}$ in the presence of a strong base such as sodium hydride. Compounds H—R$^{11}$ in this instance are cyclic amines, i.e. N-containing heteroaryl or heterocyclyl groups, where the hydrogen of H—R$^{11}$ is attached to a nitrogen atom of the residue R$^{11}$. The reaction is best carried out in an aprotic polar solvent like, for example, DMF, N-methylpyrrolidinone or DMSO at a temperature between 0° C. and room temperature.

Reaction Scheme 11

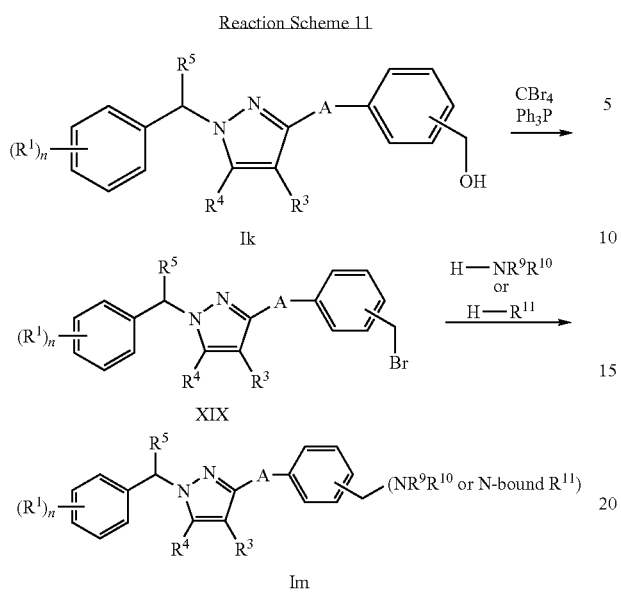

In order that this invention may be better understood, the following examples are set forth. These examples are for the purpose of illustration only, and are not to be construed as limiting the scope of the invention in any manner. All publications mentioned herein are incorporated by reference in their entirety.

Intermediates

Intermediate A

Preparation of Methyl 5-methyl-1-(4-methylbenzyl)-1H-pyrazole-3-carboxylate

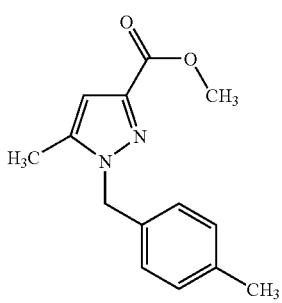

Step 1: Preparation of tert-Butyl 2-isopropylidenehydrazinecarboxylate

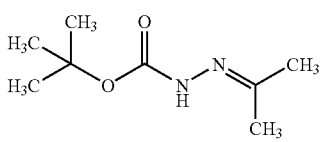

To a mechanically stirred solution of tert-butylcarbazate (450 g, 3.4 mol) in acetone (2.5 L) was added magnesium sulfate (100 g, 0.83 mol) and 100 drops of acetic acid. The mixture was warmed to reflux and stirred for 3.5 h. After being cooled to rt, the mixture was filtered and partially concentrated, at which point the product crystallized from the supersaturated solvent. The crystals were filtered and dried in a vacuum oven overnight to provide the title compound as colorless needles (463 g, 79%): $^1$H NMR (300 MHz, $d_6$-DMSO) δ 1.40 (s, 9H), 1.75 (s, 3H), 1.83 (s, 3H).

Step 2: Preparation of tert-Butyl 2-isopropylidene-1-(4-methylbenzyl)hydrazinecarboxylate

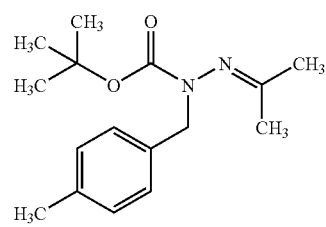 [SMILES: CC(C)=NN(Cc1ccc(C)cc1)C(=O)OC(C)(C)C]

To a mechanically stirred solution of tert-butyl 2-isopropylidene-1-(4-methylbenzyl)-hydrazinecarboxylate (Step 1, 77.6 g, 450 mmol) in toluene (1800 mL) was added powdered potassium hydroxide (32.8 g, 585 mmol) and tetrabutylammonium hydrogen sulfate (15.3 g, 45 mmol). The mixture was stirred vigorously and was warmed to 50° C., at which point p-methylbenzyl bromide (91.7 g, 495 mmol) was added portionwise. The mixture was further warmed to 80° C. and was stirred for 3 h. After being cooled to rt, the mixture was washed with water (3×500 mL) and brine (1×500 mL), was dried (MgSO$_4$), filtered and concentrated to a light yellow oil that was carried on without additional purification: $^1$H NMR (300 MHz, $d_6$-DMSO) δ 1.38 (s, 9H), 1.65 (s, 3H), 1.89 (s, 3H), 2.25 (s, 3H) 4.49 (s, 2H), 7.09-7.11 (m, 4H).

Step 3: Preparation of (4-Methylbenzyl)hydrazine dihydrochloride

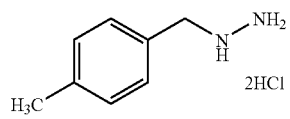

A mechanically stirred solution of tert-butyl 2-isopropylidene-1-(4-methylbenzyl)hydrazinecarboxylate (crude product from Step 2) in THF (950 mL) and HCl (3N aq., 360 mL) was warmed to reflux. After being stirred for 3 h, the yellow solution was cooled to rt and concentrated to a white solid. The crude material was dried under high vacuum overnight, was suspended in Et$_2$O, and was filtered to provide the title compound as a crystalline white solid (87.8 g, 87% for 2 steps): $^1$H NMR (300 MHz, $d_6$-DMSO) δ 2.27 (s, 3H), 4.00 (s, 2H), 7.17 (d, 2H), 7.29 (d, 2H).

Step 4: Preparation of (Methyl 5-methyl-1-(4-methylbenzyl)-1H-pyrazole-3-carboxylate

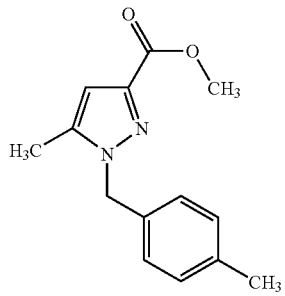

A mechanically stirred suspension of 4-(methylbenzyl)hydrazine dihydrochloride (Step 3, 81.8 g, 391 mmol) and methyl acetopyruvate (51.2 g, 356 mmol) in acetic acid (825 mL) was warmed to 90° C. and stirred for 4 h. The solid gradually dissolved, leaving an orange solution. After being cooled to rt, the reaction mixture was concentrated to an orange oil. The organic residue was diluted with EtOAc, washed with water (1×250 mL), NaHCO$_3$ (1×250 mL), and brine (1×250 mL), was dried (Na$_2$SO$_4$), filtered and concentrated to an orange oil. Purification with an ISCO CombiFlash Companion, using a gradient from 0% to 30% EtOAc in hexanes afforded the title compound as a yellow-orange oil (39 g, 45%): $^1$H NMR (300 MHz, d$_6$-DMSO) δ 2.20 (s, 3H), 2.24 (s, 3H), 3.75 (s, 3H), 5.31 (s, 2H), 6.56 (s, 1H), 7.01 (d, 2H), 7.12 (d, 2H). ES-MS m/z 245.0 (MH)$^+$, HPLC RT (Method A) 3.13 min.

Intermediate B

Preparation of 5-Methyl-1-(4-methylbenzyl)-1H-pyrazole-3-carboxylic acid

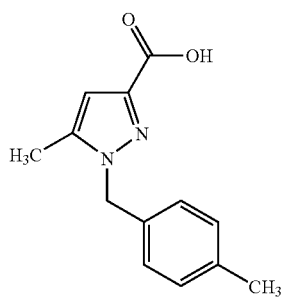

To a solution of methyl 5-methyl-1-(4-methylbenzyl)-1H-pyrazole-3-carboxylate (Intermediate A, 16.3 g, 66.7 mmol) in ethanol (500 mL) was added NaOH (1N aq., 133 mL, 133 mmol), and the mixture was heated at 70° C. for 16 h. The organic solvent was evaporated under vacuum and the residue was acidified with HCl (1N aq., 150 mL) until a white solid completely precipitated from solution. The solid was filtered, washed with water (1.5 L), and was dried in a vacuum oven to afford the title compound as a white solid (14.6 g, 95%): $^1$H NMR (300 MHz, DMSO-d$_6$) δ 7.0 (d, 2H), 7.08 (d, 2H), 6.56 (s, 1H), 5.35 (s, 2H), 2.30 (s, 3H), 2.27 (s, 3H); ES-MS m/z 231.0 (MH)$^+$, HPLC RT (Method B) 3.12 min.

Intermediate C

Preparation of 5-(5-Methyl-1H-pyrazol-3-yl)-3-[4-(trifluoromethoxy)phenyl]-1,2,4-oxadiazole

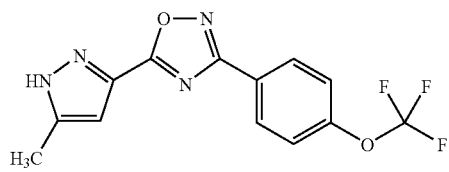

To a mechanically stirred solution of 5-methyl-1H-pyrazole-3-carboxylic acid (15.3 g, 0.121 mol) in dry DMF (600 mL) was added EDCl (23.3 g, 0.121 mol), HOBT (16.4 g, 0.121 mol) and N'-hydroxy-4-(trifluoromethoxy)benzenecarboximidamide (26.7 g, 0.121 mol). The mixture was stirred at rt for 2 h, and then warmed to 140° C. and stirred for further 5 h. After being cooled to rt, the mixture was diluted with water (2 L) and extracted with ethyl acetate.

The organic extract was successively washed with water and brine. The solvent was removed in vacuo and the residue was purified by MPLC (silica, cyclohexane/ethyl acetate 5:1→1:1). The appropriate fractions were combined and partially concentrated, at which point the product crystallized from the supersaturated solvent. Two crops of solid were obtained. The two crops were combined and dried in vacuo to provide the title compound as a colorless solid (19.7 g, 52%): $^1$H NMR (400 MHz, CDCl$_3$) δ 10.75 (broad, 1H), 8.24 (d, 2H), 7.34 (d, 2H), 6.81 (s, 1H), 2.46 (s, 3H); ES-MS m/z 311 (MH)$^+$; HPLC RT (Method H) 4.72 min.

Intermediate D

Preparation of 5-Ethyl-1-(4-methylbenzyl)-1H-pyrazole-3-carboxylic acid

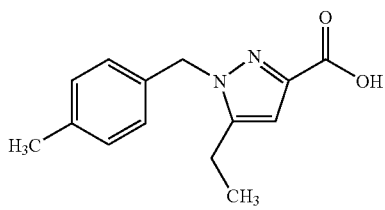 [SMILES: CCc1cc(C(=O)O)nn1Cc1ccc(C)cc1]

Step 1: Preparation of Ethyl 2,4-dioxohexanoate

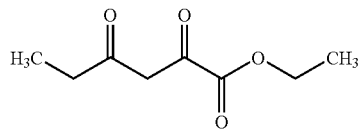

To a suspension of sodium hydride (44 g, 1.10 mol, 60% in mineral oil) dry ethanol (318 mL, 5.44 mol) was added dropwise at a temperature of 0° C. Ten minutes after the addition was completed and still at 0° C., a mixture of 2-butanone (90 mL, 1.0 mol) and diethyl oxalate (136 mL, 1.0 mol) was added dropwise. The reaction mixture was stirred at rt overnight. Then, sulfuric acid was added (4N aq., 550 mL, 1.1 mol). The crude product was extracted into diethyl ether. After washing with water and brine, the organic extract was dried over anhydrous magnesium sulfate, followed by filtration and evaporation of the solvent. The residue was subjected to distillation in vacuo. At a boiling point of 68-78° C. (2.2-2.6 mbar) the product was obtained as a colorless liquid (68.4 g, 40%): $^1$H NMR (400 MHz, CDCl$_3$) δ 14.40 (broad, 1H), 6.38 (s, 1H), 4.36 (quart, 2H), 2.53 (quart, 2H), 1.38 (t, 3H), 1.17 (t, 3H); DCI(NH$_3$)-MS m/z 173 (MH)$^+$, 190 (M+NH$_4$)$^+$; HPLC RT (Method I) 4.02 min.

Step 2: Preparation of Ethyl 5-ethyl-1-(4-methylbenzyl)-1H-pyrazole-3-carboxylate

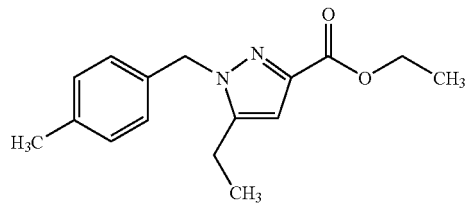 [SMILES: CCOC(=O)c1cc(CC)n(Cc2ccc(C)cc2)n1]

A solution of ethyl 2,4-dioxohexanoate (Step 1, 2.0 g, 11.6 mmol) and 4-(methylbenzyl)-hydrazine dihydrochloride (Step 3 of Intermediate A, 2.67 g, 12.8 mmol) in acetic acid (15 mL) was stirred for 4 h at 90° C. After removal of the solvent (rotavapor), the residue was subjected to MPLC (silica, cyclohexane/ethyl acetate 5:1) to afford the title compound as a highly viscous oil (1.93 g, 61%): $^1$H NMR (400 MHz, CDCl$_3$) δ 7.10 (d, 2H), 6.98 (d, 2H), 6.62 (s, 1H), 5.33 (s, 2H), 4.40 (quart, 2H), 2.48 (quart, 2H), 2.31 (s, 3H), 1.40 (t, 3H), 1.18 (t, 3H); DCI(NH$_3$)-MS m/z 273 (MH)$^+$; HPLC RT (Method I) 4.75 min.

Step 3: Preparation of 5-Ethyl-1-(4-methylbenzyl)-1H-pyrazole-3-carboxylic acid

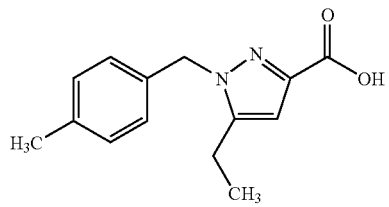 [SMILES: CCc1cc(C(=O)O)nn1Cc1ccc(C)cc1]

To a solution of ethyl 5-ethyl-1-(4-methylbenzyl)-1H-pyrazole-3-carboxylate (Step 2, 1.85 g, 6.79 mmol) in ethanol (43 mL) was added NaOH (1N aq., 13.6 mL, 13.6 mmol), and the mixture was heated at 70° C. for 3 h. The organic solvent was evaporated under vacuum and the residue was acidified with HCl (3N aq.) at 0° C. until a white solid completely precipitated from solution. The solid was filtered, washed with water, and was dried in a vacuum oven to afford the title compound as a white solid (1.53 g, 92%): $^1$H NMR (500 MHz, CDCl$_3$) δ 7.07 (d, 2H), 6.94 (d, 2H), 6.63 (s, 1H), 5.23 (s, 2H), 2.47 (quart, 2H), 2.30 (s, 3H), 1.17 (t, 3H); ES-MS m/z 245 (MH)$^+$, 262 (M+NH$_4$)$^+$; HPLC RT (Method I) 4.12 min.

Intermediate E

Preparation of 5-Ethyl-4-methyl-1-(4-methylbenzyl)-1H-pyrazole-3-carboxylic acid

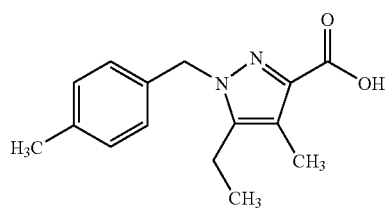 [SMILES: CCc1c(C)c(C(=O)O)nn1Cc1ccc(C)cc1]

Step 1: Preparation of Methyl 5-ethyl-4-methyl-1H-pyrazole-3-carboxylate hydrochloride

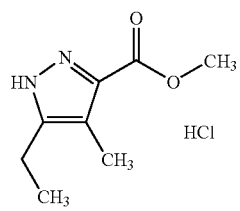

To a mechanically stirred suspension of 5-ethyl-4-methyl-1H-pyrazole-3-carboxylic acid (1.0 g, 6.49 mmol) in dry methanol (30 mL) was added chlorotrimethylsilane (2.5 mL, 19.5 mmol). The reaction mixture was heated at reflux overnight. After being cooled to rt, the solvent was removed in vacuo, and the residue was stirred in diethyl ether (20 mL) for 1 h. After filtration and vacuum drying the title compound was obtained as white crystals (832 mg, 63%): $^1$H NMR (400 MHz, CDCl$_3$) δ 10.55 (broad, 1H), 4.00 (s, 3H), 2.91 (quart, 2H), 2.32 (s, 3H), 1.35 (t, 3H); ES-MS m/z 169 (MH)$^+$; HPLC RT (Method F) 1.52 min.

Step 2: Preparation of 5-Ethyl-4-methyl-1-(4-methylbenzyl)-1H-pyrazole-3-carboxylic acid

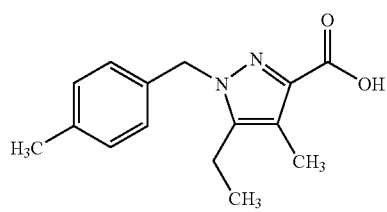 [SMILES: CCc1c(C)c(C(=O)O)nn1Cc1ccc(C)cc1]

To a mechanically stirred solution of methyl 5-ethyl-4-methyl-1H-pyrazole-3-carboxylate hydrochloride (Step 1, 825 mg, 4.03 mmol) in dry ethanol (20 mL) was added potassium tert-butoxide (1.18 g, 10.5 mmol) and a solution of 4-methylbenzyl bromide (1.12 g, 6.05 mmol) in dry ethanol (20 mL). The reaction mixture was stirred at 60° C. overnight. After being cooled to rt, LiOH (0.5N aq., 40.3 mL, 20.1 mmol) was added, and the mixture was stirred at 40° C. for additional 3 h. After being cooled to RT again, the reaction mixture was diluted with water (200 mL) and acidified with HCl (2N aq., 12.1 mL, 24.2 mmol). Extraction with dichloromethane, drying over anhydrous magnesium sulfate, filtration, evaporation of the solvent and subsequent purification by preparative HPLC afforded the title compound as a white solid (183 mg, 18%): $^1$H NMR (400 MHz, CDCl$_3$) δ 7.12 (d, 2H), 7.01 (d, 2H), 5.30 (s, 2H), 2.53 (quart, 2H), 2.32 (s, 3H), 2.22 (s, 3H), 0.98 (t, 3H); ES-MS m/z 259 (MH)$^+$; HPLC RT (Method D) 2.13 min.

Intermediate F

Preparation of 5-(5-Nitro-1H-pyrazol-3-yl)-3-[4-(trifluoromethoxy)phenyl]-1,2,4-oxadiazole

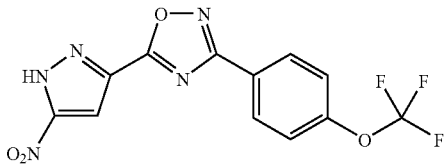

To a mechanically stirred solution of 5-nitro-1H-pyrazole-3-carboxylic acid (1.0 g, 6.24 mmol) in dry DMF (50 mL) was added EDCl (1.20 g, 6.24 mmol), HOBT (0.84 g, 6.24 mmol) and N'-hydroxy-4-(trifluoromethoxy)benzenecarboximidamide (1.37 g, 6.24 mmol). The mixture was stirred at rt for 2 h, and then warmed to 140° C. and stirred for additional 2 h. After being cooled to rt, the mixture was diluted with water (100 mL) and extracted with ethyl acetate. The organic extract was successively washed with water and brine. After drying over anhydrous magnesium sulfate and filtration, the solvent was removed in vacuo, and the residue was redissolved in warm acetonitrile (3 mL) to which tert-butyl methyl ether (2 mL) was added. The title compound precipitated and was obtained as a white solid after filtration, washing with tert-butyl methyl ether and drying in vacuo (1.2 g, 56%): $^1$H NMR (500 MHz, DMSO-d$_6$) δ 8.20 (d, 2H), 7.58 (d, 2H), 7.34 (s, 1H); ES-MS m/z 340 (M-H)$^-$; HPLC RT (Method J) 4.87 min.

Intermediate G

Preparation of 5-(5-Amino-1H-pyrazol-3-yl)-3-[4-(trifluoromethoxy)phenyl]-1,2,4-oxadiazole

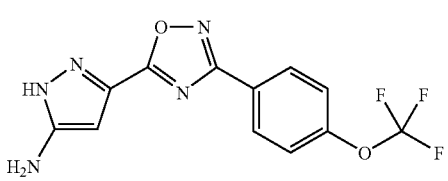

A solution of 5-(5-nitro-1H-pyrazol-3-yl)-3-[4-(trifluoromethoxy)phenyl]-1,2,4-oxadiazole (Intermediate F, 342 mg, 1.0 mmol) in ethyl acetate (43 mL) was subjected to hydrogenation using an H-Cube flow reactor (Thales Nano, Budapest, Hungary) (10% Pd/C, 30×4 mm, 1 bar H$_2$, 25° C., 1 mL/min). After evaporation of the solvent, the crude product was purified by MPLC (silica, cyclohexane/ethyl acetate 1:1) affording the title compound as a solid (322 mg, 93%): $^1$H NMR (400 MHz, DMSO-d$_6$) δ 12.49 (s, 1H), 8.19 (d, 2H), 7.49 (d, 2H), 5.93 (s, 1H), 5.44 (s, 2H); ES-MS m/z 312 (MH)$^+$; HPLC RT (Method E) 1.76 min.

Intermediate H

Preparation of 3-[4-(Trifluoromethoxy)phenyl]-5-[(5-trifluoromethyl)-1H-pyrazol-3-yl]-1,2,4-oxadiazole

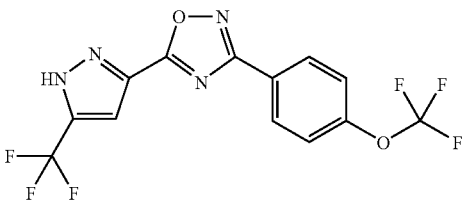 [SMILES: FC(F)(F)Oc1ccc(-c2noc(-c3cc(C(F)(F)F)[nH]n3)n2)cc1]

To a mechanically stirred solution of 5-(trifluoromethyl)-1H-pyrazole-3-carboxylic acid (1.0 g, 5.55 mmol) in dry DMF (50 mL) was added EDCl (1.07 g, 5.55 mmol), HOBT (0.75 g, 5.55 mmol) and N'-hydroxy-4-(trifluoromethoxy)benzenecarboximidamide (1.22 g, 5.55 mmol). The mixture was stirred at rt for 2 h, and then warmed to 140° C. and stirred for additional 2 h. After being cooled to rt, the mixture was diluted with water (100 mL) and extracted with ethyl acetate. The organic extract was successively washed with NaOH (0.5N aq.), water and brine. After drying over anhydrous magnesium sulfate and filtration, the solvent was removed in vacuo, and the residue was purified by MPLC (silica, cyclohexane/ethyl acetate 3:1) to afford the title compound as a white solid (1.12 g, 55%): $^1$H NMR (400 MHz, CDCl$_3$) δ 11.73 (broad, 1H), 8.19 (d, 2H), 7.38 (d, 2H), 7.37 (s, 1H); ES-MS m/z 365 (MH)$^+$; HPLC RT (Method E) 2.41 min.

Intermediate I

Preparation of N'-Hydroxy-4-(4-hydroxytetrahydro-2H-pyran-4-yl)benzenecarboximidamide hydroformiate

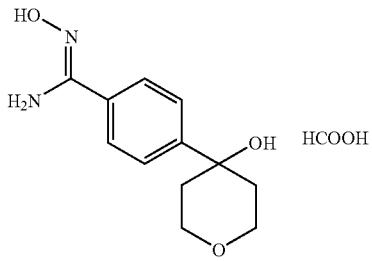 [SMILES: N/C(=N\O)c1ccc(C2(O)CCOCC2)cc1 ; "HCOOH"]

Step 1: Preparation of 4-(4-Hydroxytetrahydro-2H-pyran-4-yl)benzonitrile

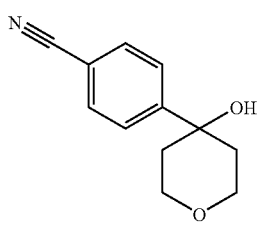 [SMILES: N#Cc1ccc(C2(O)CCOCC2)cc1]

To a solution of 4-iodobenzonitrile (5.0 g, 21.8 mmol) in dry THF (100 mL) was added 2-propyl magnesium chloride (2M solution in diethyl ether, 11 mL, 21.8 mmol) dropwise at −40° C. After stirring for 1.5 h at this temperature, the reaction mixture was cooled to −78° C. before it was canulated to a solution of 4-oxotetrahydro-2H-pyrane (3.28 g, 32.8 mmol) in dry THF (100 mL) which was likewise cooled to −78° C. After the slow addition of the Grignard reagent was completed, the reaction mixture was stirred at −78° C. for additional 10 minutes, then at 0° C. for 2 h, and finally at rt for 30 minutes. A few mL saturated aqueous NH$_4$Cl were added, and then most of the solvent was evaporated. The residue was partitioned between water and ethyl acetate (200 mL each). After separation, the aqueous layer was extracted using ethyl acetate. The combined organic layers were successively washed with water and brine. After drying over anhydrous magnesium sulfate, the solvent was evaporated and the crude material was purified by MPLC (silica, cyclohexane/ethyl acetate 2:1→1:1). The title compound was obtained as a highly viscous oil (1.19 g, 27%): $^1$H NMR (400 MHz, DMSO-d$_6$) δ 7.80 (d, 2H), 7.70 (d, 2H), 5.30 (s, 1H), 3.81-3.70 (m, 4H), 2.02-1.94 (m, 2H), 1.51-1.48 (m, 2H); DCI (NH$_3$)-MS m/z 204 (MH)$^+$, 221 (M+NH$_4$)$^+$; HPLC RT (Method I) 3.35 min.

Step 2: Preparation of N'-Hydroxy-4-(4-hydroxytetrahydro-2H-pyran-4-yl)benzenecarboximidamide hydroformiate

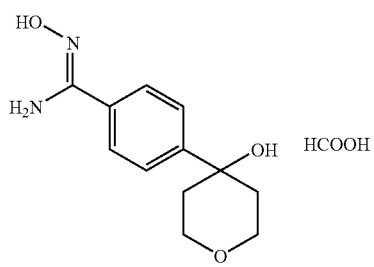 [SMILES: N/C(=N\O)c1ccc(C2(O)CCOCC2)cc1 ; "HCOOH"]

A solution of 4-(4-hydroxytetrahydro-2H-pyran-4-yl)benzonitrile (Step 1, 200 mg, 0.984 mmol), hydroxylamine hydrochloride (150 mg, 2.17 mmol) and triethylamine (219 mg, 2.17 mmol) in ethanol (5 mL) was stirred and heated at reflux for 4 h. After being cooled to rt, the reaction mixture as such was subjected to preparative HPLC, affording the pure title compound (278 mg, 99%): $^1$H NMR (500 MHz, DMSO-d$_6$) δ 9.71 (broad, 1H), 9.58 (s, 1H), 7.62 (d, 2H), 7.48 (d, 2H), 7.22 (broad, 1H), 5.78 (s, 2H), 5.07 (s, 1H), 3.80-3.75 (m, 2H), 3.72-3.68 (m, 2H), 2.00-1.93 (m, 2H), 1.53-1.49 (m, 2H); ES-MS m/z 237 (MH)$^+$; HPLC RT (Method F) 0.72 min.

Intermediate J

Preparation of 4-(4-Fluorotetrahydro-2H-pyran-4-yl)-N'-hydroxybenzenecarboximidamide

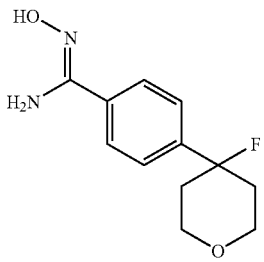 [SMILES: N/C(=N\O)c1ccc(C2(F)CCOCC2)cc1]

Step 1: Preparation of 4-(4-Fluorotetrahydro-2H-pyran-4-yl)benzonitrile

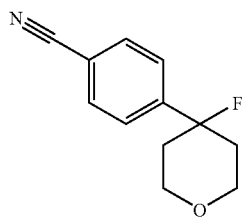 [SMILES: N#Cc1ccc(C2(F)CCOCC2)cc1]

To a suspension of 4-(4-hydroxytetrahydro-2H-pyran-4-yl)benzonitrile (Step 1 of Intermediate 1, 300 mg, 1.48 mmol) in dichloromethane (28 mL) was added dropwise N-ethyl-N-(trifluoro-λ$^4$-sulfanyl)ethanamine (586 mg, 1.77 mmol, dissolved in 2 mL dichloromethane) at a temperature of −78° C. After 30 minutes at this temperature, the reaction mixture was rapidly warmed to −20° C. by the aid of a water/ice bath for no longer than 30 seconds whereupon NaOH (1N aq., 10 mL) was added and the reaction mixture was allowed to warm to rt. The mixture was diluted with water (100 mL) and extracted with diethyl ether. The organic extract was dried with anhydrous magnesium sulfate and filtered. After evaporation of the solvent, the crude product was purified by MPLC (silica, cyclohexane/ethyl acetate 20:1→4:1) to afford the title compound in pure form (267 mg, 88%): $^1$H NMR (400 MHz, CDCl$_3$) δ 7.68 (d, 2H), 7.50 (d, 2H), 3.98-3.83 (m, 4H), 2.23-2.05 (m, 2H), 1.91-1.85 (m, 2H).

Step 2: Preparation of 4-(4-Fluorotetrahydro-2H-pyran-4-yl)-N'-hydroxybenzenecarboximidamide

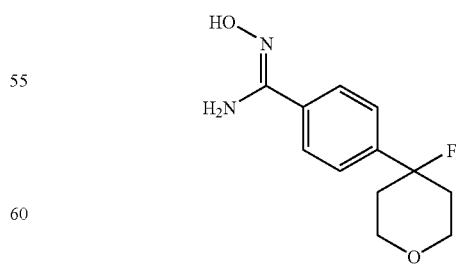

A solution of 4-(4-fluorotetrahydro-2H-pyran-4-yl)benzonitrile (Step 1, 180 mg, 0.877 mmol), hydroxylamine hydrochloride (134 mg, 1.93 mmol) and triethylamine (196 mg, 1.93 mmol) in ethanol (4.5 mL) was stirred and heated at reflux for 4 h. After being cooled to rt, the reaction mixture was diluted with water (100 mL) and extracted with ethyl acetate. The organic extract was successively washed with brine and dried over anhydrous magnesium sulfate. After filtration and evaporation of the solvent, the title compound was obtained (201 mg, 76%): $^1$H NMR (500 MHz, DMSO-$d_6$) δ 9.64 (s, 1H), 7.70 (d, 2H), 7.44 (d, 2H), 5.81 (s, 2H), 3.88-3.83 (m, 2H), 3.73-3.67 (m, 2H), 2.23-2.06 (m, 2H), 1.87-1.81 (m, 2H); DCI(NH$_3$)-MS m/z 239 (MH)$^+$; HPLC RT (Method I) 3.13 min.

Intermediate K

Preparation of N'-1-Hydroxy-4-(4-methoxytetrahydro-2H-pyran-4-yl)benzenecarboximidamide

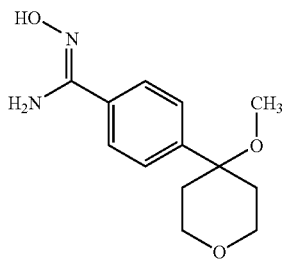 [SMILES: COC1(c2ccc(/C(N)=N/O)cc2)CCOCC1]

Step 1: Preparation of 4-(4-Methoxytetrahydro-2H-pyran-4-yl)benzonitrile

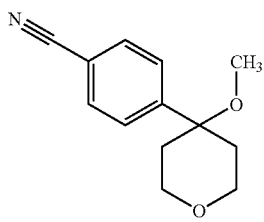 [SMILES: COC1(c2ccc(C#N)cc2)CCOCC1]

To a solution of 4-(4-hydroxytetrahydro-2H-pyran-4-yl)benzonitrile (Step 1 of Intermediate I, 300 mg, 1.48 mmol) in DMF (6.5 mL) was added sodium hydride (60% suspension in mineral oil, 65 mg, 1.62 mmol) at a temperature of ~5° C. The reaction mixture was allowed to stirr for 1 h at this temperature, before methyl iodide (110 μL, 1.77 mmol) was added. Stirring was continued over night at rt. The mixture was diluted with water and extracted with diethyl ether. The organic extract was dried with anhydrous magnesium sulfate and filtered. After evaporation of the solvent, the crude product was purified by MPLC (silica, cyclohexane/ethyl acetate 20:1→4:1) to afford the title compound in pure form (238 mg, 74%): $^1$H NMR (500 MHz, CDCl$_3$) δ 7.68 (d, 2H), 7.51 (d, 2H), 3.89-3.82 (m, 4H), 2.99 (s, 3H), 2.03-1.98 (m, 2H), 1.94-1.91 (m, 2H); DCI(NH$_3$)-MS m/z 235 (M+NH$_4$)$^+$; HPLC RT (Method I) 3.99 min.

Step 2: Preparation of N'-Hydroxy-4-(4-methoxytetrahydro-2H-pyran-4-yl)benzenecarboximidamide

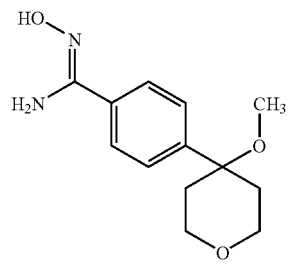 [SMILES: COC1(c2ccc(/C(N)=N/O)cc2)CCOCC1]

A solution of 4-(4-methoxytetrahydro-2H-pyran-4-yl)benzonitrile (Step 1, 200 mg, 0.921 mmol), hydroxylamine hydrochloride (141 mg, 2.03 mmol) and triethylamine (205 mg, 2.03 mmol) in ethanol (5 mL) was stirred and heated at reflux for 4 h. After being cooled to rt, the reaction mixture was diluted with water (100 mL) and extracted with ethyl acetate. The organic extract was successively washed with brine and dried over anhydrous magnesium sulfate. After filtration and evaporation of the solvent, the title compound was obtained (229 mg, 99%): $^1$H NMR (400 MHz, DMSO-$d_6$) δ 9.63 (s, 1H), 7.68 (d, 2H), 7.39 (d, 2H), 5.80 (s, 2H), 3.71-3.67 (m, 4H), 2.88 (m, 2H), 1.93-1.89 (m, 4H); DCI(NH$_3$)-MS m/z 251 (MH)$^+$; HPLC RT (Method G) 2.95 min.

Intermediate L

Preparation of 5-Methyl-1-benzyl-1H-pyrazole-3-carboxylic acid

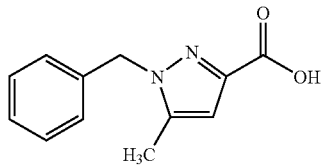 [SMILES: Cc1cc(C(=O)O)nn1Cc1ccccc1]

A mixture of methyl acetopyruvate (1.0 g, 6.94 mmol) and benzylhydrazine dihydrochloride (1.49 g, 7.63 mmol) in acetic acid (7 mL) was stirred for 4 h at 90° C. After removal of the solvent (rotavapor), the residue was subjected to MPLC (silica, cyclohexane/ethyl acetate 10:1→2:1, followed by dichloromethane/methanol 10:1). The eluate obtained with dichloromethane/methanol contained the title compound as a crude product. After evaporation of the solvent, this fraction was further purified by preparative HPLC to afford the title compound (260 mg, 17%): $^1$H NMR (400 MHz, DMSO-d$_6$) δ 12.57 (s, 1H), 7.37-7.27 (m, 3H), 7.12 (d, 2H), 6.53 (s, 1H), 5.36 (s, 2H), 2.22 (s, 3H).

Intermediate M

Preparation of [4-(Bromomethyl)phenoxy][tris(1-methylethyl)]silane

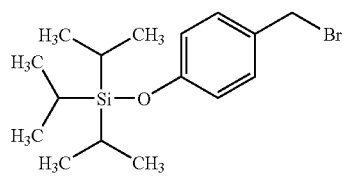 [SMILES: CC(C)[Si](Oc1ccc(CBr)cc1)(C(C)C)C(C)C]

Step 1: Preparation of Ethyl 4-{[tris(1-methylethyl)silyl]oxy}benzoate

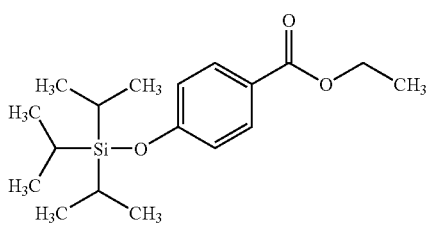 [SMILES: CCOC(=O)c1ccc(O[Si](C(C)C)(C(C)C)C(C)C)cc1]

To a solution of ethyl 4-hydroxybenzoate (5.0 g, 30.1 mmol) and imidazole (2.4 g, 35.4 mmol) in dry DMF (20 mL) was added chlorotriisopropylsilane (6.8 mL, 31 mmol) dropwise at 0° C. The mixture was stirred at rt for 16 h. Then water was added (100 mL), and the product was extracted with diethyl ether (3×100 mL). The combined organic extracts were washed with brine and dried over anhydrous magnesium sulfate. After filtration and evaporation of the solvent, the remaining crude product was purified by MPLC (silica, cyclohexane/ethyl acetate 10:1→1:1) to afford the title compound (9.66 g, 99%): $^1$H NMR (400 MHz, CDCl$_3$) δ 7.93 (d, 2H), 6.89 (d, 2H), 4.33 (quart, 2H), 1.38 (t, 3H), 1.27 (m, 1H), 1.10 (d, 18H); DCI(NH$_3$)-MS m/z 323 (MH)$^+$; HPLC RT (Method G) 6.19 min.

Step 2: Preparation of (4-{[Tris(1-methylethyl)silyl]oxy}phenyl)methanol

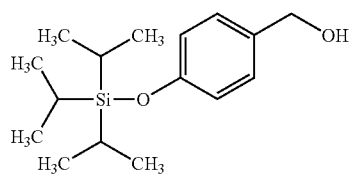

To 75 mL of dry diethyl ether was added a solution of lithium aluminium hydride (4M in diethyl ether, 14 mL, 55.8 mmol), and the solution was cooled to 0° C. A solution of ethyl 4-{[tris(1-methylethyl)silyl]oxy}benzoate (Step 1, 9.0 g, 27.9 mmol) in dry diethyl ether (90 mL) was added dropwise, maintaining the temperature below 5-10° C. After the addition was completed, stirring of the reaction mixture was continued for 1 h at 0° C. Then, still at the same temperature, a saturated aqueous solution of sodium sulfate (60 mL) was added with caution. After warming to rt, the precipitate which had formed was removed by filtration, and the residue was washed with diethyl ether. The organic layer was separated from the filtrate, and the aqueous layer was extracted with diethyl ether. The combined organic layers were washed with water and brine and dried over anhydrous magnesium sulfate. After filtration, the solvent was removed in vacuo. The crude product thus obtained was purified by MPLC (silica, cyclohexane/ethyl acetate 5:1→1:1) to afford the title compound in pure form (7.38 g, 94%): $^1$H NMR (400 MHz, CDCl$_3$) δ 7.21 (d, 2H), 6.87 (d, 2H), 4.60 (d, 2H), 1.56 (t, 1H), 1.23 (m, 1H), 1.10 (d, 18H); EI-MS m/z 280 (M)$^+$; HPLC RT (Method H) 5.33 min.

Step 3: Preparation of [4-(Bromomethyl)phenoxy][tris(1-methylethyl)]silane

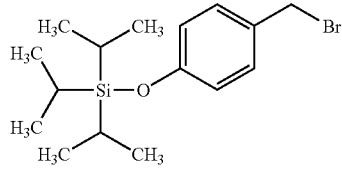

To a solution of (4-{[tris(1-methylethyl)silyl]oxy}phenyl)methanol (Step 2, 1.0 g, 3.56 mmol) in diethyl ether (20 mL) and acetonitrile (7.5 mL) was added triphenylphosphine (0.94 g, 3.57 mmol) and imidazole (243 mg, 3.57 mmol). After being cooled to 0° C., a solution of bromine (184 μL, 3.56 mmol) in diethyl ether (2.5 mL) was added dropwise. The reaction mixture was stirred at rt over night. Then water was added, and it was extracted with ethyl acetate. The organic extract was washed with water and brine, dried over anhydrous magnesium sulfate and filtered. After evaporation of the solvent, the crude material was treated with pentane. Precipitated triphenylphosphine oxide (TPPO) was removed by filtration. The solvent was evaporated in vacuo. The product thus obtained (1.42 g) still contained some TPPO (as judged by tlc) but was used for subsequent reactions without further purification.

Intermediate N

Preparation of 1-(Bromomethyl)-4-[2-(2-methoxyethoxy)ethoxy]benzene

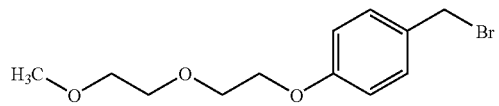 [SMILES: COCCOCCOc1ccc(CBr)cc1]

Step 1: Preparation of Ethyl 4-[2-(2-methoxyethoxy)ethoxy]benzoate

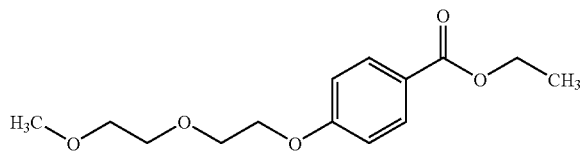 [SMILES: CCOC(=O)c1ccc(OCCOCCOC)cc1]

To a solution of ethyl 4-hydroxybenzoate (2.0 g, 12.04 mmol) in dry DME (50 mL) was added potassium carbonate (3.33 g, 24.07 mmol), potassium iodide (100 mg, 0.602 mmol) and 1-bromo-2-(2-methoxyethoxy)ethane (3.6 mL, 24.07 mmol). The mixture was stirred at reflux for 2 days. After being cooled to rt, the solids were removed by filtration and the solvent by evaporation in vacuo. The remaining crude product was purified by MPLC (silica, cyclohexane/ethyl acetate 5:1) to afford the title compound (2.17 g, 67%): $^1$H NMR (400 MHz, CDCl$_3$) δ 7.98 (d, 2H), 6.93 (d, 2H), 4.33 (quart, 2H), 4.19 (t, 2H), 3.88 (t, 2H), 3.72 (t, 2H), 3.57 (t, 2H), 3.39 (s, 3H), 1.37 (t, 3H); DCI(NH$_3$)-MS m/z 286 (M+NH$_4$)$^+$; HPLC RT (Method I) 4.14 min.

Step 2: Preparation of {4-[2-(2-Methoxyethoxy)ethoxy]phenyl}methanol

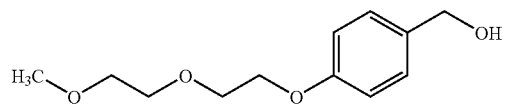 [SMILES: COCCOCCOc1ccc(CO)cc1]

To a solution of ethyl 4-[2-(2-methoxyethoxy)ethoxy]benzoate (Step 1, 1.0 g, 3.73 mmol) in 18 mL dry THF was added dropwise a solution of lithium aluminium hydride (1M in THF, 5.6 mL, 5.59 mmol) at 0° C. After the addition was completed, stirring of the reaction mixture was continued for 1 h at rt. Then, 1 g Celite was added, as was 5 mL water with caution. After the addition of sodium hydroxide (1N aq., 2 mL), the precipitate which had formed was removed by filtration. After some washing of the precipitate with ethyl acetate, the organic layer was separated from the filtrate and the aqueous layer was extracted with additional ethyl acetate. The combined organic layers were washed with water and brine and dried over anhydrous magnesium sulfate. After filtration, the solvent was removed in vacuo to yield the title compound (710 mg, 84%): $^1$H NMR (400 MHz, CDCl$_3$) δ 7.28 (d, 2H), 6.90 (d, 2H), 4.61 (s, 2H), 4.14 (t, 2H), 3.86 (t, 2H), 3.72 (t, 2H), 3.58 (t, 2H), 3.39 (s, 3H).

Step 3: Preparation of 1-(Bromomethyl)-4-[2-(2-methoxyethoxy)ethoxy]benzene

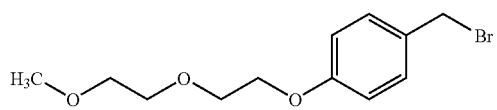 [SMILES: COCCOCCOc1ccc(CBr)cc1]

To a solution of {4-[2-(2-methoxyethoxy)ethoxy]phenyl}methanol (Step 2, 500 mg, 2.21 mmol) in 10 mL dichloromethane was added dropwise phosphorous tribromide (210 μL, 2.21 mmol) at 0° C. After the addition was completed, stirring of the reaction mixture was continued for 1 h at the same temperature. Then, water was added with caution, and it was extracted with ethyl acetate. The combined organic layers were washed with water and brine and dried over anhydrous magnesium sulfate. After filtration, the solvent was removed in vacuo to yield a crude product which was purified by MPLC (silica, cyclohexane/ethyl acetate 10:1) affording the title compound in pure form (530 mg, 83%): $^1$H NMR (400 MHz, CDCl$_3$) δ 7.31 (d, 2H), 6.88 (d, 2H), 4.50 (s, 2H), 4.13 (t, 2H), 3.85 (t, 2H), 3.71 (t, 2H), 3.58 (t, 2H), 3.40 (s, 3H); DCI(NH$_3$)-MS m/z 306/308 (M+NH$_4$)$^+$; HPLC RT (Method I) 3.20 min.

Intermediate O

Preparation of 4-(3-Fluorooxetan-3-yl)-N'-hydroxybenzenecarboximidamide

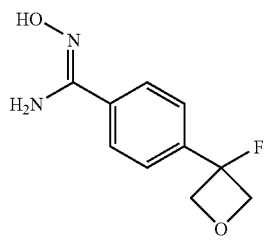 [SMILES: N/C(=N\O)c1ccc(C2(F)COC2)cc1]

Step 1: Preparation of 4-(3-Hydroxyoxetan-3-yl)benzonitrile

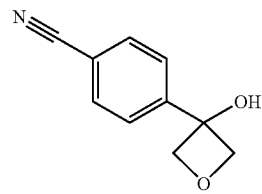 [SMILES: N#Cc1ccc(C2(O)COC2)cc1]

To a solution of 4-iodobenzonitrile (5.0 g, 21.8 mmol) in dry THF (100 mL) was added 2-propyl magnesium chloride (2M solution in diethyl ether, 11 mL, 21.8 mmol) dropwise at −40° C. After stirring for 1.5 h at this temperature, the reaction mixture was cooled to −78° C. before it was canulated to a solution of 3-oxooxetane (80% in dichloromethane, 2.95 g, 32.7 mmol; preparation described in: G. Wuitschik et al., Angew. Chem. Int. Ed. Engl. 45 (46), 7736-7739 (2006)) in dry THF (100 mL) which was likewise cooled to −78° C. After the slow addition of the Grignard reagent was completed, the reaction mixture was stirred at −78° C. for additional 10 minutes, then at 0° C. for 2 h, and finally at rt for 30 minutes. A few mL saturated aqueous NH$_4$Cl were added and then most of the solvent was evaporated. The residue was partitioned between water and ethyl acetate (200 mL each). After separation, the aqueous layer was extracted using ethyl acetate. The combined organic layers were successively washed with water and brine. After drying over anhydrous magnesium sulfate, the solvent was evaporated and the crude material was crystallized from cyclohexane/ethyl acetate 10:1. The title compound was obtained in pure form (2.42 g, 63%): $^1$H NMR (400 MHz, DMSO-$d_6$) δ 7.88 (d, 2H), 7.80 (d, 2H), 6.63 (s, 1H), 4.79 (d, 2H), 4.65 (d, 2H); DCI(NH$_3$)-MS m/z 193 (M+NH$_4$)$^+$; HPLC RT (Method I) 3.09 min.

Step 2: Preparation of 4-(3-Fluorooxetan-3-yl)benzonitrile

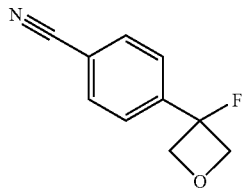 [SMILES: N#Cc1ccc(C2(F)COC2)cc1]

To a suspension of 4-(3-hydroxyoxetan-3-yl)benzonitrile (Step 1, 600 mg, 3.43 mmol) in dichloromethane (55 mL) was added dropwise N-ethyl-N-(trifluoro-λ$^4$-sulfanyl)ethanamine (662 mg, 4.11 mmol, dissolved in 5 mL dichloromethane) at a temperature of −78° C. After 30 minutes at this temperature, the reaction mixture was rapidly warmed to −20° C. by the aid of a water/ice bath for no longer than 30 seconds whereupon NaOH (1N aq., 20 mL) was added and the reaction mixture was allowed to warm to rt. The mixture was diluted with water (150 mL) and extracted with diethyl ether (3×50 mL). The organic extract was dried with anhydrous magnesium sulfate and filtered. After evaporation of the solvent, the crude product was purified by MPLC (silica, cyclohexane/ethyl acetate 8:1) to afford the title compound in pure form (495 mg, 82%): $^1$H NMR (400 MHz, CDCl$_3$) δ 7.76 (d, 2H), 7.73 (d, 2H), 5.15 (dd, 2H), 4.81 (dd, 2H); ES-MS m/z 178 (MH)$^+$; HPLC RT (Method F) 1.59 min.

Step 3: Preparation of 4-(3-Fluorooxetan-3-yl)-N'-hydroxybenzenecarboximidamide

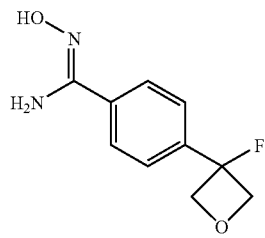 [SMILES: N/C(=N\O)c1ccc(C2(F)COC2)cc1]

A solution of 4-(3-fluorooxetan-3-yl)benzonitrile (Step 2, 450 mg, 2.54 mmol), hydroxylamine hydrochloride (388 mg, 5.59 mmol) and triethylamine (779 µL, 5.59 mmol) in ethanol (12.5 mL) was stirred and heated at reflux over night. After being cooled to rt, the reaction mixture was diluted with water (75 mL) whereupon the product precipitated. Filtration, washing with water and drying in a vacuum oven afforded a first crop of the title compound (360 mg, 67%). A second crop was obtained after concentration of the filtrate (122 mg, 21%, purity 90%): $^1$H NMR (400 MHz, DMSO-$d_6$) δ 9.71 (s, 1H), 7.77 (d, 2H), 7.54 (d, 2H), 5.87 (broad s, 2H), 4.97 (dd, 2H), 4.91 (dd, 2H); DCI(NH$_3$)-MS m/z 211 (MH)$^+$; HPLC RT (Method I) 2.64 min.

Intermediate P

Preparation of N'-Hydroxy-4-(3-methoxyoxetan-3-yl)benzenecarboximidamide

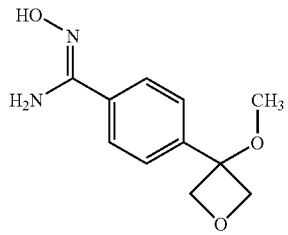 [SMILES: COC1(c2ccc(/C(N)=N/O)cc2)COC1]

Step 1: Preparation of 4-(3-Methoxyoxetan-3-yl)benzonitrile

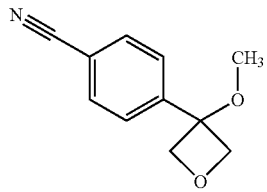

To a solution of 4-(3-hydroxyoxetan-3-yl)benzonitrile (Step 1 of Intermediate O, 600 mg, 3.43 mmol) in DMF (12.5 mL) was added sodium hydride (60% suspension in mineral oil, 151 mg, 3.77 mmol) at a temperature of ~5° C. The reaction mixture was allowed to stir for 1 h at this temperature, before methyl iodide (256 µL, 4.11 mmol) was added. Stirring was continued at rt over night. The mixture was diluted with water and extracted with diethyl ether. The organic extract was dried with anhydrous magnesium sulfate and filtered. After evaporation of the solvent, the crude product was purified by MPLC (silica, cyclohexane/ethyl acetate 20:1→4:1) to afford the title compound in pure form (566 mg, 87%): $^1$H NMR (500 MHz, DMSO-$d_6$) δ 7.93 (d, 2H), 7.68 (d, 2H), 4.81 (d, 2H), 4.73 (d, 2H), 3.05 (s, 3H); ES-MS m/z 190 (MH)$^+$; HPLC RT (Method E) 1.22 min.

Step 2: Preparation of N'-Hydroxy-4-(3-methoxyoxetan-3yl)benzenecarboximidamide

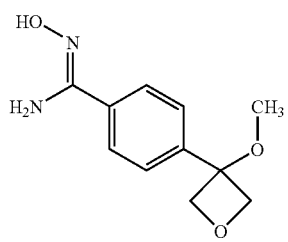 [SMILES: COC1(c2ccc(/C(N)=N/O)cc2)COC1]

A solution of 4-(3-methoxyoxetan-3-yl)benzonitrile (Step 1, 500 mg, 2.64 mmol), hydroxylamine hydrochloride (403 mg, 5.81 mmol) and triethylamine (810 μL, 5.81 mmol) in ethanol (12.5 mL) was stirred and heated at reflux for 2 h. After being cooled to rt, the reaction mixture was evaporated to dryness. The resulting material was treated with a mixture of water (5 mL) and diethyl ether (0.5 mL). The solid was isolated by filtration, washed with a small amount of cold water and dried in a vacuum oven to afford the title compound as a colorless solid (520 mg, 86%): $^1$H NMR (400 MHz, DMSO-$d_6$) δ 9.67 (s, 1H), 7.73 (d, 2H), 7.43 (d, 2H), 5.84 (broad s, 2H), 4.79-4.75 (m, 4H), 3.01 (s, 3H); DCI(NH$_3$)-MS m/z 223 (MH)$^+$; HPLC RT (Method I) 2.54 min.

Intermediate Q

Preparation of 4-(2-Fluoropropan-2-yl)-N'-hydroxybenzenecarboximidamide

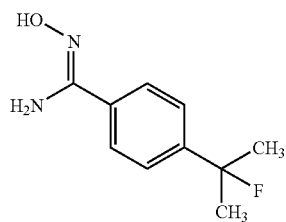

Step 1: Preparation of 4-(2-Fluoropropan-2-yl)benzonitrile

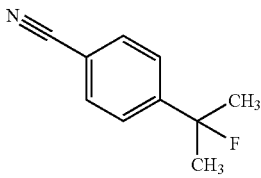

To a solution of 4-(2-hydroxypropan-2-yl)benzonitrile (1.00 g, 6.20 mmol; obtained from 4-(propan-2-yl)benzonitrile according to literature procedure: *Synth. Comm.* 2006, 36, 2145-2155) in dichloromethane (20 mL) was added diethylamino sulfur trifluoride (DAST; 1.20 g, 7.44 mmol) at a temperature of 0° C. The reaction mixture was allowed to stirr at rt for 2 h, whereupon it was diluted with water and extracted with dichloromethane. The organic extract was washed with water, dried with anhydrous magnesium sulfate and filtered. After evaporation of the solvent, the crude product was purified by MPLC (silica, cyclohexane/ethyl acetate 95:5) to afford the title compound (675 mg, 67%): $^1$H NMR (400 MHz, CDCl$_3$) δ 7.57 (d, 2H), 7.48 (d, 2H), 1.72 (s, 3H), 1.68 (s, 3H); ES-MS m/z 163, HPLC RT (Method F) 2.12 min.

Step 2: Preparation 4-(2-Fluoropropan-2-yl)-N'-hydroxybenzenecarboximidamide

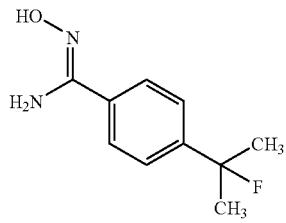

A solution of 4-(2-fluoropropan-2-yl)benzonitrile (Step 1, 675 mg, 4.14 mmol), hydroxylamine hydrochloride (632 mg, 9.10 mmol) and triethylamine (1.27 mL, 9.10 mmol) in ethanol (20 mL) was stirred and heated at reflux for 1 h. After being cooled to rt, the reaction mixture was evaporated to dryness. The resulting material was treated with ethyl acetate and the solid was filtered off. The ethyl acetate solution was washed with water and saturated sodium chloride solution, dried with anhydrous magnesium sulfate and filtered. After evaporation of the solvent, the title compound was obtained (756 mg, 93%): $^1$H NMR (400 MHz, CDCl$_3$) δ 7.62 (d, 2H), 7.41 (d, 2H), 4.89 (broad s, 2H), 1.72 (s, 3H), 1.68 (s, 3H); ES-MS m/z 197, HPLC RT (Method F) 1.04 min.

Intermediate R

Preparation of N'-Hydroxy-4-[(tetrahydro-2H-pyran-4-yloxy)methyl]benzenecarboximidamide

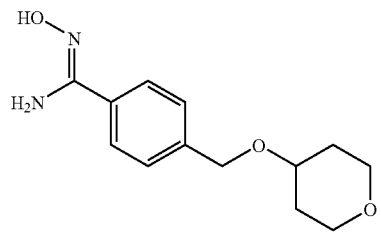 [SMILES: N/C(=N\O)c1ccc(COC2CCOCC2)cc1]

Step 1: Preparation of 4-[(Tetrahydro-2H-pyran-4-yloxy)methyl]benzonitrile

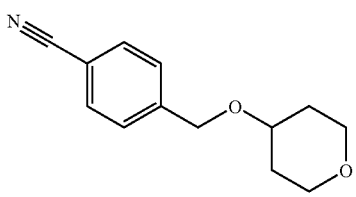 [SMILES: N#Cc1ccc(COC2CCOCC2)cc1]

To a suspension of sodium hydride (60% dispersion in mineral oil; 490 mg, 12.2 mmol) in THF (10 mL) was added a solution of tetrahydro-2H-pyran-4-ol (1.20 g, 12.2 mmol) in THF (2 mL) at rt. The reaction mixture was stirred at it for several minutes and then heated to reflux for 15 min. After cooling to rt, 4-(bromomethyl)benzonitrile (2.00 g, 10.2 mmol) was added, and the reaction mixture was stirred at it over night. Ethyl acetate was added and the mixture was washed with water. The organic layer was dried with anhydrous magnesium sulfate and filtered. After evaporation of the solvent, the crude product was purified by MPLC (silica, cyclohexane/ethyl acetate 7:3) to afford the title compound (1.57 g, 71%): $^1$H NMR (400 MHz, CDCl$_3$) δ 7.53 (d, 2H), 7.45 (d, 2H), 4.61 (s, 2H), 4.00-3.92 (m, 2H), 3.65-3.58 (m, 1H), 3.49-3.41 (m, 2H), 1.99-1.92 (m, 2H), 1.72-1.62 (m, 2H); ES-MS m/z 218, HPLC RT (Method D) 1.86 min.

Step 2: Preparation of N'-Hydroxy-4-[(tetrahydro-2H-pyran-4-yloxy)methyl]benzenecarboximidamide

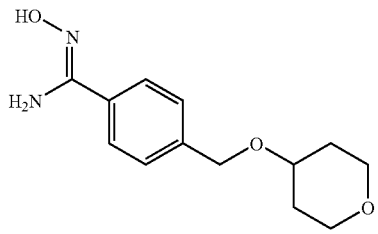 [SMILES: N/C(=N\O)c1ccc(COC2CCOCC2)cc1]

A solution of 4-[(tetrahydro-2H-pyran-4-yloxy)methyl]benzonitrile (Step 1, 1.50 g, 6.90 mmol), hydroxylamine hydrochloride (1.06 g, 15.2 mmol) and triethylamine (2.11 mL, 15.2 mmol) in ethanol (35 mL) was stirred and heated at reflux for 1 h. After being cooled to rt, the reaction mixture was evaporated to dryness. The resulting material was treated with ethyl acetate, and the solid was filtered off. The ethyl acetate solution was washed with water and saturated sodium chloride solution, dried with anhydrous magnesium sulfate and filtered. After evaporation of the solvent, the title compound was obtained (556 mg, 32%): $^1$H NMR (400 MHz, CDCl$_3$) δ 7.62 (d, 2H), 7.38 (d, 2H), 4.85 (broad s, 2H), 4.60 (s, 2H), 4.00-3.92 (m, 2H), 3.62-3.55 (m, 1H), 3.49-3.40 (m, 2H), 1.96-1.90 (m, 2H), 1.72-1.60 (m, 2H); ES-MS m/z 251, HPLC RT (Method K) 0.34 min.

Intermediate S

Preparation of tert-Butyl 4-{[4-(N'-hydroxycarbamimidoyl)benzyl]oxy}piperidine-1-carboxylate

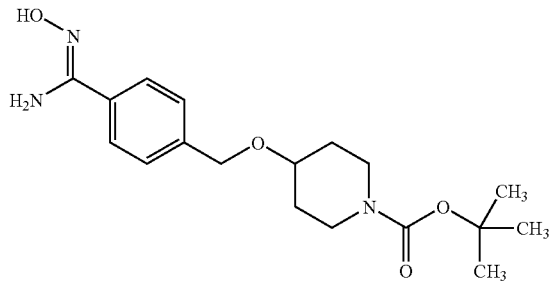 [SMILES: CC(C)(C)OC(=O)N1CCC(OCc2ccc(/C(N)=N/O)cc2)CC1]

Step 1: Preparation of tert-Butyl 4-[(4-cyanobenzyl)oxy]piperidine-1-carboxylate

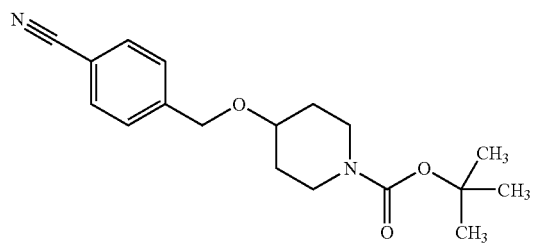 [SMILES: CC(C)(C)OC(=O)N1CCC(OCc2ccc(C#N)cc2)CC1]

To a suspension of sodium hydride (60% dispersion in mineral oil; 490 mg, 12.2 mmol) in THF (10 mL) was added a solution of tert-butyl 4-hydroxypiperidine-1-carboxylate (2.46 g, 12.2 mmol) in THF (2 mL) at rt. The reaction mixture was stirred at rt for several minutes and then heated to reflux for 15 min. After cooling to rt 4-(bromomethyl)benzonitrile (2.00 g, 10.2 mmol) was added, and the reaction mixture was stirred at rt over night. Ethyl acetate was added and the mixture was washed with water. The organic layer was dried with anhydrous magnesium sulfate and filtered. The solvent was removed and the crude product was used as such for Step 2.

Step 2: Preparation of tert-Butyl 4-{[4-(N'-hydroxycarbamimidoyl)benzyl]oxy}-piperidine-1-carboxylate

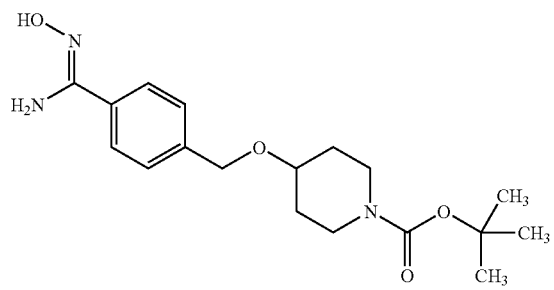 [SMILES: CC(C)(C)OC(=O)N1CCC(OCc2ccc(/C(N)=N/O)cc2)CC1]

A solution of tert-butyl 4-{[4-(N'-hydroxycarbamimidoyl)benzyl]oxy}piperidine-1-carboxylate (Step 1, 1.47 g, 4.22 mmol, purity 91%), hydroxylamine hydrochloride (646 mg, 9.30 mmol) and triethylamine (1.30 mL, 9.30 mmol) in ethanol (35 mL) was stirred and heated at reflux for 1 h. After being cooled to rt, the reaction mixture was evaporated to dryness. The resulting material was treated with ethyl acetate, and the solid was filtered off. The ethyl acetate solution was washed with water and saturated sodium chloride solution, dried with anhydrous magnesium sulfate and filtered. After evaporation of the solvent, the crude product was stirred in tert-butyl methyl ether for 15 min and filtered to obtain the title compound (1.16 g, 78%): $^1$H NMR (400 MHz, CDCl$_3$) δ 7.61 (d, 2H), 7.38 (d, 2H), 4.86 (s, 2H), 4.58 (s, 2H), 3.84-3.72 (m, 2H), 3.60-3.51 (m, 1H), 3.15-3.06 (m, 2H), 1.91-1.81 (m, 2H), 1.65-1.50 (m, 2H), 1.45 (s, 9H); ES-MS m/z 350, HPLC RT (Method F) 1.15 min.

Intermediate T

Preparation of N'-Hydroxy-4-(tetrahydro-2H-pyran-4-ylmethoxy)benzenecarboximidamide

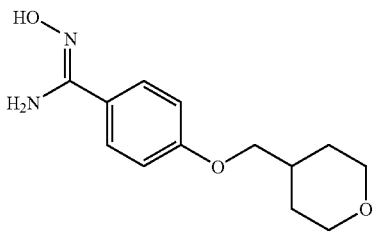 [SMILES: N/C(=N\O)c1ccc(OCC2CCOCC2)cc1]

Step 1: Preparation of 4-[(Tetrahydro-2H-pyran-4-yloxy)methyl]benzonitrile

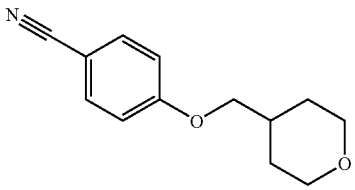 [SMILES: N#Cc1ccc(OCC2CCOCC2)cc1]

To a mixture of 4-hydroxybenzonitrile (665 mg, 5.59 mmol) and caesium carbonate (2.00 g, 6.14 mmol) in DMF (5 mL) was added 4-(bromomethyl)tetrahydro-2H-pyran (1.00 g, 5.59 mmol), and the reaction mixture was stirred at 80° C. over night. After cooling to rt, the reaction mixture was poured into water. After stirring for a few minutes, the precipitate was collected by filtration, washed with water and dried in vacuo to give the title compound (785 mg, 65%): $^1$H NMR (400 MHz, CDCl$_3$) δ 7.58 (d, 2H), 7.92 (d, 2H), 4.05-4.00 (dd, 2H), 3.82 (d, 2H), 3.48-3.41 (m, 2H), 2.15-2.02 (m, 1H), 1.78-1.72 (dd, 2H), 1.52-1.41 (m, 2H); ES-MS m/z 218, HPLC RT (Method D) 2.09 min.

Step 2: Preparation of N'-Hydroxy-4-[(tetrahydro-2H-pyran-4-yloxy)methyl]benzenecarboximidamide

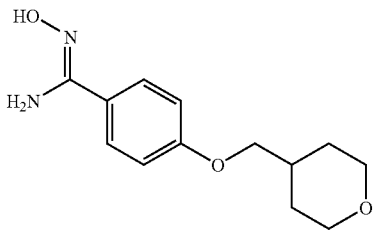 [SMILES: N/C(=N\O)c1ccc(OCC2CCOCC2)cc1]

A solution of 4-[(tetrahydro-2H-pyran-4-yloxy)methyl] benzonitrile (Step 1, 780 mg, 3.59 mmol), hydroxylamine hydrochloride (549 mg, 7.90 mmol) and triethylamine (1.10 mL, 7.90 mmol) in ethanol (20 mL) was stirred and heated at reflux for 1 h. After being cooled to rt, the reaction mixture was evaporated to dryness. The resulting material was treated with ethyl acetate, and the solid was filtered off. The ethyl acetate solution was washed with water and saturated sodium chloride solution, dried with anhydrous magnesium sulfate and filtered. After evaporation of the solvent, the crude product was stirred in hexane and filtered. After evaporation of the solvent, the title compound was obtained (857 mg, 95%): $^1$H NMR (400 MHz, CDCl$_3$) δ 7.55 (d, 2H), 7.40 (d, 2H), 4.81 (s, 2H), 4.06-3.99 (dd, 2H), 3.81 (d, 2H), 3.48-3.40 (m, 2H), 2.15-2.02 (m, 1H), 1.78-1.72 (dd, 2H), 1.52-1.40 (m, 2H); ES-MS m/z 251, HPLC RT (Method E) 0.56 min.

Intermediate U

Preparation of tert-Butyl 4-{[4-(N'-hydroxycarbamimidoyl)phenoxy]methyl}-piperidine-1-carboxylate

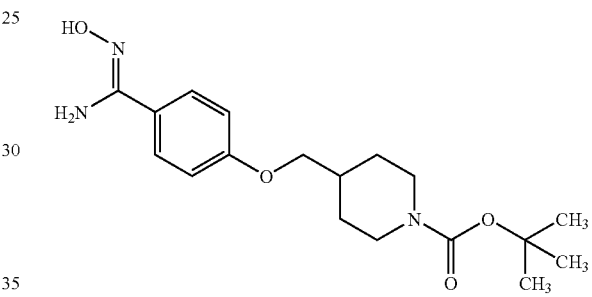

Step 1: Preparation of tert-Butyl 4-[(4-cyanophenoxy)methyl]piperidine-1-carboxylate

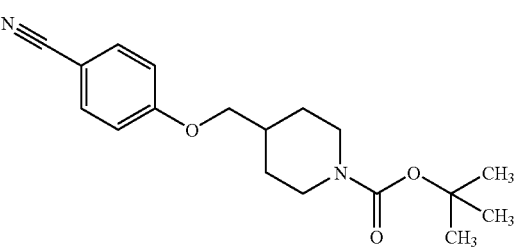 [SMILES: CC(C)(C)OC(=O)N1CCC(COc2ccc(C#N)cc2)CC1]

To a suspension of sodium hydride (60% dispersion in mineral oil; 316 mg, 7.91 mmol) in DMF (10 mL) was added in portions 4-hydroxybenzonitrile (856 mg, 7.19 mmol). After stirring for 15 min at rt, tert-butyl 4-(bromomethyl) piperidine-1-carboxylate (2.00 g, 7.19 mmol) was added, and the reaction mixture was stirred at 80° C. for 1 h and at 150° C. for a further 1 h. After cooling to rt, water was added, and the mixture was stirred for 15 min. The solid was filtered off, water was added again, and the mixture was stirred for further 15 min and then filtered again. This procedure was repeated once again. Finally, the solids obtained were dried in vacuo to give the title compound (1.47 g, 59%): ES-MS m/z 317, HPLC RT (Method F) 2.54 min.

Step 2: Preparation of tert-Butyl 4-{[4-(N'-hydroxycarbamimidoyl)phenoxy]methyl}-piperidine-1-carboxylate

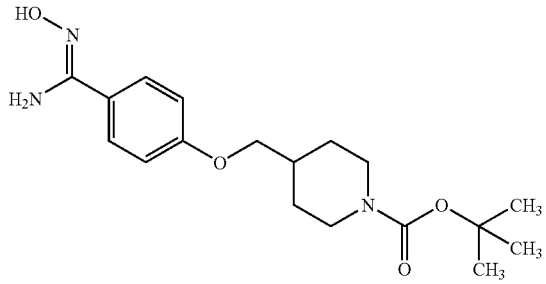 [SMILES: CC(C)(C)OC(=O)N1CCC(COc2ccc(/C(N)=N/O)cc2)CC1]

A solution of tert-butyl 4-[(4-cyanophenoxy)methyl]piperidine-1-carboxylate (Step 1, 1.47 g, 4.22 mmol, purity 91%), hydroxylamine hydrochloride (646 mg, 9.30 mmol) and triethylamine (1.30 mL, 9.30 mmol) in ethanol (24 mL) was stirred and heated at reflux for 1 h. After being cooled to rt, the reaction mixture was evaporated to dryness. The resulting material was treated with ethyl acetate, and the solid was filtered off. The ethyl acetate solution was washed with water and saturated sodium chloride solution, dried with anhydrous magnesium sulfate and filtered. After evaporation of the solvent, the crude product was stirred in tert-butyl methyl ether. The solid was filtered off and dried in vacuo to give the title compound (1.16 g, 78%): $^1$H NMR (400 MHz, CDCl$_3$) δ 7.53 (d, 2H), 6.89 (d, 2H), 4.82 (s, 2H), 4.22-4.08 (broad m, 2H), 3.81 (d, 2H), 2.81-2.66 (m, 2H), 2.02-1.90 (m, 1H), 1.85-1.78 (d, 2H), 1.46 (s, 9H), 1.35-1.18 (m, 2H); ES-MS m/z 350, HPLC RT (Method D) 1.56 min.

By using the method described above for Intermediate U, and by substituting the appropriate starting materials (which were either purchased from commercial sources or were synthesized according to the literature procedures cited), Intermediates V-FF found in the table below were similarly prepared.

| Intermediate Number | Structure | HPLC RT (min) | MS m/z (MH+) | Method |
|---|---|---|---|---|
| V | ![structure] | 0.96 | 243 | F |

$^1$H NMR (400 MHz, CDCl$_3$) δ 7.92 (d, 2H), 7.83 (d, 2H), 7.43 (broad s, 1H), 4.92 (broad s, 2H), 3.25-3.15 (m, 1H), 1.31 (d, 6H).
The corresponding nitrile starting material can be synthesized according to Chem. Eur. J. 2006, 12 (30), 7782-7796.

| W | ![structure] | 0.23 | 216 | F |

$^1$H NMR (400 MHz, DMSO-d$_6$) δ 9.88 (s, 1H), 7.87-7.78 (dd, 4H), 7.39 (s, 2H), 5.94 (s, 2H).

| X | ![structure] | 0.78 | 195 | F |

$^1$H NMR (400 MHz, DMSO-d$_6$) δ 9.51 (s, 1H), 7.59 (d, 2H), 7.42 (d, 2H), 5.74 (s, 2H), 5.01 (s, 1H), 1.41 (s, 6H).
The corresponding nitrile starting material can be synthesized according to Synth. Comm. 2006, 36, 2145-2155.

-continued

| Intermediate Number | Structure | HPLC RT (min) | MS m/z (MH+) | Method |
|---|---|---|---|---|
| Y | (4-(trifluoromethylsulfonyl)phenyl)-N'-hydroxybenzamidine structure | 1.57 | 269 | F |

¹H NMR (400 MHz, DMSO-d₆) δ 10.26 (s, 1H), 8.17-8.09 (dd, 4H), 6.12 (s, 2H).

| Z | (4-(methylthio)phenyl)-N'-hydroxybenzamidine structure | 0.91 | 183 | F |

¹H NMR (400 MHz, DMSO-d₆) δ 9.60 (s, 1H), 7.61 (d, 2H), 7.22 (d, 2H), 5.79 (s, 2H).

| AA | (4-(phenylthio)phenyl)-N'-hydroxybenzamidine structure | 0.87 | 245 | K |

¹H NMR (400 MHz, DMSO-d₆) δ 9.70 (s, 1H), 7.63 (s, 1H), 7.60 (d, 1H), 7.41-7.28 (m, 7H), 5.82 (s, 2H).
The corresponding nitrile starting material can be synthesized according to Org. Lett. 2006, 8 (24), 5613-5616.

| BB | tert-butyl (4-(N'-hydroxycarbamimidoyl)phenyl)carbamate structure | 1.21 | 252 | F |

¹H NMR (400 MHz, DMSO-d₆) δ 9.45 (s, 1H), 9.41 (s, 1H), 7.52 (d, 2H), 7.42 (d, 2H), 5.70 (s, 2H), 1.48 (s, 9H).
The corresponding nitrile starting material can be synthesized according to WO 2005/118587.

| CC | tert-butyl 4-(4-(N'-hydroxycarbamimidoyl)phenyl)-4-hydroxypiperidine-1-carboxylate structure | 0.91 | 336 | E |

¹H NMR (400 MHz, DMSO-d₆) δ 9.55 (s, 1H), 7.61 (d, 2H), 7.45 (d, 2H), 5.75 (s, 2H), 5.10 (s, 1H), 3.88-3.80 (broad m, 2H), 3.20-3.05 (broad m, 2H), 1.82-1.75 (m, 2H), 1.61-1.55 (m, 2H), 1.40 (s, 9H).

| Intermediate Number | Structure | HPLC RT (min) | MS m/z (MH+) | Method |
|---|---|---|---|---|
| DD | HO-N, H₂N, phenyl-S-CF₃ | 1.42 | 237 | F |

¹H NMR (400 MHz, DMSO-d₆) δ 9.90 (s, 1H), 7.80 (d, 2H), 7.72 (d, 2H), 5.94 (s, 2H).

| EE | HO-N, H₂N, phenyl-S(O)₂-N(CH₃)₂ | 0.92 | 244 | F |

¹H NMR (400 MHz, DMSO-d₆) δ 9.96 (s, 1H), 7.92 (d, 2H), 7.72 (d, 2H), 5.99 (s, 2H), 2.62 (s, 6H).

| FF | HO-N, H₂N, phenyl-CH₂OH | 0.24 | 167 | F |

¹H NMR (400 MHz, DMSO-d₆) δ 9.55 (s, 1H), 7.62 (d, 2H), 7.29 (d, 2H), 5.78 (s, 2H), 5.20 (t, 1H), 4.50 (d, 2H).

Intermediate GG

Preparation of 3-[4-(2-Fluoropropan-2-yl)phenyl]-5-(5-methyl-1H-pyrazol-3-yl)-1,2,4-oxadiazole

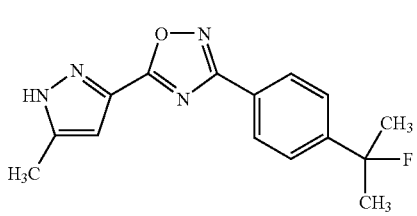 [SMILES: Cc1cc(-c2nc(-c3ccc(C(C)(C)F)cc3)no2)n[nH]1]

To a mechanically stirred solution of 5-methyl-1H-pyrazole-3-carboxylic acid (1.59 g, 12.64 mmol) in dry DMF (64 mL) was added EDCl (2.42 g, 12.64 mmol), HOBT (1.71 g, 12.64 mmol) and 4-(2-fluoropropan-2-yl)-N'-hydroxybenzenecarboximidamide (Intermediate Q, 2.48 g, 12.64 mmol). The mixture was stirred at rt for 2 h, and then heated to 140° C. and stirred for additional 1 h. After being cooled to it, the solvent was removed under reduced pressure. Ethyl acetate (150 mL) and 2% aqueous citric acid solution (150 mL) were added, and the organic phase was separated and washed with saturated aqueous sodium bicarbonate solution (150 mL) and saturated aqueous sodium chloride solution. After drying over anhydrous magnesium sulfate and filtration, the solvent was removed in vacuo and the residue was purified by MPLC (silica, cyclohexane/ethyl acetate 3:1) to afford the title compound (2.48 g, 64%): ¹H NMR (400 MHz, DMSO-d₆) δ 13.54 (broad s, 1H), 8.08 (d, 2H), 7.62 (d, 2H), 6.81 (s, 1H), 2.33 (s, 3H), 1.72 (s, 3H), 1.68 (s, 3H); ES-MS m/z 287 (MH)⁺; HPLC RT (Method F) 2.19 min.

By using the method described above for Intermediate GG, and by substituting the appropriate starting materials, specifically by using 5-methyl-1H-pyrazole-3-carboxylic acid and N'-hydroxy-4-[(trifluoromethyl)sulfonyl]benzenecarboximidamide (Intermediate Y) or 4-(4-fluorotetrahydro-2H-pyran-4-yl)-N'-hydroxybenzenecarboximidamide (Intermediate J) or N'-hydroxy-4-(3-methoxyoxetan-3-yl)benzenecarboximidamide (Intermediate P) as reaction partners, Intermediates HH-JJ found in the table below were similarly prepared.

| Intermediate Number | Structure | HPLC RT (min) | MS m/z (MH+) | Method |
|---|---|---|---|---|
| aHH | ![structure] | 1.25 | 359 | K |

$^1$H NMR (400 MHz, DMSO-d$_6$) δ 13.62 (broad s, 1H), 8.49 (d, 2H), 8.38 (d, 2H), 6.83 (s, 1H), 2.34 (s, 3H).

| II | ![structure] | 4.24 | 329 | H |

$^1$H NMR (400 MHz, CDCl$_3$) δ 10.73 (broad, 1H), 8.20 (d, 2H), 7.52 (d, 2H), 6.81 (s, 1H), 4.00-3.88 (m, 4H), 2.45 (s, 3H), 2.30-2.11 (m, 2H), 1.98-1.91 (m, 2H).

| JJ | ![structure] | 0.99 | 313 | K |

$^1$H NMR (400 MHz, DMSO-d$_6$) δ 13.54 (broad s, 1H), 8.13 (d, 2H), 7.69 (d, 2H), 6.81 (s, 1H), 4.83 (d, 2H), 4.78 (d, 2H), 3.08 (s, 3H), 2.35 (s, 3H).

Intermediate KK

Preparation of N'-Hydroxy-5-methyl-1-(4-methylbenzyl)-1H-pyrazole-3-carboximidamide

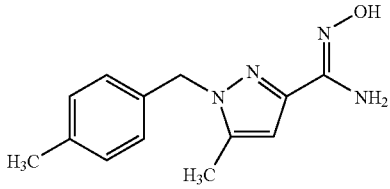 [SMILES: Cc1ccc(Cn2nc(/C(N)=N/O)cc2C)cc1]

Step 1: Preparation of 5-Methyl-1-(4-methylbenzyl)-1H-pyrazole-3-carboxamide

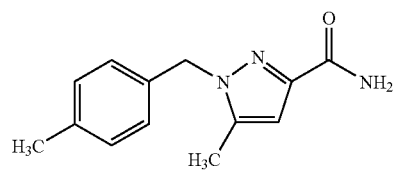 [SMILES: Cc1ccc(Cn2nc(C(N)=O)cc2C)cc1]

To a mechanically stirred solution of 5-methyl-1-(4-methylbenzyl)-1H-pyrazole-3-carboxylic acid (Intermediate B, 500 mg, 2.17 mmol) in dichloromethane (15 mL) was added dropwise oxalylchloride (950 μL, 10.9 mmol) and one drop DMF. After stirring at rt for 1 h, all volatiles were removed in vacuo. The crude acid chloride thus obtained was re-dissolved in dioxane (10 mL) and added dropwise to aqueous ammonia (33%, 6.4 mL) at 0° C. After the addition was complete, the reaction mixture was stirred at rt for 30 minutes. A white precipitate formed which was collected by filtration and washed with water. The title compound was obtained after drying in vacuo (436 mg, 89%): $^1$H NMR (400 MHz, DMSO-d$_6$) δ 7.37 (broad s, 1H), 7.14 (d, 2H, and broad s, 1H), 7.02 (d, 2H), 6.43 (s, 1H), 5.28 (s, 2H), 2.27 (s, 3H), 2.19 (s, 3H); ES-MS m/z 230 (MH)$^+$; HPLC RT (Method E) 1.39 min.

Step 2: Preparation of 5-Methyl-1-(4-methylbenzyl)-1H-pyrazole-3-carbonitrile

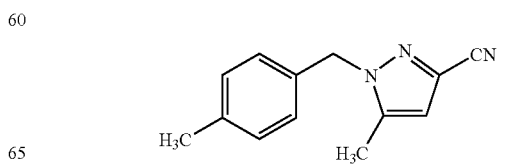

To a mechanically stirred solution of 5-methyl-1-(4-methylbenzyl)-1H-pyrazole-3-carboxamide (Step 1, 200 mg, 0.872 mmol) and N,N-diisopropylethylamine (760 µL, 4.36 mmol) in dichloromethane (10 mL) was added dropwise trifluoromethanesulfonic acid anhydride (266 µL, 1.57 mmol) at 0° C. After stirring for 30 minutes at this temperature, all volatiles were removed in vacuo. Then, in a first purification step, the crude product was subjected to preparative HPLC, followed by a second purification using MPLC (silica, dichloromethane) to afford the title compound in pure form (140 mg, 76%): $^1$H NMR (400 MHz, CDCl$_3$) δ 7.13 (d, 2H), 7.02 (d, 2H), 6.43 (s, 1H), 5.27 (s, 2H), 2.33 (s, 3H), 2.21 (s, 3H); ES-MS m/z 211 (M)$^+$; HPLC RT (Method J) 4.54 min.

Step 3: Preparation of N'-Hydroxy-5-methyl-1-(4-methylbenzyl)-1H-pyrazole-3-carboximidamide

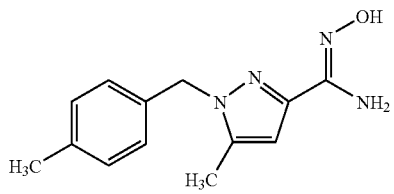 [SMILES: Cc1ccc(Cn2nc(/C(N)=N/O)cc2C)cc1]

In analogy to the procedure described in Step 2 of Intermediate J, 5-methyl-1-(4-methylbenzyl)-1H-pyrazole-3-carbonitrile (Step 2, 148 mg, 0.701 mmol) was converted to the title compound (150 mg, 88%): $^1$H NMR (400 MHz, CDCl$_3$) δ 7.12 (d, 2H), 6.97 (d, 2H), 6.95 (broad, 1H), 6.33 (s, 1H), 5.23 (s, 2H), 5.17 (broad s, 2H), 2.31 (s, 3H), 2.17 (s, 3H); DCI (NH$_3$)-MS m/z 245 (MH)$^+$; HPLC RT (Method I) 3.67 min.

Intermediate LL

Preparation of 3-[4-(Bromomethyl)phenyl]-5-[5-methyl-1-(4-methylbenzyl)-1H-pyrazol-3-yl]-1,2,4-oxadiazole

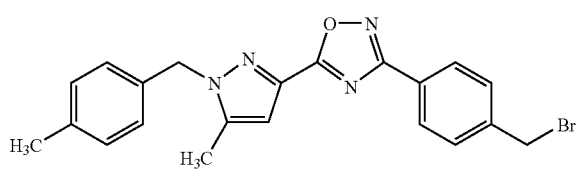 [SMILES: Cc1ccc(Cn2nc(-c3nc(-c4ccc(CBr)cc4)no3)cc2C)cc1]

To a mechanically stirred solution of (4-{5-[5-methyl-1-(4-methylbenzyl)-1H-pyrazol-3-yl]-1,2,4-oxadiazol-3-yl}phenyl)methanol (Example 110, 1.50 g, 4.16 mmol) in dichloromethane (60 mL) was added tetrabromomethane (1.66 g, 5.00 mmol) and triphenyl-phosphane (1.64 g, 6.24 mmol). The mixture was stirred at rt for 5 h and then partly concentrated under reduced pressure. The solid formed was filtered off and dried under reduced pressure to yield the title compound. The filtrate was concentrated and purified by MPLC (silica, cyclohexane/ethyl acetate 9:1) to afford another batch of the title compound (combined 1.55 g, 88%): $^1$H-NMR (400 MHz, DMSO-d$_6$) δ 8.07 (d, 2H), 7.66 (d, 2H), 7.17 (d, 2H), 7.12 (d, 2H), 6.90 (s, 1H), 5.42 (s, 2H), 4.70 (s, 2H), 2.32 (s, 3H). 2.28 (s, 3H); ES-MS m/z 423 (MH)$^+$; HPLC RT (Method D) 3.05 min.

EXAMPLES

Example 1

Preparation of 5-[5-Methyl-1-(4-methylbenzyl)-1)-1H-pyrazol-3-yl]-3-[4-(trifluoromethoxy)phenyl]-1,2,4-oxadiazole

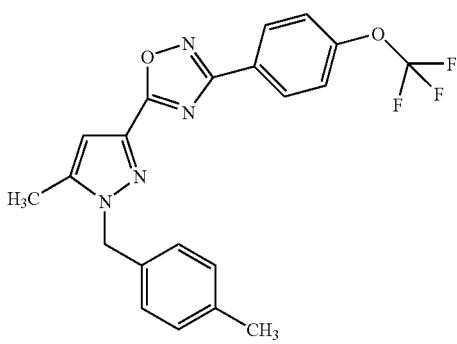 [SMILES: Cc1ccc(Cn2nc(-c3nc(-c4ccc(OC(F)(F)F)cc4)no3)cc2C)cc1]

A mixture of 5-methyl-1-(4-methylbenzyl)-1H-pyrazole-3-carboxylic acid (Intermediate B, 3.8 g, 16.5 mmol), EDCl (3.80 g, 19.8 mmol) and HOBT (2.68 g, 19.80 mmol) in DMF (100 mL) was stirred at rt for 30 min. N'-hydroxy-4-(trifluoromethoxy)benzeneamidine (4.36 g, 19.80 mmol) was added, and the mixture was stirred at rt for 1 h and then the reaction mixture was heated to 140° C. for 2 h. The reaction mixture was cooled and water (400 mL) and ethyl acetate (300 mL) were added. The layers were separated and the organic layer was washed with water (2×200 mL) and then dried with magnesium sulfate. The solvent was evaporated, and the residue was purified using silica and a gradient elution from 100% hexane to 40% ethyl acetate in hexane to afford the title compound as a white solid (3.0 g, 44%): $^1$H NMR (400 MHz, DMSO-d$_6$) δ 8.20 (d, 2H), 7.60 (d, 2H), 7.18 (d, 2H), 7.10 (d, 2H), 6.92 (s, 1H), 5.44 (s, 2H), 2.38 (s, 3H), 2.32 (s, 3H); ES-MS m/z 415.02 (MH)$^+$, HPLC RT (Method B) 4.20 min.

By using the method described above for Example 1, and by substituting the appropriate starting materials, Examples 2-13 found in the table below were similarly prepared.

| Example Number | Structure | HPLC RT (min) | MS m/z (MH+) | Method |
|---|---|---|---|---|
| 2 | 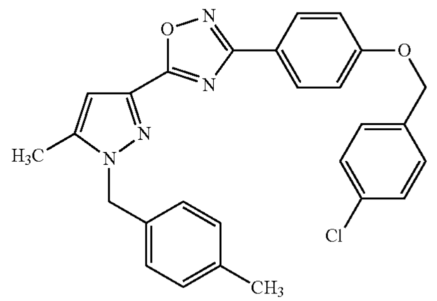 [SMILES: Cc1ccc(Cn2nc(-c3nc(-c4ccc(OCc5ccc(Cl)cc5)cc4)no3)cc2C)cc1] | 4.75 | 471.26 | A |
| 3 | 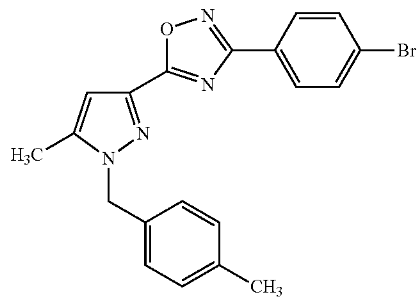 [SMILES: Cc1ccc(Cn2nc(-c3nc(-c4ccc(Br)cc4)no3)cc2C)cc1] | 4.17 | 409.10 | B |
| 4 | 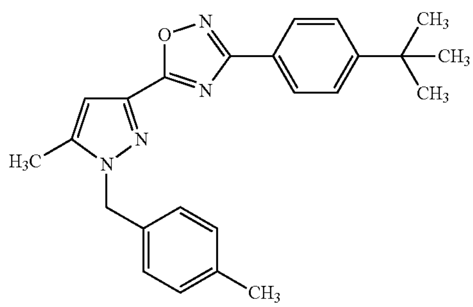 [SMILES: Cc1ccc(Cn2nc(-c3nc(-c4ccc(C(C)(C)C)cc4)no3)cc2C)cc1] | 4.86 | 387.31 | A |

¹H NMR (400 MHz, DMSO-d₆, δ/ppm): 8.00 (d, 2H), 7.61 (d, 2H), 7.18 (d, 2H), 7.10 (d, 2H), 6.90 (s, 1H), 5.43 (s, 2H), 2.32 (s, 3H), 2.28 (s, 3H), 1.32 (s, 9H).

| 5 | | 5.09 | 491.30 | A |
| 6 | | 4.39 | 428.54 | A |

-continued

| Example Number | Structure | HPLC RT (min) | MS m/z (MH+) | Method |
|---|---|---|---|---|
| 7 | 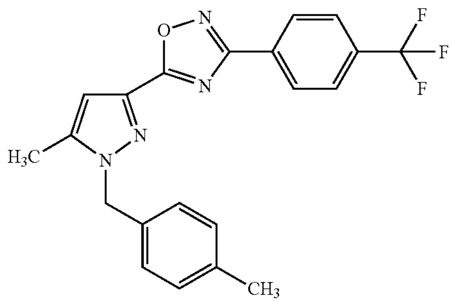 [SMILES: Cc1ccc(Cn2nc(-c3nc(-c4ccc(C(F)(F)F)cc4)no3)cc2C)cc1] | 4.44 | 398.98 | B |
| 8 | 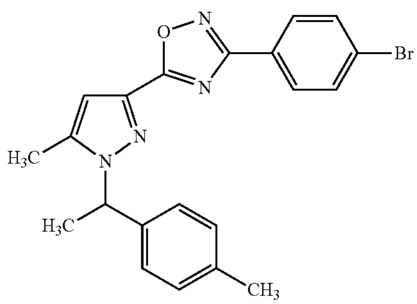 | 4.63 | 424.81 | B |
| 9 | 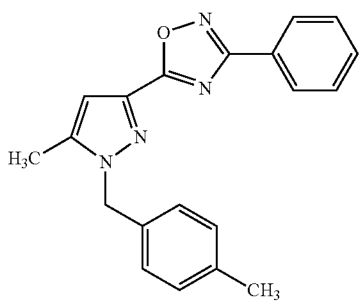 [SMILES: Cc1ccc(Cn2nc(-c3nc(-c4ccccc4)no3)cc2C)cc1] | 4.06 | 331.11 | B |
| 10 | 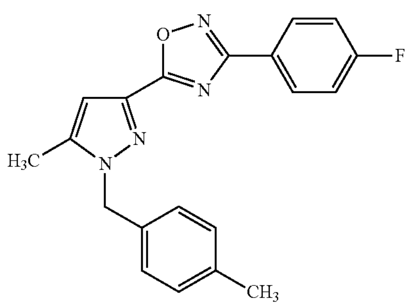 [SMILES: Cc1ccc(Cn2nc(-c3nc(-c4ccc(F)cc4)no3)cc2C)cc1] | 4.12 | 349.08 | B |
| 11 | 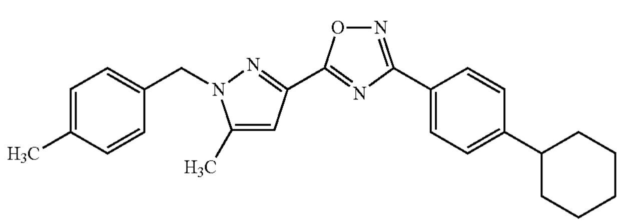 [SMILES: Cc1ccc(Cn2nc(-c3nc(-c4ccc(C5CCCCC5)cc4)no3)cc2C)cc1] | 6.26 | 413 | H |

$^1$H NMR (400 MHz, DMSO-$d_6$, δ/ppm): 7.98 (d, 2H), 7.43 (d, 2H), 7.18 (d, 2H), 7.10 (d, 2H), 6.90 (s, 1H), 5.43 (s, 2H), 2.63-2.56 (m, 1H), 2.32 (s, 3H), 2.28 (s, 3H), 1.84-1.79 (m, 4H), 1.73-1.69 (m, 1H), 1.50-1.33 (m, 4H), 1.30-1.20 (m, 1H).

| Example Number | Structure | HPLC RT (min) | MS m/z (MH+) | Method |
|---|---|---|---|---|
| 12 | 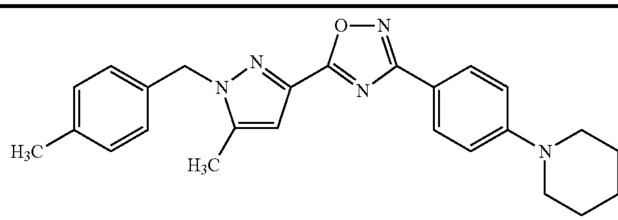 | 4.49 | 414 | J |

$^1$H NMR (500 MHz, DMSO-d$_6$, δ/ppm): 7.87 (d, 2H), 7.18 (d, 2H), 7.10 (d, 2H), 7.04 (d, 2H), 6.87 (s, 1H), 5.42 (s, 2H), 2.33-3.30 (m, 4H), 2.31 (s, 3H), 2.28 (s, 3H), 1.60 (m, 6H).

| 13 | | 5.65 | 457 | G |

$^1$H NMR (400 MHz, DMSO-d$_6$, δ/ppm): 7.98 (d, 2H), 7.84 (d, 2H), 7.18 (d, 2H), 7.10 (d, 2H), 6.90 (s, 1H), 5.43 (s, 2H), 2.32 (s, 3H), 2.27 (s, 3H).

Example 14

Preparation of 4-{5-[5-Methyl-1-(4-methylbenzyl)-1H-pyrazol-3-yl]-1,2,4-oxadiazol-3-yl}pyridine

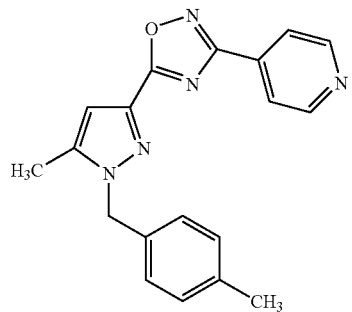 [SMILES: Cc1ccc(Cn2nc(-c3nc(-c4ccncc4)no3)cc2C)cc1]

Step 1: Preparation of 5-Methyl-1-(4-methylbenzyl)-1H-pyrazole-3-carbonyl chloride

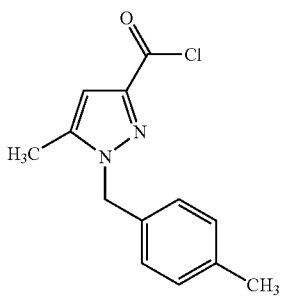

5-methyl-1-(4-methylbenzyl)-1H-pyrazole-3-carboxylic acid (Intermediate B, 390 mg, 1.69 mmol), was dissolved in dichloromethane (26 mL) and cooled to 0° C. Oxalyl chloride was added (0.79 mL, 8.47 mmol) along with 1 drop of DMF. The ice bath was removed and the mixture was stirred at rt for 30 min before the solvent was evaporated. The residue was used in the next step with no further purification or characterization.

Step 2: Preparation of 4-{5-[5-Methyl-1-(4-methyl-benzyl)-1H-pyrazol-3-yl]-1,2,4-oxadiazol-3-yl}pyridine

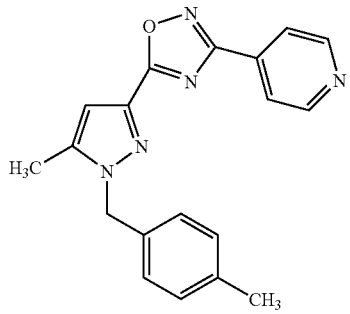 [SMILES: Cc1ccc(Cn2nc(-c3nc(-c4ccncc4)no3)cc2C)cc1]

To a solution of 5-methyl-1-(4-methylbenzyl)-1H-pyrazole-3-carbonyl chloride (Step 1, 65 mg, 0.26 mmol) in dichloromethane (4 mL) at 0° C. was added N'-hydroxypyridine-4-amidine (43 mg, 0.31 mmol) along with triethyl amine (0.073 mL). The mixture was stirred for 16 h at rt. The mixture was evaporated to dryness and DMF (3 mL) was added along with EDCl (75 mg, 0.392 mmol) and the mixture was stirred at 140° C. for 2 h. The reaction mixture was cooled and water (100 mL) and ethyl acetate (100 mL) was added. The layers were separated and the organic layer was washed with water (2×200 mL) and then dried with magnesium sulfate. The solvent was evaporated and the residue was purified with an ISCO CombiFlash Companion using gradient elution from 100% hexane to 40% ethyl acetate in hexane to afford the title compound as a white solid (65 mg, 75%): $^1$H NMR (300 MHz, CD$_2$Cl$_2$) δ 8.80 (d, 2H), 8.20 (d, 2H), 7.20 (d, 2H), 7.10 (d, 2H), 6.82 (s, 1H), 5.40 (s, 2H), 2.35 (m, 6H); ES-MS m/z 332.25 (MH)$^+$, HPLC RT (Method B) 3.34 min.

By using the method described above for Example 14, and by substituting the appropriate starting materials, Examples 15-17 found in the table below were similarly prepared.

A solution of 2,2,2-trifluoroethanol (175 mg, 1.75 mmol) in DMF (2 ml) was added to sodium hydride (117 mg of a 60% suspension in mineral oil, 2.94 mmol). The mixture was stirred at 50° C. for 15 minutes. Then, 3-(4-iodophenyl)-5-[5-methyl-1-(4-methylbenzyl)-1H-pyrazol-3-yl]-1,2,4-oxadiazole (Example 13, 200 mg, 0.44 mmol) and copper(I) iodide (167 mg, 0.88 mmol) were added and the reaction mixture was stirred at 110° C. for one hour. The reaction mixture was cooled and water (100 mL) and ethyl acetate

| Example Number | Structure | HPLC RT (min) | MS m/z (MH+) | Method |
|---|---|---|---|---|
| 15 | 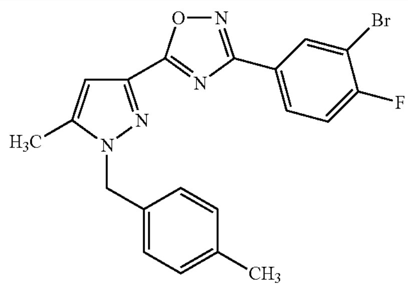 [SMILES: Cc1ccc(Cn2nc(-c3nc(-c4ccc(F)c(Br)c4)no3)cc2C)cc1] | 4.26 | 428.97 | B |
| 16 | 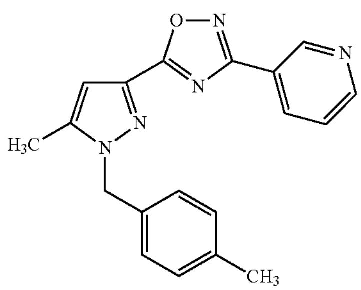 [SMILES: Cc1ccc(Cn2nc(-c3nc(-c4cccnc4)no3)cc2C)cc1] | 3.50 | 332.28 | B |
| 17 | 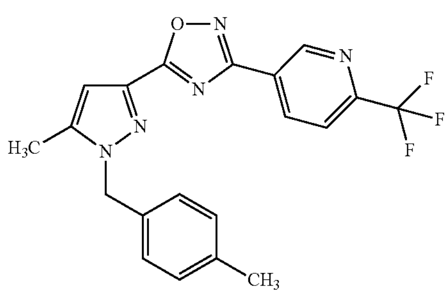 [SMILES: Cc1ccc(Cn2nc(-c3nc(-c4ccc(C(F)(F)F)nc4)no3)cc2C)cc1] | 4.10 | 400.17 | A |

Example 18

Preparation of 5-[5-Methyl-1-(4-methylbenzyl)-1H-pyrazol-3-yl]-3-[4-(2,2,2-trifluoroethoxy)phenyl]-1,2,4-oxadiazole

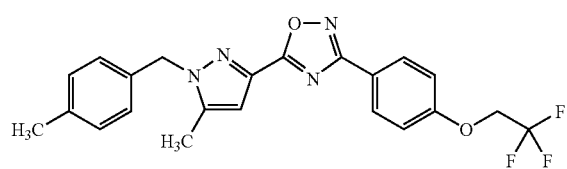 [SMILES: Cc1ccc(Cn2nc(-c3nc(-c4ccc(OCC(F)(F)F)cc4)no3)cc2C)cc1]

(100 mL) was added. The layers were separated and the organic layer was washed with water and brine and then dried with magnesium sulfate. The solvent was evaporated and the residue was purified, first using preparative HPLC and then via flash chromatography (silica, gradient elution from cyclohexane/ethyl acetate 10:1 to 3:1) to afford the title compound as a white solid (33 mg, 18%): $^1$H NMR (400 MHz, CDCl$_3$) δ 8.19 (d, 2H), 7.13 (d, 2H), 7.07 (d, 2H), 7.03 (d, 2H), 6.78 (s, 1H), 5.42 (s, 2H), 4.42 (quart, 2H), 2.32 (s, 3H), 2.26 (s, 3H); ES-MS m/z 429 (MH)$^+$, HPLC RT (Method D) 3.19 min.

By using the method described above for Example 18, and by substituting the appropriate starting materials, Example 19 found in the table below was similarly prepared.

| Example Number | Structure | HPLC RT (min) | MS m/z (MH+) | Method |
|---|---|---|---|---|
| 19 | 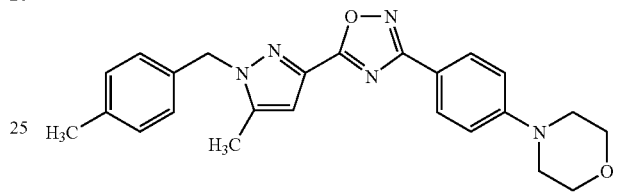 | 3.44 | 415 | D |

¹H NMR (400 MHz, CDCl₃, δ/ppm): 8.11 (d, 2H), 7.13 (d, 2H), 7.07 (d, 2H), 6.95 (d, 2H), 6.78 (s, 1H), 5.40 (s, 2H), 4.85-4.81 (m, 1H), 2.31 (s, 3H), 2.26 (s, 3H), 1.99-1.77 (m, 6H), 1.69-1.60 (m, 2H).

Example 20

Preparation of 3-(4-Isopropoxyphenyl)-5-[5-methyl-1-(4-methylbenzyl)-1H-pyrazol-3-yl]-1,2,4-oxadiazole

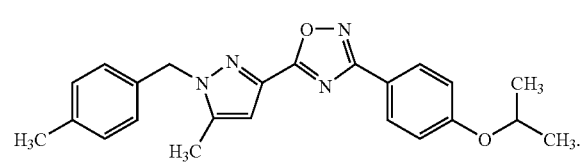 [SMILES: Cc1ccc(Cn2nc(-c3nc(-c4ccc(OC(C)C)cc4)no3)cc2C)cc1]

A mixture of 3-(4-iodophenyl)-5-[5-methyl-1-(4-methylbenzyl)-1H-pyrazol-3-yl]-1,2,4-oxadiazole (Example 13, 200 mg, 0.44 mmol), 2-propanol (1 ml, 13.06 mmol), copper (I) iodide (8.4 mg, 0.04 mmol), phenanthroline (16 mg, 0.09 mmol) and cesium carbonate (286 mg, 0.88 mmol) was stirred at 100° C. for five hours in a microwave reactor (CEM Discover). The reaction mixture was cooled and water (50 mL) and ethyl acetate (50 mL) was added. The layers were separated and the organic layer was washed with water and brine and then dried with magnesium sulfate. The solvent was evaporated and the residue was purified using preparative HPLC to afford the title compound as a white solid (30 mg, 16%): ¹H NMR (400 MHz, CDCl₃) δ 8.12 (d, 2H), 7.13 (d, 2H), 7.07 (d, 2H), 6.97 (d, 2H), 6.79 (s, 1H), 5.41 (s, 2H), 4.63 (sept, 1H), 2.33 (s, 3H), 2.26 (s, 3H), 1.38 (d, 6H); ES-MS m/z 389 (MH)⁺, HPLC RT (Method E) 2.67 min.

Example 21

Preparation of 4-(4-{5-[5-Methyl-1-(4-methylbenzyl)-1H-pyrazol-3-yl]-1,2,4-oxadiazol-3-yl}phenyl)morpholine

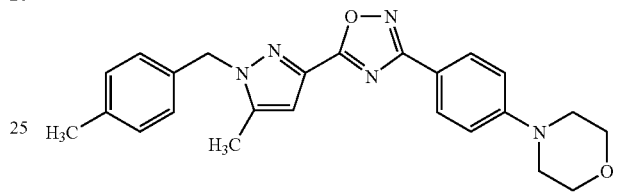

A mixture of 3-(4-iodophenyl)-5-[5-methyl-1-(4-methylbenzyl)-1H-pyrazol-3-yl]-1,2,4-oxadiazole (Example 13, 200 mg, 0.44 mmol), morpholine (76 μl, 0.88 mmol), potassium carbonate (121 mg, 0.88 mmol), tris(dibenzylideneacetone)dipalladium (13 mg, 0.014 mmol), 2-(dicyclohexylphosphino)-2',4',6'-tri-tert-butyl-1,1'-biphenyl (21 mg 0.044 mmol), DMF (1 ml) and tert-butanol (4 ml) was stirred at 80° C. for 15 h. The reaction mixture was cooled and water (100 mL) and ethyl acetate (100 mL) was added. The layers were separated and the organic layer was washed with water and brine and then dried with magnesium sulfate. The solvent was evaporated and the residue was purified, first using preparative HPLC, then via flash chromatography (silica, cyclohexane/ethyl acetate, 10:1→2:1) to afford the title compound as a white solid (37 mg, 20%): ¹H NMR (400 MHz, CDCl₃) δ 8.11 (d, 2H), 7.13 (d, 2H), 7.07 (d, 2H), 6.97 (d, 2H), 6.78 (s, 1H), 5.41 (s, 2H), 3.88 (m, 4H), 3.28 (m, 4H), 2.33 (s, 3H), 2.25 (s, 3H); ES-MS m/z 416 (MH)⁺, HPLC RT (Method D) 2.95 min.

By using the method described above for Example 21, and by substituting the appropriate starting materials, Example 22 found in the table below was similarly prepared.

| Example Number | Structure | HPLC RT (min) | MS m/z (MH+) | Method |
|---|---|---|---|---|
| 22 | 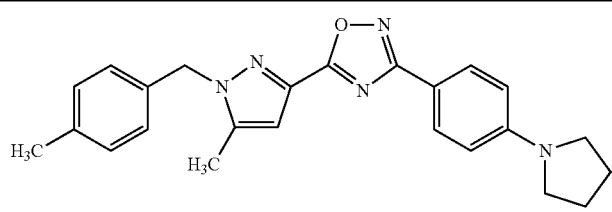 | 3.31 | 400 | D |

¹H NMR (400 MHz, CDCl₃, δ/ppm): 8.08 (d, 2H), 7.13 (d, 2H), 7.07 (d, 2H), 6.79 (s, 1H), 6.75 (d, 2H), 5.41 (s, 2H), 3.45-3.42 (m, 4H), 2.32 (s, 3H), 2.27 (s, 3H), 2.10-2.17 (m, 4H).

Example 23

Preparation of N,N-Diethyl-4-{5-[5-methyl-1-(4-methylbenzyl)-1H-pyrazol-3-yl]-1,2,4-oxadiazol-3-yl}aniline

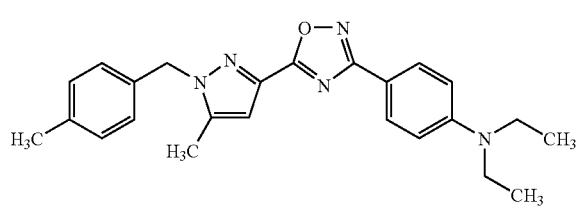 [SMILES: CCN(CC)c1ccc(-c2noc(-c3cc(C)n(Cc4ccc(C)cc4)n3)n2)cc1]

A mixture of 3-(4-iodophenyl)-5-[5-methyl-1-(4-methylbenzyl)-1H-pyrazol-3-yl]-1,2,4-oxadiazole (Example 13, 250 mg, 0.55 mmol), diethylamine (113 µl, 1.1 mmol), sodium tert-butylat (74 mg, 0.77 mmol), palladium(II) acetate (25 mg, 0.11 mmol), 2-(dicyclohexylphosphino)-1,1'-biphenyl (19 mg, 0.06 mmol) and toluene (3 ml) was stirred at 80° C. for 15 h. The reaction mixture was cooled and water (100 mL) and ethyl acetate (100 mL) was added. The layers were separated and the organic layer was washed with water and brine and then dried with magnesium sulfate. The solvent was evaporated and the residue was purified, first using preparative HPLC, then via flash chromatography (silica, cyclohexane/ethyl acetate, 10:1→1:1) to afford the title compound as a white solid (42 mg, 19%): $^1$H NMR (400 MHz, CDCl$_3$) δ 8.03 (d, 2H), 7.12 (d, 2H), 7.07 (d, 2H), 6.78 (s, 1H), 6.71 (d, 2H), 5.40 (s, 2H), 3.41 (quart, 4H), 2.32 (s, 3H), 2.25 (s, 3H), 1.20 (t, 6H); ES-MS m/z 402 (MH)$^+$, HPLC RT (Method E) 2.68 min.

Example 24

Preparation of 1-(4-{5-[5-Methyl-1-(4-methylbenzyl)-1H-pyrazol-3-yl]-1,2,4-oxadiazol-3-yl}phenyl)pyrrolidin-2-one A mixture of 3-(4-iodophenyl)-5-[5-methyl-1-(4-methylbenzyl)-1H-pyrazol-3-yl]-1,2,4-oxadiazole (Example 13, 200 mg, 0.44 mmol), pyrrolidinone (67 µl, 0.88 mmol), potassium phosphate (186 mg, 0.88 mmol), copper(I) iodide (25 mg, 0.13 mmol), N,N'-dimethylethylenediamine (28 µl, 0.26 mmol) and 1,4-dioxane (4 ml) was stirred at 70° C. for 15 h. The reaction mixture was cooled and water (100 mL) and ethyl acetate (100 mL) was added. The layers were separated and the organic layer was washed with water and brine and then dried with magnesium sulfate. The solvent was evaporated and the residue was purified using preparative HPLC, to afford the title compound as a white solid (73 mg, 40%): $^1$H NMR (400 MHz, CDCl$_3$) δ 8.21 (d, 2H), 7.79 (d, 2H), 7.13 (d, 2H), 7.08 (d, 2H), 6.79 (s, 1H), 5.41 (s, 2H), 3.93 (t, 2H), 2.65 (t, 2H), 2.33 (s, 3H), 2.26 (s, 3H), 2.20 (quint, 2H); ES-MS m/z 414 (MH)$^+$, HPLC RT (Method E) 4.82 min.

By using the method described above for Example 24, and by substituting the appropriate starting materials, Examples 25-28 found in the table below were similarly prepared.

| Example Number | Structure | HPLC RT (min) | MS m/z (MH+) | Method |
|---|---|---|---|---|
| 25 | 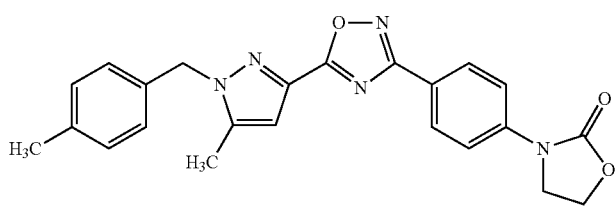 [SMILES: Cc1ccc(Cn2nc(-c3nc(-c4ccc(N5CCOC5=O)cc4)no3)cc2C)cc1]<br>$^1$H NMR (400 MHz, DMSO-d$_6$, δ/ppm): 8.09 (d, 2H), 7.79 (d, 2H), 7.17 (d, 2H), 7.10 (d, 2H), 6.90 (s, 1H), 5.43 (s, 2H), 4.48 (dd, 2H), 4.13 (dd, 2H), 2.32 (s, 3H), 2.28 (s, 3H). | 2.73 | 416 | D |
| 26 | 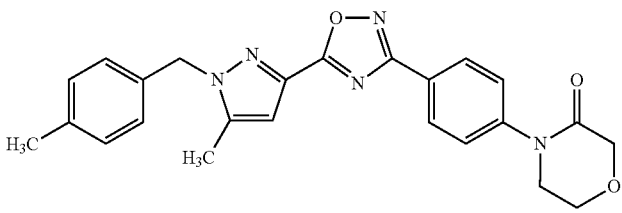 [SMILES: Cc1ccc(Cn2nc(-c3nc(-c4ccc(N5CCOCC5=O)cc4)no3)cc2C)cc1]<br>$^1$H NMR (400 MHz, CDCl$_3$, δ/ppm): 8.27 (d, 2H), 7.51 (d, 2H), 7.13 (d, 2H), 7.07 (d, 2H), 6.80 (s, 1H), 5.41 (s, 2H), 4.37 (s, 2H), 4.07 (dd, 2H), 3.83 (dd, 2H), 2.32 (s, 3H), 2.26 (s, 3H). | 4.56 | 430 | G |

| Example Number | Structure | HPLC RT (min) | MS m/z (MH+) | Method |
|---|---|---|---|---|
| 27 | 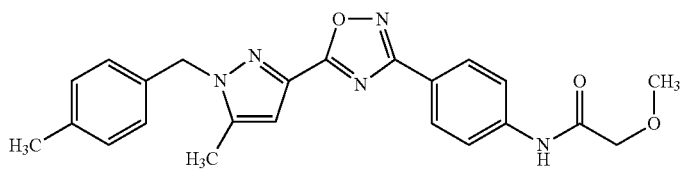 | 2.70 | 418 | D |

¹H-NMR (400 MHz, DMSO-d₆, δ/ppm): 8.01 (d, 2H), 7.89 (d, 2H), 7.18 (d, 2H), 7.10 (d, 2H), 6.89 (s, 1H), 5.43 (s, 2H), 4.05 (s, 2H), 3.39 (s, 3H), 2.32 (s, 3H), 2.28 (s, 3H).

| | | | | |
|---|---|---|---|---|
| 28 | 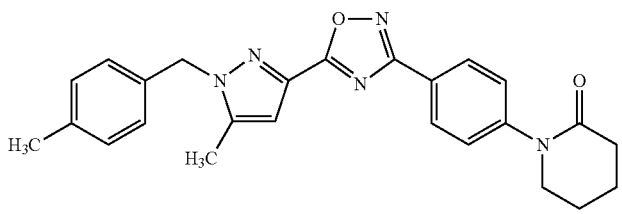 [SMILES: Cc1ccc(Cn2nc(-c3nc(-c4ccc(N5CCCCC5=O)cc4)no3)cc2C)cc1] | 4.72 | 428 | I |

¹H NMR (400 MHz, CDCl₃, δ/ppm): 8.22 (d, 2H), 7.41 (d, 2H), 7.13 (d, 2H), 7.07 (d, 2H), 6.79 (s, 1H), 5.41 (s, 2H), 3.72-3.69 (m, 2H), 2.61-2.58 (m, 2H), 2.32 (s, 3H), 2.26 (s, 3H), 2.01-1.92 (m, 4H).

Example 29

Preparation of 2-[5-Methyl-1-(4-methylbenzyl)-1H-pyrazol-3-yl]-5-phenyl-1,3-benzoxazole

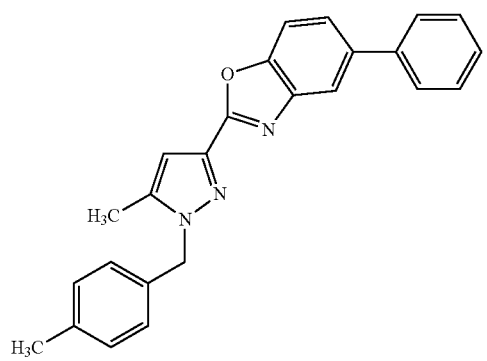 [SMILES: Cc1ccc(Cn2nc(-c3nc4cc(-c5ccccc5)ccc4o3)cc2C)cc1]

A flask containing 5-methyl-1-(4-methylbenzyl)-1H-pyrazole-3-carboxylic acid (Intermediate B, 5.0 g, 21.7 mmol), 3-aminobiphenyl-4-ol (4.0 g, 21.7 mmol) and trimethylsilyl polyphosphate (40 g) was heated at 180° C. for 30 min, and then the reaction mixture was poured into ice water (1 L). The mixture was stirred for 1 h and was extracted with dichloromethane (2 L). The layers were separated and the organic layer was washed with brine (2×1 L) and dried with sodium sulfate. The solvent was evaporated, and the residue was purified with an ISCO CombiFlash Companion using gradient elution from 100% hexane to 20% ethyl acetate in hexane to afford the title compound as a white solid (2.19 g, 27%): ¹H NMR (300 MHz, CD₂Cl₂) δ 7.94 (d, 1H), 7.66 (m, 4H), 7.48 (t, 2H), 7.39 (m, 1H), 7.14 (dd, 4H), 6.82 (s, 1H), 5.37 (s, 2H), 2.34 (s, 3H), 2.32 (s, 3H); ES-MS m/z 380.2 (MH)⁺, HPLC RT (Method A) 4.25 min.

By using the method described above for Example 29, and by substituting the appropriate starting materials, Examples 30-36 found in the table below were similarly prepared.

| Example Number | Structure | HPLC RT (min) | MS m/z (MH+) | Method |
|---|---|---|---|---|
| 30 | 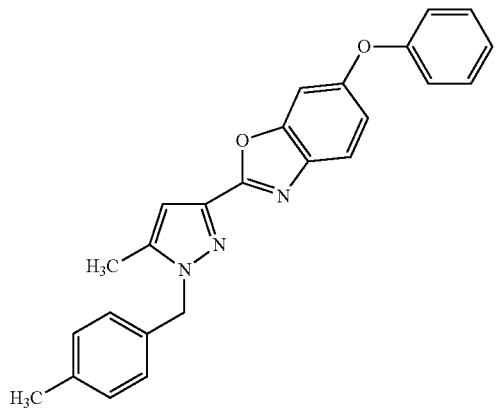 [SMILES: Cc1ccc(Cn2nc(-c3nc4ccc(Oc5ccccc5)cc4o3)cc2C)cc1] | 4.13 | 396.3 | A |
| 31 | 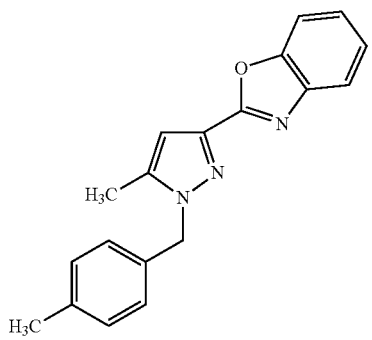 [SMILES: Cc1ccc(Cn2nc(-c3nc4ccccc4o3)cc2C)cc1] | 3.83 | 304.2 | A |
| 32 | 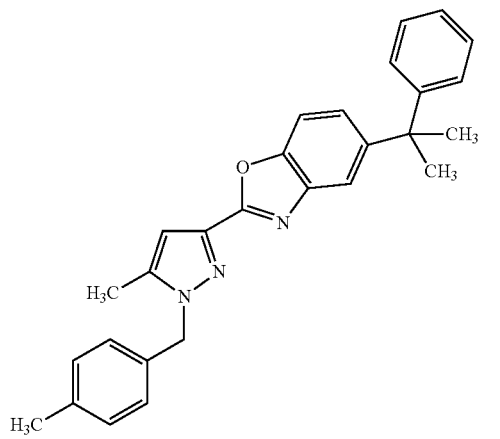 [SMILES: Cc1ccc(Cn2nc(-c3nc4cc(C(C)(C)c5ccccc5)ccc4o3)cc2C)cc1] | 4.55 | 422.1 | A |

-continued

| Example Number | Structure | HPLC RT (min) | MS m/z (MH+) | Method |
|---|---|---|---|---|
| 33 | 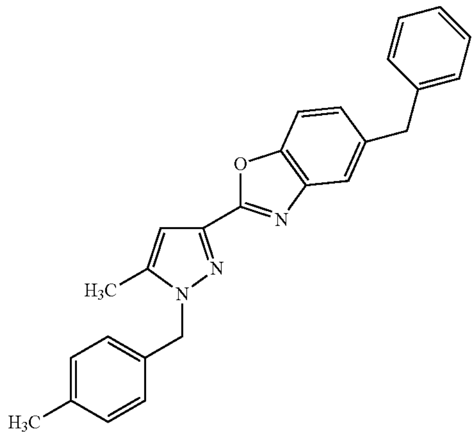 [SMILES: Cc1ccc(Cn2nc(-c3nc4cc(Cc5ccccc5)ccc4o3)cc2C)cc1] | 4.20 | 394.1 | A |
| 34 | 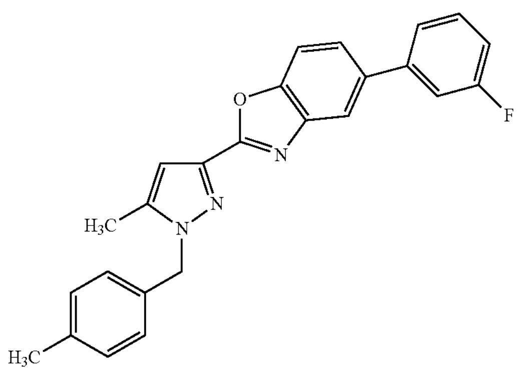 [SMILES: Cc1ccc(Cn2nc(-c3nc4cc(-c5cccc(F)c5)ccc4o3)cc2C)cc1] | 4.26 | 398.2 | A |
| 35 | 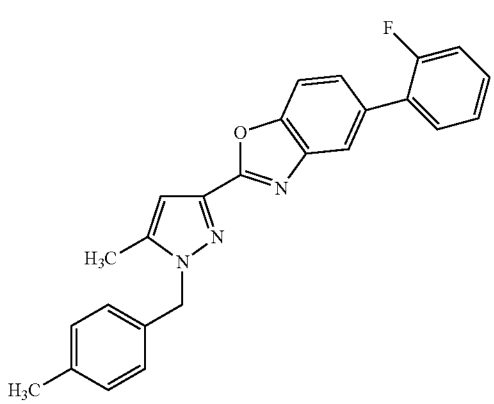 [SMILES: Cc1ccc(Cn2nc(-c3nc4cc(-c5ccccc5F)ccc4o3)cc2C)cc1] | 4.29 | 398.2 | A |

| Example Number | Structure | HPLC RT (min) | MS m/z (MH+) | Method |
|---|---|---|---|---|
| 36 | 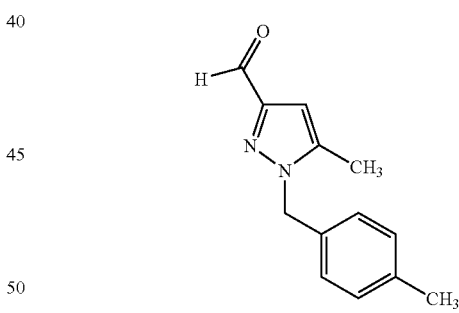 | 4.44 | 414.2 | A |

Example 37

Preparation of 6-Bromo-2-[5-methyl-1-(4-methylbenzyl)-1H-pyrazol-3-yl]-1H-benzimidazole

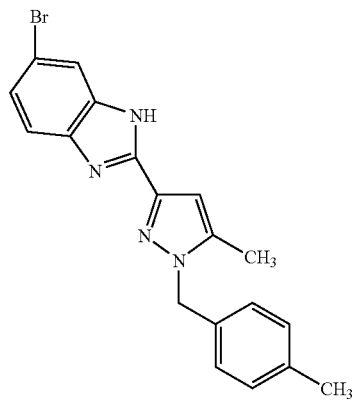 [SMILES: Cc1ccc(Cn2nc(-c3nc4ccc(Br)cc4[nH]3)cc2C)cc1]

Step 1: Preparation of [5-Methyl-1-(4-methylbenzyl)-1H-pyrazol-3-yl]methanol

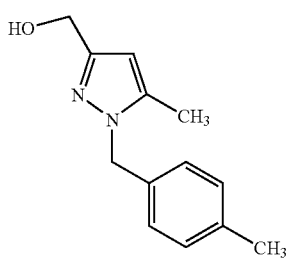 [SMILES: Cc1ccc(Cn2nc(CO)cc2C)cc1]

To a solution of methyl 5-methyl-1-(4-methylbenzyl)-1H-pyrazole-3-carboxylate (Intermediate A, 5.0 g, 20.5 mmol) in THF (100 mL) at 0° C. was added a solution of lithium aluminum hydride (15.4 mL, 30.7 mmol, 2.0 M in THF) dropwise. The mixture was stirred at rt for 1 h. Celite® (3 g) was added to the mixture, followed by water (5 mL) dropwise and sodium hydroxide (1.0 N, 5 mL). The mixture was filtered through a pad of Celite® washing throroughly with ethyl acetate. The combined organics were diluted with ethyl acetate, washed with water (1×150 mL) and brine (1×150 mL), dried over $Na_2SO_4$, filtered and concentrated to dryness to afford the title compound as a light yellow solid (4.2 g, 95%): $^1$H NMR (300 MHz, DMSO-$d_6$) δ 7.10 (d, 2H), 6.96 (d, 2H), 5.98 (s, 1H), 5.14 (s, 2H), 4.89 (t, 1H), 4.29 (d, 2H), 2.24 (s, 3H), 2.14 (s, 3H); ES-MS m/z 217.03, HPLC RT (Method A) 2.96 min.

Step 2: Preparation of 5-Methyl-1-(4-methylbenzyl)-1H-pyrazole-3-carbaldehyde

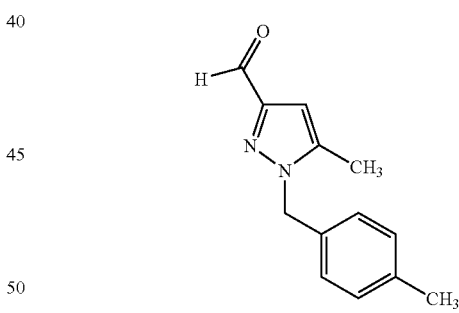

To a stirred solution of oxalyl chloride (1.69 mL, 19.4 mmol) in dichloromethane (10 mL) at −78° C. was added DMSO (3.45 mL, 18.6 mmol) as a solution in dichloromethane (5 mL) dropwise over a period of 10 min. To this reaction mixture was added [5-methyl-1-(4-methylbenzyl)-1H-pyrazol-3-yl]methanol (Step 1, 4.2 g, 19.42 mmol) as a solution in dichloromethane (50 mL) dropwise over a period of 30 min. The mixture was stirred at −78° C. for 1.5 h. and triethylamine (13.5 mL, 97.1 mmol) in dichloromethane (5 mL) was then added dropwise. The resultant mixture was warmed to 0° C. and stirred for 20 min. To this mixture was added water (25 mL) dropwise, followed by dichloromethane (100 mL). The organic layer was separated, and the aqueous layer was extracted with dichloromethane (1×100 mL). The combined organic extracts were washed with HCl (0.5 M aq., 1×50 mL), dried (Na₂SO₄), and filtered. The organic layer was passed through a small plug of silica gel using ethyl acetate as eluent, and was concentrated under reduced pressure to afford the title compound as a yellow oil (3.7 g, 89%): ¹H NMR (300 MHz, DMSO-d₆) δ 9.80 (s, 1H), 7.12 (d, 2H), 7.03 (d, 2H), 6.57 (s, 1H), 5.36 (s, 2H), 2.25 (s, 3H), 2.23 (s, 3H): ES-MS m/z 214.98, HPLC RT (Method A) 3.33 min.

Step 3: Preparation of 6-Bromo-2-[5-methyl-1-(4-methylbenzyl)-1H-pyrazol-3-yl]-1H-benzimidazole

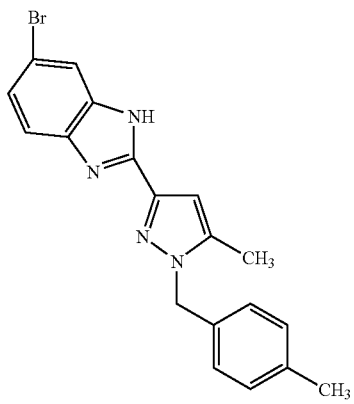 [SMILES: Cc1ccc(Cn2nc(-c3nc4ccc(Br)cc4[nH]3)cc2C)cc1]

To a solution of 5-methyl-1-(4-methylbenzyl)-1H-pyrazole-3-carbaldehyde (Step 2, 700 mg, 3.27 mmol) in DMF (25 mL) was added 4-bromo-o-phenylenediamine (1.2 g, 6.53 mmol) followed by sodium bisulfite (679 mg, 6.53 mmol), and the resulting mixture was heated at 110° C. for 5 h. After being cooled to rt, the reaction mixture was diluted with water. The aqueous phase was extracted with ethyl acetate (3×50 mL), and the combined organics were washed with water (1×50 mL) and brine (1×50 mL), dried (Na₂SO₄), filtered, and concentrated to dryness. The crude material was then purified with an ISCO CombiFlash Companion using gradient elution from 0% to 50% EtOAc in hexanes to afford the title compound as a mixture of regioisomers as a light yellow solid (600 mg, 48%): ¹H NMR (300 MHz, DMSO-d₆) δ 11.76 (m, 1H), 11.60 (s, 1H), 7.35-7.77 (m, 2H), 7.27-7.30 (m, 1H), 7.13 (d, 2H), 7.04 (d, 2H), 6.69 (s, 1H), 5.36 (s, 2H), 2.27 (s, 3H), 2.24 (s, 3H); ES-MS m/z 381.20, HPLC RT (Method B) 3.20 min.

By using the method described above for Example 37, and by substituting the appropriate starting materials, Examples 38-58 found in the table below were similarly prepared.

| Example Number | Structure | HPLC RT (min) | MS m/z (MH+) | Method |
|---|---|---|---|---|
| 38 | 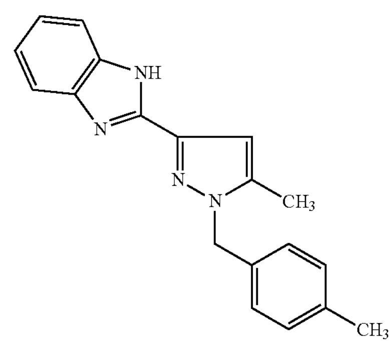 [SMILES: Cc1ccc(Cn2nc(-c3nc4ccccc4[nH]3)cc2C)cc1] | 2.84 | 303.19 | B |
| 39 | 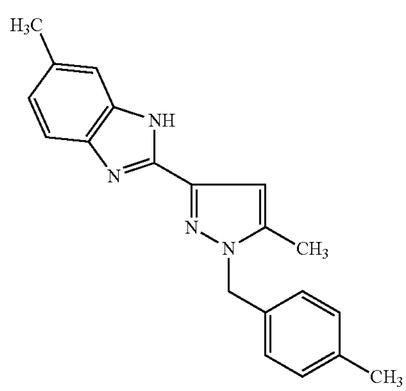 [SMILES: Cc1ccc(Cn2nc(-c3nc4ccc(C)cc4[nH]3)cc2C)cc1] | 3.01 | 317.22 | B |

-continued

| Example Number | Structure | HPLC RT (min) | MS m/z (MH+) | Method |
|---|---|---|---|---|
| 40 | 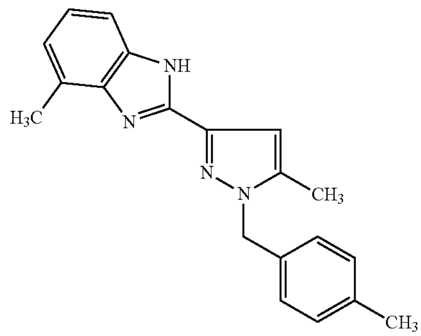 | 2.98 | 317.20 | B |
| 41 | 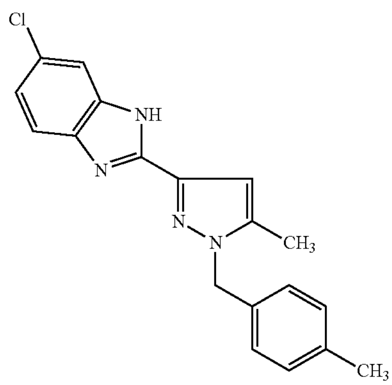 [SMILES: Cc1ccc(Cn2nc(-c3nc4ccc(Cl)cc4[nH]3)cc2C)cc1] | 3.17 | 337.18 | B |
| 42 | 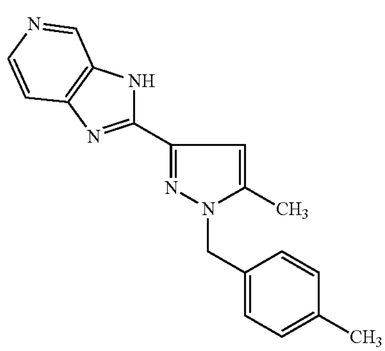 [SMILES: Cc1ccc(Cn2nc(-c3nc4ccncc4[nH]3)cc2C)cc1] | 1.91 | 304.21 | B |
| 43 | 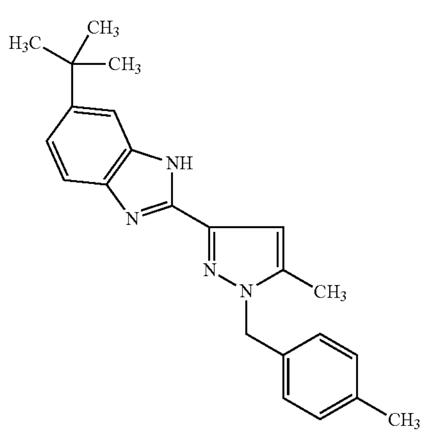 [SMILES: Cc1ccc(Cn2nc(-c3nc4ccc(C(C)(C)C)cc4[nH]3)cc2C)cc1] | 2.88 | 359.21 | A |

-continued

| Example Number | Structure | HPLC RT (min) | MS m/z (MH+) | Method |
|---|---|---|---|---|
| 44 | 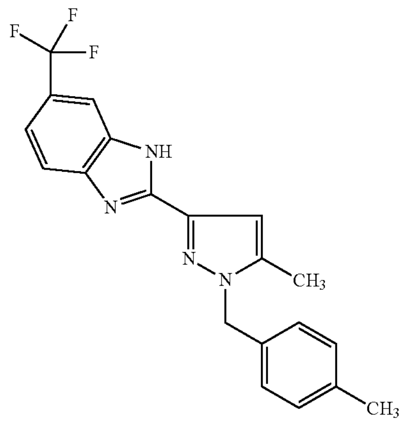 [SMILES: Cc1ccc(Cn2nc(-c3nc4ccc(C(F)(F)F)cc4[nH]3)cc2C)cc1] | 3.16 | 371.09 | A |
| 45 | 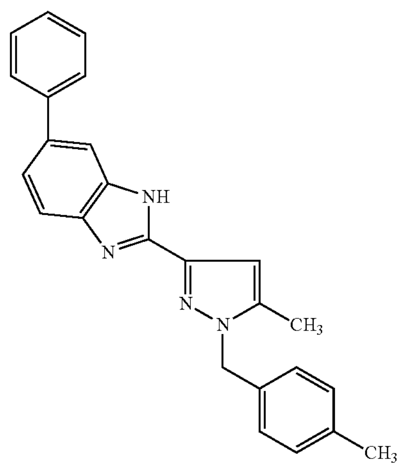 [SMILES: Cc1ccc(Cn2nc(-c3nc4ccc(-c5ccccc5)cc4[nH]3)cc2C)cc1] | 2.93 | 379.14 | A |
| 46 | 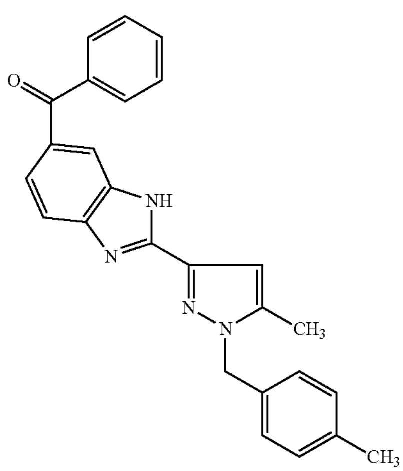 [SMILES: Cc1ccc(Cn2nc(-c3nc4ccc(C(=O)c5ccccc5)cc4[nH]3)cc2C)cc1] | 3.06 | 407.16 | A |

-continued
| Example Number | Structure | HPLC RT (min) | MS m/z (MH+) | Method |
|---|---|---|---|---|
| 47 | 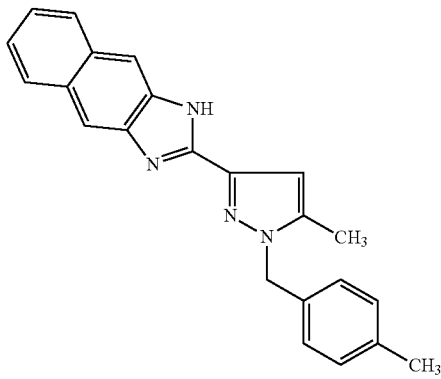 [SMILES: Cc1ccc(Cn2nc(-c3nc4cc5ccccc5cc4[nH]3)cc2C)cc1] | 2.81 | 353.16 | A |
| 48 | 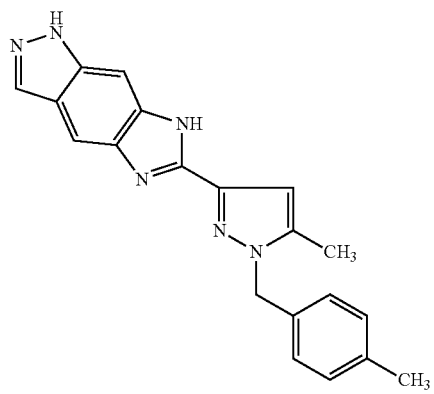 [SMILES: Cc1ccc(Cn2nc(-c3nc4cc5cn[nH]c5cc4[nH]3)cc2C)cc1] | 2.43 | 343.13 | A |
| 49 | 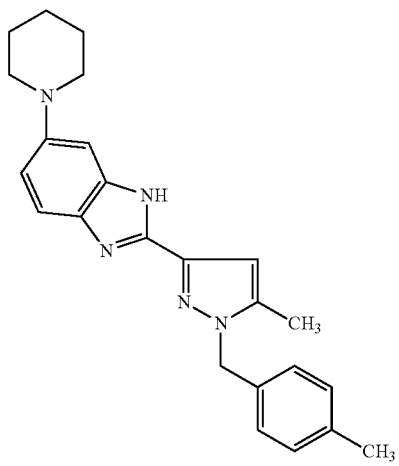 | 2.61 | 386.32 | B |

-continued
| Example Number | Structure | HPLC RT (min) | MS m/z (MH+) | Method |
|---|---|---|---|---|
| 50 | 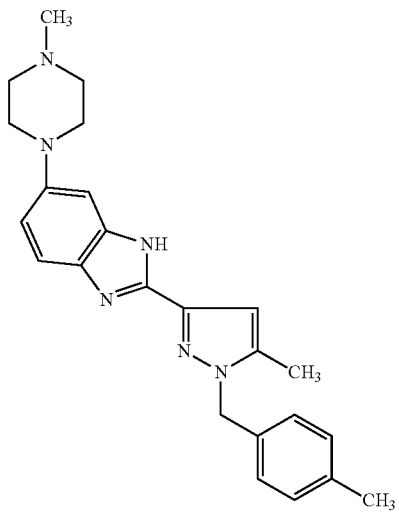 [SMILES: Cc1ccc(Cn2nc(-c3nc4ccc(N5CCN(C)CC5)cc4[nH]3)cc2C)cc1] | 2.13 | 401.18 | B |
| 51 | 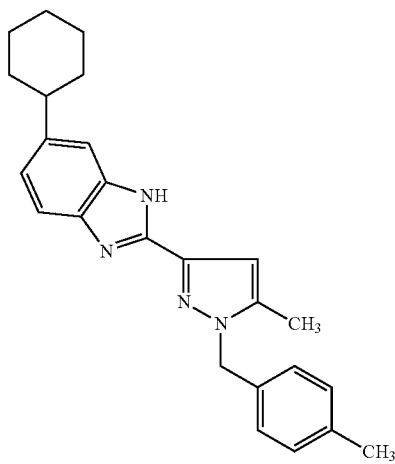 [SMILES: Cc1ccc(Cn2nc(-c3nc4ccc(C5CCCCC5)cc4[nH]3)cc2C)cc1] | 3.07 | 385.24 | A |
| 52 | 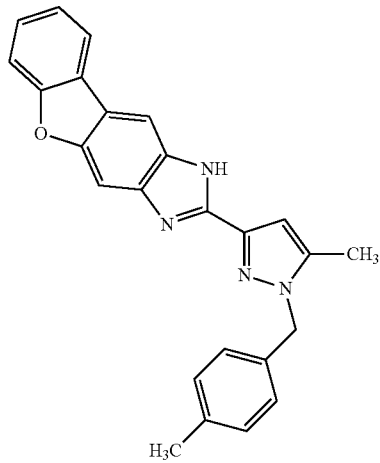 [SMILES: Cc1ccc(Cn2nc(-c3nc4cc5oc6ccccc6c5cc4[nH]3)cc2C)cc1] | 2.97 | 393.17 | A |

-continued
| Example Number | Structure | HPLC RT (min) | MS m/z (MH+) | Method |
|---|---|---|---|---|
| 53 | 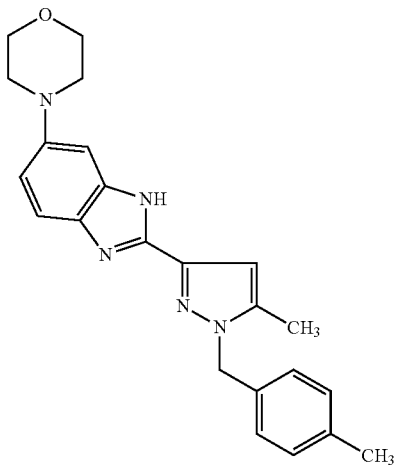 [SMILES: Cc1ccc(Cn2nc(-c3nc4ccc(N5CCOCC5)cc4[nH]3)cc2C)cc1] | 3.18 | 388.26 | B |
| 54 | 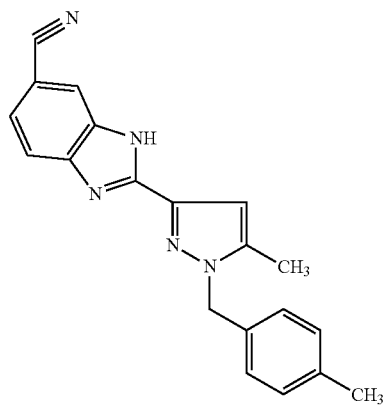 [SMILES: Cc1ccc(Cn2nc(-c3nc4ccc(C#N)cc4[nH]3)cc2C)cc1] | 3.01 | 328.05 | A |
| 55 | 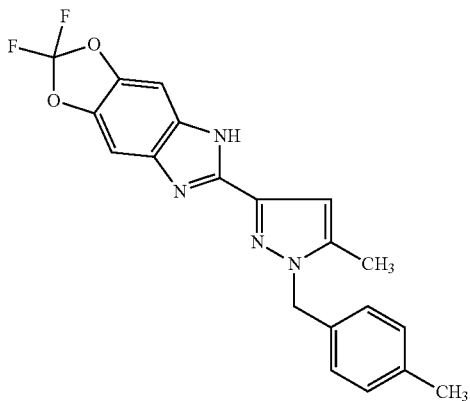 [SMILES: Cc1ccc(Cn2nc(-c3nc4cc5c(cc4[nH]3)OC(F)(F)O5)cc2C)cc1] | 3.05 | 383.13 | A |

| Example Number | Structure | HPLC RT (min) | MS m/z (MH+) | Method |
|---|---|---|---|---|
| 56 | 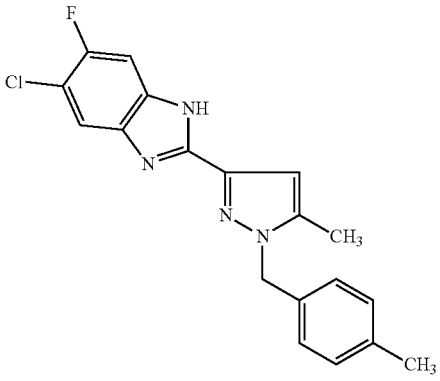 [SMILES: Cc1ccc(Cn2nc(-c3nc4cc(Cl)c(F)cc4[nH]3)cc2C)cc1] | 3.13 | 355.12 | A |
| 57 | 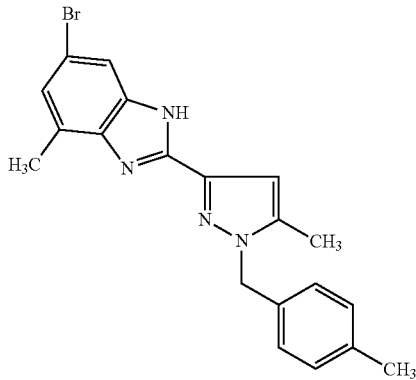 | 2.99 | 395.15 | B |
| 58 | 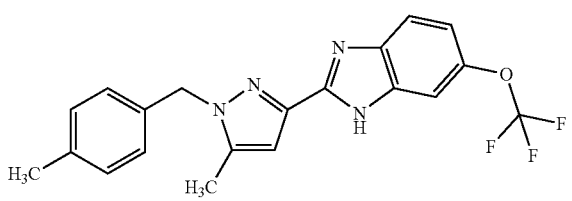 [SMILES: Cc1ccc(Cn2nc(-c3nc4ccc(OC(F)(F)F)cc4[nH]3)cc2C)cc1] | 4.40 | 387 | I |
$^1$H NMR (400 MHz, DMSO-d$_6$, δ/ppm): 12.97 (broad, 1H), 7.69 and 7.50 (2 × d, together 1H), 7.59 and 7.36 (2 × s, together 1H), 7.17 (d, 2H), 7.14 (d, 1H), 7.09 (d, 2H), 6.73 (s, 1H), 5.49 (s, 2H), 2.30 (s, 3H), 2.28 (s, 3H).

Example 59

Preparation of 6-(4-Fluorophenyl)-2-[5-methyl-1-(4-methylbenzyl)-1H-pyrazol-3-yl]-1H-benzimidazole

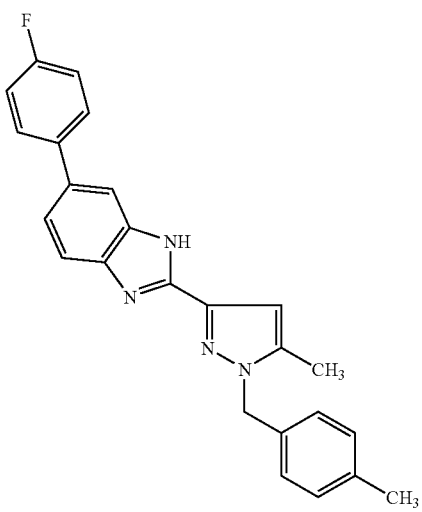 [SMILES: Cc1ccc(Cn2nc(-c3nc4ccc(-c5ccc(F)cc5)cc4[nH]3)cc2C)cc1]

Step 1: Preparation of 6-Bromo-2-[5-methyl-1-(4-methylbenzyl)-1H-pyrazol-3-yl]-1-{[2-(trimethylsilyl)ethoxy]methyl}-1H-benzimidazole

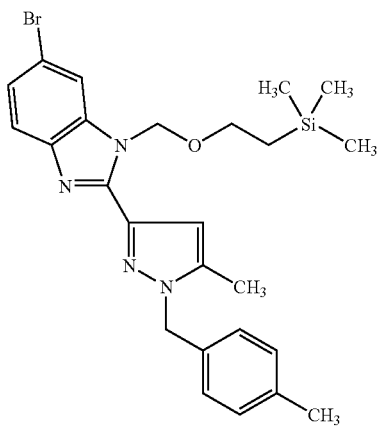 [SMILES: Cc1ccc(Cn2nc(-c3nc4ccc(Br)cc4n3COCC[Si](C)(C)C)cc2C)cc1]

To a solution of 6-bromo-2-[5-methyl-1-(4-methylbenzyl)-1H-pyrazol-3-yl]-1H-benzimidazole (Example 37, 600 mg, 1.57 mmol) in dichloromethane (20 mL) were added diisopropylethylamine (0.82 mL, 4.72 mmol) and 2-(trimethylsilyl)ethoxymethyl chloride (0.36 mL, 2.36 mmol) and the resulting mixture was stirred at rt for 16 h. Water was then added and the mixture was extracted with dichloromethane (1×50 mL), dried over Na$_2$SO$_4$, filtered and concentrated to dryness. The residue was then purified with an ISCO CombiFlash Companion using gradient elution from 0% to 30% EtOAc in hexanes to afford the title compound as a white solid (560 mg, 70%, mixture of two regioisomers): Isomer 1 (less polar): $^1$H NMR (300 MHz, DMSO-d$_6$) δ 8.05 (d, 1H), 7.78 (d, 1H), 7.60-7.63 (dd, 1H), 7.31-7.36 (m, 4H), 6.95 (s, 1H), 6.34 (s, 2H), 5.57 (s, 2H), 3.61 (t, 2H), 2.50 (s, 3H), 2.46 (s, 3H), 0.91 (t, 2H), 0.00 (s, 9H); ES-MS m/z 512.21, HPLC RT (Method C) 4.05 min. Isomer 2 (more polar): $^1$H NMR (300 MHz, DMSO-d$_6$) δ 8.05 (d, 1H), 7.79 (d, 1H), 7.59-7.62 (dd, 1H), 7.31-7.34 (m, 4H), 6.94 (s, 1H), 6.35 (s, 2H), 5.57 (s, 2H), 3.61 (t, 2H), 2.50 (s, 3H), 2.47 (s, 3H), 0.92 (t, 2H), 0.00 (s, 9H); ES-MS m/z 512.11, HPLC RT (Method B) 4.03 min.

Step 2: Preparation of 6-(4-Fluorophenyl)-2-[5-methyl-1-(4-methylbenzyl)-1H-pyrazol-3-yl]-1H-benzimidazole

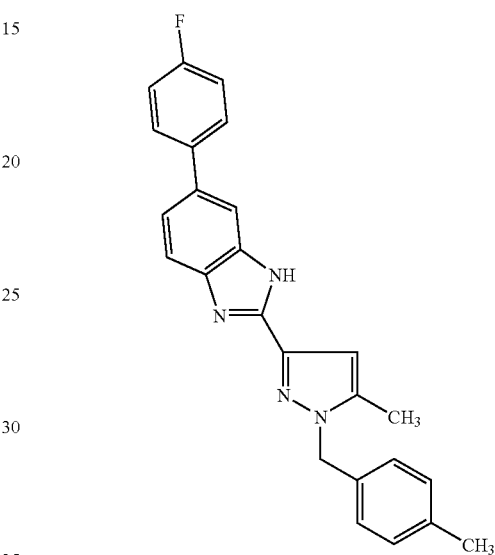

To a solution of 6-bromo-2-[5-methyl-1-(4-methylbenzyl)-1H-pyrazol-3-yl]-1-{[2-(trimethylsilyl)ethoxy]methyl}-1H-benzimidazole (Step 1, 150 mg, 0.29 mmol) in dioxane (5 mL) was added (4-fluorophenyl)boronic acid (49 mg, 0.35 mmol) followed by sodium carbonate solution (2.0 M aq., 0.44 mL, 0.88 mmol), and the resultant mixture was freed from oxygen by bubbling a gentle stream of nitrogen through the solution for 10 min. Tetrakis(triphenylphosphine)palladium(0) (34 mg, 0.03 mmol) was then added and the mixture was refluxed for 5 hr. After being cooled to rt, the mixture was diluted with ethyl acetate (50 mL) and washed with water (1×25 mL). The combined organics were dried (Na$_2$SO$_4$), filtered, and concentrated under reduced pressure. The resulting crude material was suspended in dichloromethane (2 mL), TFA (2 mL) was added, and the mixture was stirred at rt for 16 h. The volatiles were removed under reduced pressure and the crude product was purified by HPLC eluting with a gradient from 20% to 80% acetonitrile in water containing 0.1% TFA. The combined fractions were then diluted with ethyl acetate and washed with sat. NaHCO$_3$ solution (1×50 mL), dried (Na$_2$SO$_4$), filtered, and concentrated under reduced pressure to afford the title compound as a light yellow solid (44 mg, 38%): $^1$H NMR (300 MHz, CD$_3$OD) δ 7.75 (bs, 1H), 7.63-7.69 (m, 3H), 7.52 (dd, 1H), 7.11-7.20 (m, 6H), 6.78 (s, 1H), 5.40 (s, 2H), 2.30 (s, 6H); ES-MS m/z 397.22, HPLC RT (Method B) 3.21 min.

By using the method described above for Example 59, and by substituting the appropriate starting materials, Examples 60-64 found in the table below were similarly prepared.

| Example Number | Structure | HPLC RT (min) | MS m/z (MH+) | Method |
|---|---|---|---|---|
| 60 | 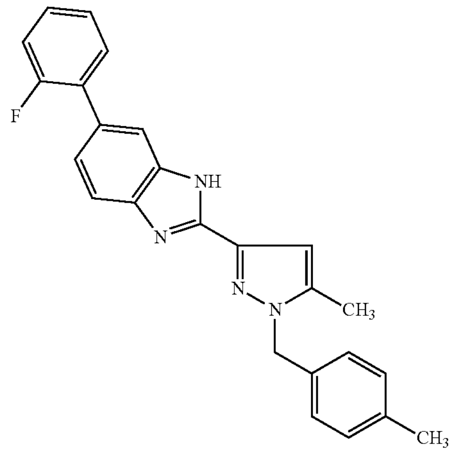 [SMILES: Cc1ccc(Cn2nc(-c3nc4ccc(-c5ccccc5F)cc4[nH]3)cc2C)cc1] | 2.96 | 397.14 | A |
| 61 | 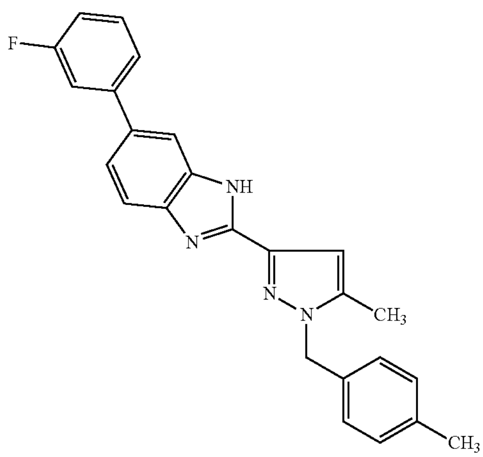 [SMILES: Cc1ccc(Cn2nc(-c3nc4ccc(-c5cccc(F)c5)cc4[nH]3)cc2C)cc1] | 3.18 | 397.24 | B |
| 62 | 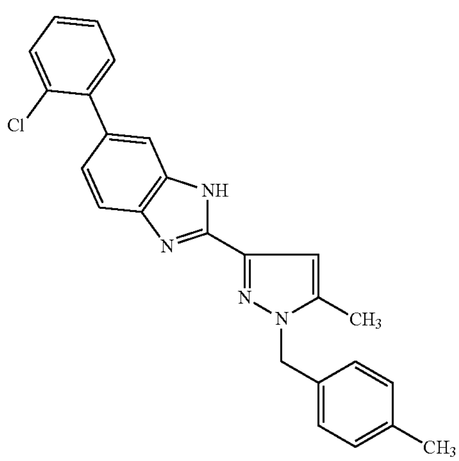 [SMILES: Cc1ccc(Cn2nc(-c3nc4ccc(-c5ccccc5Cl)cc4[nH]3)cc2C)cc1] | 3.20 | 413.30 | B |

| Example Number | Structure | HPLC RT (min) | MS m/z (MH+) | Method |
|---|---|---|---|---|
| 63 | 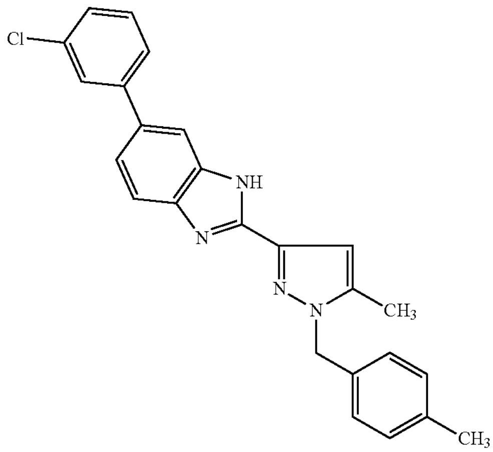 [SMILES: Cc1ccc(Cn2nc(-c3nc4ccc(-c5cccc(Cl)c5)cc4[nH]3)cc2C)cc1] | 3.23 | 413.25 | B |
| 64 | 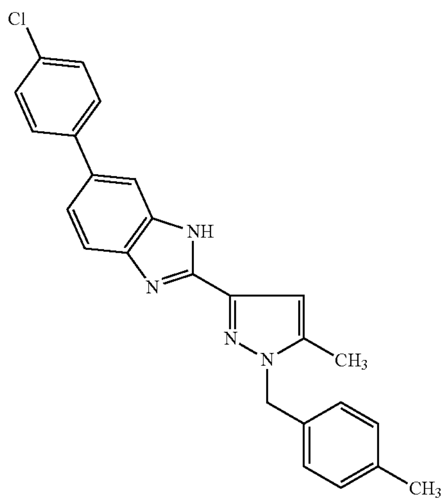 [SMILES: Cc1ccc(Cn2nc(-c3nc4ccc(-c5ccc(Cl)cc5)cc4[nH]3)cc2C)cc1] | 3.24 | 413.23 | B |

Example 65

Preparation of 5-Methyl-1-(4-methylbenzyl)-3-{4-[4-(trifluoromethoxy)phenyl]-1H-imidazol-2-yl}-1H-pyrazole

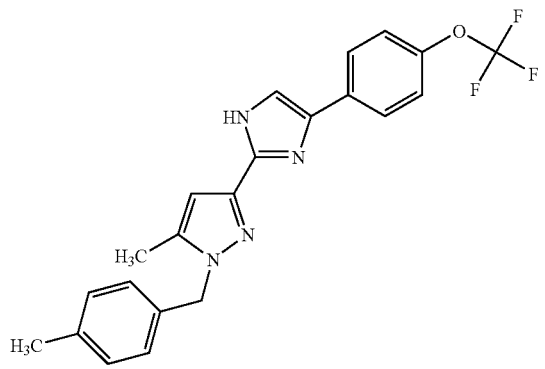 [SMILES: Cc1ccc(Cn2nc(-c3nc(-c4ccc(OC(F)(F)F)cc4)c[nH]3)cc2C)cc1]

To a solution of 5-methyl-1-(4-methylbenzyl)-1H-pyrazole-3-carboxylic acid (Intermediate B, 150 mg, 0.65 mmol) in ethanol (4 mL) was added cesium carbonate (212 mg, 0.65 mmol). The mixture was stirred for 30 min at rt, and then evaporated under reduced pressure. To a solution of the resultant salt in DMF (8 mL) was added 2-bromo-1-[4-(trifluoromethoxy)phenyl]ethanone (184 mg, 0.65 mmol). The mixture was stirred for 2 h at rt, and was concentrated under reduced pressure. The residue was suspended in ethyl acetate (10 mL), the mixture was filtered, and the solid washed thoroughly with ethyl acetate. The filtrate was concentrated under reduced pressure, the crude material was dissolved in xylene (15 mL), and ammonium acetate (502 mg, 6.5 mmol) was added. The resultant mixture was heated at reflux for 2 h in a flask fitted with a Dean-Stark trap. After being cooled to rt, the mixture was diluted with water, and the aqueous phase was extracted with ethyl acetate (1×50 mL), dried (Na$_2$SO$_4$), and the crude material was purified with an ISCO CombiFlash Companion using gradient elution from 0% to 50% EtOAc in hexanes to afford the title compound as a yellow solid (140 mg, 52%): $^1$H NMR (300 MHz, DMSO-d$_6$) δ 12.53 (s, 1H), 7.88 (d, 2H), 7.64 (s, 1H), 7.29 (d, 2H), 7.14 (d, 2H), 7.01 (d, 2H), 6.52 (s, 1H), 5.30 (s, 2H), 2.24 (s, 3H), 2.23 (s, 3H); ES-MS m/z 413.22, HPLC RT (Method B) 3.13 min.

By using the method described above for Example 65, and by substituting the appropriate starting materials, Examples 66-68 found in the table below were similarly prepared.

| Example Number | Structure | HPLC RT (min) | MS m/z (MH+) | Method |
|---|---|---|---|---|
| 66 | 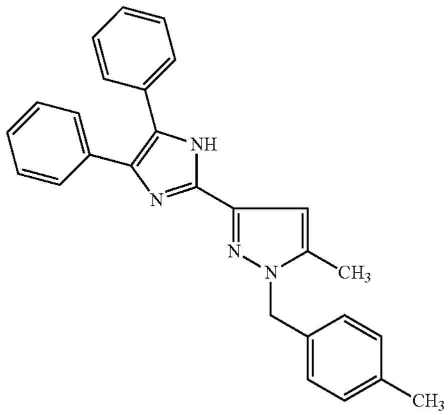 [SMILES: Cc1ccc(Cn2nc(-c3nc(-c4ccccc4)c(-c4ccccc4)[nH]3)cc2C)cc1] | 2.94 | 405.19 | A |
| 67 | 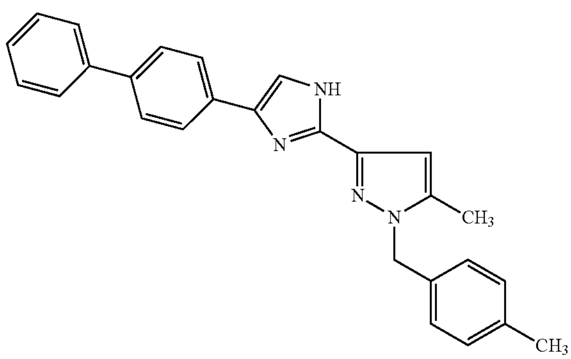 [SMILES: Cc1ccc(Cn2nc(-c3nc(-c4ccc(-c5ccccc5)cc4)c[nH]3)cc2C)cc1] | 3.01 | 405.16 | A |
| 68 | 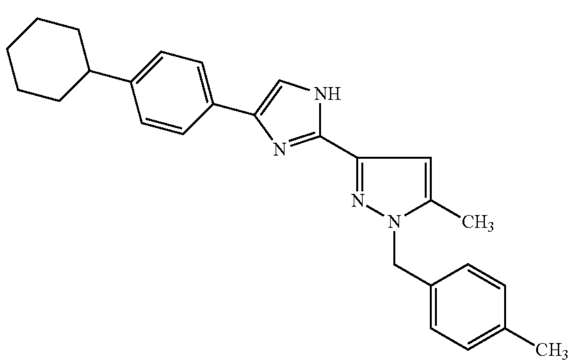 [SMILES: Cc1ccc(Cn2nc(-c3nc(-c4ccc(C5CCCCC5)cc4)c[nH]3)cc2C)cc1] | 3.28 | 411.22 | A |

Example 69

Preparation of 2-[5-Methyl-1-(4-methylbenzyl)-1H-pyrazol-3-yl]-4-phenyl-4,5-dihydro-1,3-oxazole

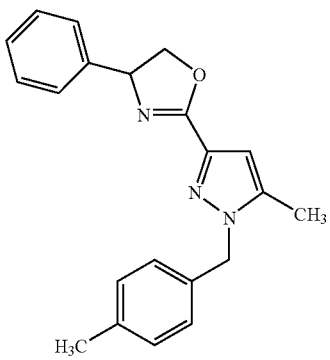 [SMILES: Cc1ccc(Cn2nc(C3=NC(c4ccccc4)CO3)cc2C)cc1]

Step 1: Preparation of N-[(1R)-2-Hydroxy-1-phenylethyl]-5-methyl-1-(4-methylbenzyl)-1H-pyrazole-3-carboxamide

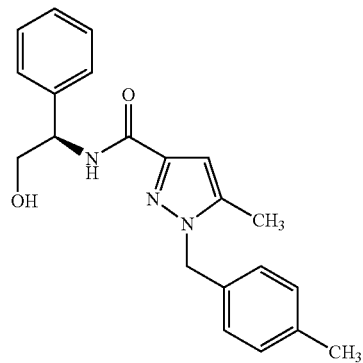 [SMILES: Cc1ccc(Cn2nc(C(=O)N[C@@H](CO)c3ccccc3)cc2C)cc1]

To a solution of 5-methyl-1-(4-methylbenzyl)-1H-pyrazole-3-carboxylic acid (Intermediate B, 250 mg, 1.08 mmol) in DMF (5 mL) was added O-(7-Azabenzotriazol-1-yl)-N,N,N',N'-tetramethyluronium $PF_6$ (619 mg, 1.63 mmol), and the mixture was stirred at rt for 30 min. To this reaction mixture was then added (D)-(−)-2-phenylglycinol (198 mg, 2.17 mmol) in DMF (5 mL) followed by triethylamine (1.21 mL, 8.69 mmol), and the mixture was stirred at rt for 16 h. Water (10 mL) was added, and the mixture was extracted with ethyl acetate (1×25 mL), dried ($Na_2SO_4$), filtered, and concentrated to dryness. The crude material was purified with an ISCO CombiFlash Companion using gradient elution from 20% to 100% EtOAc in hexanes to afford the title compound as a white solid (370 mg, 97%): $^1$H NMR (300 MHz, DMSO-$d_6$) δ 8.14 (d, 1H), 7.19-7.34 (m, 5H), 7.12 (d, 2H), 6.98 (d, 2H), 6.44 (s, 1H), 5.32 (s, 2H), 4.93-4.96 (m, 2H), 3.64-3.68 (m, 2H), 2.25 (s, 3H), 2.17 (s, 3H); ES-MS m/z 350.11, HPLC RT (Method B) 3.32 min.

Step 2: Preparation of 2-[5-Methyl-1-(4-methylbenzyl)-1H-pyrazol-3-yl]-4-phenyl-4,5-dihydro-1,3-oxazole

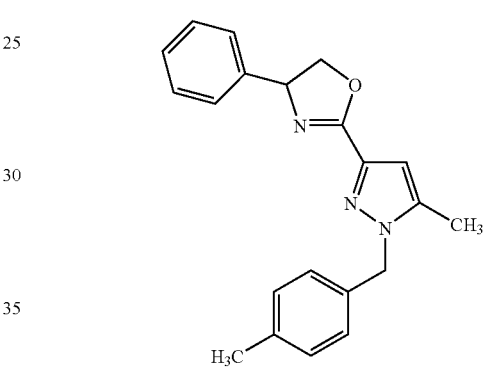

A mixture of N-[(1R)-2-hydroxy-1-phenylethyl]-5-methyl-1-(4-methylbenzyl)-1H-pyrazole-3-carboxamide (Step 1, 350 mg, 1.0 mmol) and carbomethoxysulfamoyltriethylammonium hydroxide inner salt (Burgess' reagent, 310 mg, 1.03 mmol) in THF (20 mL) was heated at 70° C. for 1 h. After being cooled to rt, the mixture was diluted with water (10 mL), and the organic phase was extracted with ethyl acetate (1×25 mL), washed with brine (1×25 mL), dried ($Na_2SO_4$), filtered, and concentrated to dryness. The crude was then purified with an ISCO CombiFlash Companion using gradient elution from 0% to 20% EtOAc in hexanes to afford the title compound as a yellow oil (230 mg, 69%): $^1$H NMR (300 MHz, DMSO-$d_6$) δ 7.31-7.34 (m, 2H), 7.24-7.28 (m, 3H), 7.12 (d, 2H), 7.01 (d, 2H), 6.52 (s, 1H), 5.27-5.32 (m, 1H), 5.29 (s, 2H), 4.69-4.75 (m, 1H), 4.06-4.12 (m, 1H), 2.25 (s, 3H), 2.22 (s, 3H); ES-MS m/z 332.20, HPLC RT (Method B) 3.20 min.

By using the method described above for Example 69, and by substituting the appropriate starting materials, Examples 70-73 found in the table below were similarly prepared.

| Example Number | Structure | HPLC RT (min) | MS m/z (MH+) | Method |
|---|---|---|---|---|
| 70 | 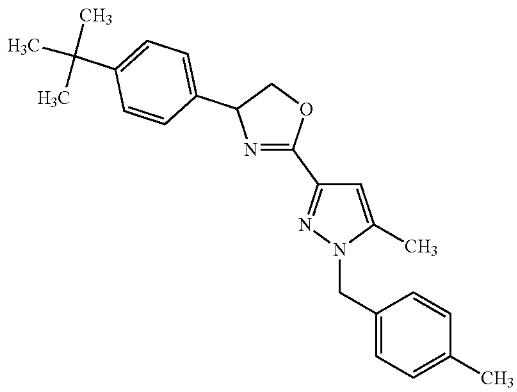 [SMILES: Cc1ccc(Cn2nc(C3=NC(c4ccc(C(C)(C)C)cc4)CO3)cc2C)cc1] | 3.84 | 388.22 | B |

¹H NMR (400 MHz, DMSO-d₆, δ/ppm): 7.37 (d, 2H), 7.19 (d, 2H), 7.16 (d, 2H), 7.03 (d, 2H), 6.52 (s, 1H), 5.31 (s, 2H), 5.28 (dd, 1H), 4.71 (dd, 1H), 4.11 (dd, 1H), 2.28 (s, 3H), 2.23 (s, 3H), 1.27 (s, 9H).

| 71 | | 2.57 | 298.49 | A |
| 72 | | 3.13 | 380.51 | A |
| 73 | | 2.35 | 416 | E |

¹H NMR (400 MHz, DMSO-d₆, δ/ppm): 7.41 (d, 2H), 7.35 (d, 2H), 7.16 (d, 2H), 7.04 (d, 2H), 6.55 (s, 1H), 5.39 (dd, 1H), 5.32 (s, 2H), 4.75 (dd, 1H), 4.12 (dd, 1H), 2.28 (s, 3H), 2.24 (s, 3H)

Example 74

Preparation of 2-[5-Methyl-1-(4-methylbenzyl)-1H-pyrazol-3-yl]-4-phenyl-1,3-oxazole

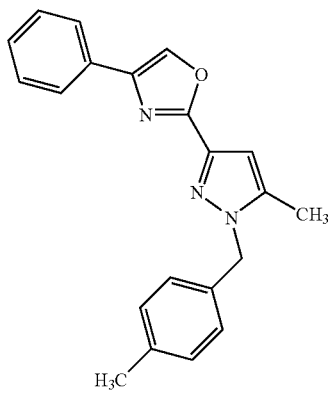 [SMILES: Cc1ccc(Cn2nc(-c3nc(-c4ccccc4)co3)cc2C)cc1]

A solution of 2-[5-methyl-1-(4-methylbenzyl)-1H-pyrazol-3-yl]-4-phenyl-4,5-dihydro-1,3-oxazole (Example 69, 100 mg, 0.3 mmol) in dioxane (10 mL) was treated with 2,3-dichloro-5,6-dicyano-1,4-benzoquinone (137 mg, 0.6 mmol), and the resultant mixture was heated at reflux for 16 h. After being cooled to rt, the mixture was diluted with water (10 mL), extracted with ethyl acetate (1×25 mL), washed with NaOH (0.5 N aq., 1×25 mL) and brine (1×25 mL), dried ($Na_2SO_4$), filtered, and concentrated to dryness. The crude material was purified by HPLC eluting with a gradient from 20% to 80% acetonitrile in water containing 0.1% TFA. The combined fractions were then diluted with ethyl acetate and washed with $NaHCO_3$ (sat. aq., 1×25 mL) dried ($Na_2SO_4$) and concentrated under reduced pressure to afford the title compound as a white solid (15 mg, 15%): $^1$H NMR (300 MHz, $CD_3OD$) δ 8.19 (s, 1H), 7.73 (d, 2H), 7.29-7.35 (m, 2H), 7.21-7.25 (m, 1H), 7.04 (d, 2H), 6.95 (d, 2H), 6.62 (s, 1H), 5.28 (s, 2H), 2.20 (s, 3H), 2.18 (s, 3H); ES-MS m/z 330.12, HPLC RT (Method B) 3.89 min.

By using the method described above for Example 74, and by substituting the appropriate starting materials, Examples 75 and 76 found in the table below were similarly prepared.

| Example Number | Structure | HPLC RT (min) | MS m/z (MH+) | Method |
|---|---|---|---|---|
| 75 | 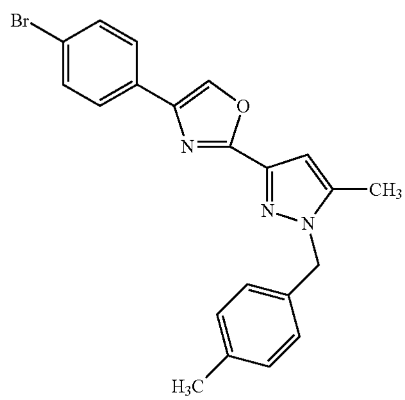 [SMILES: Cc1ccc(Cn2nc(-c3nc(-c4ccc(Br)cc4)co3)cc2C)cc1] | 4.17 | 408.09 | A |

$^1$H NMR (400 MHz, DMSO-$d_6$, δ/ppm): 8.69 (s, 1H), 7.79 (d, 2H), 7.65 (d, 2H), 7.17 (d, 2H), 7.08 (d, 2H), 6.68 (s, 1H), 5.36 (s, 2H), 2.29 (s, 3H), 2.27 (s, 3H).

| | | | | |
|---|---|---|---|---|
| 76 | | 4.59 | 440.26 | A |

Example 77

Preparation of 4-(4-tert-Butylphenyl)-2-[5-methyl-1-(4-methylbenzyl)-1H-pyrazol-3-yl]-1,3-oxazole

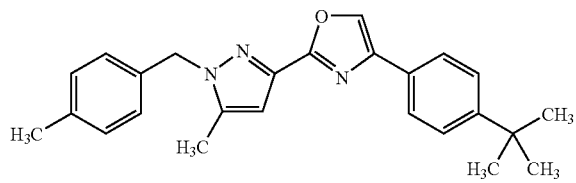 [SMILES: Cc1ccc(Cn2nc(-c3nc(-c4ccc(C(C)(C)C)cc4)co3)cc2C)cc1]

A solution of 4-(4-tert-butylphenyl)-2-[5-methyl-1-(4-methylbenzyl)-1H-pyrazol-3-yl]-4,5-dihydro-1,3-oxazole (Example 70, 100 mg, 0.26 mmol) in THF (2 mL) was treated with manganese dioxide (45 mg, 0.52 mmol), and the resultant mixture was stirred to reflux. Further portions of manganese dioxide (45 mg and 90 mg) were added after 2.5 and 4.5 h. After a total of 6.5 h, the mixture was cooled to rt, diluted with 2 ml THF and filtered over a pad of celite. The filtrate was concentrated in vacuo, re-disolved in dichloromethane and successively washed with aqueous HCl (1.0 N) and water, dried ($MgSO_4$), filtered, and concentrated to dryness. The crude material was purified by flash chromatography (silica) eluting with cyclohexane/ethyl acetate 2:1. The combined product fractions were then further purified by preparative HPLC to afford the title compound as a white solid (49 mg, 50%): $^1$H NMR (400 MHz, DMSO-$d_5$) δ 8.58 (s, 1H), 7.75 (d, 2H), 7.47 (d, 2H), 7.18 (d, 2H), 7.08 (d, 2H), 6.67 (s, 1H), 5.37 (s, 2H), 2.29 (s, 3H), 2.28 (s, 3H), 1.31 (s, 9H); ES-MS m/z 386, HPLC RT (Method E) 2.81 min.

By using the method described above for Example 77, and by substituting the appropriate starting materials, Example 78 found in the table below was similarly prepared.

phosphate (156 mg, 0.74 mmol), palladium(II) chloride (3.3 mg, 0.02 mmol) and 2-(dicyclohexylphosphino)-1,1'-biphenyl (9.7 mg, 0.03 mmol) in 1,2-dimethoxyethane (3 ml) was heated to reflux for 18 h. After cooling to rt, the mixture was filtered over a pad of celite. The filtrate was diluted with ethyl acetate and successively washed with 0.1 N aqueous HCl and water. The organic layer was dried ($MgSO_4$), filtered and concentrated to dryness. The crude material was purified by preparative HPLC. The combined product fractions were then further purified by flash chromatography (silica) eluting with cyclohexane/ethyl acetate 5:1 to afford the title compound as a white solid (17 mg, 11%): $^1$H NMR (400 MHz, DMSO-$d_6$) δ 8.42 (s, 1H), 7.63 (d, 2H), 7.17 (d, 2H), 7.08 (d, 2H), 6.98 (d, 2H), 6.65 (s, 1H), 5.35 (s, 2H), 3.19 (m, 4H), 2.28 (s, 6H), 1.64-1.52 (m, 6H); ES-MS m/z 413, HPLC RT (Method D) 2.65 min.

Example 80

Preparation of 4-(4-Cyclohex-1-en-1-ylphenyl)-2-[5-methyl-1-(4-methylbenzyl)-1H-pyrazol-3-yl]-1,3-oxazole

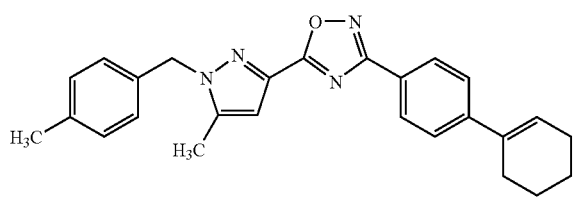 [SMILES: Cc1ccc(Cn2nc(-c3nc(-c4ccc(C5=CCCCC5)cc4)no3)cc2C)cc1]

| Example Number | Structure | HPLC RT (min) | MS m/z (MH+) | Method |
|---|---|---|---|---|
| 78 | 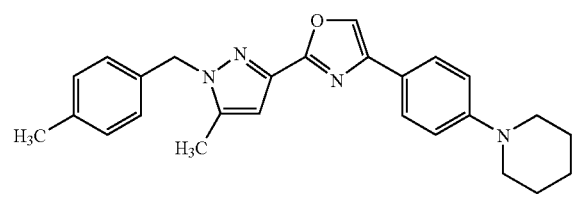 $^1$H NMR (400 MHz, DMSO-$d_6$, δ/ppm): 8.70 (s, 1H), 7.95 (d, 2H), 7.46 (d, 2H), 7.17 (d, 2H), 7.08 (d, 2H), 6.69 (s, 1H), 5.37 (s, 2H), 2.29 (s, 3H), 2.28 (s, 3H). | 2.89 | 414 | F |

Example 79

Preparation of 1-(4-{2-[5-Methyl-1-(4-methylbenzyl)-1H-pyrazol-3-yl]-1,3-oxazol-4-yl}-phenyl)piperidine A mixture of 4-(4-bromophenyl)-2-[5-methyl-1-(4-methylbenzyl)-1H-pyrazol-3-yl]-1,3-oxazole (Example 75, 150 mg, 0.37 mmol), piperidine (44 μl, 0.44 mmol), potassium A mixture of 4-(4-bromophenyl)-2-[5-methyl-1-(4-methylbenzyl)-1H-pyrazol-3-yl]-1,3-oxazole (Example 75, 200 mg, 0.49 mmol), 2-cyclohex-1-en-1-yl-4,4,5,5-tetramethyl-1,3,2-dioxaborolane (158 μl, 0.74 mmol), sodium carbonate (0.49 ml, 2M aqueous solution, 0.98 mmol) and tetrakis(triphenylphosphino)palladium(0) (57 mg, 0.05 mmol) in 1,2-dimethoxyethane (3 ml) was heated to reflux for 18 h. After cooling to rt, the mixture was filtered over a pad of celite. The filtrate was diluted with ethyl acetate and successively washed with 0.1 N aqueous HCl and water. The organic layer was dried ($MgSO_4$), filtered and concentrated to dryness. The crude material was purified by preparative HPLC to afford the title compound as a white solid (115 mg, 57%): $^1$H NMR (400 MHz, DMSO-$d_6$) δ 8.60 (s, 1H), 7.78 (d, 2H), 7.49 (d, 2H), 7.17 (d, 2H), 7.08 (d, 2H), 6.67 (s, 1H), 6.23 (m, 1H), 5.37 (s, 2H), 2.41-2.37 (m, 2H), 2.28 (s, 3H), 2.27 (s, 3H), 2.22-2.17 (m, 2H), 1.77-1.70 (m, 2H), 1.64-1.59 (m, 2H); ES-MS m/z 410, HPLC RT (Method D) 3.48 min.

Example 81

Preparation of 4-(4-Cyclohex-1-ylphenyl)-2-[5-methyl-1-(4-methylbenzyl)-1H-pyrazol-3-yl]-1,3-oxazole

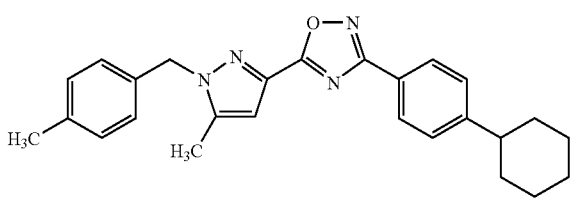

A solution of 4-(4-cyclohex-1-en-1-ylphenyl)-2-[5-methyl-1-(4-methylbenzyl)-1H-pyrazol-3-yl]-1,3-oxazole (Example 80, 30 mg, 0.073 mmol) in ethanol (1.5 ml) was hydrogenated in a continuous-flow reactor (H-cube, Thales Nano, Hungary) at an hydrogen pressure of 1 bar at rt with a flow rate of 1 ml/min using palladium (10% on charcoal) as a stationary phase. After evaporation of the solvent, the crude material was purified by preparative HPLC to afford the title compound as a white solid (13 mg, 43%): $^1$H NMR (400 MHz, DMSO-$d_6$) δ 8.57 (s, 1H), 7.72 (d, 2H), 7.29 (d, 2H), 7.17 (d, 2H), 7.07 (d, 2H), 6.67 (s, 1H), 5.36 (s, 2H), 3.51-3.40 (m, 1H), 2.29 (s, 3H), 2.28 (s, 3H), 1.82-1.69 (m, 4H), 1.48-1.22 (m, 6H); ES-MS m/z 412, HPLC RT (Method D) 3.52 min.

By using the method described above for Example 1, and by substituting the appropriate starting materials, Examples 82-114 found in the table below were similarly prepared.

| Example Number | Structure | HPLC RT (min) | MS m/z (MH+) | Method |
|---|---|---|---|---|
| 82 | 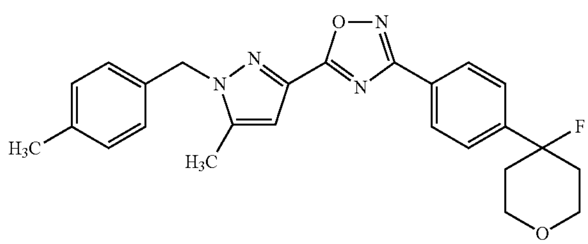 [SMILES: Cc1ccc(Cn2nc(-c3nc(-c4ccc(C5(F)CCOCC5)cc4)no3)cc2C)cc1] | 5.29 | 433 | I |

$^1$H NMR (400 MHz, CDCl$_3$, δ/ppm): 8.23 (d, 2H), 7.52 (d, 2H), 7.13 (d, 2H), 7.08 (d, 2H), 6.80 (s, 1H), 5.41 (s, 2H), 3.99-3.87 (m, 4H), 2.32 (s, 3H), 2.27 (s, 3H), 2.29-2.11 (m, 2H), 1.97-1.91 (m, 2H).

| 83 | | 2.43 | 445 | E |

$^1$H NMR (500 MHz, CDCl$_3$, δ/ppm): 8.21 (d, 2H), 7.52 (d, 2H), 7.13 (d, 2H), 7.07 (d, 2H), 6.80 (s, 1H), 5.42 (s, 2H), 3.92-3.83 (m, 4H), 3.02 (s, 3H), 2.32 (s, 3H), 2.26 (s, 3H), 2.20-2.04 (m, 2H), 2.01-1.98 (m, 2H).

| 84 | | 3.00 | 401 | E |

$^1$H NMR (500 MHz, CDCl$_3$, δ/ppm): 8.13 (d, 2H), 7.50 (d, 2H), 7.13 (d, 2H), 7.06 (d, 2H), 6.83 (s, 1H), 5.41 (s, 2H), 2.57 (quart, 2H), 2.32 (s, 3H), 1.37 (s, 9H), 1.24 (t, 3H).

-continued
| Example Number | Structure | HPLC RT (min) | MS m/z (MH+) | Method |
|---|---|---|---|---|
| 85 | 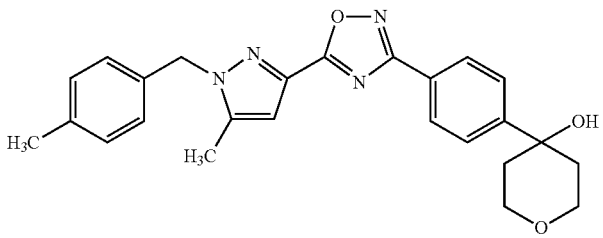 [SMILES: Cc1ccc(Cn2nc(-c3nc(-c4ccc(C5(O)CCOCC5)cc4)no3)cc2C)cc1] ¹H NMR (500 MHz, CDCl₃, δ/ppm): 8.21 (d, 2H), 7.62 (d, 2H), 7.13 (d, 2H), 7.07 (d, 2H), 6.80 (s, 1H), 5.40 (s, 2H), 3.99-3.89 (m, 4H), 2.33 (s, 3H), 2.27 (s, 3H), 2.28-2.19 (m, 2H), 1.73-1.70 (m, 2H), 1.68 (s, 1H). | 2.50 | 431 | D |
| 86 | 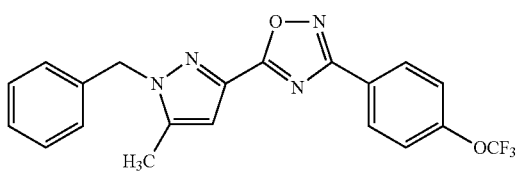 [SMILES: Cc1cc(-c2nc(-c3ccc(OC(F)(F)F)cc3)no2)nn1Cc1ccccc1] ¹H NMR (400 MHz, CDCl₃, δ/ppm): 8.26 (d, 2H), 7.35-7.30 (m, 5H), 7.17 (d, 2H), 6.80 (s, 1H), 5.47 (s, 2H), 2.27 (s, 3H). | 5.30 | 401 | J |
| 87 | 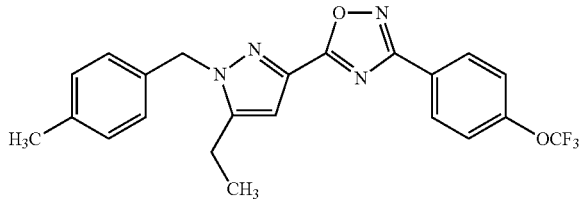 [SMILES: CCc1cc(-c2nc(-c3ccc(OC(F)(F)F)cc3)no2)nn1Cc1ccc(C)cc1] ¹H NMR (400 MHz, CDCl₃, δ/ppm): 8.26 (d, 2H), 7.33 (d, 2H), 7.13 (d, 2H), 7.06 (d, 2H), 6.82 (s, 1H), 5.42 (s, 2H), 2.57 (quart, 2H), 2.32 (s, 3H), 1.25 (t, 3H). | 2.87 | 429 | E |
| 88 | 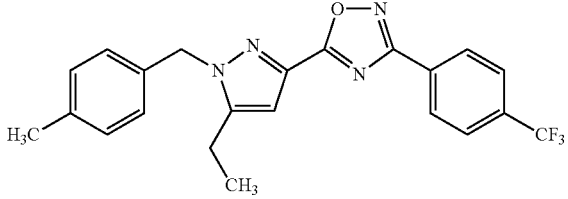 [SMILES: CCc1cc(-c2nc(-c3ccc(C(F)(F)F)cc3)no2)nn1Cc1ccc(C)cc1] ¹H NMR (400 MHz, CDCl₃, δ/ppm): 8.35 (d, 2H), 7.76 (d, 2H), 7.13 (d, 2H), 7.07 (d, 2H), 6.84 (s, 1H), 5.42 (s, 2H), 2.58 (quart, 2H), 2.32 (s, 3H), 1.25 (t, 3H). | 2.84 | 413 | E |
| 89 | 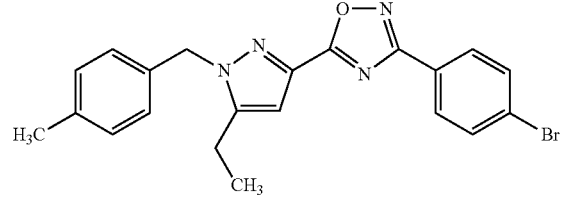 [SMILES: CCc1cc(-c2nc(-c3ccc(Br)cc3)no2)nn1Cc1ccc(C)cc1] ¹H NMR (400 MHz, CDCl₃, δ/ppm): 8.09 (d, 2H), 7.73 (d, 2H), 7.13 (d, 2H), 7.06 (d, 2H), 6.82 (s, 1H), 5.41 (s, 2H), 2.58 (quart, 2H), 2.32 (s, 3H), 1.25 (t, 3H). | 2.84 | 423/425 | E |

| Example Number | Structure | HPLC RT (min) | MS m/z (MH+) | Method |
|---|---|---|---|---|
| 90 | 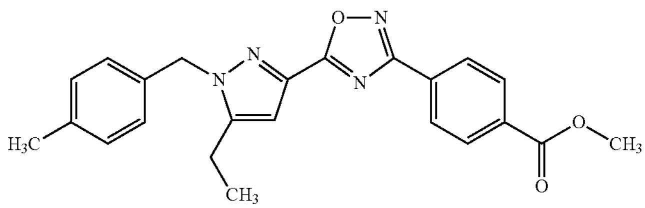 | 2.62 | 403 | E |

¹H NMR (400 MHz, CDCl₃, δ/ppm): 8.30 (d, 2H), 8.17 (d, 2H), 7.13 (d, 2H), 7.07 (d, 2H), 6.83 (s, 1H), 5.42 (s, 2H), 3.97 (s, 3H), 2.58 (quart, 2H), 2.32 (s, 3H), 1.25 (t, 3H).

| 91 | | 1.75 | 443 | K |

¹H NMR (400 MHz, CDCl₃, δ/ppm): 8.27 (d, 2H), 7.33 (d, 2H), 7.12 (d, 2H), 7.07 (d, 2H), 5.42 (s, 2H), 2.61 (quart, 2H), 2.37 (s, 3H), 2.31 (s, 3H), 1.00 (t, 3H).

| 92 | | 2.62 | 390 | E |

¹H NMR (400 MHz, CDCl₃, δ/ppm): 8.42 (d, 2H), 8.37 (d, 2H), 7.13 (d, 2H), 7.07 (d, 2H), 6.86 (s, 1H), 5.41 (s, 2H), 2.59 (quart, 2H), 2.32 (s, 3H), 1.26 (t, 3H).

| 93 | | 2.78 | 437 | D |

¹H NMR (400 MHz, DMSO-d₆, δ/ppm): 8.25 (d, 2H), 8.09 (d, 2H), 7.18 (d, 2H), 7.12 (d, 2H), 6.92 (s, 1H), 5.43 (s, 2H), 3.56-3.48 (m, 1H), 2.32 (s, 3H), 2.29 (s, 3H), 1.21-1.19 (d, 6H).

| 94 | | 2.42 | 410 | D |

¹H NMR (400 MHz, DMSO-d₆, δ/ppm): 8.27 (d, 2H), 8.02 (d, 2H), 7.54 (s, 2H), 7.18 (d, 2H), 7.12 (d, 2H), 6.92 (s, 1H), 5.43 (s, 2H), 2.32 (s, 3H), 2.29 (s, 3H).

| Example Number | Structure | HPLC RT (min) | MS m/z (MH+) | Method |
|---|---|---|---|---|
| 95 | 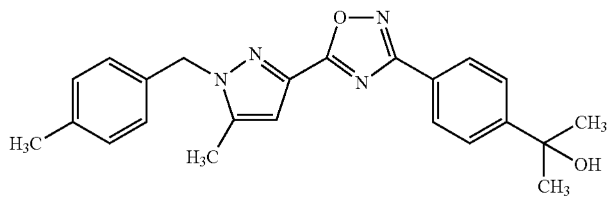 [SMILES: Cc1ccc(Cn2nc(-c3nc(-c4ccc(C(C)(C)O)cc4)no3)cc2C)cc1] | 2.20 | 389 | E |

¹H NMR (400 MHz, CDCl₃, δ/ppm): 8.18 (d, 2H), 7.61 (d, 2H), 7.13 (d, 2H), 7.07 (d, 2H), 6.80 (s, 1H), 5.40 (s, 2H), 2.32 (s, 3H), 2.27 (s, 3H), 1.82 (s, 1H), 1.61 (s, 6H).

| 96 | | 1.59 | 463 | K |

¹H NMR (400 MHz, DMSO-d₆, δ/ppm): 8.50 (d, 2H), 8.37 (d, 2H), 7.18 (d, 2H), 7.11 (d, 2H), 6.95 (s, 1H), 5.45 (s, 2H), 2.32 (s, 3H), 2.28 (s, 3H).

| 97 | | 1.54 | 377 | K |

¹H NMR (400 MHz, DMSO-d₆, δ/ppm): 7.98 (d, 2H), 7.43 (d, 2H), 7.17 (d, 2H), 7.11 (d, 2H), 6.89 (s, 1H), 5.42 (s, 2H), 2.52 (s, 3H), 2.31 (s, 3H), 2.28 (s, 3H).

| 98 | | 2.93 | 560 | E |

¹H NMR (400 MHz, CDCl₃, δ/ppm): 8.16 (d, 2H), 7.40 (d, 2H), 7.12 (d, 2H), 7.08 (d, 2H), 6.79 (s, 1H), 5.40 (s, 2H), 4.82 (s, 2H), 2.32 (s, 3H), 2.28 (s, 3H), 1.46 (s, 18H).

| 99 | | 1.30 | 409 | K |

¹H NMR (400 MHz, CDCl₃, δ/ppm): 8.32 (d, 2H), 8.14 (d, 2H), 7.17 (d, 2H), 7.11 (d, 2H), 6.92 (s, 1H), 5.45 (s, 2H), 3.30 (s, 3H), 2.32 (s, 3H), 2.28 (s, 3H).

-continued

| Example Number | Structure | HPLC RT (min) | MS m/z (MH+) | Method |
|---|---|---|---|---|
| 100 | 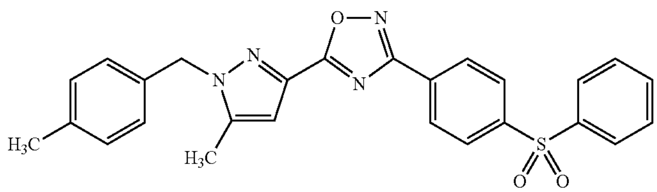 [SMILES: Cc1ccc(Cn2nc(-c3nc(-c4ccc(S(=O)(=O)c5ccccc5)cc4)no3)cc2C)cc1] | 3.31 | 439 | D |

¹H NMR (400 MHz, DMSO-d₆, δ/ppm): 7.97 (d, 1H), 7.92 (s, 1H), 7.62-7.56 (m, 1H), 7.52 (d, 1H), 7.49-7.36 (m, 5H), 7.18 (d, 2H), 7.11 (d, 2H), 6.90 (s, 1H), 5.42 (s, 2H), 2.32 (s, 3H), 2.28 (s, 3H).

| 101 | | 1.53 | 446 | K |

¹H NMR (400 MHz, CDCl₃, δ/ppm): 8.14 (d, 2H), 7.49 (d, 2H), 7.13 (d, 2H), 7.08 (d, 2H), 6.78 (s, 1H), 6.62 (s, 1H), 5.40 (s, 2H), 2.32 (s, 3H), 2.28 (s, 3H), 1.55 (s, 9H).

| 102 | | 2.94 | 430 | D |

¹H NMR (400 MHz, CDCl₃, δ/ppm): 8.19 (d, 2H), 7.60 (d, 2H), 7.12 (d, 2H), 7.08 (d, 2H), 6.79 (s, 1H), 5.40 (s, 2H), 4.20-4.00 (m, 2H), 3.32-3.20 (m, 2H), 2.32 (s, 3H), 2.27 (s, 3H), 2.10-2.00 (m, 2H), 1.80-1.72 (m, 3H), 1.49 (s, 9H).

| 103 | | 3.08 | 391 | D |

¹H NMR (400 MHz, CDCl₃, δ/ppm): 8.20 (d, 2H), 7.50 (d, 2H), 7.12 (d, 2H), 7.08 (d, 2H), 6.79 (s, 1H), 5.41 (s, 2H), 2.32 (s, 3H), 2.27 (s, 3H), 1.75 (s, 3H), 1.71 (s, 3H).

| 104 | | 2.86 | 445 | D |

¹H NMR (400 MHz, CDCl₃, δ/ppm): 8.20 (d, 2H), 7.48 (d, 2H), 7.13 (d, 2H), 7.08 (d, 2H), 6.79 (s, 1H), 5.41 (s, 2H), 4.62 (s, 2H), 4.01-3.96 (m, 2H), 3.65-3.60 (m, 1H), 3.50-3.41 (m, 2H), 2.32 (s, 3H), 2.27 (s, 3H), 2.00-1.92 (m, 2H), 1.72-1.62 (m, 2H).

| Example Number | Structure | HPLC RT (min) | MS m/z (MH+) | Method |
|---|---|---|---|---|
| 105 | 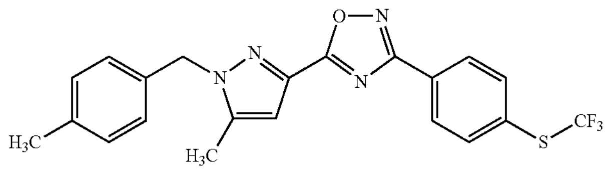 [SMILES: Cc1ccc(Cn2nc(-c3nc(-c4ccc(SC(F)(F)F)cc4)no3)cc2C)cc1] | 1.68 | 431 | K |

¹H NMR (400 MHz, DMSO-d₆, δ/ppm): 8.21 (d, 2H), 7.92 (d, 2H), 7.18 (d, 2H), 7.11 (d, 2H), 6.91 (s, 1H), 5.45 (s, 2H), 2.32 (s, 3H), 2.28 (s, 3H).

| 106 | | 2.74 | 544 | E |

¹H NMR (400 MHz, CDCl₃, δ/ppm): 8.19 (d, 2H), 7.46 (d, 2H), 7.12 (d, 2H), 7.08 (d, 2H), 6.79 (s, 1H), 5.40 (s, 2H), 4.62 (s, 2H), 3.82-3.72 (m, 2H), 3.62-3.56 (m, 1H), 3.16-3.08 (m, 2H), 2.32 (s, 3H), 2.27 (s, 3H), 1.92-1.84 (m, 2H), 1.67-1.56 (m, 2H), 1.46 (s, 9H).

| 107 | | 3.03 | 445 | D |

¹H NMR (400 MHz, CDCl₃, δ/ppm): 8.12 (d, 2H), 7.12 (d, 2H), 7.08 (d, 2H), 6.98 (d, 2H), 6.78 (s, 1H), 5.41 (s, 2H), 4.06-4.00 (dd, 2H), 3.87 (d, 2H), 3.50-3.42 (dd, 2H), 2.32 (s, 3H), 2.27 (s, 3H), 2.18-2.03 (m, 1H), 1.82-1.75 (d, 2H), 1.55-1.42 (m, 2H).

| 108 | | 2.88 | 544 | E |

¹H NMR (400 MHz, CDCl₃, δ/ppm): 8.12 (d, 2H), 7.12 (d, 2H), 7.07 (d, 2H), 6.97 (d, 2H), 6.78 (s, 1H), 5.41 (s, 2H), 4.25-4.10 (m, 2H), 3.87 (d, 2H), 2.82-2.70 (m, 2H), 2.32 (s, 3H), 2.27 (s, 3H), 2.05-1.92 (m, 1H), 1.88-1.81 (d, 2H), 1.48 (s, 9H), 1.35-1.22 (m, 2H).

| 109 | | 2.81 | 438 | D |

¹H NMR (400 MHz, DMSO-d₆, δ/ppm): 8.32 (d, 2H), 7.96 (d, 2H), 7.18 (d, 2H), 7.12 (d, 2H), 6.92 (s, 1H), 5.45 (s, 2H), 2.68 (s, 6H), 2.32 (s, 3H), 2.27 (s, 3H).

| Example Number | Structure | HPLC RT (min) | MS m/z (MH+) | Method |
|---|---|---|---|---|
| 110 | 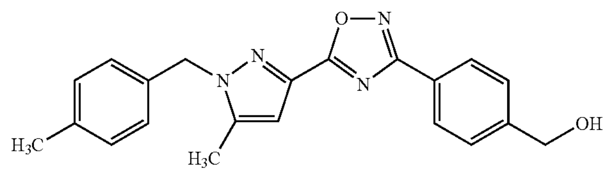 [SMILES: Cc1ccc(Cn2nc(-c3nc(-c4ccc(CO)cc4)no3)cc2C)cc1] | 2.47 | 361 | D |
| | ¹H NMR (400 MHz, DMSO-d₆, δ/ppm): 8.02 (d, 2H), 7.52 (d, 2H), 7.18 (d, 2H), 7.12 (d, 2H), 6.90 (s, 1H), 5.44 (s, 2H), 5.40-5.36 (t, 1H), 4.60 (d, 2H), 2.32 (s, 3H), 2.27 (s, 3H). | | | |
| 111 | 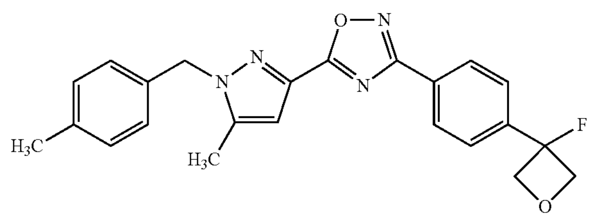 [SMILES: Cc1ccc(Cn2nc(-c3nc(-c4ccc(C5(F)COC5)cc4)no3)cc2C)cc1] | 2.83 | 405 | D |
| | ¹H NMR (400 MHz, DMSO-d₆, δ/ppm): 8.18 (d, 2H), 7.79 (d, 2H), 7.18 (d, 2H), 7.11 (d, 2H), 6.91 (s, 1H), 5.44 (s, 2H), 5.06-4.91 (m, 4H), 2.32 (s, 3H), 2.28 (s, 3H). | | | |
| 112 | 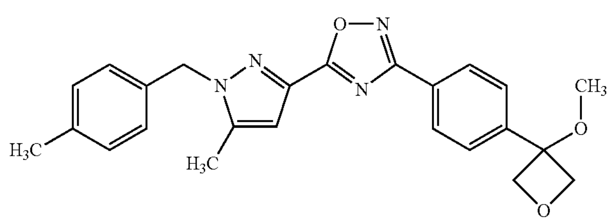 | 2.29 | 417 | E |
| | ¹H NMR (400 MHz, DMSO-d₆, δ/ppm): 8.14 (d, 2H), 7.69 (d, 2H), 7.18 (d, 2H), 7.10 (d, 2H), 6.92 (s, 1H), 5.45 (s, 2H), 4.82 (d, 2H), 4.79 (d, 2H), 3.09 (s, 3H), 2.32 (s, 3H), 2.27 (s, 3H). | | | |
| 113 | 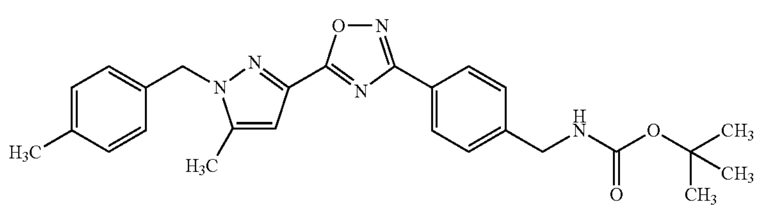 [SMILES: Cc1ccc(Cn2nc(-c3nc(-c4ccc(CNC(=O)OC(C)(C)C)cc4)no3)cc2C)cc1] | 2.94 | 460 | D |
| | ¹H NMR (400 MHz, DMSO-d₆, δ/ppm): 8.01 (d, 2H), 7.52-7.48 (t, 1H), 7.42 (d, 2H), 7.18 (d, 2H), 7.11 (d, 2H), 6.90 (s, 1H), 5.43 (s, 2H), 4.22 (d, 2H), 2.32 (s, 3H), 2.28 (s, 3H), 1.41 (s, 9H). | | | |
| 114 | 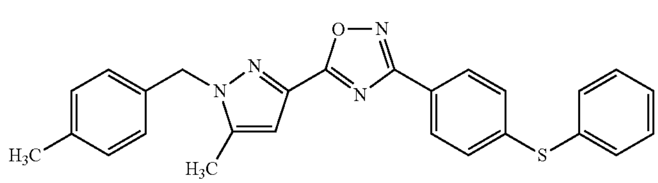 [SMILES: Cc1ccc(Cn2nc(-c3nc(-c4ccc(Sc5ccccc5)cc4)no3)cc2C)cc1] | 3.31 | 439 | D |
| | ¹H NMR (400 MHz, DMSO-d₆, δ/ppm): 7.97 (d, 1H), 7.92 (s, 1H), 7.59 (t, 1H), 7.51 (d, 1H), 7.47-7.38 (m, 5H), 7.17 (d, 2H), 7.10 (d, 2H), 6.38 (s, 1H), 5.43 (s, 2H), 2.30 (s, 3H), 2.27 (s, 3H). | | | |

By using the method described above for Example 18, and by substituting the appropriate starting materials, Examples 115 and 116 found in the table below were similarly prepared.

inert atmosphere of argon over night. In order to increase solubility, DMF (100 µL) was added, and stirring was continued at 120° C. for 24 h. After being cooled to rt, water (5

| Example Number | Structure | HPLC RT (min) | MS m/z (MH+) | Method |
|---|---|---|---|---|
| 115 | 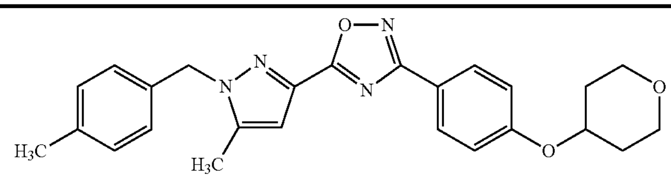 | 3.09 | 431 | D |
| | $^1$H NMR (400 MHz, CDCl$_3$, δ/ppm): 8.13 (d, 2H), 7.13 (d, 2H), 7.08 (d, 2H), 7.00 (d, 2H), 6.78 (s, 1H), 5.41 (s, 2H), 4.61-4.56 (m, 1H), 4.03-3.97 (m, 2H), 3.64-3.58 (m, 2H), 2.31 (s, 3H), 2.25 (s, 3H), 2.09-2.02 (m, 2H), 1.87-1.79 (m, 2H). | | | |
| 116 | 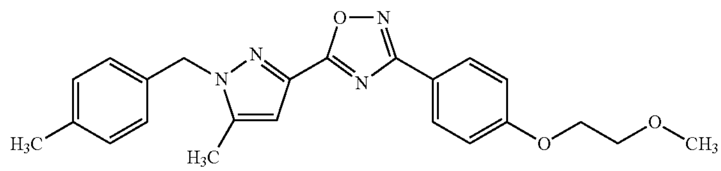 | 2.98 | 405 | D |
| | $^1$H NMR (400 MHz, CDCl$_3$, δ/ppm): 8.13 (d, 2H), 7.13 (d, 2H), 7.07 (d, 2H), 7.02 (d, 2H), 6.78 (s, 1H), 5.39 (s, 2H), 4.21-4.18 (m, 2H), 3.80-3.77 (m, 2H), 3.47 (s, 3H), 2.32 (s, 3H), 2.26 (s, 3H). | | | |

By using the method described above for Example 21, and by substituting the appropriate starting materials, Example 117 found in the table below was similarly prepared.

mL) was added and the product was extracted with ethyl acetate. After the organic extract had been washed with brine and dried over anhydrous magnesium sulfate, it was filtered

| Example Number | Structure | HPLC RT (min) | MS m/z (MH+) | Method |
|---|---|---|---|---|
| 117 | 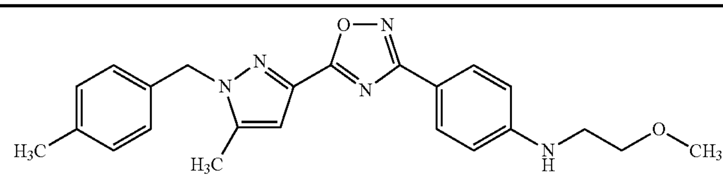 | 2.28 | 404 | E |
| | $^1$H NMR (400 MHz, CDCl$_3$, δ/ppm): 8.03 (d, 2H), 7.13 (d, 2H), 7.07 (d, 2H), 6.77 (s, 1H), 6.68 (d, 2H), 5.39 (s, 2H), 3.65-3.62 (m, 2H), 3.41 (s, 3H), 3.38-3.35 (m, 2H), 2.32 (s, 3H), 2.24 (s, 3H). | | | |

Example 118

Preparation of 3-[4-(1H-Imidazol-1-yl)phenyl]-5-[5-methyl-1-(4-methylbenzyl)-1H-pyrazol-3-yl]-1,2,4-oxadiazole

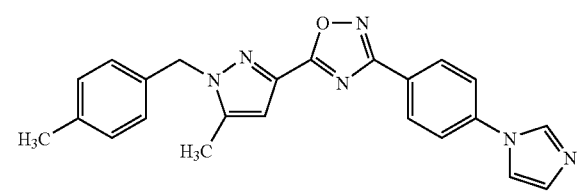 [SMILES: Cc1ccc(Cn2nc(-c3nc(-c4ccc(-n5ccnc5)cc4)no3)cc2C)cc1]

A suspension of 3-(4-iodophenyl)-5-[5-methyl-1-(4-methylbenzyl)-1H-pyrazol-3-yl]-1,2,4-oxadiazole (Example 13, 250 mg, 0.548 mmol), imidazole (56 mg, 0.822 mmol), caesium carbonate (197 mg, 0.603 mmol), copper-(I) trifluoromethanesulfonate (15 mg; 0.027 mmol), dibenzylideneacetone (6.7 mg, 0.027 mmol) and 1,10-phenanthroline (99 mg, 0.548 mmol) in toluene (1 mL) was heated to reflux under an and concentrated in vacuo. The residue was subjected to preparative HPLC to afford the title compound in pure form (20 mg, 9%): $^1$H NMR (400 MHz, CDCl$_3$) δ 8.33 (d, 2H), 7.98 (broad s, 1H), 7.53 (d, 2H), 7.38 (broad s, 1H), 7.26 (broad s, 1H, partially obscured by CHCl$_3$ signal), 7.14 (d, 2H), 7.08 (d, 2H), 6.81 (s, 1H), 5.41 (s, 2H), 2.32 (s, 3H), 2.28 (s, 3H); ES-MS m/z 397, HPLC RT (Method K) 1.06 min.

Example 119

Preparation of 4-[(5-Methyl-3-{3-[4-(trifluoromethoxy)phenyl]-1,2,4-oxadiazol-5-yl}-1H-pyrazol-1-yl)methyl]phenol

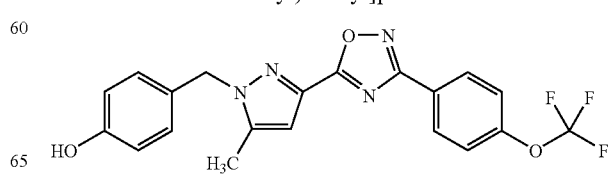

Step 1: Preparation of 5-[5-Methyl-1-(4-{[tris(1-methylethyl)silyl]oxy}benzyl)-1H-pyrazol-3-yl]-3-[4-(trifluoromethoxy)phenyl]-1,2,4-oxadiazole

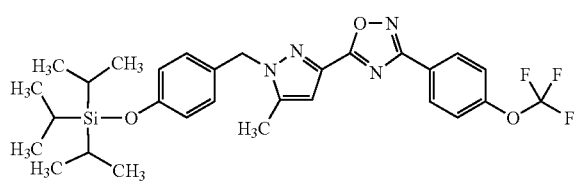 [SMILES: Cc1cc(-c2nc(-c3ccc(OC(F)(F)F)cc3)no2)nn1Cc1ccc(O[Si](C(C)C)(C(C)C)C(C)C)cc1]

To a mechanically stirred solution of 5-(5-methyl-1H-pyrazol-3-yl)-3-[4-(trifluoromethoxy)-phenyl]-1,2,4-oxadiazole (Intermediate C, 600 mg, 1.93 mmol) and [4-(bromomethyl)-phenoxy][tris(1-methylethyl)]silane (Intermediate M, 1.11 g, 2.90 mmol) in dry THF (15 mL) was added potassium tert-butoxide (239 mg, 2.13 mmol) at a temperature of 0° C. The cooling bath was removed, and the reaction mixture was stirred at rt overnight. After the addition of water (75 mL), the crude product was extracted into ethyl acetate (3×75 mL). The combined organic extracts were successively washed with water and brine, dried over anhydrous magnesium sulfate, followed by filtration and evaporation of the solvent. The residue was subjected to preparative HPLC to afford the title compound (519 mg, 47%) and, additionally, a considerable amount of the product of the next step (180 mg, 22%) which was formed by cleavage of the silicon-oxygen bond under the acidic HPLC conditions.

Step 2: Preparation of 4-[(5-Methyl-3-{3-[4-(trifluoromethoxy)phenyl]-1,2,4-oxadiazol-5-yl}-1H-pyrazol-1-yl)-methyl]phenol

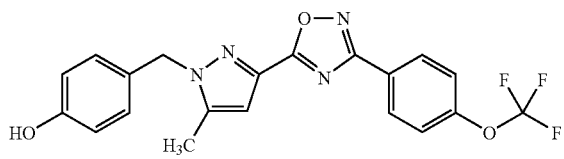

To a solution of 5-[5-methyl-1-(4-{[tris(1-methylethyl)silyl]oxy}benzyl)-1H-pyrazol-3-yl]-3-[4-(trifluoromethoxy)phenyl]-1,2,4-oxadiazole (Step 1, 500 mg, 0.873 mmol) in THF (20 mL) was added a solution of tetrabutylammonium fluoride (1M in THF, 960 µl, 0.96 mmol) at a temperature of 0° C. The cooling bath was removed, and the reaction mixture was stirred at rt for 1 h. After the addition of water (100 µL), most of the organic solvent was removed in vacuo and replaced by methanol (1 mL). The crude mixture was subjected to preparative HPLC to afford the title compound in pure form (416 mg, 67%): $^1$H NMR (400 MHz, CDCl$_3$) δ 8.24 (d, 2H), 7.32 (d, 2H), 7.07 (d, 2H), 6.79 (d, 2H), 6.78 (s, 1H), 5.61 (broad, 1H), 5.35 (s, 2H), 2.28 (s, 3H); ES-MS m/z 417, HPLC RT (Method J) 4.78 min.

Example 120

Preparation of 5-[1-(4-Chlorobenzyl)-5-methyl-1H-pyrazol-3-yl]-3-[4-(trifluoromethoxy)phenyl]-1,2,4-oxadiazole

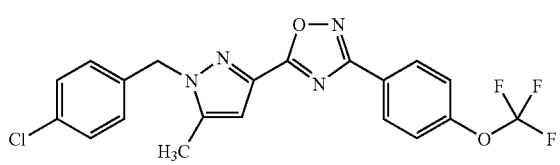

To a mechanically stirred solution of 5-(5-methyl-1H-pyrazol-3-yl)-3-[4-(trifluoromethoxy)-phenyl]-1,2,4-oxadiazole (Intermediate C, 60 mg, 0.193 mmol) and 1-(bromomethyl)-4-chlorobenzene (53 mg, 0.215 mmol) in dry THF (2 mL) was added potassium tert-butoxide (24 mg, 0.213 mmol) at a temperature of 0° C. The cooling bath was removed, and the reaction mixture was stirred at rt over night. After the addition of DMF (1 mL), the complete reaction mixture was subjected to preparative HPLC affording the title compound in pure form (68 mg, 81%): $^1$H NMR (400 MHz, CDCl$_3$) δ 8.25 (d, 2H), 7.33 (d, 2H), 7.31 (d, 2H), 7.11 (d, 2H), 6.82 (s, 1H), 5.42 (s, 2H), 2.27 (s, 3H); ES-MS m/z 435, HPLC RT (Method K) 1.63 min.

By using the method described above for Example 120, and by substituting the appropriate starting materials, Examples 121-135 found in the table below were similarly prepared.

| Example Number | Structure | HPLC RT (min) | MS m/z (MH+) | Method |
|---|---|---|---|---|
| 121 | ![structure] | 1.47 | 426 | K |

$^1$H NMR (400 MHz, CDCl$_3$, δ/ppm): 8.24 (d, 2H), 7.65 (d, 2H), 7.33 (d, 2H), 7.24 (d, 2H), 6.85 (s, 1H), 5.50 (s, 2H), 2.29 (s, 3H).

| Example Number | Structure | HPLC RT (min) | MS m/z (MH+) | Method |
|---|---|---|---|---|
| 122 | 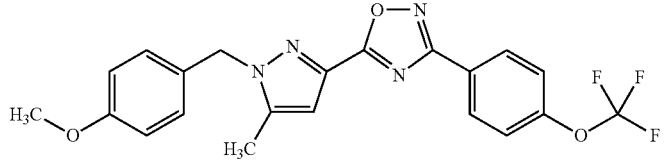 [SMILES: COc1ccc(Cn2nc(-c3nc(-c4ccc(OC(F)(F)F)cc4)no3)cc2C)cc1] <br> ¹H NMR (400 MHz, CDCl₃, δ/ppm): 8.25 (d, 2H), 7.33 (d, 2H), 7.13 (d, 2H), 6.86 (d, 2H), 6.80 (s, 1H), 5.39 (s, 2H), 3.78 (s, 3H), 2.27 (s, 3H). | 3.06 | 431 | D |
| 123 | 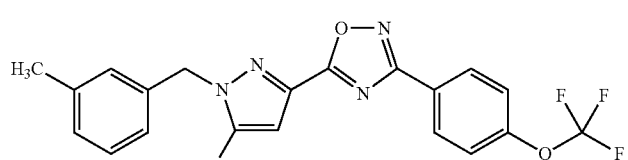 <br> ¹H NMR (400 MHz, CDCl₃, δ/ppm): 8.25 (d, 2H), 7.32 (d, 2H), 7.22 (t, 1H), 7.10 (d, 1H), 6.99 (s, 1H), 6.96 (d, 1H), 6.80 (s, 1H), 5.42 (s, 2H), 2.31 (s, 3H), 2.27 (s, 3H). | 1.62 | 415 | K |
| 124 | 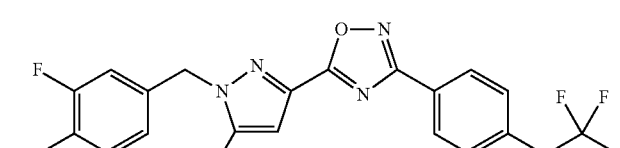 <br> ¹H NMR (400 MHz, CDCl₃, δ/ppm): 8.25 (d, 2H), 7.33 (d, 2H), 7.14 (t, 1H), 6.86-6.79 (m, 3H), 5.40 (s, 2H), 2.27 (s, 3H), 2.24 (s, 3H). | 2.75 | 433 | E |
| 125 | 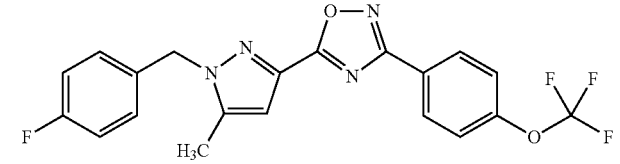 [SMILES: Cc1cc(-c2nc(-c3ccc(OC(F)(F)F)cc3)no2)nn1Cc1ccc(F)cc1] <br> ¹H NMR (400 MHz, CDCl₃, δ/ppm): 8.25 (d, 2H), 7.33 (d, 2H), 7.17 (dd, 1H), 7.03 (t, 1H), 6.81 (s, 1H), 5.43 (s, 2H), 2.27 (s, 3H). | 1.56 | 419 | K |
| 126 | 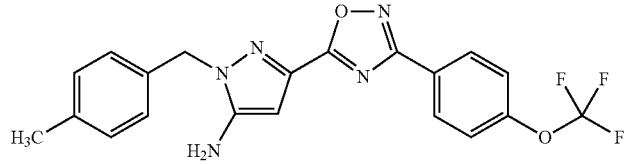 <br> ¹H NMR (400 MHz, CDCl₃, δ/ppm): 8.25 (d, 2H), 7.33 (d, 2H), 7.18 (d, 2H), 7.14 (d, 2H), 6.28 (s, 1H), 5.33 (s, 2H), 3.53 (s, 2H), 2.27 (s, 3H). | 1.44 | 416 | K |
| 127 | 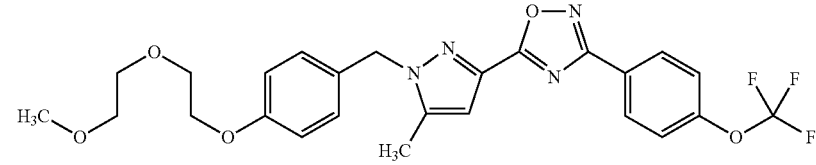 [SMILES: COCCOCCOc1ccc(Cn2nc(-c3nc(-c4ccc(OC(F)(F)F)cc4)no3)cc2C)cc1] <br> ¹H NMR (400 MHz, CDCl₃, δ/ppm): 8.25 (d, 2H), 7.33 (d, 2H), 7.11 (d, 2H), 6.87 (d, 2H), 6.79 (s, 1H), 5.38 (s, 2H), 4.11 (dd, 2H), 3.83 (dd, 2H), 3.70 (dd, 2H), 3.56 (dd, 2H), 3.38 (s, 3H), 2.27 (s, 3H). | 2.74 | 519 | F |

| Example Number | Structure | HPLC RT (min) | MS m/z (MH+) | Method |
|---|---|---|---|---|
| 128 | 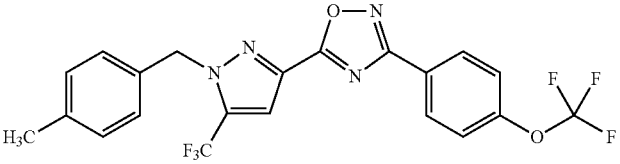 [SMILES: Cc1ccc(Cn2nc(-c3nc(-c4ccc(OC(F)(F)F)cc4)no3)cc2C(F)(F)F)cc1] | 1.76 | 469 | K |
| | $^1$H NMR (400 MHz, CDCl$_3$, δ/ppm): 8.23 (d, 2H), 7.37 (s, 1H), 7.35 (d, 2H), 7.21 (d, 2H), 7.15 (d, 2H), 5.55 (s, 2H), 2.33 (s, 3H). | | | |
| 129 | 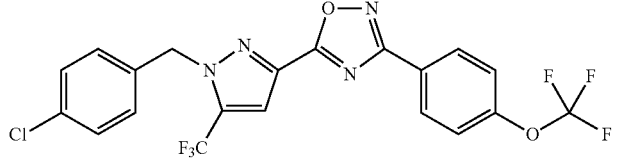 | 1.76 | 489 | K |
| | $^1$H NMR (400 MHz, CDCl$_3$, δ/ppm): 8.23 (d, 2H), 7.39 (s, 1H), 7.34 (d, 2H), 7.33 (d, 2H), 7.25 (d, 2H), 5.54 (s, 2H). | | | |
| 130 | 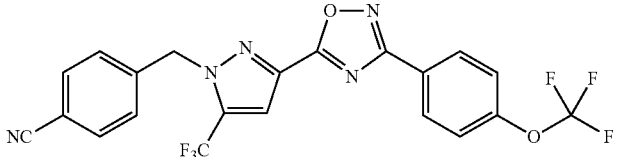 | 3.13 | 480 | D |
| | $^1$H NMR (500 MHz, CDCl$_3$, δ/ppm): 8.22 (d, 2H), 7.67 (d, 2H), 7.42 (s, 1H), 7.38 (d, 2H), 7.35 (d, 2H), 5.63 (s, 2H). | | | |
| 131 | 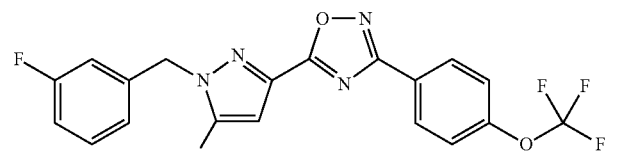 | 1.57 | 419 | K |
| | $^1$H NMR (400 MHz, CDCl$_3$, δ/ppm): 8.25 (d, 2H), 7.33 (d, 2H), 7.32-7.29 (m, 1H), 7.02-6.97 (m, 1H), 6.96-6.93 (m, 1H), 6.86-6.82 (m, 1H), 6.83 (s, 1H), 5.45 (s, 2H), 2.29 (s, 3H). | | | |
| 132 | 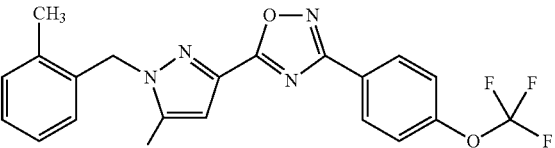 | 1.61 | 415 | K |
| | $^1$H NMR (400 MHz, CDCl$_3$, δ/ppm): 8.25 (d, 2H), 7.33 (d, 2H), 7.21-7.19 (m, 2H), 7.13-7.10 (m, 1H), 6.85 (s, 1H), 6.61-6.59 (m, 1H), 5.45 (s, 2H), 2.37 (s, 3H), 2.24 (s, 3H). | | | |
| 133 | 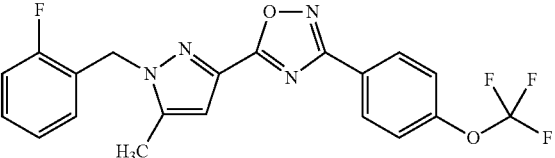 | 3.13 | 419 | D |
| | $^1$H NMR (400 MHz, CDCl$_3$, δ/ppm): 8.25 (d, 2H), 7.32 (d, 2H), 7.32-7.26 (m, 1H), 7.12-7.01 (m, 3H), 6.81 (s, 1H), 5.50 (s, 2H), 2.32 (s, 3H). | | | |

| Example Number | Structure | HPLC RT (min) | MS m/z (MH+) | Method |
|---|---|---|---|---|
| 134 | 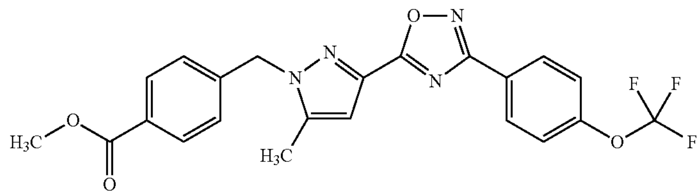 [SMILES: COC(=O)c1ccc(Cn2nc(-c3nc(-c4ccc(OC(F)(F)F)cc4)no3)cc2C)cc1] | 1.53 | 459 | K |

$^1$H NMR (400 MHz, CDCl$_3$, δ/ppm): 8.25 (d, 2H), 8.01 (d, 2H), 7.35 (d, 2H), 7.24 (d, 2H), 6.84 (s, 1H), 5.41 (s, 2H), 3.91 (s, 3H), 2.26 (s, 3H).

| Example Number | Structure | HPLC RT (min) | MS m/z (MH+) | Method |
|---|---|---|---|---|
| 135 | | 1.65 | 469 | K |

$^1$H NMR (400 MHz, CDCl$_3$, δ/ppm): 8.25 (d, 2H), 7.60 (d, 2H), 7.33 (d, 2H), 7.27 (d, 2H), 6.83 (s, 1H), 5.51 (s, 2H), 2.30 (s, 3H).

Example 136

Preparation of 5-[5-Methyl-1-(4-methylbenzyl)-1H-pyrazol-3-yl]-3-{4-[(trifluoromethyl)-sulfinyl]phenyl}-1,2,4-oxadiazole

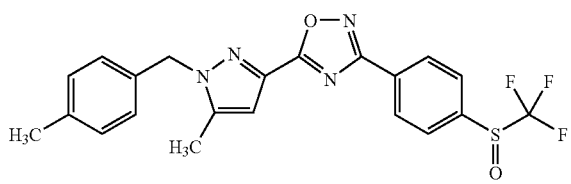 [SMILES: Cc1ccc(Cn2nc(-c3nc(-c4ccc(S(=O)C(F)(F)F)cc4)no3)cc2C)cc1]

To a mechanically stirred solution of 5-[5-methyl-1-(4-methylbenzyl)-1H-pyrazol-3-yl]-3-{4-[(trifluoromethyl) sulfanyl]phenyl}-1,2,4-oxadiazole (Example 105, 570 mg, 1.32 mmol) in dichloromethane (215 mL) was added 3-chloroperoxybenzoic acid (408 mg, 1.66 mmol) at a temperature of 0° C. The reaction mixture was stirred over night at the same temperature. Then saturated aqueous sodium bicarbonate solution (80 mL) was added, and the mixture was extracted with dichloromethane (3×30 mL). The combined organic extracts were dried over anhydrous sodium sulfate. After filtration and evaporation of the solvent, the title compound was obtained as a white solid after purification by MPLC (silica, cyclohexane/ethyl acetate 4:1) (346 mg, 59%): $^1$H NMR (400 MHz, DMSO-d$_6$) δ 8.38 (d, 2H), 8.11 (d, 2H), 7.18 (d, 2H), 7.12 (d, 2H), 6.92 (s, 1H), 5.43 (s, 2H), 2.32 (s, 3H), 2.27 (s, 3H); ES-MS m/z 447, HPLC RT (Method E) 2.44 min.

By using the method described above for Example 136, and by substituting the appropriate starting materials, Example 137 found in the table below was similarly prepared.

| Example Number | Structure | HPLC RT (min) | MS m/z (MH+) | Method |
|---|---|---|---|---|
| 137 | 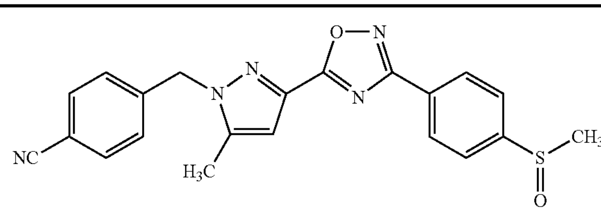 | 1.22 | 393 | K |

$^1$H NMR (400 MHz, DMSO-d$_6$, δ/ppm): 8.26 (d, 2H), 7.90 (d, 2H), 7.18 (d, 2H), 7.11 (d, 2H), 6.92 (s, 1H), 5.44 (s, 2H), 2.82 (s, 3H), 2.32 (s, 3H), 2.28 (s, 3H).

Example 138

Preparation of 5-[5-Methyl-1-(4-methylbenzyl)-1H-pyrazol-3-yl]-3-[4-(phenylsulfinyl)-phenyl]-1,2,4-oxadiazole

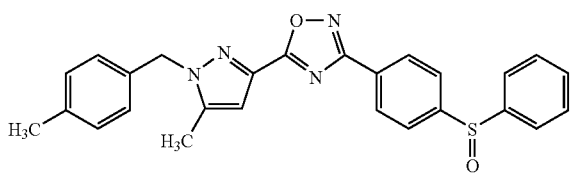 [SMILES: Cc1ccc(Cn2nc(-c3nc(-c4ccc(S(=O)c5ccccc5)cc4)no3)cc2C)cc1]

To a mechanically stirred solution of 5-[5-methyl-1-(4-methylbenzyl)-1H-pyrazol-3-yl]-3-[4-(phenylsulfanyl)phenyl]-1,2,4-oxadiazole (Example 114, 350 mg, 0.798 mmol) in THF (3 mL) was added vanadium trichloride (6 mg, 0.04 mmol) and hydrogen peroxide (30% in water, 82 µL, 0.798 mmol). The reaction mixture was stirred at rt for 5 h, before another 40 µL (0.4 mmol) of the hydrogen peroxide solution were added. Stirring was continued at rt over night. Then water (30 mL) was added, and the mixture was extracted with ethyl acetate (3×30 mL). The combined organic extracts were dried over anhydrous sodium sulfate. After filtration and evaporation of the solvent, the crude product was purified by MPLC (silica, cyclohexane/ethyl acetate 3:1), followed by precipitation using acetonitril/water 3:1 affording a first crop of the title compound (29 mg, 8%). A second crop was obtained from the mother liquor after preparative HPLC (26 mg, 7%): $^1$H NMR (400 MHz, DMSO-$d_6$) δ 8.39 (s, 1H), 8.18 (d, 1H), 7.96 (d, 1H), 7.81 (d, 2H), 7.78-7.74 (m, 1H), 7.60-7.50 (m, 3H), 7.18 (d, 2H), 7.12 (d, 2H), 6.94 (s, 1H), 5.44 (s, 2H), 2.32 (s, 3H), 2.28 (s, 3H); ES-MS m/z 455, HPLC RT (Method D) 2.78 min.

Example 139

Preparation of 1-(4-{5-[5-Methyl-1-(4-methylbenzyl)-1H-pyrazol-3-yl]-1,2,4-oxadiazol-3-yl}phenyl)methanamine

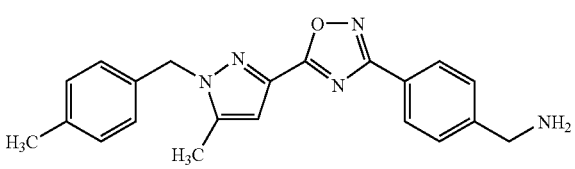 [SMILES: Cc1ccc(Cn2nc(-c3nc(-c4ccc(CN)cc4)no3)cc2C)cc1]

To a mechanically stirred solution of di-tert-butyl (4-{5-[5-methyl-1-(4-methylbenzyl)-1H-pyrazol-3-yl]-1,2,4-oxadiazol-3-yl}benzyl)imidodicarbonate (Example 98, 2.73 g, 4.88 mmol) in dichloromethane (37 mL) was added trifluoroacetic acid (3.7 mL, 48.8 mmol). After the reaction mixture had been stirred at rt for 3 h, water (50 mL) was added, and it was extracted with dichloromethane (3×30 mL). The aqueous phase was then made alkaline (pH 10) by addition of potassium carbonate. It was extracted with dichloromethane (3×30 mL). The combined organic extracts were dried over anhydrous sodium sulfate. After filtration and evaporation of the solvent, the title compound was obtained (1.28 g, 73%): $^1$H NMR (400 MHz, DMSO-$d_6$) δ 8.02 (d, 2H), 7.55 (d, 2H), 7.18 (d, 2H), 7.11 (d, 2H), 6.90 (s, 1H), 5.43 (s, 2H), 3.85 (s, 2H), 2.32 (s, 3H), 2.28 (s, 3H); ES-MS m/z 360, HPLC RT (Method D) 1.56 min.

Example 140

Preparation of 5-[5-Methyl-1-(4-methylbenzyl)-1H-pyrazol-3-yl]-3-[4-(1H-pyrrol-1-yl-methyl)phenyl]-1,2,4-oxadiazole

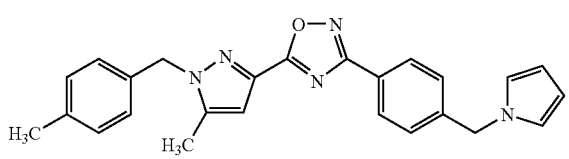 [SMILES: Cc1ccc(Cn2nc(-c3nc(-c4ccc(Cn5cccc5)cc4)no3)cc2C)cc1]

To a solution of acetic acid (348 µL, 6.08 mmol) in water (194 µL) were added successively pyridine (491 µL, 6.08 mmol), 1-(4-{5-[5-methyl-1-(4-methylbenzyl)-1H-pyrazol-3-yl]-1,2,4-oxadiazol-3-yl}phenyl)methanamine (Example 139, 130 mg, 0.362 mmol) and 2,5-dimethoxytetrahydrofuran (47 µL, 0.362 mmol). The reaction mixture was heated to 100° C. for 20 h. After being cooled to rt, water (50 mL) was added, and the mixture was extracted with ethyl acetate (3×30 mL). The combined organic extracts were dried over anhydrous sodium sulfate. After filtration and evaporation of the solvent, the crude product was first subjected to MPLC (silica, cyclohexane/ethyl acetate 4:1) and then to preparative HPLC affording the title compound as a white solid (48 mg, 31%): NMR (400 MHz, DMSO-$d_6$) δ 8.02 (d, 2H), 7.35 (d, 2H), 7.18 (d, 2H), 7.11 (d, 2H), 6.91 (s, 1H), 6.86 (t, 2H), 6.05 (t, 2H), 5.42 (s, 2H), 5.21 (s, 2H), 2.32 (s, 3H), 2.27 (s, 3H); ES-MS m/z 410, HPLC RT (Method K) 1.54 min.

Example 141

Preparation of 3-(4-{5-[5-Methyl-1-(4-methylbenzyl)-1H-pyrazol-3-yl]-1,2,4-oxadiazol-3-yl}phenyl)imidazolidin-4-one

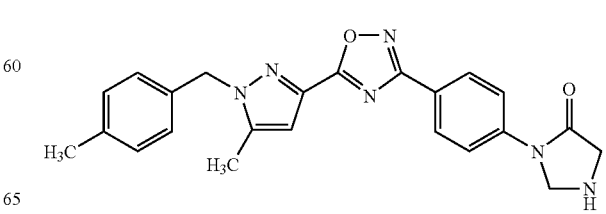

Step 1: Preparation of 4-{5-[5-Methyl-1-(4-methyl-benzyl)-1H-pyrazol-3-yl]-1,2,4-oxadiazol-3-yl}aniline

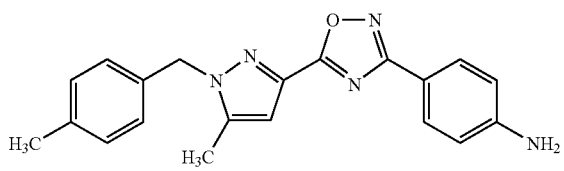 [SMILES: Cc1ccc(Cn2nc(-c3nc(-c4ccc(N)cc4)no3)cc2C)cc1]

To a solution of tert-butyl (4-{5-[5-methyl-1-(4-methylbenzyl)-1H-pyrazol-3-yl]-1,2,4-oxadiazol-3-yl}phenyl)carbamate (Example 101, 1.0 g, 2.25 mmol) in dichloromethane (20 mL) was added trifluoroacetic acid (5 mL). The reaction mixture was stirred at rt for 1 h. The solvent was removed in vacuo and the residue was re-dissolved in ethyl acetate. After washing with saturated aqueous sodium bicarbonate, the solvent was removed and the title compound was obtained as an off-white solid (770 mg, 99%): $^1$H NMR (400 MHz, CDCl$_3$) δ 8.00 (d, 2H), 7.13 (d, 2H), 7.07 (d, 2H), 6.76 (s, 1H), 6.73 (d, 2H), 5.40 (s, 2H), 3.92 (broad, 2H), 2.32 (s, 3H), 2.23 (s, 3H); ES-MS m/z 346, HPLC RT (Method D) 2.48 min.

Step 2: Preparation of 2-Bromo-N-(4-{5-[5-methyl-1-(4-methylbenzyl)-1H-pyrazol-3-yl]-1,2,4-oxadiazol-3-yl}phenyl)acetamide

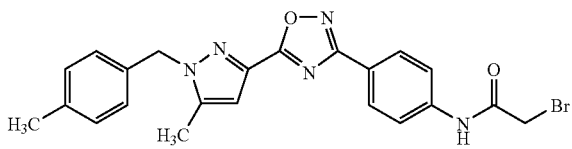 [SMILES: Cc1ccc(Cn2nc(-c3nc(-c4ccc(NC(=O)CBr)cc4)no3)cc2C)cc1]

To a solution of 4-{5-[5-methyl-1-(4-methylbenzyl)-1H-pyrazol-3-yl]-1,2,4-oxadiazol-3-yl}-aniline (Step 1, 150 mg, 0.434 mmol) and N,N-diisopropylethylamine (113 μL, 0.651 mmol) in dichloromethane (5 mL) was added bromoacetyl bromide (46 μL, 0.521 mmol) dropwise at a temperature of 0° C. After 5 minutes, the reaction mixture was allowed to warm to rt. After a further 2 h, the reaction mixture was diluted with an equal volume of dichloromethane, and 20 mL water were added. After separation of the organic from the aqueous layer, the organic phase was dried over anhydrous sodium sulfate. Subsequent filtration and evaporation of the solvent yielded the title compound which was obtained in pure form after stirring with cyclohexane (195 mg, 96%): $^1$H NMR (400 MHz, DMSO-d$_6$) δ 10.70 (s, 1H), 8.03 (d, 2H), 7.80 (d, 2H), 7.18 (d, 2H), 7.10 (d, 2H), 6.90 (s, 1H), 5.44 (s, 2H), 4.09 (s, 2H), 2.32 (s, 3H), 2.28 (s, 3H); ES-MS m/z 466/468, HPLC RT (Method F) 2.45 min.

Step 3: Preparation of 3-(4-{5-[5-Methyl-1-(4-methylbenzyl)-1H-pyrazol-3-yl]-1,2,4-oxadiazol-3-yl}phenyl)imidazolidin-4-one

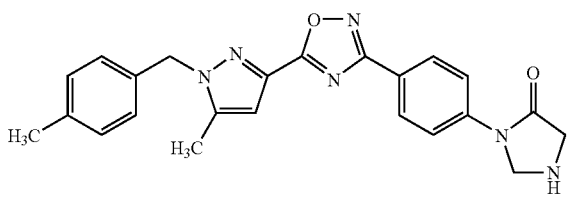 [SMILES: Cc1ccc(Cn2nc(-c3nc(-c4ccc(N5CNCC5=O)cc4)no3)cc2C)cc1]

To a solution of 2-bromo-N-(4-{5-[5-methyl-1-(4-methylbenzyl)-1H-pyrazol-3-yl]-1,2,4-oxadiazol-3-yl}phenyl)acetamide (Step 2, 190 mg, 0.407 mmol) in ethanol (4 mL) was added hexamethylenetetramine (286 mg, 2.04 mmol). The reaction mixture was stirred and heated at reflux for 2.5 h. After being cooled to rt, the solvent was evaporated, and the residue was subjected to preparative HPLC. The crude product thus obtained was treated with a mixture of ethyl acetate and saturated aqueous sodium bicarbonate. The layers were separated and the aqueous layer was extracted with ethyl acetate. The combined organic extracts were dried over anhydrous sodium sulfate. Subsequent filtration and evaporation of the solvent yielded the title compound which was obtained in pure form after stirring with cyclohexane (84 mg, 50%): $^1$H NMR (400 MHz, CDCl$_3$) δ 8.23 (d, 2H), 7.70 (d, 2H), 7.13 (d, 2H), 7.07 (d, 2H), 6.79 (s, 1H), 5.40 (s, 2H), 4.92 (s, 2H), 3.69 (s, 2H), 2.32 (s, 3H), 2.25 (s, 3H); ES-MS m/z 415, HPLC RT (Method E) 1.62 min.

By using the method described above for Example 120, and by substituting the appropriate starting materials, Examples 142-164 found in the table below were similarly prepared.

| Example Number | Structure | HPLC RT (min) | MS m/z (MH+) | Method |
|---|---|---|---|---|
| 142 | 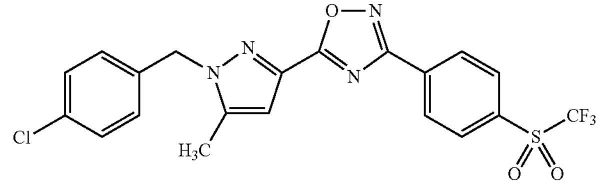 [SMILES: Cc1cc(-c2nc(-c3ccc(S(=O)(=O)C(F)(F)F)cc3)no2)nn1Cc1ccc(Cl)cc1] | 2.85 | 483 | F |

$^1$H-NMR (400 MHz, DMSO-d$_6$, δ/ppm): 8.51 (d, 2H), 8.36 (d, 2H), 7.44 (d, 2H), 7.23 (d, 2H), 6.97 (s, 1H), 5.52 (s, 2H), 2.32 (s, 3H).

-continued

| Example Number | Structure | HPLC RT (min) | MS m/z (MH+) | Method |
|---|---|---|---|---|
| 143 | 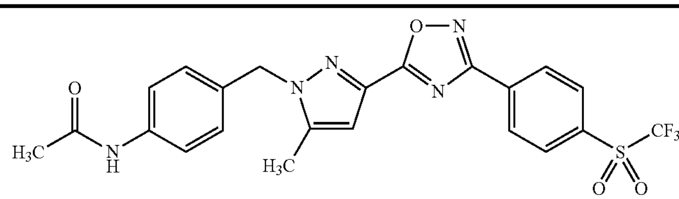 | 2.40 | 506 | F |

$^1$H-NMR (400 MHz, DMSO-$d_6$, δ/ppm): 9.98 (s, 1H), 8.51 (d, 2H), 8.38 (d, 2H), 7.56 (d, 2H), 7.18 (d, 2H), 6.95 (s, 1H), 5.42 (s, 2H), 2.32 (s, 3H), 2.01 (s, 3H).

| 144 | | 2.61 | 474 | F |
|---|---|---|---|---|

$^1$H-NMR (400 MHz, DMSO-$d_6$, δ/ppm): 8.51 (d, 2H), 8.36 (d, 2H), 7.87 (d, 2H), 7.36 (d, 2H), 7.01 (s, 1H), 5.65 (s, 2H), 2.34 (s, 3H).

| 145 | | 2.58 | 479 | E |
|---|---|---|---|---|

$^1$H-NMR (400 MHz, DMSO-$d_6$, δ/ppm): 8.50 (d, 2H), 8.37 (d, 2H), 7.20 (d, 2H), 7.92 (d, 2H), 5.42 (s, 2H), 3.72 (s, 3H), 2.33 (s, 3H).

| 146 | | 2.79 | 515 | F |
|---|---|---|---|---|

$^1$H-NMR (400 MHz, DMSO-$d_6$, δ/ppm): 8.49 (d, 2H), 8.37 (d, 2H), 7.45-7.40 (m, 1H), 7.30 (t, 1H), 7.26 (d, 2H), 7.04 (d, 1H), 6.98 (s, 1H), 5.48 (s, 2H), 2.37 (s, 3H).

| 147 | | 2.73 | 507 | F |
|---|---|---|---|---|

$^1$H-NMR (400 MHz, DMSO-$d_6$, δ/ppm): 8.50 (d, 2H), 8.37 (d, 2H), 7.91 (d, 1H), 7.82 (s, 1H), 7.56-7.51 (m, 1H), 7.49 (d, 1H), 6.99 (s, 1H), 5.62 (s, 2H), 3.83 (s, 3H), 2.33 (s, 3H).

| 148 | | 2.82 | 411 | F |
|---|---|---|---|---|

$^1$H-NMR (400 MHz, DMSO-$d_6$, δ/ppm): 8.09 (d, 2H), 7.62 (d, 2H), 7.43 (d, 2H), 7.22 (d, 2H), 6.92 (s, 1H), 5.51 (s, 2H), 2.32 (s, 3H), 1.72 (s, 3H), 1.67 (s, 3H).

| Example Number | Structure | HPLC RT (min) | MS m/z (MH+) | Method |
|---|---|---|---|---|
| 149 | 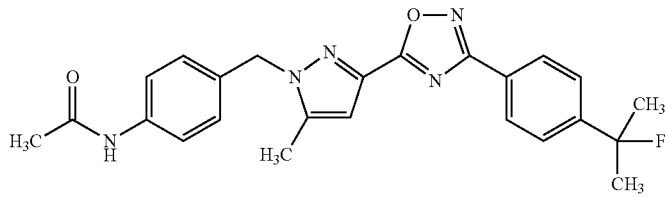 [SMILES: CC(=O)Nc1ccc(Cn2nc(-c3nc(-c4ccc(C(C)(C)F)cc4)no3)cc2C)cc1] | 2.51 | 434 | D |
¹H-NMR (400 MHz, DMSO-d₆, δ/ppm): 9.96 (s, 1H), 8.08 (d, 2H), 7.62 (d, 2H), 7.56 (d, 2H), 7.15 (d, 2H), 6.91 (s, 1H), 5.41 (s, 2H), 2.32 (s, 3H), 2.01 (s, 3H), 1.72 (s, 3H), 1.67 (s, 3H).
| 150 | 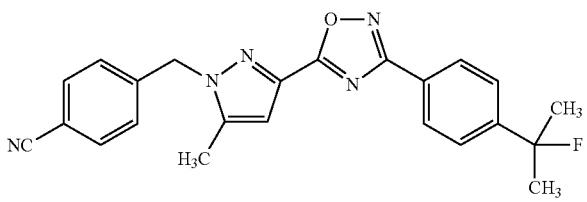 [SMILES: Cc1cc(-c2nc(-c3ccc(C(C)(C)F)cc3)no2)nn1Cc1ccc(C#N)cc1] | 2.58 | 402 | F |
¹H-NMR (400 MHz, DMSO-d₆, δ/ppm): 8.04 (d, 2H), 7.85 (d, 2H), 7.62 (d, 2H), 7.33 (d, 2H), 6.96 (s, 1H), 5.62 (s, 2H), 2.32 (s, 3H), 1.72 (s, 3H), 1.68 (s, 3H).
| 151 | 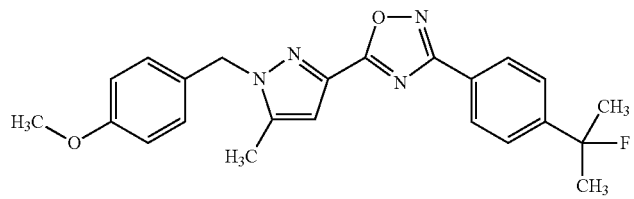 [SMILES: COc1ccc(Cn2nc(-c3nc(-c4ccc(C(C)(C)F)cc4)no3)cc2C)cc1] | 2.89 | 407 | D |
¹H-NMR (400 MHz, DMSO-d₆, δ/ppm): 8.09 (d, 2H), 7.62 (d, 2H), 7.19 (d, 2H), 6.93-6.88 (m, 3H), 5.41 (s, 2H), 3.72 (s, 3H), 2.33 (s, 3H), 1.72 (s, 3H), 1.67 (s, 3H).
| 152 | 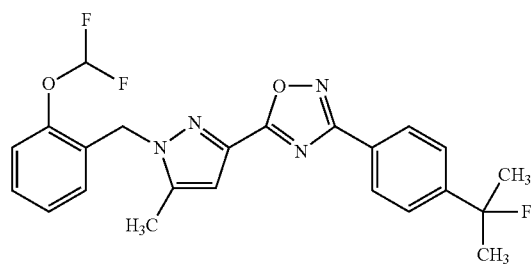 [SMILES: Cc1cc(-c2nc(-c3ccc(C(C)(C)F)cc3)no2)nn1Cc1ccccc1OC(F)F] | 2.76 | 443 | F |
¹H-NMR (400 MHz, DMSO-d₆, δ/ppm): 8.08 (d, 2H), 7.62 (d, 2H), 7.45-7.38 (m, 1H), 7.30 (t, 1H), 7.25 (d, 2H), 7.01 (d, 1H), 6.93 (s, 1H), 5.47 (s, 2H), 2.37 (s, 3H), 1.72 (s, 3H), 1.67 (s, 3H).
| 153 | 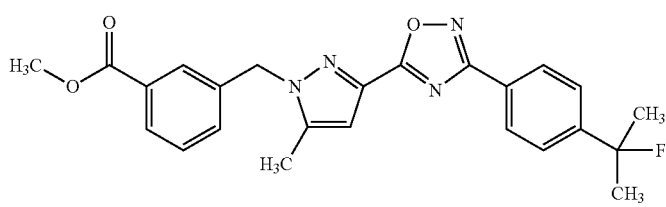 [SMILES: COC(=O)c1cccc(Cn2nc(-c3nc(-c4ccc(C(C)(C)F)cc4)no3)cc2C)c1] | 2.69 | 435 | F |
¹H-NMR (400 MHz, DMSO-d₆, δ/ppm): 8.09 (d, 2H), 7.91 (d, 1H), 7.82 (s, 1H), 7.62 (d, 2H), 7.55-7.51 (m, 1H), 7.48 (d, 1H), 6.94 (s, 1H), 5.61 (s, 2H), 3.83 (s, 3H), 2.32 (s, 3H), 1.72 (s, 3H), 1.67 (s, 3H).

| Example Number | Structure | HPLC RT (min) | MS m/z (MH+) | Method |
|---|---|---|---|---|
| 154 | 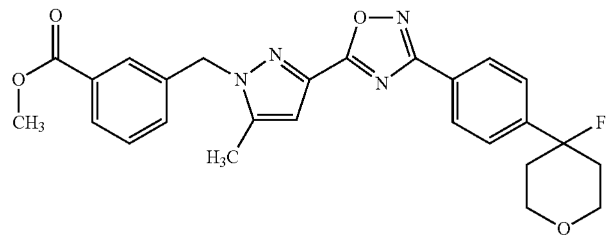 [SMILES: COC(=O)c1cccc(Cn2nc(-c3nc(-c4ccc(C5(F)CCOCC5)cc4)no3)cc2C)c1] | 2.33 | 477 | E |

¹H-NMR (400 MHz, CDCl₃, δ/ppm): 8.23 (d, 2H), 7.98 (dd, 1H), 7.89 (d, 1H), 7.52 (d, 2H), 7.43 (dd, 1H), 7.33 (dd, 1H), 6.83 (s, 1H), 5.50 (s, 2H), 4.00-3.87 (m, 4H), 3.91 (s, 3H), 2.29 (s, 3H), 2.30-2.11 (m, 2H), 1.98-1.92 (m, 2H).

| 155 | | 2.24 | 444 | E |

¹H-NMR (400 MHz, CDCl₃, δ/ppm): 8.22 (d, 2H), 7.64 (d, 2H), 7.53 (d, 2H), 7.25 (d, 2H), 6.86 (s, 1H), 5.51 (s, 2H), 4.00-3.87 (m, 4H), 2.29 (s, 3H), 2.30-2.11 (m, 2H), 1.97-1.92 (m, 2H).

| 156 | | 4.98 | 449 | H |

¹H-NMR (400 MHz, CDCl₃, δ/ppm): 8.22 (d, 2H), 7.52 (d, 2H), 7.13 (d, 2H), 6.86 (d, 2H), 6.79 (s, 1H), 5.39 (s, 2H), 4.00-3.87 (m, 4H), 3.79 (s, 3H), 2.28 (s, 3H), 2.29-2.11 (m, 2H), 1.98-1.92 (m, 2H).

| 157 | | 2.92 | 453 | D |

¹H-NMR (400 MHz, CDCl₃, δ/ppm): 8.22 (d, 2H), 7.52 (d, 2H), 7.31 (d, 2H), 7.11 (d, 2H), 6.82 (s, 1H), 5.42 (s, 2H), 4.00-3.87 (m, 4H), 2.28 (s, 3H), 2.29-2.11 (m, 2H), 1.97-1.92 (m, 2H).

| 158 | | 2.61 | 459 | E |

¹H-NMR (400 MHz, CDCl₃, δ/ppm): 8.26 (d, 2H), 7.98 (dd, 1H), 7.89 (d, 1H), 7.42 (dd, 1H), 7.33 (dd, 1H, and d, 2H), 7.33 (dd, 1H), 6.83 (s, 1H), 5.50 (s, 2H), 3.92 (s, 3H), 2.29 (s, 3H).

| Example Number | Structure | HPLC RT (min) | MS m/z (MH+) | Method |
|---|---|---|---|---|
| 159 | 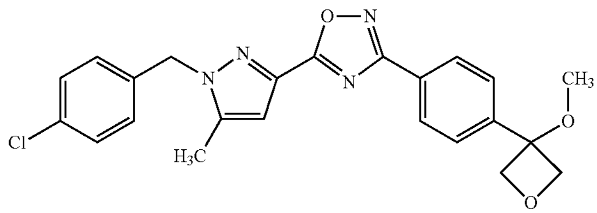 [SMILES: COC1(c2ccc(-c3noc(-c4cc(C)n(Cc5ccc(Cl)cc5)n4)n3)cc2)COC1] | 2.71 | 437 | D |

¹H-NMR (400 MHz, CDCl₃, δ/ppm): 8.27 (d, 2H), 7.60 (d, 2H), 7.31 (d, 2H), 7.11 (d, 2H), 6.83 (s, 1H), 5.42 (s, 2H), 4.97 (d, 2H), 4.85 (d, 2H), 3.18 (s, 3H), 2.29 (s, 3H).

| 160 | | 2.85 | 485 | D |

¹H-NMR (400 MHz, DMSO-d₆, δ/ppm): 8.09 (d, 2H), 7.17 (d, 2H), 7.44-7.40 (m, 1H), 7.29 (t, 1H), 7.27-7.22 (m, 2H), 7.01 (dd, 1H), 6.93 (s, 1H), 5.47 (s, 2H), 3.90-3.83 (m, 2H), 3.74-3.68 (m, 2H), 2.38 (s, 3H), 2.29-2.21 (m, 1H), 2.18-2.10 (m, 1H), 1.91-1.83 (m, 2H).

| 161 | | 3.08 | 467 | D |

¹H-NMR (400 MHz, CDCl₃, δ/ppm): 8.24 (d, 2H), 7.34-7.30 (m, 3H), 7.18-7.13 (m, 2H), 6.90 (dd, 1H), 6.83 (s, 1H), 6.61 (t, 1H), 5.51 (s, 2H), 2.31 (s, 3H).

| 162 | | 1.22 | 476 | K |

¹H-NMR (400 MHz, CDCl₃, δ/ppm): 8.22 (d, 2H), 7.52 (d, 2H), 7.48 (d, 2H), 7.19 (broad s, 1H), 7.13 (d, 2H), 6.80 (s, 1H), 5.40 (s, 2H), 4.00-3.87 (m, 4H), 2.26 (s, 3H), 2.30-2.21 (m, 1H), 2.17 (s, 3H), 2.20-2.11 (m, 1H), 1.98-1.91 (m, 2H).

| Example Number | Structure | HPLC RT (min) | MS m/z (MH+) | Method |
|---|---|---|---|---|
| 163 | 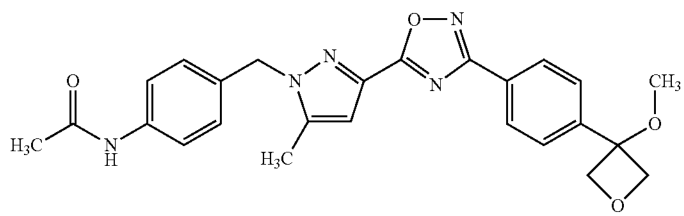 [SMILES: COC1(c2ccc(-c3noc(-c4cc(C)n(Cc5ccc(NC(C)=O)cc5)n4)n3)cc2)COC1] | 4.20 | 460 | H |

¹H-NMR (400 MHz, CDCl₃, δ/ppm): 8.26 (d, 2H), 7.60 (d, 2H), 7.47 (d, 2H), 7.19 (broad s, 1H), 7.14 (d, 2H), 6.81 (s, 1H), 5.42 (s, 2H), 4.97 (d, 2H), 4.85 (d, 2H), 3.18 (s, 3H), 2.27 (s, 3H), 2.17 (s, 3H).

| 164 | | 2.85 | 527 | E |

¹H-NMR (400 MHz, CDCl₃, δ/ppm): 8.25 (d, 2H), 7.68 (d, 2H), 7.32 (d, 2H), 6.91 (d, 2H), 6.81 (s, 1H), 5.40 (s, 2H), 2.26 (s, 3H).

Example 165

Preparation of 3-[5-Methyl-1-(4-methylbenzyl)-1H-pyrazol-3-yl]-5-[4-(trifluoromethoxy)phenyl]-1,2,4-oxadiazole

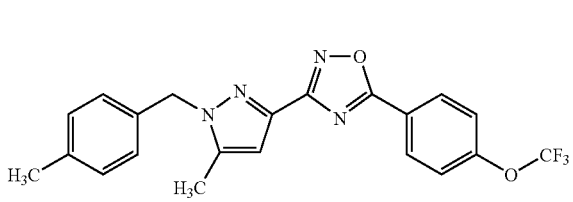 [SMILES: Cc1ccc(Cn2nc(-c3noc(-c4ccc(OC(F)(F)F)cc4)n3)cc2C)cc1]

To a mechanically stirred solution of N'-hydroxy-5-methyl-1-(4-methylbenzyl)-1H-pyrazole-3-carboximidamide (Intermediate KK, 110 mg, 0.45 mmol) and triethylamine (188 μL, 1.35 mmol) in dichloromethane (4 mL) was added 4-(trifluoromethyoxy)benzoyl chloride (101 mg, 0.45 mmol) at a temperature of 0° C. After stirring at rt for 1 h, when analytical HPLC indicated complete conversion of the starting materials, all volatiles were removed in vacuo. The residue was re-dissolved in DMSO (6 mL) and heated to 140° C. for 30 minutes in a microwave oven (CEM Discover). Then, the reaction mixture was diluted with a few mL of methanol and subjected to preparative HPLC. The title compound was obtained in pure form (110 mg, 59%): ¹H NMR (400 MHz, CDCl₃) δ 8.32 (d, 2H), 7.37 (d, 2H), 7.12 (d, 2H), 7.05 (d, 2H), 6.71 (s, 1H), 5.40 (s, 2H), 2.31 (s, 3H), 2.23 (s, 3H); ES-MS m/z 415 (MH)⁺; HPLC RT (Method K) 1.58 min.

Example 166

Preparation of 1-Methyl-3-(4-{5-[5-methyl-1-(4-methylbenzyl)-1H-pyrazol-3-yl]-1,2,4-oxadiazol-3-yl}phenyl)imidazolidin-4-one

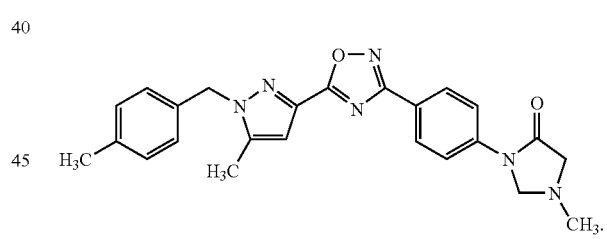

A mixture of 3-(4-{5-[5-methyl-1-(4-methylbenzyl)-1H-pyrazol-3-yl]-1,2,4-oxadiazol-3-yl}-phenyl)imidazolidin-4-one (Example 141, 50 mg, 0.12 mmol) and aqueous formaldehyde solution (37%, 0.09 mL, 1.21 mmol) in acetic acid (0.5 mL) was stirred at rt for 15 min and then cooled to 0° C. Sodium triacetoxyborohydride (384 mg, 1.81 mmol) was added, and the mixture was stirred for 1 h at 0° C. and then at rt over night. Dichloromethane was added, and the mixture was extracted twice with saturated aqueous sodium bicarbonate solution, whereupon it was dried over magnesium sulfate and concentrated under reduced pressure. The residue was subjected to preparative HPLC (RP-18 column; acetonitrile/water gradient containing 0.1% trifluoroacetic acid). The product-containing fractions were combined, and the solvent was partly removed which resulted in precipitation of a solid. A neutral pH was established by adding saturated aqueous sodium bicarbonate solution, and the mixture was stirred for 30 min whereupon the solid was filtered off and dried under reduced pressure to yield the title compound (30 mg, 59%): ¹H NMR (400 MHz, CDCl₃) δ 8.22 (d, 2H), 7.69 (d, 2H), 7.12 (d, 2H), 7.08 (d, 2H), 6.80 (s, 1H), 5.41 (s, 2H), 4.61 (s, 2H), 3.48 (s, 2H), 2.58 (s, 3H), 2.33 (s, 3H), 2.27 (s, 3H); ES-MS m/z 429 (MH)⁺, HPLC RT (Method D) 2.31 min.

Example 167

Preparation of 1-(4-{5-[5-Methyl-1-(4-methylbenzyl)-1H-pyrazol-3-yl]-1,2,4-oxadiazol-3-yl}benzyl)piperidine

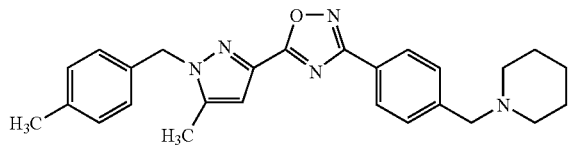 [SMILES: Cc1ccc(Cn2nc(-c3nc(-c4ccc(CN5CCCCC5)cc4)no3)cc2C)cc1]

To a mechanically stirred solution of piperidine (24 mg, 0.28 mmol) in DMF (1.5 mL) at 0° C. was added sodium hydride (60% dispersion in mineral oil, 11.3 mg, 0.28 mmol), and the mixture was stirred at 0° C. for 30 min. 3-[4-(Bromomethyl)phenyl]-5-[5-methyl-1-(4-methylbenzyl)-1H-pyrazol-3-yl]-1,2,4-oxadiazole (Intermediate LL, 100 mg, 0.24 mmol) was added, and the mixture was stirred at rt over night whereupon it was directly subjected to preparative HPLC (RP-18 column; acetonitrile/water gradient containing 0.1% trifluoroacetic acid). The product-containing fractions were combined and the solvent was partly removed. A neutral pH was established by adding saturated aqueous sodium bicarbonate solution, and the mixture was extracted three times with ethyl acetate (20 mL each). The combined organic fractions were dried over sodium sulfate, filtered and concentrated under reduced pressure to afford the title compound (62 mg, 61%): ¹H-NMR (400 MHz, DMSO-d₆) δ 8.01 (d, 2H), 7.50 (d, 2H), 7.17 (d, 2H), 7.12 (d, 2H), 6.90 (s, 1H), 5.42 (s, 2H), 3.50 (s, 2H), 2.42-2.30 (m, 4H), 2.32 (s, 3H), 2.28 (s, 3H), 1.55-1.47 (m, 4H), 1.44-1.35 (m, 2H); ES-MS m/z 428 (MH)⁺; HPLC RT (Method K) 1.10 min.

By using the method described above for Example 167, and by substituting the appropriate starting materials, Examples 168-171 found in the table below were similarly prepared.

| Example Number | Structure | HPLC RT (min) | MS m/z (MH+) | Method |
|---|---|---|---|---|
| 168 | [structure: morpholine analog] ¹H NMR (400 MHz, DMSO-d₆): δ 8.00 (d, 2H), 7.52 (d, 2H), 7.18 (d, 2H), 7.12 (d, 2H), 6.90 (s, 1H), 5.42 (s, 2H), 3.63-3.58 (m, 4H), 3.56 (s, 2H), 2.41-2.37 (m, 4H), 2.32 (s, 3H), 2.28 (s, 3H). | 1.04 | 430 | K |
| 169 | [structure: azetidine analog] ¹H NMR (400 MHz, DMSO-d₆): δ 8.02 (d, 2H), 7.46 (d, 2H), 7.18 (d, 2H), 7.11 (d, 2H), 6.90 (s, 1H), 5.42 (s, 2H), 3.61 (s, 2H), 3.20-3.12 (t, 4H), 2.32 (s, 3H), 2.28 (s, 3H), 2.04-1.96 (quin, 2H). | 1.37 | 400 | E |
| 170 | [structure: diisopropylamine analog] ¹H NMR (400 MHz, DMSO-d₆): δ 7.98 (d, 2H), 7.55 (d, 2H), 7.18 (d, 2H), 7.11 (d, 2H), 6.90 (s, 1H), 5.42 (s, 2H), 3.69 (s, 2H), 3.02-2.95 (m, 2H), 2.32 (s, 3H), 2.28 (s, 3H), 1.00 (d, 12H). | 1.46 | 444 | E |
| 171 | [structure: N-methyl-isopropylamine analog] ¹H NMR (400 MHz, DMSO-d₆): δ 8.01 (d, 2H), 7.51 (d, 2H), 7.17 (d, 2H), 7.11 (d, 2H), 6.90 (s, 1H), 5.45 (s, 2H), 3.58 (s, 2H), 2.90-2.81 (m, 1H), 2.32 (s, 3H), 2.28 (s, 3H), 2.08 (s, 3H), 1.02 (d, 6H). | 1.41 | 416 | E |

IUPAC Names of compounds of the tables above:

| Example Number | IUPAC Name |
|---|---|
| 1 | 5-[5-methyl-1-(4-methylbenzyl)-1H-pyrazol-3-yl]-3-[4-(trifluoromethoxy)phenyl]-1,2,4-oxadiazole |
| 2 | 3-{4-[(4-chlorobenzyl)oxy]phenyl}-5-[5-methyl-1-(4-methylbenzyl)-1H-pyrazol-3-yl]-1,2,4-oxadiazole |
| 3 | 3-(4-bromophenyl)-5-[5-methyl-1-(4-methylbenzyl)-1H-pyrazol-3-yl]-1,2,4-oxadiazole |
| 4 | 3-(4-tert-butylphenyl)-5-[5-methyl-1-(4-methyl-benzyl)-1H-pyrazol-3-yl]-1,2,4-oxadiazole |
| 5 | 5-[5-methyl-1-(4-methylbenzyl)-1H-pyrazol-3-yl]-3-[4'-(trifluoromethoxy)biphenyl-4-yl]-1,2,4-oxadiazole |
| 6 | 3-methyl-1-(4-{5-[5-methyl-1-(4-methylbenzyl)-1H-pyrazol-3-yl]-1,2,4-oxadiazol-3-yl}phenyl)piperidine |
| 7 | 5-[5-methyl-1-(4-methylbenzyl)-1H-pyrazol-3-yl]-3-[4-(trifluoromethyl)phenyl]-1,2,4-oxadiazole |
| 8 | 3-(4-bromophenyl)-5-{5-methyl-1-[1-(4-methyl-phenyl)ethyl]-1H-pyrazol-3-yl}-1,2,4-oxadiazole |
| 9 | 5-[5-methyl-1-(4-methylbenzyl)-1H-pyrazol-3-yl]-3-phenyl-1,2,4-oxadiazole |
| 10 | 3-(4-fluorophenyl)-5-[5-methyl-1-(4-methylbenzyl)-1H-pyrazol-3-yl]-1,2,4-oxadiazole |
| 11 | 3-(4-cyclohexylphenyl)-5-[5-methyl-1-(4-methyl-benzyl)-1H-pyrazol-3-yl]-1,2,4-oxadiazole |
| 12 | 1-(4-{5-[5-methyl-1-(4-methylbenzyl)-1H-pyrazol-3-yl]-1,2,4-oxadiazol-3-yl}phenyl)piperidine |
| 13 | 3-(4-iodophenyl)-5-[5-methyl-1-(4-methylbenzyl)-1H-pyrazol-3-yl]-1,2,4-oxadiazole |
| 14 | 4-{5-[5-methyl-1-(4-methylbenzyl)-1H-pyrazol-3-yl]-1,2,4-oxadiazol-3-yl}pyridine |
| 15 | 3-(3-bromo-4-fluorophenyl)-5-[5-methyl-1-(4-methylbenzyl)-1H-pyrazol-3-yl]-1,2,4-oxadiazole |
| 16 | 3-{5-[5-methyl-1-(4-methylbenzyl)-1H-pyrazol-3-yl]-1,2,4-oxadiazol-3-yl}pyridine |
| 17 | 5-{5-[5-methyl-1-(4-methylbenzyl)-1H-pyrazol-3-yl]-1,2,4-oxadiazol-3-yl}-2-(trifluoromethyl)pyridine |
| 18 | 5-[5-methyl-1-(4-methylbenzyl)-1H-pyrazol-3-yl]-3-[4-(2,2,2-trifluoroethoxy)phenyl]-1,2,4-oxadiazole |
| 19 | 3-[4-(cyclopentyloxy)phenyl]-5-[5-methyl-1-(4-methylbenzyl)-1H-pyrazol-3-yl]-1,2,4-oxadiazole |
| 20 | 3-(4-isopropoxyphenyl)-5-[5-methyl-1-(4-methyl-benzyl)-1H-pyrazol-3-yl]-1,2,4-oxadiazole |
| 21 | 4-(4-{5-[5-methyl-1-(4-methylbenzyl)-1H-pyrazol-3-yl]-1,2,4-oxadiazol-3-yl}phenyl)morpholine |
| 22 | 5-[5-methyl-1-(4-methylbenzyl)-1H-pyrazol-3-yl]-3-(4-pyrrolidin-1-ylphenyl)-1,2,4-oxadiazole |
| 23 | N,N-diethyl-4-{5-[5-methyl-1-(4-methylbenzyl)-1H-pyrazol-3-yl]-1,2,4-oxadiazol-3-yl}aniline |
| 24 | 1-(4-{5-[5-methyl-1-(4-methylbenzyl)-1H-pyrazol-3-yl]-1,2,4-oxadiazol-3-yl}phenyl)pyrrolidin-2-one |
| 25 | 3-(4-{5-[5-methyl-1-(4-methylbenzyl)-1H-pyrazol-3-yl]-1,2,4-oxadiazol-3-yl}phenyl)-1,3-oxazolidin-2-one |
| 26 | 4-(4-{5-[5-methyl-1-(4-methylbenzyl)-1H-pyrazol-3-yl]-1,2,4-oxadiazol-3-yl}phenyl)morpholin-3-one |
| 27 | 2-methoxy-N-(4-{5-[5-methyl-1-(4-methylbenzyl)-1H-pyrazol-3-yl]-1,2,4-oxadiazol-3-yl}phenyl)acetamide |
| 28 | 1-(4-{5-[5-methyl-1-(4-methylbenzyl)-1H-pyrazol-3-yl]-1,2,4-oxadiazol-3-yl}phenyl)piperidin-2-one |
| 29 | 2-[5-methyl-1-(4-methylbenzyl)-1H-pyrazol-3-yl]-5-phenyl-1,3-benzoxazole |
| 30 | 2-[5-methyl-1-(4-methylbenzyl)-1H-pyrazol-3-yl]-6-phenoxy-1,3-benzoxazole |
| 31 | 2-[5-methyl-1-(4-methylbenzyl)-1H-pyrazol-3-yl]-1,3-benzoxazole |
| 32 | 2-[5-methyl-1-(4-methylbenzyl)-1H-pyrazol-3-yl]-5-(1-methyl-1-phenylethyl)-1,3-benzoxazole |
| 33 | 5-benzyl-2-[5-methyl-1-(4-methylbenzyl)-1H-pyrazol-3-yl]-1,3-benzoxazole |
| 34 | 5-(3-fluorophenyl)-2-[5-methyl-1-(4-methylbenzyl)-1H-pyrazol-3-yl]-1,3-benzoxazole |
| 35 | 5-(2-fluorophenyl)-2-[5-methyl-1-(4-methylbenzyl)-1H-pyrazol-3-yl]-1,3-benzoxazole |
| 36 | 5-(3-chlorophenyl)-2-[5-methyl-1-(4-methylbenzyl)-1H-pyrazol-3-yl]-1,3-benzoxazole |
| 37 | 6-bromo-2-[5-methyl-1-(4-methylbenzyl)-1H-pyrazol-3-yl]-1H-benzimidazole |
| 38 | 2-[5-methyl-1-(4-methylbenzyl)-1H-pyrazol-3-yl]-1H-benzimidazole |
| 39 | 6-methyl-2-[5-methyl-1-(4-methylbenzyl)-1H-pyrazol-3-yl]-1H-benzimidazole |
| 40 | 4-methyl-2-[5-methyl-1-(4-methylbenzyl)-1H-pyrazol-3-yl]-1H-benzimidazole |
| 41 | 6-chloro-2-[5-methyl-1-(4-methylbenzyl)-1H-pyrazol-3-yl]-1H-benzimidazole |
| 42 | 2-[5-methyl-1-(4-methylbenzyl)-1H-pyrazol-3-yl]-3H-imidazo[4,5-c]pyridine |
| 43 | 6-tert-butyl-2-[5-methyl-1-(4-methylbenzyl)-1H-pyrazol-3-yl]-1H-benzimidazole |
| 44 | 2-[5-methyl-1-(4-methylbenzyl)-1H-pyrazol-3-yl]-6-(trifluoromethyl)-1H-benzimidazole |
| 45 | 2-[5-methyl-1-(4-methylbenzyl)-1H-pyrazol-3-yl]-6-phenyl-1H-benzimidazole |
| 46 | {2-[5-methyl-1-(4-methylbenzyl)-1H-pyrazol-3-yl]-1H-benzimidazol-6-yl}(phenyl)methanone |
| 47 | 2-[5-methyl-1-(4-methylbenzyl)-1H-pyrazol-3-yl]-1H-naphtho[2,3-d]imidazole |
| 48 | 6-[5-methyl-1-(4-methylbenzyl)-1H-pyrazol-3-yl]-1,7-dihydroimidazo[4,5-f]indazole |
| 49 | 2-[5-methyl-1-(4-methylbenzyl)-1H-pyrazol-3-yl]-6-piperidin-1-yl-1H-benzimidazole |
| 50 | 2-[5-methyl-1-(4-methylbenzyl)-1H-pyrazol-3-yl]-6-(4-methylpiperazin-1-yl)-1H-benzimidazole |
| 51 | 6-cyclohexyl-2-[5-methyl-1-(4-methylbenzyl)-1H-pyrazol-3-yl]-1H-benzimidazole |
| 52 | 2-[5-methyl-1-(4-methylbenzyl)-1H-pyrazol-3-yl]-1H-[1]benzofuro[2,3-f]benzimidazole |
| 53 | 2-[5-methyl-1-(4-methylbenzyl)-1H-pyrazol-3-yl]-6-morpholin-4-yl-1H-benzimidazole |
| 54 | 2-[5-methyl-1-(4-methylbenzyl)-1H-pyrazol-3-yl]-1H-benzimidazole-6-carbonitrile |
| 55 | 2,2-difluoro-6-[5-methyl-1-(4-methylbenzyl)-1H-pyrazol-3-yl]-5H-[1,3]dioxolo[4,5-f]benzimidazole |
| 56 | 5-chloro-6-fluoro-2-[5-methyl-1-(4-methylbenzyl)-1H-pyrazol-3-yl]-1H-benzimidazole |
| 57 | 6-bromo-4-methyl-2-[5-methyl-1-(4-methylbenzyl)-1H-pyrazol-3-yl]-1H-benzimidazole |
| 58 | 2-[5-methyl-1-(4-methylbenzyl)-1H-pyrazol-3-yl]-6-(trifluoromethoxy)-1H-benzimidazole |
| 59 | 6-(4-fluorophenyl)-2-[5-methyl-1-(4-methylbenzyl)-1H-pyrazol-3-yl]-1H-benzimidazole |
| 60 | 6-(2-fluorophenyl)-2-[5-methyl-1-(4-methylbenzyl)-1H-pyrazol-3-yl]-1H-benzimidazole |
| 61 | 6-(3-fluorophenyl)-2-[5-methyl-1-(4-methylbenzyl)-1H-pyrazol-3-yl]-1H-benzimidazole |
| 62 | 6-(2-chlorophenyl)-2-[5-methyl-1-(4-methylbenzyl)-1H-pyrazol-3-yl]-1H-benzimidazole |
| 63 | 6-(3-chlorophenyl)-2-[5-methyl-1-(4-methylbenzyl)-1H-pyrazol-3-yl]-1H-benzimidazole |
| 64 | 6-(4-chlorophenyl)-2-[5-methyl-1-(4-methylbenzyl)-1H-pyrazol-3-yl]-1H-benzimidazole |
| 65 | 5-methyl-1-(4-methylbenzyl)-3-{4-[4-(trifluoro-methoxy)phenyl]-1H-imidazol-2-yl}-1H-pyrazole |
| 66 | 3-(4,5-diphenyl-1H-imidazol-2-yl)-5-methyl-1-(4-methylbenzyl)-1H-pyrazole |
| 67 | 3-(4-biphenyl-4-yl-1H-imidazol-2-yl)-5-methyl-1-(4-methylbenzyl)-1H-pyrazole |
| 68 | 3-[4-(4-cyclohexylphenyl)-1H-imidazol-2-yl]-5-methyl-1-(4-methylbenzyl)-1H-pyrazole |
| 69 | 2-[5-methyl-1-(4-methylbenzyl)-1H-pyrazol-3-yl]-4-phenyl-4,5-dihydro-1,3-oxazole |
| 70 | 4-(4-tert-butylphenyl)-2-[5-methyl-1-(4-methyl-benzyl)-1H-pyrazol-3-yl]-4,5-dihydro-1,3-oxazole |
| 71 | 4-isopropyl-2-[5-methyl-1-(4-methylbenzyl)-1H-pyrazol-3-yl]-4,5-dihydro-1,3-oxazole |
| 72 | 4-(4-chlorobenzyl)-2-[5-methyl-1-(4-methylbenzyl)-1H-pyrazol-3-yl]-4,5-dihydro-1,3-oxazole |
| 73 | 2-[5-methyl-1-(4-methylbenzyl)-1H-pyrazol-3-yl]-4-[4-(trifluoromethoxy)phenyl]-4,5-dihydro-1,3-oxazole |
| 74 | 2-[5-methyl-1-(4-methylbenzyl)-1H-pyrazol-3-yl]-4-phenyl-1,3-oxazole |
| 75 | 4-(4-bromophenyl)-2-[5-methyl-1-(4-methylbenzyl)-1H-pyrazol-3-yl]-1,3-oxazole |

| Example Number | IUPAC Name |
|---|---|
| 76 | 4-(4'-chlorobiphenyl-4-yl)-2-[5-methyl-1-(4-methylbenzyl)-1H-pyrazol-3-yl]-1,3-oxazole |
| 77 | 4-(4-tert-butylphenyl)-2-[5-methyl-1-(4-methylbenzyl)-1H-pyrazol-3-yl]-1,3-oxazole |
| 78 | 2-[5-methyl-1-(4-methylbenzyl)-1H-pyrazol-3-yl]-4-[4-(trifluoromethoxy)phenyl]-1,3-oxazole |
| 79 | 1-(4-{2-[5-methyl-1-(4-methylbenzyl)-1H-pyrazol-3-yl]-1,3-oxazol-4-yl}phenyl)piperidine |
| 80 | 4-(4-cyclohex-1-en-1-ylphenyl)-2-[5-methyl-1-(4-methylbenzyl)-1H-pyrazol-3-yl]-1,3-oxazole |
| 81 | 4-(4-cyclohex-1-ylphenyl)-2-[5-methyl-1-(4-methylbenzyl)-1H-pyrazol-3-yl]-1,3-oxazole |
| 82 | 3-[4-(4-fluorotetrahydro-2H-pyran-4-yl)phenyl]-5-[5-methyl-1-(4-methylbenzyl)-1H-pyrazol-3-yl]-1,2,4-oxadiazole |
| 83 | 3-[4-(4-methoxytetrahydro-2H-pyran-4-yl)phenyl]-5-[5-methyl-1-(4-methylbenzyl)-1H-pyrazol-3-yl]-1,2,4-oxadiazole |
| 84 | 3-(4-tert-butylphenyl)-5-[5-ethyl-1-(4-methylbenzyl)-1H-pyrazol-3-yl]-1,2,4-oxadiazole |
| 85 | 4-(4-5-[5-methyl-1-(4-methylbenzyl)-1H-pyrazol-3-yl]-1,2,4-oxadiazol-3-ylphenyl)tetrahydro-2H-pyran-4-ol |
| 86 | 5-(1-benzyl-5-methyl-1H-pyrazol-3-yl)-3-[4-(trifluoromethoxy)phenyl]-1,2,4-oxadiazole |
| 87 | 5-[5-ethyl-1-(4-methylbenzyl)-1H-pyrazol-3-yl]-3-[4-(trifluoromethoxy)phenyl]-1,2,4-oxadiazole |
| 88 | 5-[5-ethyl-1-(4-methylbenzyl)-1H-pyrazol-3-yl]-3-[4-(trifluoromethyl)phenyl]-1,2,4-oxadiazole |
| 89 | 3-(4-bromophenyl)-5-[5-ethyl-1-(4-methylbenzyl)-1H-pyrazol-3-yl]-1,2,4-oxadiazole |
| 90 | methyl 4-5-[5-ethyl-1-(4-methylbenzyl)-1H-pyrazol-3-yl]-1,2,4-oxadiazol-3-ylbenzoate |
| 91 | 5-[5-ethyl-4-methyl-1-(4-methylbenzyl)-1H-pyrazol-3-yl]-3-[4-(trifluoromethoxy)phenyl]-1,2,4-oxadiazole |
| 92 | 5-[5-ethyl-1-(4-methylbenzyl)-1H-pyrazol-3-yl]-3-(4-nitrophenyl)-1,2,4-oxadiazole |
| 93 | 3-4-[(1-methylethyl)sulfonyl]phenyl-5-[5-methyl-1-(4-methylbenzyl)-1H-pyrazol-3-yl]-1,2,4-oxadiazole |
| 94 | 4-5-[5-methyl-1-(4-methylbenzyl)-1H-pyrazol-3-yl]-1,2,4-oxadiazol-3-ylbenzenesulfonamide |
| 95 | 2-(4-5-[5-methyl-1-(4-methylbenzyl)-1H-pyrazol-3-yl]-1,2,4-oxadiazol-3-ylphenyl)propan-2-ol |
| 96 | 5-[5-methyl-1-(4-methylbenzyl)-1H-pyrazol-3-yl]-3-4-[(trifluoromethyl)sulfonyl]phenyl-1,2,4-oxadiazole |
| 97 | 5-[5-methyl-1-(4-methylbenzyl)-1H-pyrazol-3-yl]-3-[4-(methylsulfanyl)phenyl]-1,2,4-oxadiazole |
| 98 | di-tert-butyl (4-5-[5-methyl-1-(4-methylbenzyl)-1H-pyrazol-3-yl]-1,2,4-oxadiazol-3-ylbenzyl)imidodicarbonate |
| 99 | 5-[5-methyl-1-(4-methylbenzyl)-1H-pyrazol-3-yl]-3-[4-(methylsulfonyl)phenyl]-1,2,4-oxadiazole |
| 100 | 5-[5-methyl-1-(4-methylbenzyl)-1H-pyrazol-3-yl]-3-[4-(phenylsulfonyl)phenyl]-1,2,4-oxadiazole |
| 101 | tert-butyl (4-5-[5-methyl-1-(4-methylbenzyl)-1H-pyrazol-3-yl]-1,2,4-oxadiazol-3-ylphenyl)carbamate |
| 102 | tert-butyl 4-hydroxy-4-(4-5-[5-methyl-1-(4-methylbenzyl)-1H-pyrazol-3-yl]-1,2,4-oxadiazol-3-ylphenyl)piperidine-1-carboxylate |
| 103 | 3-[4-(1-fluoro-1-methylethyl)phenyl]-5-[5-methyl-1-(4-methylbenzyl)-1H-pyrazol-3-yl]-1,2,4-oxadiazole |
| 104 | 5-[5-methyl-1-(4-methylbenzyl)-1H-pyrazol-3-yl]-3-4-[(tetrahydro-2H-pyran-4-yloxy)methyl]phenyl-1,2,4-oxadiazole |
| 105 | 5-[5-methyl-1-(4-methylbenzyl)-1H-pyrazol-3-yl]-3-4-[(trifluoromethyl)sulfanyl]phenyl-1,2,4-oxadiazole |
| 106 | tert-butyl 4-[(4-5-[5-methyl-1-(4-methylbenzyl)-1H-pyrazol-3-yl]-1,2,4-oxadiazol-3-ylbenzyl)oxy]piperidine-1-carboxylate |
| 107 | 5-[5-methyl-1-(4-methylbenzyl)-1H-pyrazol-3-yl]-3-[4-(tetrahydro-2H-pyran-4-ylmethoxy)phenyl]-1,2,4-oxadiazole |
| 108 | tert-butyl 4-[(4-5-[5-methyl-1-(4-methylbenzyl)-1H-pyrazol-3-yl]-1,2,4-oxadiazol-3-ylphenoxy)methyl]piperidine-1-carboxylate |
| 109 | N,N-dimethyl-4-5-[5-methyl-1-(4-methylbenzyl)-1H-pyrazol-3-yl]-1,2,4-oxadiazol-3-ylbenzenesulfonamide |
| 110 | (4-5-[5-methyl-1-(4-methylbenzyl)-1H-pyrazol-3-yl]-1,2,4-oxadiazol-3-ylphenyl)methanol |
| 111 | 3-[4-(3-fluorooxetan-3-yl)phenyl]-5-[5-methyl-1-(4-methylbenzyl)-1H-pyrazol-3-yl]-1,2,4-oxadiazole |
| 112 | 3-[4-(3-methoxyoxetan-3-yl)phenyl]-5-[5-methyl-1-(4-methylbenzyl)-1H-pyrazol-3-yl]-1,2,4-oxadiazole |
| 113 | tert-butyl (4-5-[5-methyl-1-(4-methylbenzyl)-1H-pyrazol-3-yl]-1,2,4-oxadiazol-3-ylbenzyl)carbamate |
| 114 | 5-[5-methyl-1-(4-methylbenzyl)-1H-pyrazol-3-yl]-3-[4-(phenylsulfanyl)phenyl]-1,2,4-oxadiazole |
| 115 | 5-[5-methyl-1-(4-methylbenzyl)-1H-pyrazol-3-yl]-3-[4-(tetrahydro-2H-pyran-4-yloxy)phenyl]-1,2,4-oxadiazole |
| 116 | 3-[4-(2-methoxyethoxy)phenyl]-5-[5-methyl-1-(4-methylbenzyl)-1H-pyrazol-3-yl]-1,2,4-oxadiazole |
| 117 | N-(2-methoxyethyl)-4-5-[5-methyl-1-(4-methylbenzyl)-1H-pyrazol-3-yl]-1,2,4-oxadiazol-3-ylaniline |
| 118 | 3-[4-(1H-imidazol-1-yl)phenyl]-5-[5-methyl-1-(4-methylbenzyl)-1H-pyrazol-3-yl]-1,2,4-oxadiazole |
| 119 | 4-[(5-methyl-3-3-[4-(trifluoromethoxy)phenyl]-1,2,4-oxadiazol-5-yl-1H-pyrazol-1-yl)methyl]phenol |
| 120 | 5-[1-(4-chlorobenzyl)-5-methyl-1H-pyrazol-3-yl]-3-[4-(trifluoromethoxy)phenyl]-1,2,4-oxadiazole |
| 121 | 4-[(5-methyl-3-3-[4-(trifluoromethoxy)phenyl]-1,2,4-oxadiazol-5-yl-1H-pyrazol-1-yl)methyl]benzonitrile |
| 122 | 5-[1-(4-methoxybenzyl)-5-methyl-1H-pyrazol-3-yl]-3-[4-(trifluoromethoxy)phenyl]-1,2,4-oxadiazole |
| 123 | 5-[5-methyl-1-(3-methylbenzyl)-1H-pyrazol-3-yl]-3-[4-(trifluoromethoxy)phenyl]-1,2,4-oxadiazole |
| 124 | 5-[1-(3-fluoro-4-methylbenzyl)-5-methyl-1H-pyrazol-3-yl]-3-[4-(trifluoromethoxy)phenyl]-1,2,4-oxadiazole |
| 125 | 5-[1-(4-fluorobenzyl)-5-methyl-1H-pyrazol-3-yl]-3-[4-(trifluoromethoxy)phenyl]-1,2,4-oxadiazole |
| 126 | 1-(4-methylbenzyl)-3-3-[4-(trifluoromethoxy)phenyl]-1,2,4-oxadiazol-5-yl-1H-pyrazol-5-amine |
| 127 | 5-(1-4-[2-(2-methoxyethoxy)ethoxy]benzyl-5-methyl-1H-pyrazol-3-yl)-3-[4-(trifluoromethoxy)phenyl]-1,2,4-oxadiazole |
| 128 | 5-[1-(4-methylbenzyl)-5-(trifluoromethyl)-1H-pyrazol-3-yl]-3-[4-(trifluoromethoxy)phenyl]-1,2,4-oxadiazole |
| 129 | 5-[1-(4-chlorobenzyl)-5-(trifluoromethyl)-1H-pyrazol-3-yl]-3-[4-(trifluoromethoxy)phenyl]-1,2,4-oxadiazole |
| 130 | 4-[3-3-[4-(trifluoromethoxy)phenyl]-1,2,4-oxadiazol-5-yl-5-(trifluoromethyl)-1H-pyrazol-1-yl]methylbenzonitrile |
| 131 | 5-[1-(3-fluorobenzyl)-5-methyl-1H-pyrazol-3-yl]-3-[4-(trifluoromethoxy)phenyl]-1,2,4-oxadiazole |
| 132 | 5-[5-methyl-1-(2-methylbenzyl)-1H-pyrazol-3-yl]-3-[4-(trifluoromethoxy)phenyl]-1,2,4-oxadiazole |
| 133 | 5-[1-(2-fluorobenzyl)-5-methyl-1H-pyrazol-3-yl]-3-[4-(trifluoromethoxy)phenyl]-1,2,4-oxadiazole |
| 134 | methyl 4-[(5-methyl-3-3-[4-(trifluoromethoxy)phenyl]-1,2,4-oxadiazol-5-yl-1H-pyrazol-1-yl)methyl]benzoate |
| 135 | 5-5-methyl-1-[4-(trifluoromethyl)benzyl]-1H-pyrazol-3-yl-3-[4-(trifluoromethoxy)phenyl]-1,2,4-oxadiazole |
| 136 | 5-[5-methyl-1-(4-methylbenzyl)-1H-pyrazol-3-yl]-3-4-[(trifluoromethyl)sulfinyl]phenyl-1,2,4-oxadiazole |
| 137 | 5-[5-methyl-1-(4-methylbenzyl)-1H-pyrazol-3-yl]-3-[4-(methylsulfinyl)phenyl]-1,2,4-oxadiazole |
| 138 | 5-[5-methyl-1-(4-methylbenzyl)-1H-pyrazol-3-yl]-3-[4-(phenylsulfinyl)phenyl]-1,2,4-oxadiazole |
| 139 | 1-(4-5-[5-methyl-1-(4-methylbenzyl)-1H-pyrazol-3-yl]-1,2,4-oxadiazol-3-ylphenyl)methanamine |
| 140 | 5-[5-methyl-1-(4-methylbenzyl)-1H-pyrazol-3-yl]-3-[4-(1H-pyrrol-1-ylmethyl)phenyl]-1,2,4-oxadiazole |
| 141 | 3-(4-5-[5-methyl-1-(4-methylbenzyl)-1H-pyrazol-3-yl]-1,2,4-oxadiazol-3-ylphenyl)imidazolidin-4-one |
| 142 | 5-[1-(4-chlorobenzyl)-5-methyl-1H-pyrazol-3-yl]-3-4-[(trifluoromethyl)sulfonyl]phenyl-1,2,4-oxadiazole |

| Example Number | IUPAC Name |
|---|---|
| 143 | N-(4-[5-methyl-3-(3-4-[(trifluoromethyl)sulfonyl]-phenyl-1,2,4-oxadiazol-5-yl)-1H-pyrazol-1-yl]-methylphenyl)acetamide |
| 144 | 4-[5-methyl-3-(3-4-[(trifluoromethyl)sulfonyl]phenyl-1,2,4-oxadiazol-5-yl)-1H-pyrazol-1-yl]methyl-benzonitrile |
| 145 | 5-[1-(4-methoxybenzyl)-5-methyl-1H-pyrazol-3-yl]-3-4-[(trifluoromethyl)sulfonyl]phenyl-1,2,4-oxadiazole |
| 146 | 5-1-[2-(difluoromethoxy)benzyl]-5-methyl-1H-pyrazol-3-yl-3-4-[(trifluoromethyl)sulfonyl]phenyl-1,2,4-oxadiazole |
| 147 | methyl 3-[5-methyl-3-(3-4-[(trifluoromethyl)sulfonyl]-phenyl-1,2,4-oxadiazol-5-yl)-1H-pyrazol-1-yl]-methylbenzoate |
| 148 | 5-[1-(4-chlorobenzyl)-5-methyl-1H-pyrazol-3-yl]-3-[4-(2-fluoropropan-2-yl)phenyl]-1,2,4-oxadiazole |
| 149 | N-4-[(3-3-[4-(2-fluoropropan-2-yl)phenyl]-1,2,4-oxadiazol-5-yl-5-methyl-1H-pyrazol-1-yl)methyl]-phenylacetamide |
| 150 | 4-[(3-3-[4-(2-fluoropropan-2-yl)phenyl]-1,2,4-oxadiazol-5-yl-5-methyl-1H-pyrazol-1-yl)methyl]-benzonitrile |
| 151 | 3-[4-(2-fluoropropan-2-yl)phenyl]-5-[1-(4-methoxy-benzyl)-5-methyl-1H-pyrazol-3-yl]-1,2,4-oxadiazole |
| 152 | 5-1-[2-(difluoromethoxy)benzyl]-5-methyl-1H-pyrazol-3-yl-3-[4-(2-fluoropropan-2-yl)phenyl]-1,2,4-oxadiazole |
| 153 | methyl 3-[(3-3-[4-(2-fluoropropan-2-yl)phenyl]-1,2,4-oxadiazol-5-yl-5-methyl-1H-pyrazol-1-yl)methyl]-benzoate |
| 154 | methyl 3-[(3-3-[4-(4-fluorotetrahydro-2H-pyran-4-yl)phenyl]-1,2,4-oxadiazol-5-yl-5-methyl-1H-pyrazol-1-yl)methyl]benzoate |
| 155 | 4-[(3-3-[4-(4-fluorotetrahydro-2H-pyran-4-yl)-phenyl]-1,2,4-oxadiazol-5-yl-5-methyl-1H-pyrazol-1-yl)methyl]benzonitrile |
| 156 | 3-[4-(4-fluorotetrahydro-2H-pyran-4-yl)phenyl]-5-[1-(4-methoxybenzyl)-5-methyl-1H-pyrazol-3-yl]-1,2,4-oxadiazole |
| 157 | 5-[1-(4-chlorobenzyl)-5-methyl-1H-pyrazol-3-yl]-3-[4-(4-fluorotetrahydro-2H-pyran-4-yl)phenyl]-1,2,4-oxadiazole |
| 158 | methyl 3-[(5-methyl-3-3-[4-(trifluoromethoxy)-phenyl]-1,2,4-oxadiazol-5-yl-1H-pyrazol-1-yl)-methyl]benzoate |
| 159 | 5-[1-(4-chlorobenzyl)-5-methyl-1H-pyrazol-3-yl]-3-[4-(3-methoxyoxetan-3-yl)phenyl]-1,2,4-oxadiazole |
| 160 | 5-1-[2-(difluoromethoxy)benzyl]-5-methyl-1H-pyrazol-3-yl-3-[4-(4-fluorotetrahydro-2H-pyran-4-yl)-phenyl]-1,2,4-oxadiazole |
| 161 | 5-1-[2-(difluoromethoxy)benzyl]-5-methyl-1H-pyrazol-3-yl-3-[4-(trifluoromethoxy)phenyl]-1,2,4-oxadiazole |
| 162 | N-4-[(3-3-[4-(4-fluorotetrahydro-2H-pyran-4-yl)-phenyl]-1,2,4-oxadiazol-5-yl-5-methyl-1H-pyrazol-1-yl)methyl]phenylacetamide |
| 163 | N-4-[(3-3-[4-(3-methoxyoxetan-3-yl)phenyl]-1,2,4-oxadiazol-5-yl-5-methyl-1H-pyrazol-1-yl)methyl]-phenylacetamide |
| 164 | 5-[1-(4-iodobenzyl)-5-methyl-1H-pyrazol-3-yl]-3-[4-(trifluoromethoxy)phenyl]-1,2,4-oxadiazole |
| 165 | 3-[5-methyl-1-(4-methylbenzyl)-1H-pyrazol-3-yl]-5-[4-(trifluoromethoxy)phenyl]-1,2,4-oxadiazole |
| 166 | 1-methyl-3-(4-5-[5-methyl-1-(4-methylbenzyl)-1H-pyrazol-3-yl]-1,2,4-oxadiazol-3-ylphenyl)-imidazolidin-4-one |
| 167 | 1-(4-5-[5-methyl-1-(4-methylbenzyl)-1H-pyrazol-3-yl]-1,2,4-oxadiazol-3-ylbenzyl)piperidine |
| 168 | 4-(4-5-[5-methyl-1-(4-methylbenzyl)-1H-pyrazol-3-yl]-1,2,4-oxadiazol-3-ylbenzyl)morpholine |
| 169 | 3-[4-(azetidin-1-ylmethyl)phenyl]-5-[5-methyl-1-(4-methylbenzyl)-1H-pyrazol-3-yl]-1,2,4-oxadiazole |
| 170 | N-(4-5-[5-methyl-1-(4-methylbenzyl)-1H-pyrazol-3-yl]-1,2,4-oxadiazol-3-ylbenzyl)-N-(propan-2-yl)-propan-2-amine |
| 171 | N-methyl-N-(4-5-[5-methyl-1-(4-methylbenzyl)-1H-pyrazol-3-yl]-1,2,4-oxadiazol-3-ylbenzyl)propan-2-amine |

Biological Evaluation

Demonstration of the activity of the compounds of the present invention may be accomplished through in vitro, ex vivo, and in vivo assays that are well known in the art. For example, to demonstrate the activity of the compounds of the present invention, the following assays may be used.

Biological Assays

HIF-Luciferase Assay:

HCT-116 cells stably transfected with a Luciferase reporter gene under the control of HIF-responsive element were plated in white 96- or 384-well plates at 30,000 or 5,000 cells/well, respectively, in 50 µL/well media (RPMI with 10% fetal bovine serum and 100 µg/mL Hygromycin). Cells were incubated overnight at 37° C. in a humidified incubator containing 5% $CO_2$ under normal oxygen. The next day test compounds were added to the wells at various concentrations (0-10 µM, 0.1% final DMSO concentration) and placed in a hypoxic chamber overnight at 1% oxygen. Following the exposure to hypoxic conditions, 50 µL/well of Bright Glo reagent (Promega, Wisconsin, USA) was added to the wells and luminescence was measured after 5 min. Cells incubated under normal oxygen levels were used as background control. Compounds that have an $IC_{50} \leq 1$ µM in this assay include those of Examples 1, 2, 3, 4, 5, 6, 7, 9, 10, 11, 12, 14, 17, 18, 20, 21, 24, 25, 26, 27, 29, 30, 31, 34, 35, 36, 37, 44, 45, 46, 49, 51, 52, 55, 58, 59, 60, 61, 62, 63, 64, 65, 67, 68, 74, 75, 76, and 77. Compounds that have $IC_{50}$ values between 1 µM and 10 µM include those of Examples 8, 16, 38, 39, 40, 41, 42, 43, 47, 48, 53, 54, 56, 57, 66, 69, and 72. Those that have measured $IC_{50}$ values >10 include those of examples 15, 32, 33, 50, 70, and 71. Individual $IC_{50}$ values of some representative Examples are listed in the table below.

Table: Activity in the HIF-Luciferase Assay

| Example Number | $IC_{50}$ [µmol/L] |
|---|---|
| 1 | 0.03 |
| 4 | 0.005 |
| 18 | 0.03 |
| 24 | 0.08 |
| 59 | 0.005 |
| 64 | 0.003 |
| 67 | 0.008 |
| 68 | 0.006 |
| 77 | 0.02 |
| 81 | 0.05 |
| 103 | 0.01 |
| 105 | 0.03 |
| 120 | 0.02 |
| 121 | 0.03 |
| 140 | 0.04 |

MSD Total HIF-1α Singleplex Assay:

HCT-116 cells were cultured for 24 h in collagen coated 96-well cell culture plates ($3 \times 10^4$ cells per well). Compounds diluted to appropriate concentrations in culture medium were added (100 µl/well), and cells were cultured for another 24 h at 1% oxygen concentration in the atmosphere. Controls were cultured under normoxic conditions. Cell culture medium was removed and cells were washed with buffer and lysed with lysis buffer containing detergent. 80 µl of lysate was added to MSD detection plates coated previously with anti-HIF-1α antibodies and blocked with 150 µl/well of blocking solution. After 1 h at room temperature, wells were washed 4-times with 200 µl Tris-Wash-buffer. 25 µl of SULFO-TAG detection antibody against HIF-1α was added at 10 nM and incubated for 1 h. After washing 4-times with wash-buffer, 150 µl of READ Buffer T was added, and the signal was measured using a redox measure instrument (SECTOR). $IC_{50}$ concentrations were analyzed according to standard methods used in the field.

In Vivo Efficacy Studies: Staged Human Xenograft Models

Staged human xenograft models grown in mice or rats are used to evaluate compound efficacy. To generate tumors, cells harvested from mid-log phase cultures or tumor fragments from in vivo passage are injected s.c. in the flank of athymic mice or rats.

Treatment administered p.o. or i.v. is initiated when all mice in each experiment had established tumors. The general health of animals is monitored and mortality is recorded daily. Tumor dimensions and body weights are recorded two to three times a week starting with the first day of treatment. Tumor weights are calculated using the equation (l×w2)/2, where l and w refer to the larger and smaller dimensions collected at each measurement. Anti-tumor efficacy is measured as tumor growth inhibition (TGI). TGI is calculated by the equation [1−(T/C)]*100, where T and C represent the mean tumor size of the treated (T) and untreated or vehicle control (C) groups, respectively, at the end of treatment.

It is believed that one skilled in the art, using the preceeding information and information available in the art, can utilize the present invention to its fullest extent. Those skilled in the art will recognize that the invention may be practiced with variations on the disclosed structures, materials, compositions and methods without departing from the spirit or scope of the invention as it is set forth herein and such variations are regarded as within the ambit of the invention. The compounds described in the examples are intended to be representative of the invention, and it will be understood that the scope of the invention is not limited by the scope of the examples. The topic headings set forth above are meant as guidance where certain information can be found in the application, but are not intended to be the only source in the application where information on such topics can be found. All publications and patents cited above are incorporated herein by reference.

REFERENCES

Globocan 2002 Report
IARC International Agency for Research on Cancer: Globocan 2002, http://www-dep.iarc.fr/globocan/downloads.htm
American Cancer Society, Cancer Facts and Figures 2005
American Cancer Society: *Cancer Facts and Figures* 2007, http://www.cancer.org/docroot/STT/content/STT_1x_Cancer_Facts_Figures_2007.asp
Gibbs J B, 2000
Gibbs J B: Mechanism-based target identification and drug discovery in cancer research, *Science* 2000, 287 (5460), 1969-1973.
Semenza and Wang, 1992
Semenza G L, Wang G L: A nuclear factor induced by hypoxia via de novo protein synthesis binds to the human erythropoietin gene enhancer at a site required for transcriptional activation, *Mol. Cell. Biol.* 1992, 12 (12), 5447-5454.
Wang and Semenza, 1995
Wang G L, Semenza G L: Purification and characterization of hypoxia-inducible factor 1, *J. Biol. Chem.* 1995, 270 (3), 1230-1237.
Wang, Jiang et al., 1995
Wang G L, Jiang O H, Rue E A, Semenza G L; Hypoxia-inducible factor 1 is a basic-helix-loop-helix-PAS heterodimer regulated by cellular O2 tension, *PNAS* 1995, 92 (12), 5510-5514.
Jiang, Rue et al., 1996
Jiang B H, Rue E, Wang G L, Roe R, Semenza G L: Dimerization, DNA binding, and transactivation properties of hypoxia-inducible factor 1, *J. Biol. Chem.* 1996, 271 (30), 17771-17778.
Makino, Cao et al., 2001
Makino Y, Cao R, Svensson K, Bertilsson G, Asman M, Tanaka H, Cao Y, Poellinger L: *Nature* 2001, 414 (6863), 550-554.
Jiang, Semenza et al., 1996
Jiang B H, Semenza G L, Bauer C, Marti H H: Hypoxia-inducible factor 1 levels vary exponentially over a physiologically relevant range of O2 tension, *Am. J. Physiol.* 1996, 271, 1172-1180.
Maxwell, Wiesener et al., 1999
Maxwell P H, Wiesener M S, Chang G W, Clifford S C, Vaux E C, Cockman M E, Wykoff C C, Ratcliffe P J: The tumour suppressor protein VHL targets hypoxia-inducible factors for oxygen-dependent proteolysis, *Nature* 1999, 399 (6733), 271-275.
Hirota and Semenza, 2006
Hirota K, Semenza GL: Regulation of angiogenesis by hypoxia-inducible factor 1, *Crit. Rev. Oncol. Hematol.* 2006, 59 (1), 15-26.
Chen, Zhao et al., 2003
Chen J, Zhao S, Nakada K, Kuge Y, Tamaki N, Okada F, Wang J, Shindo M, Higashino F, Takeda K, Asaka M, Katoh H, Sugiyama T, Hosokawa M, Kobayashi M: Dominant-negative hypoxia-inducible factor-1alpha reduces tumorigenicity of pancreatic cancer cells through the suppression of glucose metabolism, *Am. J. Pathol.* 2003, 162 (4), 1283-1291.
Stoeltzing, McCarty et al., 2004
Stoeltzing O, McCarty M F, Wey J S, Fan F, Liu W, Belcheva A, Bucana C D, Semenza G L, Ellis L M: Role of hypoxia-inducible factor-1alpha in gastric cancer cell growth, angiogenesis, and vessel maturation, *J. Natl. Cancer Inst.* 2004, 96 (12), 946-956.
Li, Lin et al., 2005
Li L, Lin X, Stayer M, Shoemaker A, Semizarov D, Fesik S W, Shen Y: Evaluating hypoxia-inducible factor-1alpha as a cancer therapeutic target via inducible RNA interference in vivo, *Cancer Res.* 2005, 65 (16), 7249-7258.
Mizukami, Jo et al., 2005
Mizukami Y, Jo W S, Duerr E M, Gala M, Li J, Zhang X, Zimmer M A, Iliopoulos O, Zukerberg L R, Kohgo Y, Lynch M P, Rueda B R, Chung D C: Induction of interleukin-8 preserves the angiogenic response in HIF-1alpha-deficient colon cancer cells, *Nat. Med.* 2005, 11 (9), 992-997.
Li, Shi et al., 2006
Li J, Shi M, Cao Y, Yuan W, Pang T, Li B, Sun Z, Chen L, Zhao R C: Knockdown of hypoxia-inducible factor-1alpha in breast carcinoma MCF-7 cells results in reduced tumor growth and increased sensitivity to methotrexate, *Biochem. Biophys. Res. Commun.* 2006, 342, 1341-1351.

What is claimed is:

1. A compound having the formula:

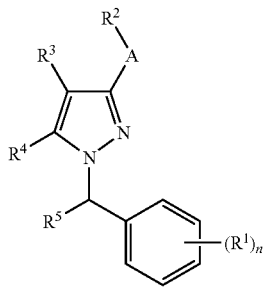

or a physiologically acceptable salt thereof, wherein:

A is heteroaryl optionally substituted with halogen or phenyl, or is heterocyclyl;

n is an integer from 0-3;

$R^1$ at each occurrence is independently halogen, —$NR^6C(O)R^7$, —$C(O)R^6$, —$C(O)OR^6$, —$OC(O)R^6$, —$OR^6$, —$SR^6$, —$S(O)R^6$, —$SO_2R^6$, cyano, nitro, —$C(O)NR^6R^7$, —$SO_2NR^6R^7$, or —$NR^6R^7$, or $R^1$ is independently aryl, heteroaryl, heterocyclyl, alkyl or cycloalkyl each optionally substituted with one or more halogen, $OR^6$ or $NR^6R^7$ groups;

$R^2$ is aryl optionally substituted with 1, 2 or 3 $R^8$ groups or heteroaryl optionally substituted with 1, 2 or 3 $R^8$ groups, when A is mono- or bicyclic heteroaryl or mono- or bicyclic heterocyclyl, or $R^2$ is hydrogen, halogen, cyano, alkyl optionally substituted with up to 3 fluoro atoms, alkyloxy optionally substituted with up to 3 fluoro atoms, cycloalkyl, aryloxy, aroyl, aralkyl optionally substituted with halogen, or heterocyclyl optionally substituted with alkyl, when A is bi- or tricyclic heteroaryl or mono-, bi- or tricyclic heterocyclyl;

$R^3$ and $R^4$ are each independently hydrogen, halogen, —$OR^6$, —$SR^6$, —$NR^6R^7$, alkyl optionally substituted with one or more halogen, $R^6$, —$OR^6$ or —$NR^6R^7$ groups, or cycloalkyl optionally substituted with one or more halogen, $R^6$, —$OR^6$ or —$NR^6R^7$ groups;

$R^5$ is hydrogen, oxo, or alkyl optionally substituted with one or more halogen, —$OR^6$ or —$NR^6R^7$ groups;

each occurrence of $R^6$ or $R^7$ may be the same or different and is independently hydrogen, or aryl, heteroaryl, heterocyclyl, alkyl, or cycloalkyl each of which may be optionally substituted with one or more hydrogen, halogen, —$OR^9$ or —$NR^9R^{10}$ groups;

each occurrence of $R^8$ may be the same or different and is independently hydrogen, halogen, —$NR^9C(O)R^{10}$, —$NR^9C(O)OR^{10}$, —$C(O)R^9$, —$C(O)OR^9$, —$OC(O)R^9$, —$OR^9$, —$SR^9$, —$S(O)R^9$, —$SO_2R^9$, cyano, nitro, —$C(O)NR^9R^{10}$, —$SO_2NR^9R^{10}$, —$NR^9R^{10}$, or aryl, heteroaryl, heterocyclyl, alkyl, or cycloalkyl, each of which may be optionally substituted with one or more halogen, $R^{11}$, —$OR^9$ or —$NR^9R^{10}$ groups;

each occurrence of $R^9$ and $R^{10}$ may be the same or different and is independently hydrogen, or aryl, heteroaryl, heterocyclyl, alkyl, cycloalkyl, aralkyl, or heterocyclylalkyl each of which may be optionally substituted with one or more hydrogen, halogen, hydroxyl, alkyloxy, cycloalkyloxy, aryloxy, amino, alkylamino, cycloalkylamino, arylamino, alkyl, cycloalkyl, alkylcarbonyl or alkoxycarbonyl groups;

each occurrence of $R^{11}$ may be the same or different and is independently hydrogen, oxo, aryl, heteroaryl, heterocyclyl, alkyl, cycloalkyl, —$C(O)R^9$, —$C(O)OR^9$, —$NR^{12}C(O)R^{13}$, —$N[C(O)R^{13}]_2$, —$NR^{12}C(O)OR^{13}$, or —$N[C(O)OR^{13}]_2$;

$R^{12}$ is hydrogen or alkyl; and $R^{13}$ is alkyl.

2. The compound of claim 1, wherein

A is heteroaryl or heterocyclyl;

n is an integer from 0-3;

$R^1$ at each occurrence is independently halogen, —$NR^6C(O)R^7$, —$C(O)R^6$, —$C(O)OR^6$, —$OC(O)R^6$, —$OR^6$, —$SR^6$, cyano, nitro, —$C(O)NR^6R^7$, —$SO_2NR^6R^7$, or —$NR^6R^7$, or $R^1$ is independently aryl, heteroaryl, heterocyclyl, alkyl or cycloalkyl each optionally substituted with one or more halogen, $OR^6$ or $NR^6R^7$ groups;

$R^2$ is aryl optionally substituted with 1, 2 or 3 $R^8$ groups or heteroaryl optionally substituted with 1, 2 or 3 $R^8$ groups;

$R^3$ and $R^4$ are each independently hydrogen, halogen, —$OR^6$, —$SR^6$, —$NR^6R^7$, alkyl optionally substituted with one or more halogen, $R^6$, —$OR^6$ or —$NR^6R^7$ groups, or cycloalkyl optionally substituted with one or more halogen, $R^6$, —$OR^6$ or —$NR^6R^7$ groups;

$R^5$ is hydrogen, oxo, or alkyl optionally substituted with one or more halogen, —$OR^6$ or —$NR^6R^7$ groups;

each occurrence of $R^6$ or $R^7$ may be the same or different and is independently hydrogen, or aryl, heteroaryl, heterocyclyl, alkyl, or cycloalkyl each of which may be optionally substituted with one or more hydrogen, halogen, —$OR^9$ or —$NR^9R^{10}$ groups;

each occurrence of $R^8$ may be the same or different and is independently hydrogen, halogen, —$NR^9C(O)R^{10}$, —$C(O)R^9$, —$C(O)OR^9$, —$OC(O)R^9$, —$OR^9$, —$SR^9$, cyano, nitro, —$C(O)NR^9R^{10}$, —$SO_2NR^9R^{10}$, —$NR^9R^{10}$, or aryl, heteroaryl, heterocyclyl, alkyl, or cycloalkyl each of which may be optionally substituted with one or more halogen, $R^{11}$, —$OR^9$ or —$NR^9R^{10}$ groups; and each occurrence of $R^9$ and $R^{10}$ may be the same or different and is independently hydrogen, or aryl, heteroaryl, heterocyclyl, alkyl, or cycloalkyl each of which may be optionally substituted with one or more hydrogen, halogen, hydroxyl, alkyloxy, cycloalkyloxy, aryloxy, amino, alkylamino, cycloalkylamino, or arylamino groups;

each occurrence of $R^{11}$ may be the same or different and is independently hydrogen, halogen, aryl, oxo, heteroaryl, heterocyclyl, alkyl, cycloalkyl, hydroxyl, alkyloxy, cycloalkyloxy, aryloxy, amino, alkylamino, cycloalkylamino, or arylamino groups.

3. The compound of claim 2 having the formula

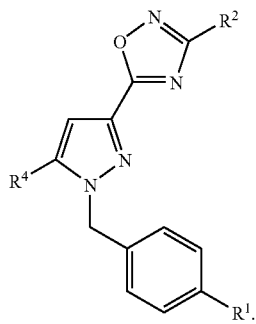

4. The compound of claim 3, wherein

R¹ is hydrogen, fluorine, chlorine, methyl, ethyl, propyl, isopropyl, tert.-butyl, cyclopropyl, methoxy, ethoxy, isopropoxy, trifluoromethyl, or trifluoromethoxy;

R² is aryl optionally substituted with 1, 2 or 3 R⁸ groups or heteroaryl optionally substituted with 1, 2 or 3 R⁸ groups; and R⁴ is hydrogen, fluorine, chlorine, methoxy, ethoxy, propoxy, isopropoxy, cyclopropyloxy, dimethylamino, methyl, ethyl, propyl, isopropyl, tert.-butyl, cyclopropyl, methoxymethyl, or methoxyethyl.

5. The compound of claim 2 having the formula

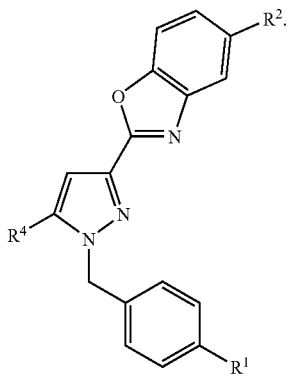

6. The compound of claim 5, wherein

R¹ is hydrogen, fluorine, chlorine, methyl, ethyl, propyl, isopropyl, tert.-butyl, cyclopropyl, methoxy, ethoxy, isopropoxy, trifluoromethyl, or trifluoromethoxy;

R² is aryl optionally substituted with 1, 2 or 3 R⁸ groups or heteroaryl optionally substituted with 1, 2 or 3 R⁸ groups; and R⁴ is hydrogen, fluorine, chlorine, methoxy, ethoxy, propoxy, isopropoxy, cyclopropyloxy, dimethylamino, methyl, ethyl, propyl, isopropyl, tert.-butyl, cyclopropyl, methoxymethyl, or methoxyethyl.

7. The compound of claim 2 having the formula

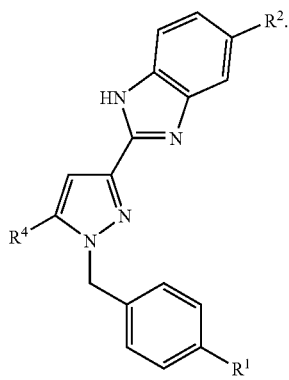

8. The compound of claim 7, wherein

R¹ is hydrogen, fluorine, chlorine, methyl, ethyl, propyl, isopropyl, tert.-butyl, cyclopropyl, methoxy, ethoxy, isopropoxy, trifluoromethyl, or trifluoromethoxy;

R² is aryl optionally substituted with 1, 2 or 3 R⁸ groups or heteroaryl optionally substituted with 1, 2 or 3 R⁸ groups; and R⁴ is hydrogen, fluorine, chlorine, methoxy, ethoxy, propoxy, isopropoxy, cyclopropyloxy, dimethylamino, methyl, ethyl, propyl, isopropyl, tert.-butyl, cyclopropyl, methoxymethyl, or methoxyethyl.

9. The compound of claim 2 having the formula

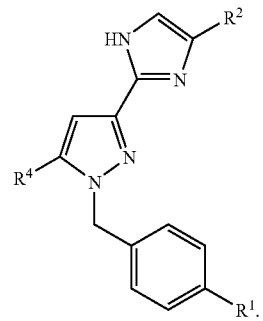

10. The compound of claim 9, wherein

R¹ is hydrogen, fluorine, chlorine, methyl, ethyl, propyl, isopropyl, tert.-butyl, cyclopropyl, methoxy, ethoxy, isopropoxy, trifluoromethyl, or trifluoromethoxy;

R² is aryl optionally substituted with 1, 2 or 3 R⁸ groups or heteroaryl optionally substituted with 1, 2 or 3 R⁸ groups; and R⁴ is hydrogen, fluorine, chlorine, methoxy, ethoxy, propoxy, isopropoxy, cyclopropyloxy, dimethylamino, methyl, ethyl, propyl, isopropyl, tert.-butyl, cyclopropyl, methoxymethyl, or methoxyethyl.

11. The compound of claim 2 having the formula

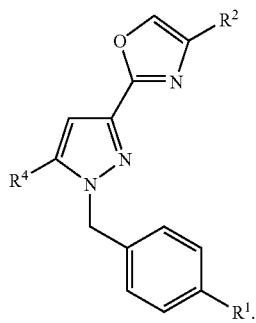

12. The compound of claim 11, wherein
$R^1$ is hydrogen, fluorine, chlorine, methyl, ethyl, propyl, isopropyl, tert.-butyl, cyclopropyl, methoxy, ethoxy, isopropoxy, trifluoromethyl, or trifluoromethoxy;
$R^2$ is aryl optionally substituted with 1, 2 or 3 $R^8$ groups or heteroaryl optionally substituted with 1, 2 or 3 $R^8$ groups; and
$R^4$ is hydrogen, fluorine, chlorine, methoxy, ethoxy, propoxy, isopropoxy, cyclopropyloxy, dimethylamino, methyl, ethyl, propyl, isopropyl, tert.-butyl, cyclopropyl, methoxymethyl, or methoxyethyl.

13. A pharmaceutical composition comprising a compound according to claim 1 or a physiologically acceptable salt thereof and a pharmaceutically acceptable diluent or carrier.

14. A method of modulating the HIF-1α pathway in cells comprising contacting a cell with one or more compounds of claim 1.

15. A method of treating a transcription factor HIF-mediated hyperproliferative disorder in a mammal comprising administering to a mammal in need thereof a therapeutically effective amount of one or more compounds of claim 1.

16. The method of claim 15 wherein the transcription factor HIF-mediated hyperproliferative disorder is cancer of the breast, respiratory tract, brain, reproductive organs, digestive tract, urinary tract, eye, liver, skin, head and neck, thyroid, parathyroid or a distant metastasis of a solid tumor.

17. A method of treating a transcription factor HIF-mediated angiogenesis disorder in a mammal comprising administering to a mammal in need thereof a therapeutically effective amount of one or more compounds of claim 1.

18. The method of claim 17 wherein the transcription factor HIF-mediated angiogenesis disorder is diabetic retinopathy, ischemic retinal-vein occlusion, retinopathy of prematurity, age-related macular degeneration (AMD), neovascular glaucoma, psoriasis, retrolental fibroplasias, angiofibroma, inflammation, rheumatoid arthritis (RA), restenosis, in-stent restenosis or vascular graft restenosis.

19. A method of treating a transcription factor HIF-mediated disorder in a mammal comprising administering to a mammal in need thereof a therapeutically effective amount of one or more compounds of claim 1.

20. The method of claim 19 wherein the transcription factor HIF-mediated disorder is a transient or chronic ischemic cardiovascular disease, such as cardiac heart failure, myocardial infarction, arrhythmia and apoplexy, a fibrotic disease of the kidney or the lung, the loss of nerve function after traumatic crushing or severing, or Chuwash polycythemia.

* * * * *